(12) United States Patent
Njoroge et al.

(10) Patent No.: US 7,342,041 B2
(45) Date of Patent: Mar. 11, 2008

(54) 3,4-(CYCLOPENTYL)-FUSED PROLINE COMPOUNDS AS INHIBITORS OF HEPATITIS C VIRUS NS3 SERINE PROTEASE

(75) Inventors: F. George Njoroge, Warren, NJ (US); Srikanth Venkatraman, Woodbridge, NJ (US); Ashok Arasappan, Bridgewater, NJ (US); Francisco Velazquez, Clinton, NJ (US); Viyyoor M. Girijavallabhan, Parippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 74 days.

(21) Appl. No.: 11/064,757

(22) Filed: Feb. 24, 2005

(65) Prior Publication Data

US 2005/0197301 A1    Sep. 8, 2005

Related U.S. Application Data

(60) Provisional application No. 60/548,655, filed on Feb. 27, 2004.

(51) Int. Cl.
*A61K 31/401* (2006.01)
*C07D 207/08* (2006.01)

(52) U.S. Cl. ............... 514/423; 544/143; 544/295; 544/357; 544/373; 546/200; 546/277.1; 548/181; 548/235; 548/537; 549/59; 549/473

(58) Field of Classification Search ............... 514/423; 548/537, 181, 235; 544/143, 295, 357, 373; 546/200, 277.1; 549/59, 473
See application file for complete search history.

(56) References Cited

U.S. PATENT DOCUMENTS 6,608,027 B1    8/2003    Tsantrizos et al.

FOREIGN PATENT DOCUMENTS

| EP | 1 157 998 A1 | 11/2001 |
|---|---|---|
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 01/74768 | 10/2001 |
| WO | WO 01/77113 | 10/2001 |
| WO | WO 01/81325 | 11/2001 |
| WO | WO 02/08187 | 1/2002 |
| WO | WO 02/08244 | 1/2002 |
| WO | WO 02/08244 A2 | 1/2002 |
| WO | WO 02/08256 | 1/2002 |
| WO | WO 08/08251 | 1/2002 |
| WO | WP 02/08198 | 1/2002 |
| WO | WO 02/18369 A2 | 3/2002 |
| WO | WO 02/48172 | 6/2002 |
| WO | WO 03/062265 A2 | 7/2003 |

OTHER PUBLICATIONS

U.S. Appl. No. 10/052,386, filed Jan. 18, 2002.*
Han, Wei, et al., "Alpha-Ketoamides, Alpha-Ketoesters and Alpha-Diketones . . . ," Bioorganic & Medicinal Chemistry Letters 10:711-713 (2000).
Landro, James A., et al., "Mechanistic Role of an NS4A . . . ," Biochemistry 36:9340-9348 (1997).
Marchetti, Antonella, et al., "Synthesis of Two Novel . . . ," Synlett S1:1000-1002 (1999).
PCT International Search Report dated Jul. 29, 2005 for corresponding PCT Application No. PCT/US2005/005778.
Chen, Shu-Hui, et al., "Synthesis and Evaluation . . . ," Bioorganic & Medicinal Chemistry Letters 3531-36 (2003).
Lamar, Jason, et al., "Novel P4 truncated . . . ," Bioorganic & Medicinal Chemistry Letters 14:263-66 (2004).
Smith, R.M., et al., "Structure-based design . . . ," Journal of Viral Hepatitis 10:405-412 (2003).

* cited by examiner

*Primary Examiner*—Rebecca Anderson
*Assistant Examiner*—Joseph R. Kosack
(74) *Attorney, Agent, or Firm*—Serena Farquharson-Torres; Palaiyur S. Kalyanaraman

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

34 Claims, No Drawings

3,4-(CYCLOPENTYL)-FUSED PROLINE COMPOUNDS AS INHIBITORS OF HEPATITIS C VIRUS NS3 SERINE PROTEASE

FIELD OF THE INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention additionally discloses novel compounds containing bicyclic P2 moieties as inhibitors of the HCV NS3/NS4a serine protease. This application claims priority from U.S. provisional application Ser. No. 60/548,655 filed Feb. 27, 2004.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed. (See, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e. trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, eg., Pizzi et al. (1994) *Proc. Natl. Acad. Sci (USA)* 91:888-892, Failla et al. (1996) *Folding & Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinàs-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPSTI-C3) and minibody repertoires (MBip) (Dimasi et al. (1997) *J. Virol.* 71:7461-7469), $cV_HE2$ (a "camelized" variable domain antibody fragment) (Martin et al.(1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (U.S. Pat. No. 6,608, 027, Assignee: Boehringer Ingelheim (Canada) Ltd.; Published Oct. 12, 2000) which discloses peptide derivatives of the formula:

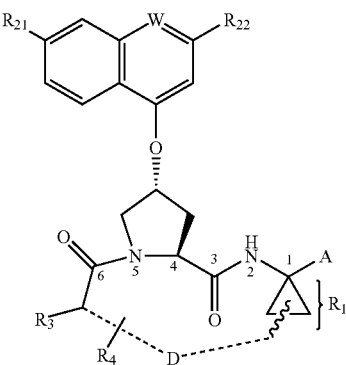

Reference is made to A. Marchetti et al, Synlett, S1, 1000-1002 (1999) describing the synthesis of bicylic analogs of an inhibitor of HCV NS3 protease. A compound disclosed therein has the formula:

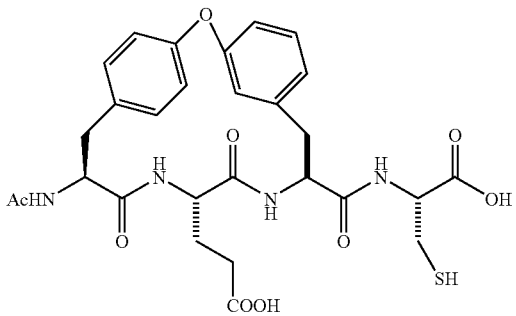

Reference is also made to W. Han et al, *Bioorganic & Medicinal Chem. Lett,* (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

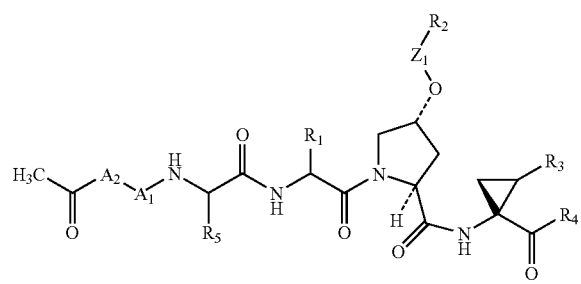

where the various elements are defined therein. An illustrative compound of that series is:

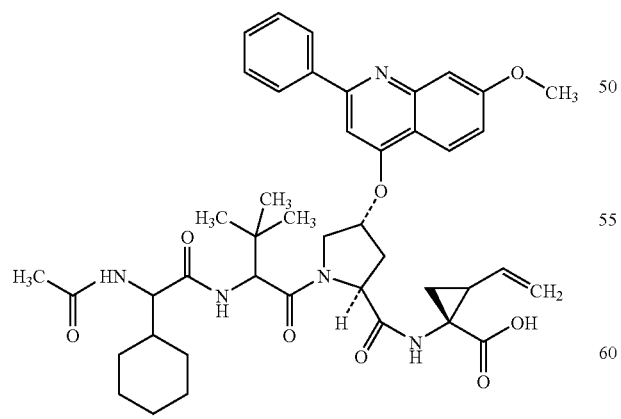

Reference is also made to WO 00/09543 (Assignee: Boehringer Ingelheim Limited; Published Feb. 24, 2000) which discloses peptide derivatives of the formula:

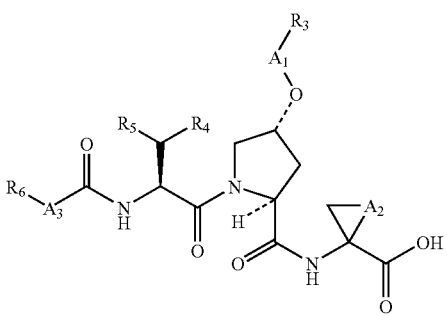

where the various elements are defined therein. An illustrative compound of that series is:

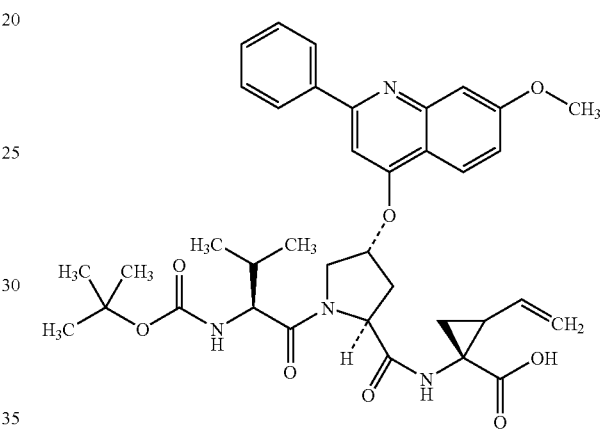

Reference is also made to U.S. Pat. No. 6,608,027 (Boehringer Ingelheim, Canada) which discloses NS3 protease inhibitors of the type:

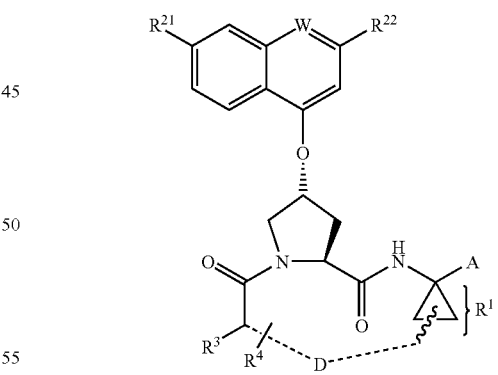

wherein the various moieties are defined therein.

Current therapies for hepatitis C include interferon-α (INF$_\alpha$) and combination therapy with ribavirin and interferon. See, e.g., Beremguer et al. (1998) *Proc. Assoc. Am. Physicians* 110(2):98-112. These therapies suffer from a low sustained response rate and frequent side effects. See, e.g. Hoofnagle et al. (1997) *N. Engl. J. Med.* 336:347. Currently, no vaccine is available for HCV infection.

Reference is further made to WO 01/74768 (Assignee: Vertex Pharmaceuticals Inc) published Oct. 11, 2001, which discloses certain compounds of the following general formula (R is defined therein) as NS3-serine protease inhibitors of Hepatitis C virus:

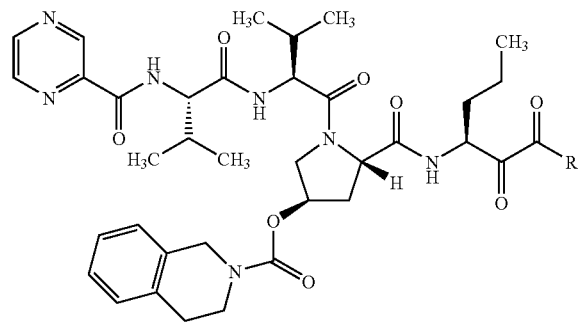

A specific compound disclosed in the aforementioned WO 01/74768 has the following formula:

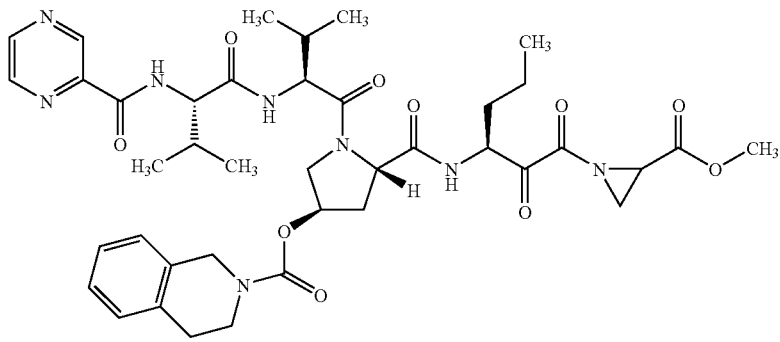

PCT Publications WO 01/77113; WO 01/081325; WO 02/08198; WO 02/08256; WO 02/08187; WO 02/08244; WO 02/48172; WO 02/08251; and pending U.S. patent application Ser. No.10/052,386, filed Jan. 18, 2002, disclose various types of peptides and/or other compounds as NS-3 serine protease inhibitors of hepatitis C virus. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment or prevention of HCV or amelioration of one or more of the symptoms of hepatitis C using one or more such compounds or one or more such formulations. Also provided are methods of modulating the interaction of an HCV polypeptide with HCV protease. Among the compounds provided herein, compounds that inhibit HCV NS3/NS4a serine protease activity are preferred. The present invention discloses a compound, or enantiomers, stereoisomers, rotamers, tautomers, diastereomers or racemates of said compound, or a pharmaceutically acceptable salt, solvate or ester of said compound, said compound having the general structure shown in structural Formula 1:

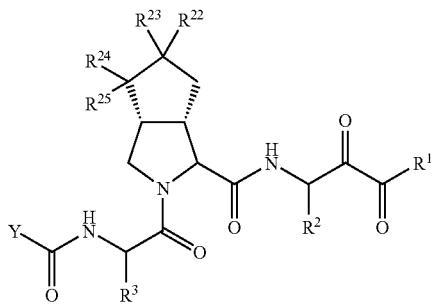

Formula 1 wherein:

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl, or alternately $R^9$ and $R^{10}$ in $NR^9R^{10}$ are connected to each other such that $NR^9R^{10}$ forms a four to eight-membered heterocyclyl, and likewise independently alternately $R^9$ and $R^{10}$ in $CHR^9R^{10}$ are connected to each other such that $CHR^9R^{10}$ forms a four to eight-membered cycloalkyl;

$R^2$ and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

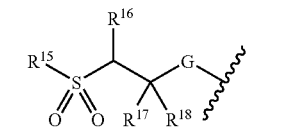 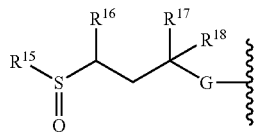

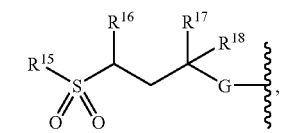 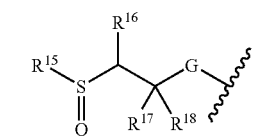

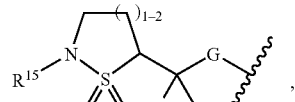

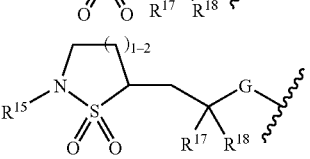

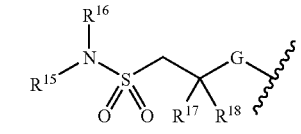 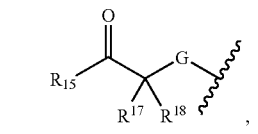

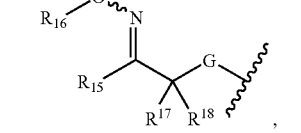 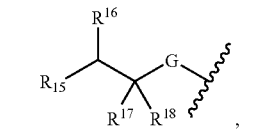

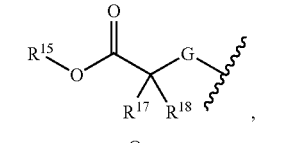 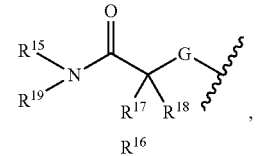

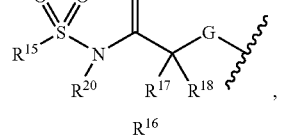 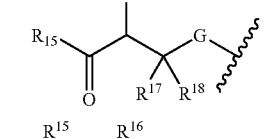

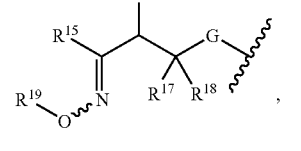 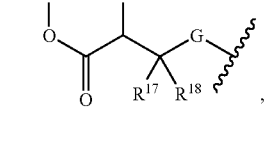

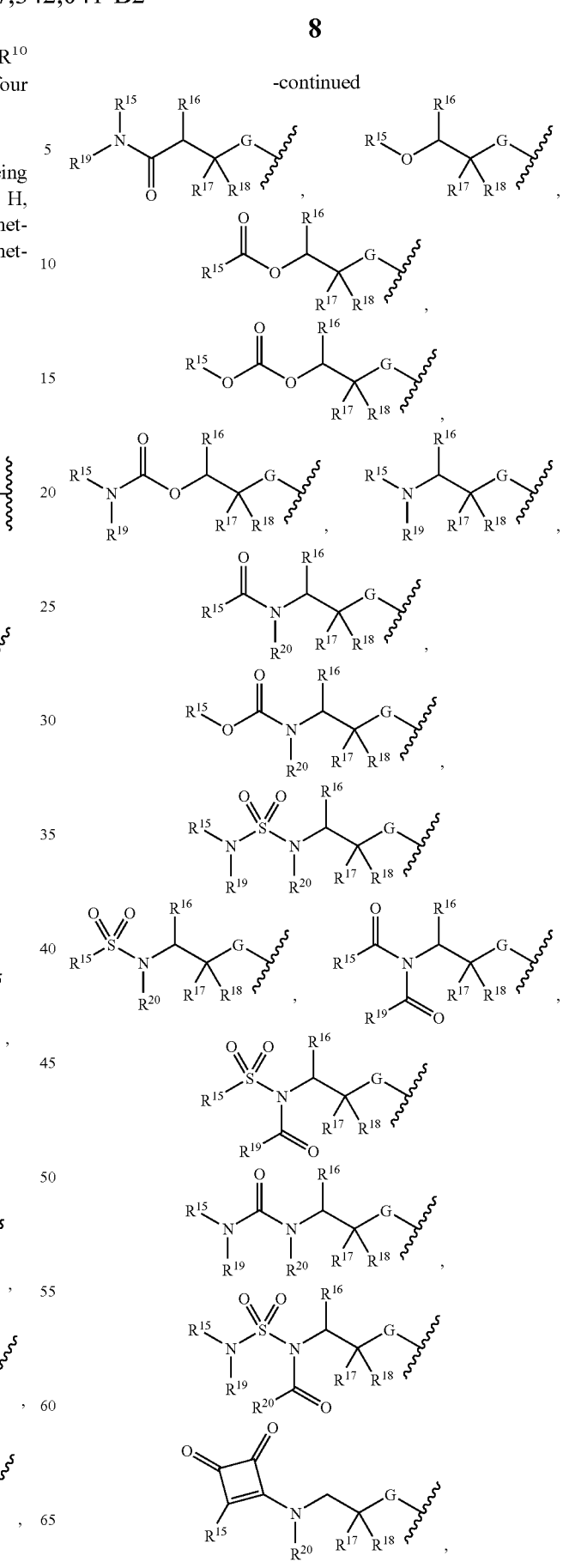

-continued

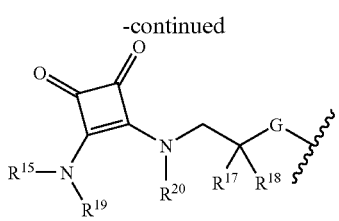

wherein G is NH or O; and $R^{15}$, $R^{16}$, $R^{17}$, $R^{18}$, $R^{19}$, $R^{20}$, $R^{21}$, $R^{22}$, $R^{23}$, $R^{24}$ and $R^{25}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; (iv) likewise independently $R^{15}$ and $R^{20}$ are connected to each other to form a four to eight-membered heterocyclyl; (v) likewise independently $R^{22}$ and $R^{23}$ are connected to each other to form a three to eight-membered cycloalkyl or a four to eight-membered heterocyclyl; and (vi) likewise independently $R^{24}$ and $R^{25}$ are connected to each other to form a three to eight-membered cycloalkyl or a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In the above-noted definitions, preferred alkyl is made of one to ten carbon atoms, preferred alkenyl or alkynyl is made of two to ten carbon atoms, preferred cycloalkyl is made of three to eight carbon atoms, and preferred heteroalkyl, heteroaryl or heterocycloalkyl (heterocyclyl) has one to six oxygen, nitrogen, sulfur, or phosphorus atoms.

The compounds represented by Formula I, by themselves or in combination with one or more other suitable agents disclosed herein, can be useful for treating diseases such as, for example, HCV, HIV, AIDS (Acquired Immune Deficiency Syndrome), and related disorders, as well as for modulating the activity of hepatitis C virus (HCV) protease, preventing HCV, or ameliorating one or more symptoms of hepatitis C. Such modulation, treatment, prevention or amelioration can be done with the inventive compounds as well as with pharmaceutical compositions or formulations comprising such compounds. Without being limited to theory, it is believed that the HCV protease may be the NS3 or NS4a protease. The inventive compounds can inhibit such protease. They can also modulate the processing of hepatitis C virus (HCV) polypeptide.

DETAILED DESCRIPTION

In an embodiment, the present invention discloses compounds which are represented by structural Formula 1 or a pharmaceutically acceptable salt, solvate or ester thereof, wherein the various moieties are as defined above.

In another embodiment, $R^1$ is $NR^9R^{10}$, and $R^9$ is H, $R^{10}$ is H, or $R^{14}$ wherein $R^{14}$ is H, alkyl, aryl, heteroalkyl, heteroaryl, cycloalkyl, alkyl-aryl, alkyl-heteroaryl, aryl-alkyl, alkenyl, alkynyl or heteroaryl-alkyl.

In another embodiment, $R^{14}$ is selected from the group consisting of:

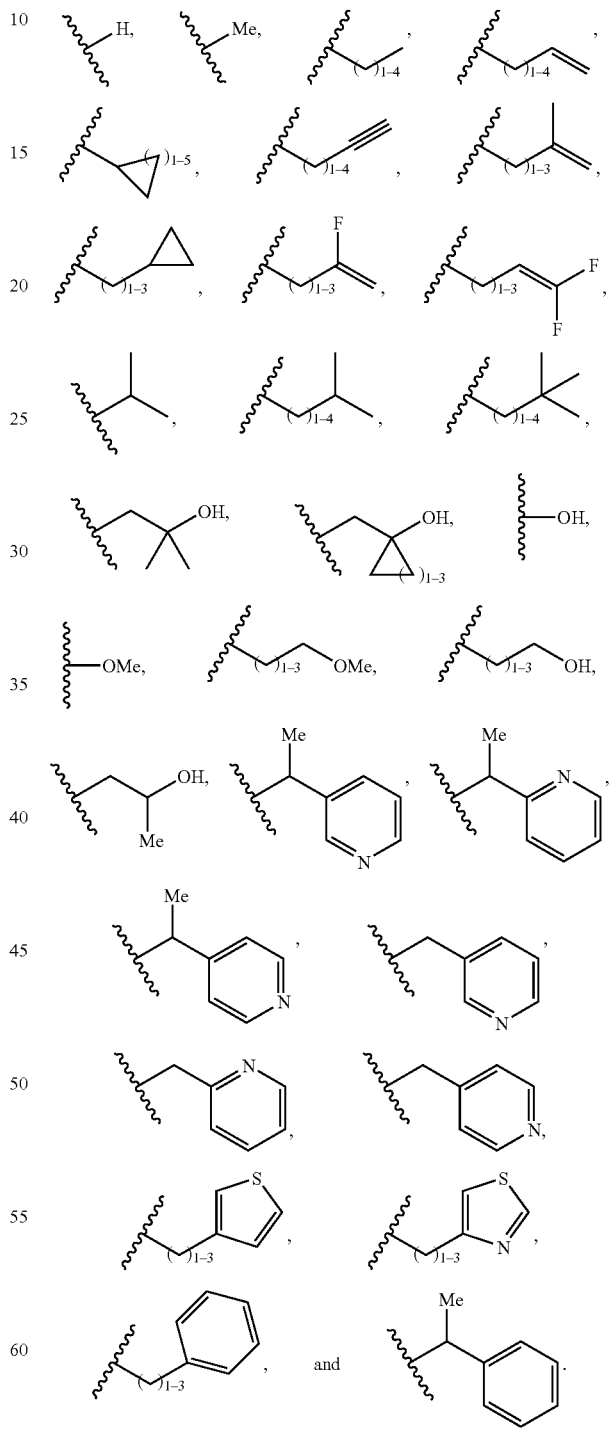

In another embodiment, $R^2$ is selected from the group consisting of the following moieties:

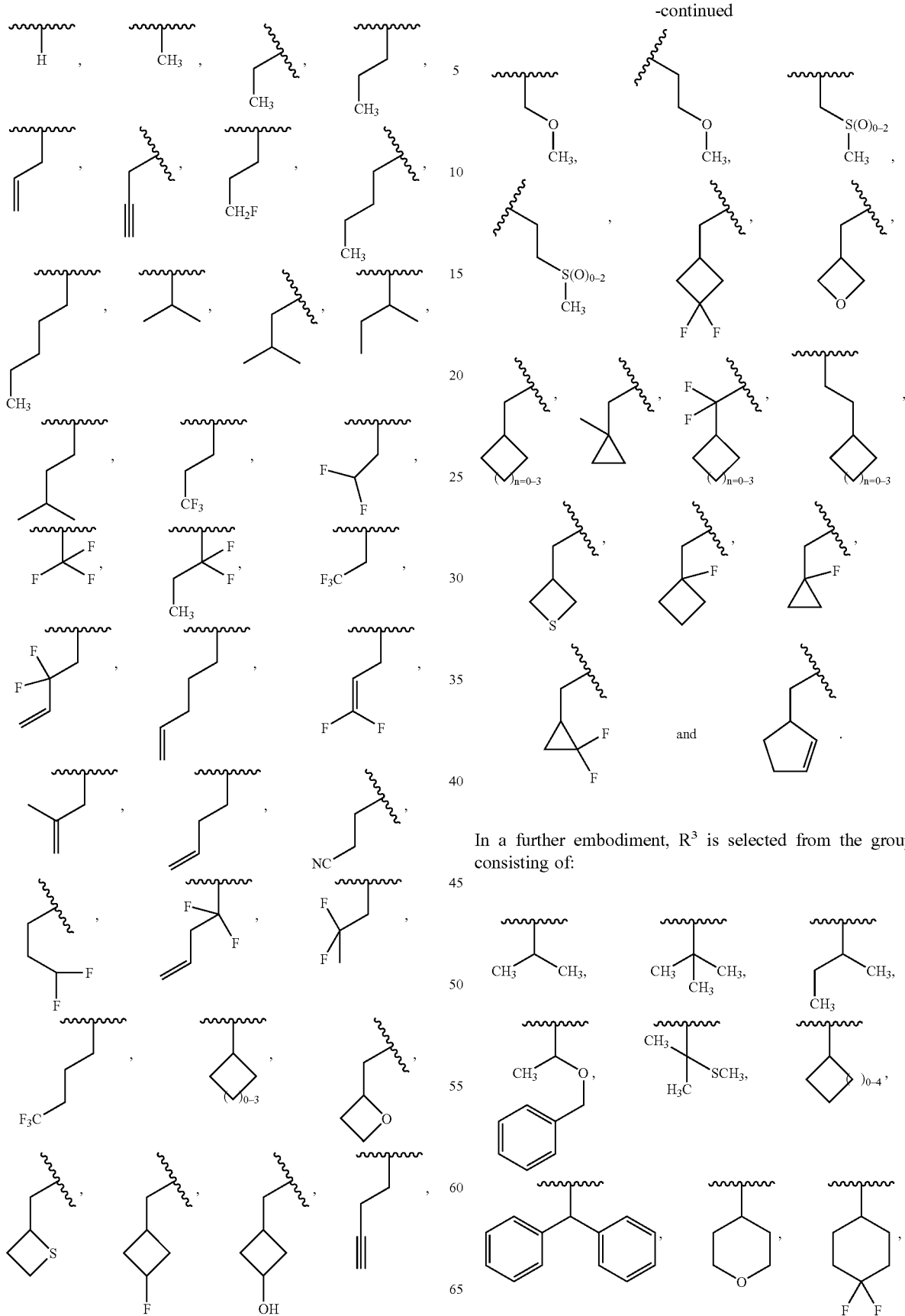
In a further embodiment, $R^3$ is selected from the group consisting of:

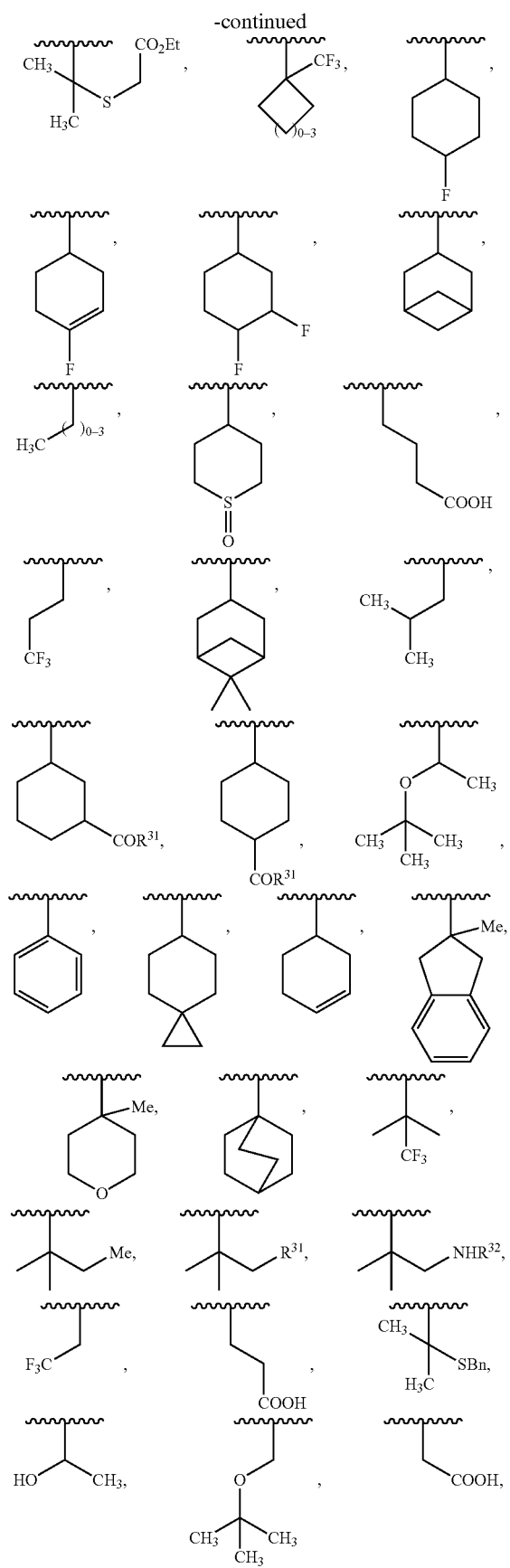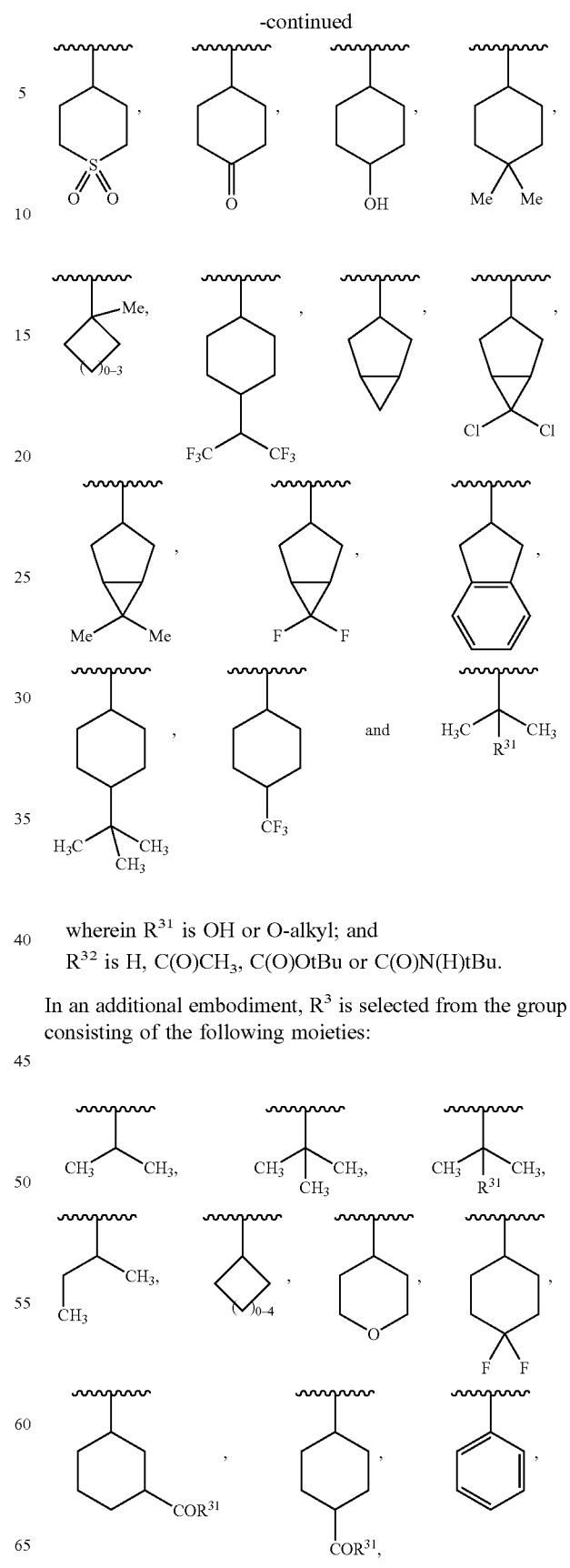
wherein $R^{31}$ is OH or O-alkyl; and
$R^{32}$ is H, C(O)CH$_3$, C(O)OtBu or C(O)N(H)tBu.
In an additional embodiment, $R^3$ is selected from the group consisting of the following moieties:

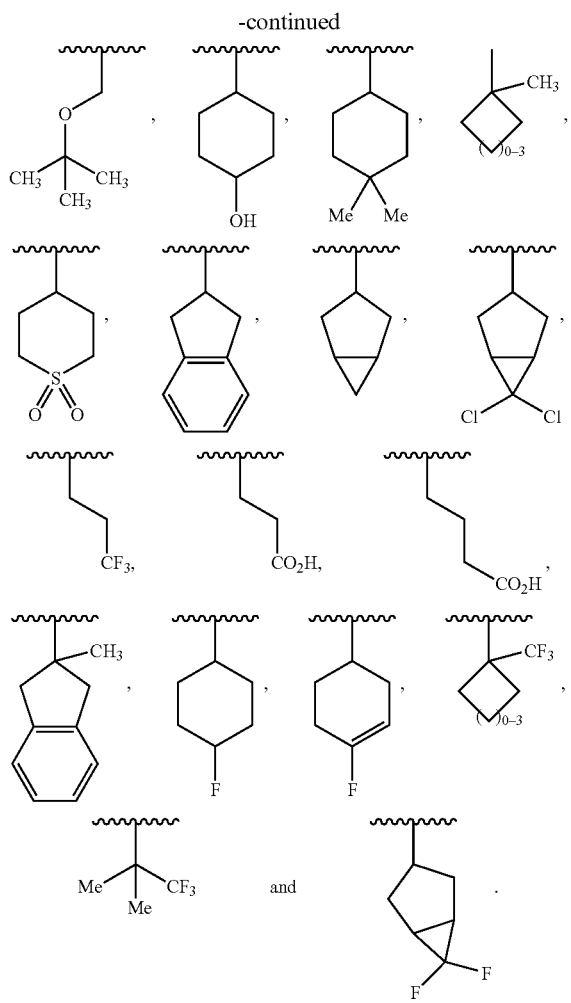
In an yet another embodiment, G is NH.
In a further embodiment, Y is selected from the following moieties:
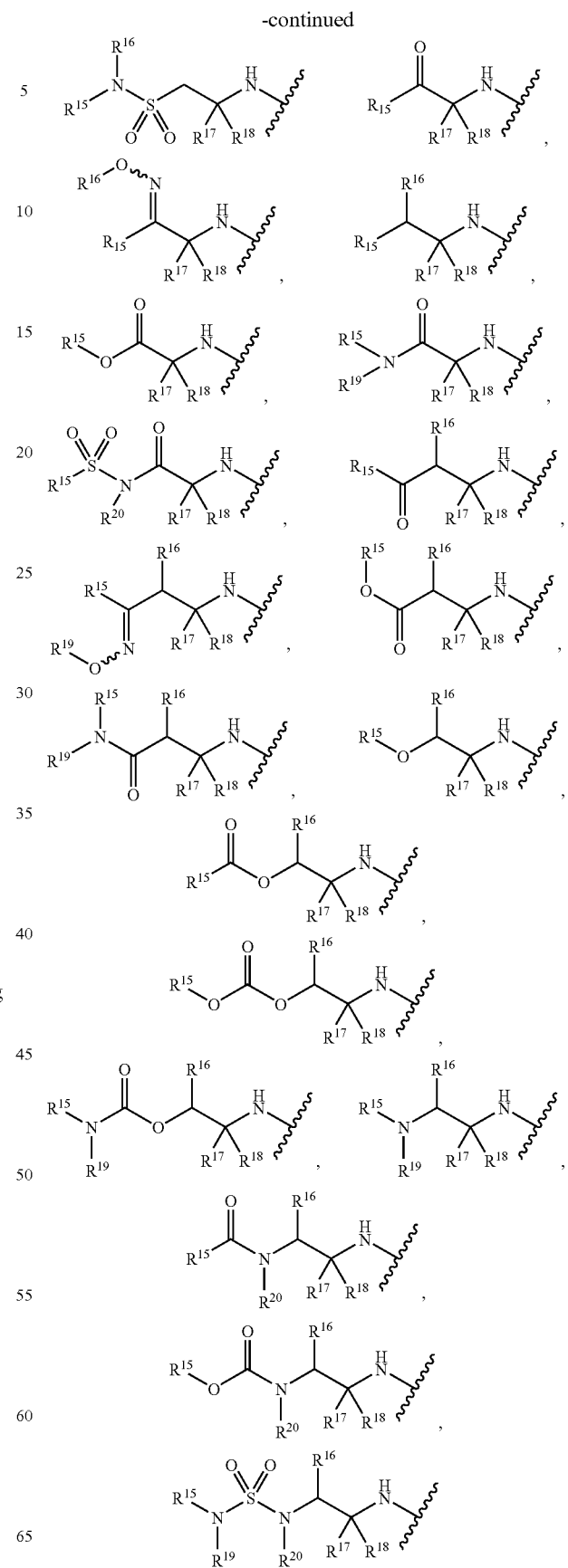

-continued

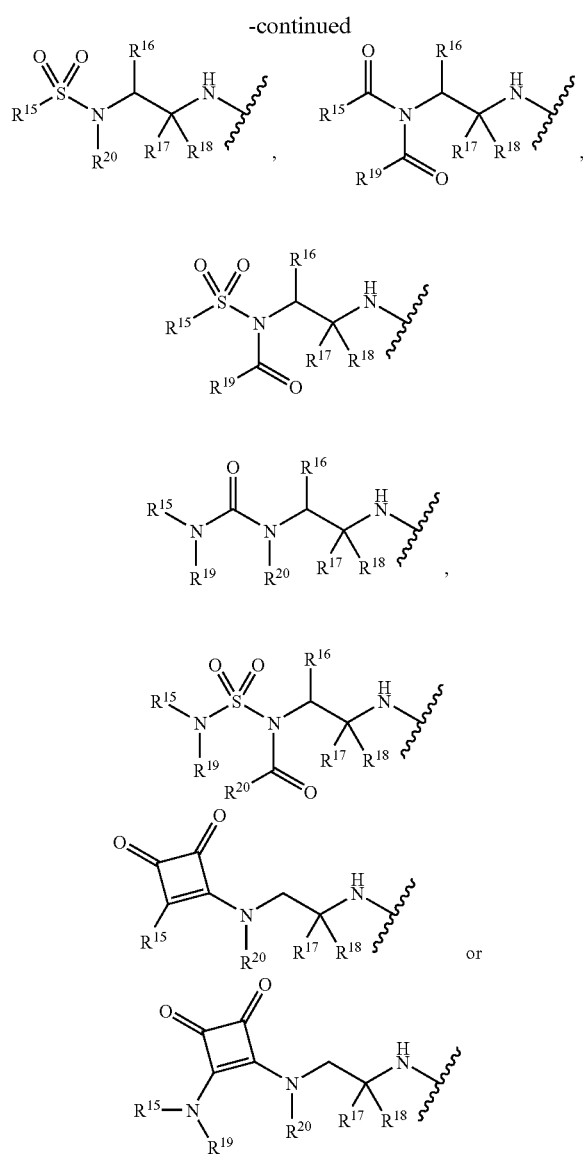

wherein $R^{15}$, $R^{16}$, $R^{17}$, $R^{18}$, $R^{19}$, $R^{20}$, $R^{21}$, $R^{22}$, $R^{23}$, $R^{24}$, and $R^{25}$ each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In a still additional embodiment, the moiety:

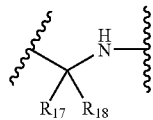

is selected from the following:

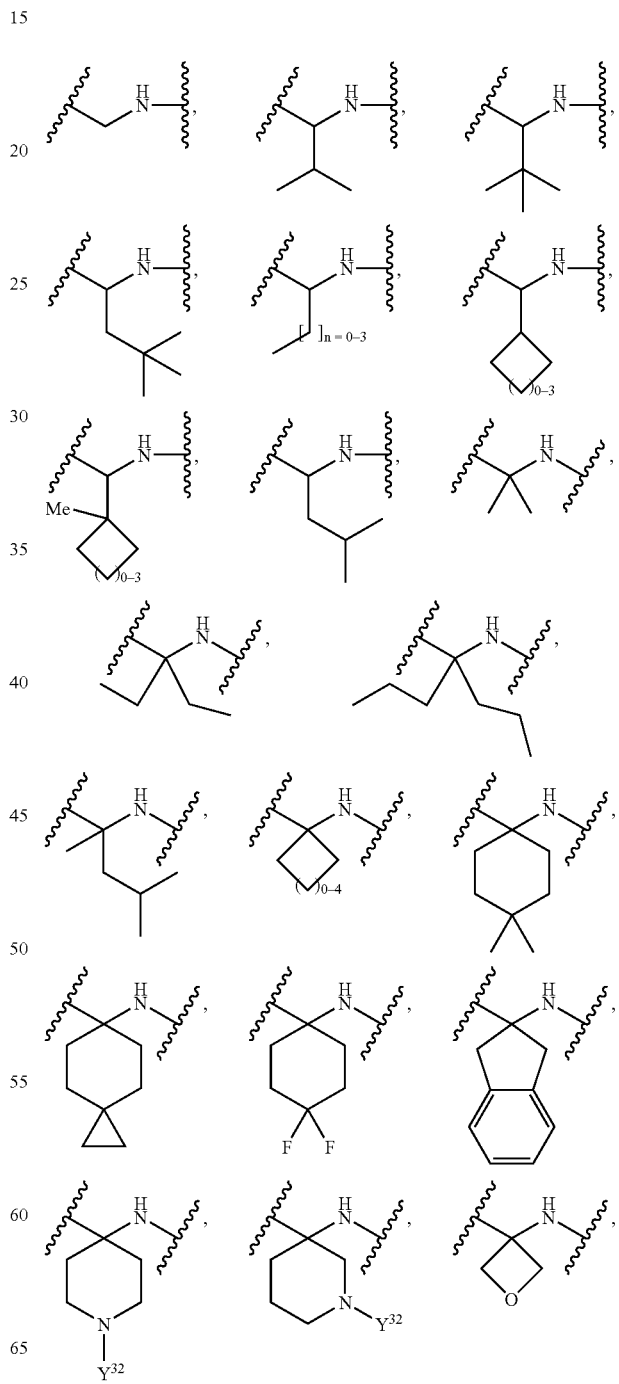

-continued wherein Y³² is selected from the group consisting of:

In a further embodiment, Y is selected from:

-continued
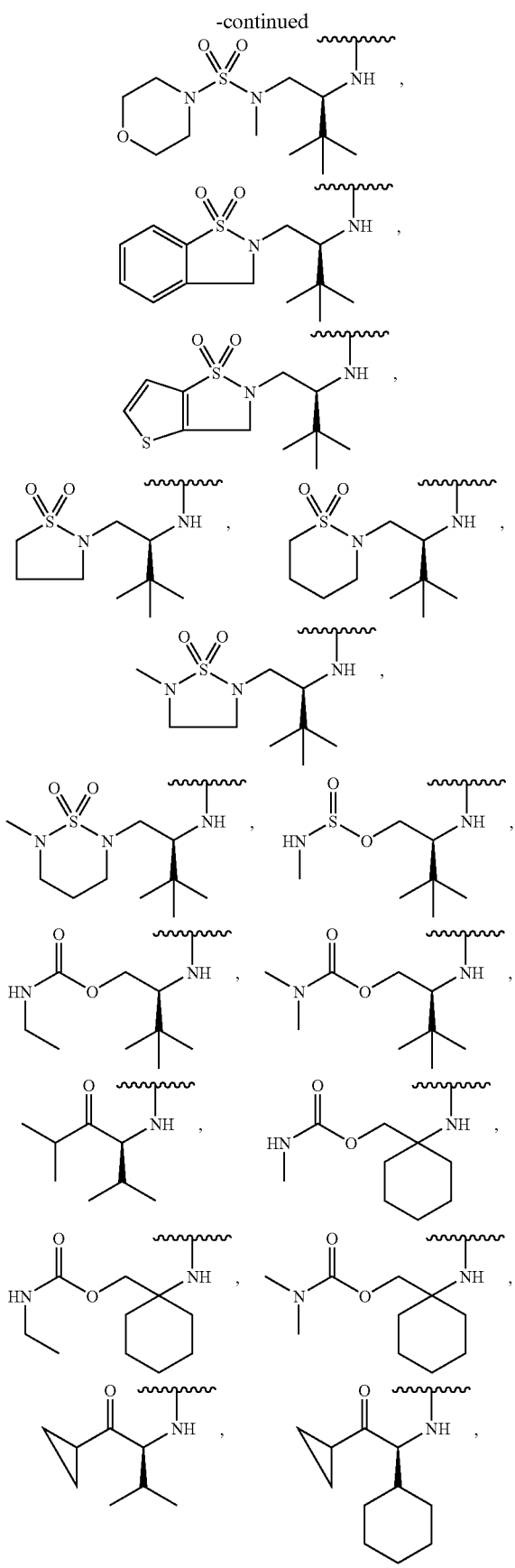
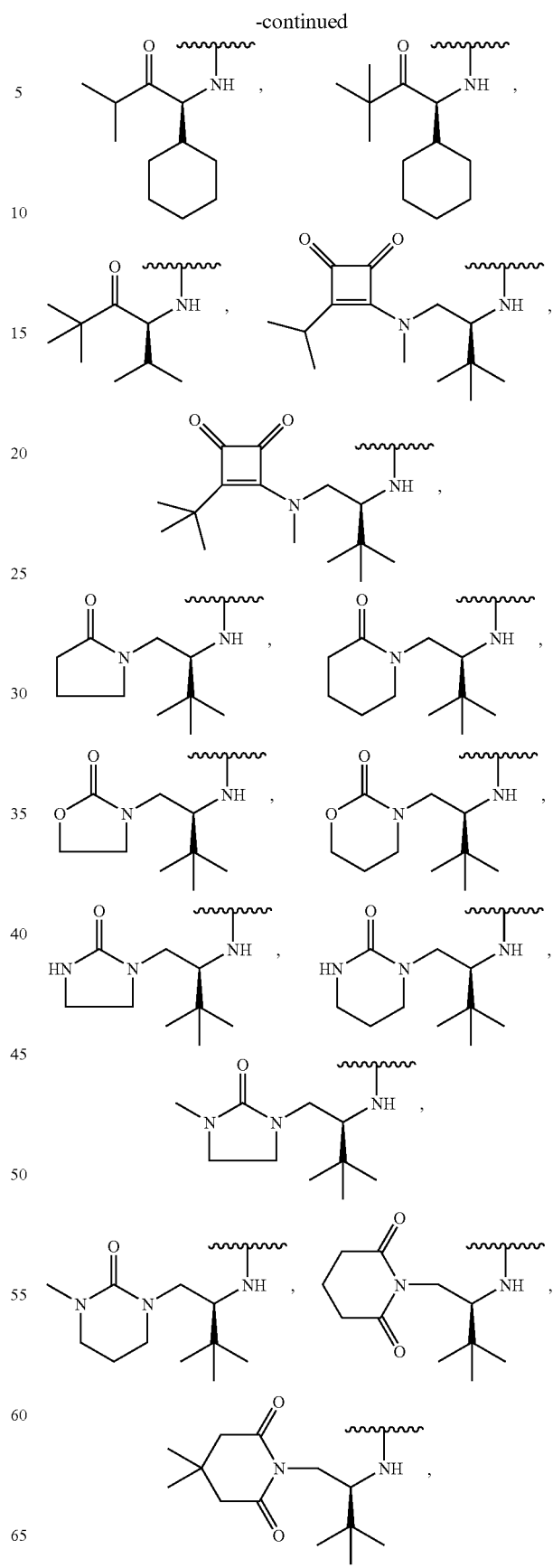

-continued
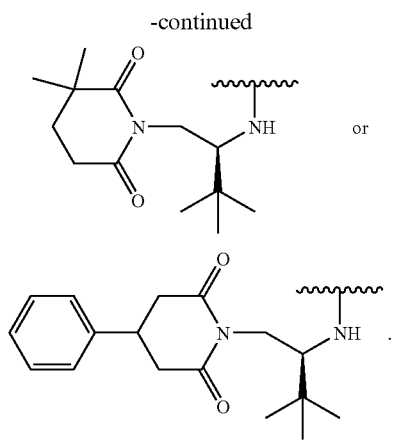
or
In an additional embodiment, the moiety:
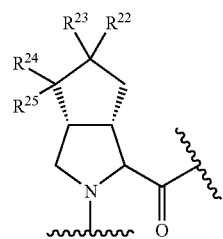
is selected from the following structures:
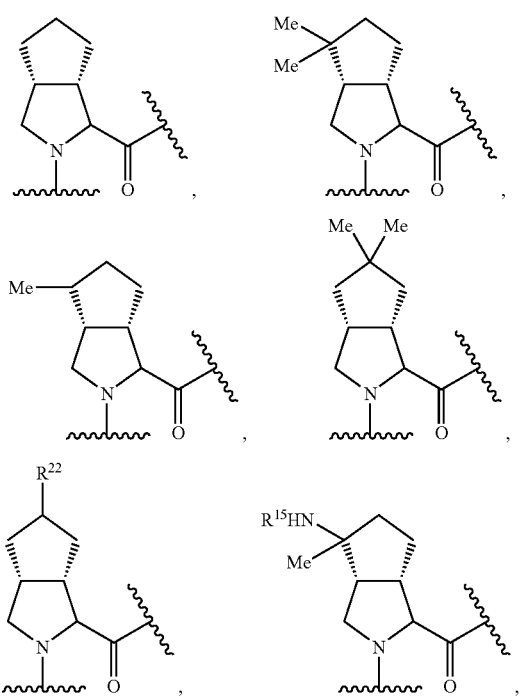
-continued
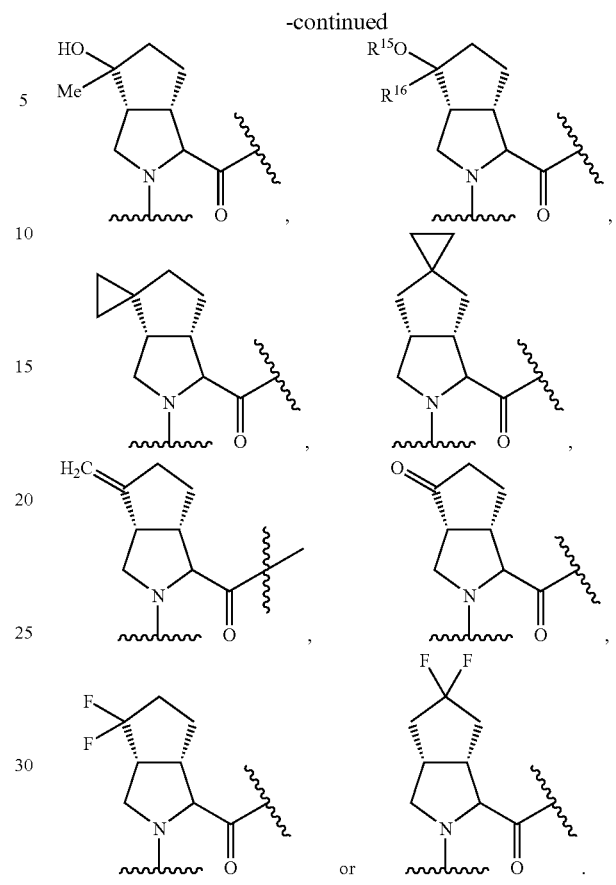
In a still additional embodiment, $R^1$ is $NHR^{14}$, where $R^{14}$ is selected from the group consisting of:

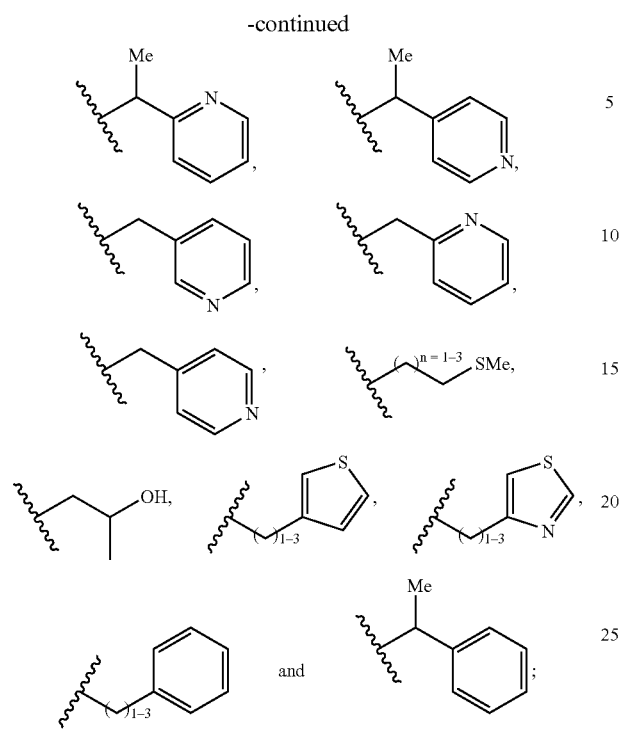
$R^2$ is selected from the group consisting of the following moieties:
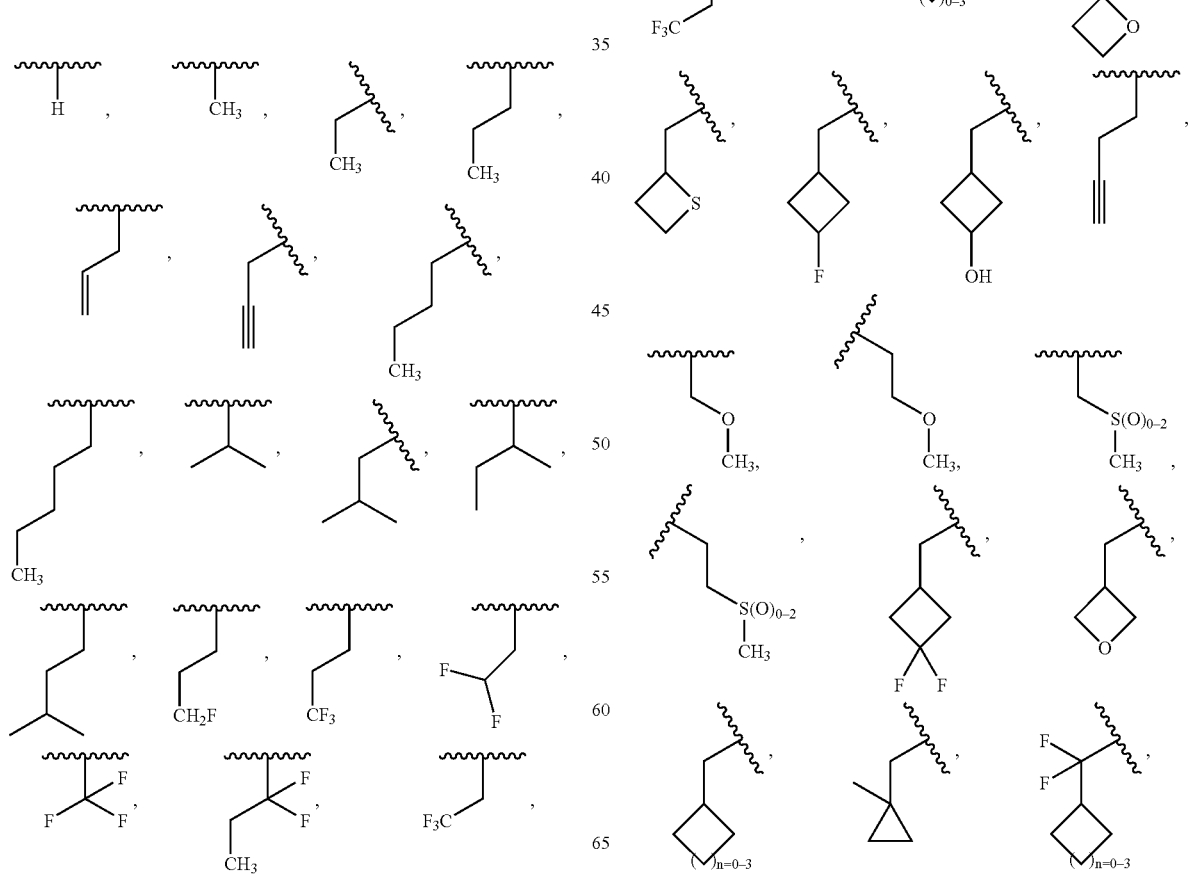

$R^3$ is selected from the group consisting of the following moieties:

the moiety:

is selected from

-continued
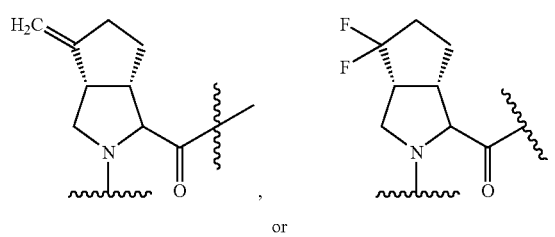
or
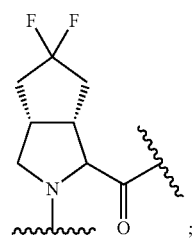
and Y is selected from:
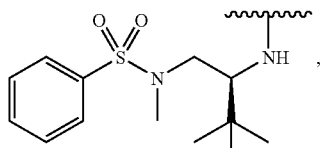
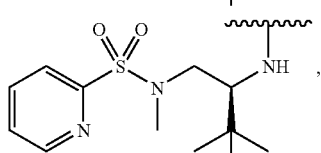
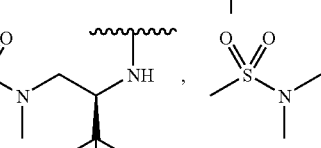
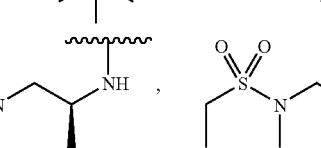
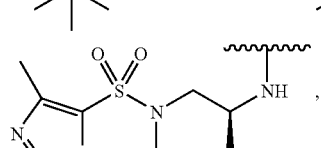
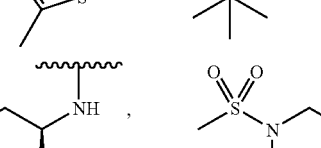
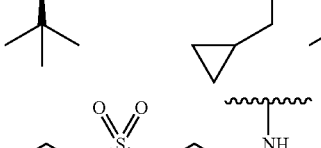
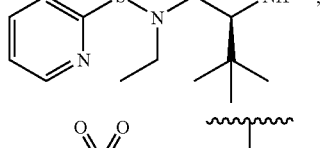
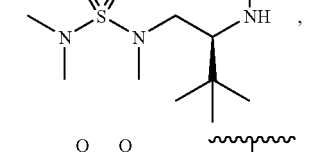
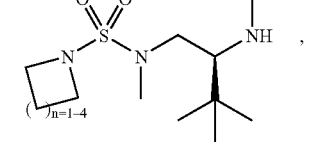
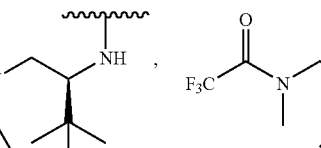

-continued
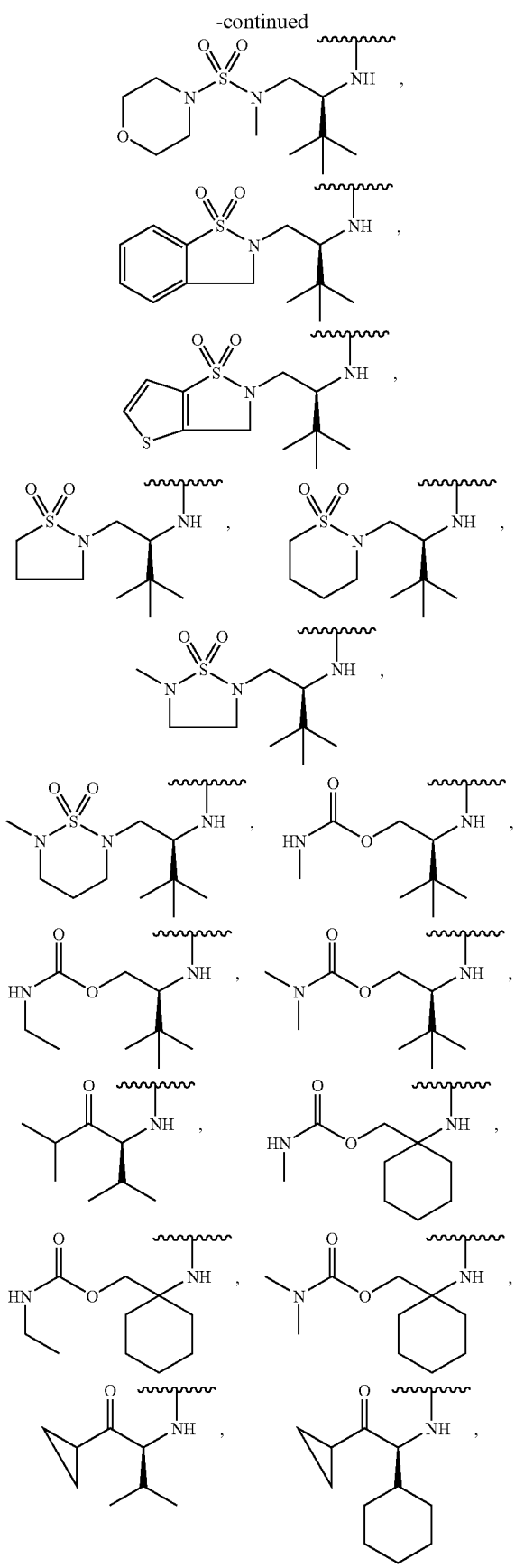
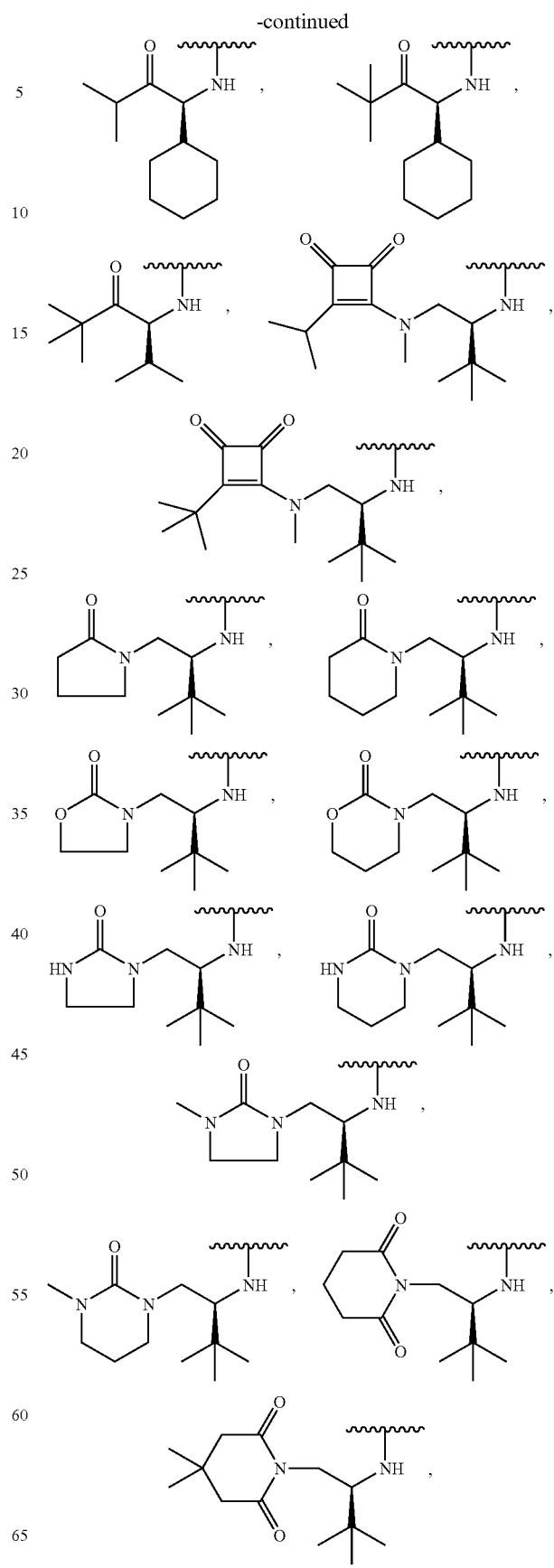

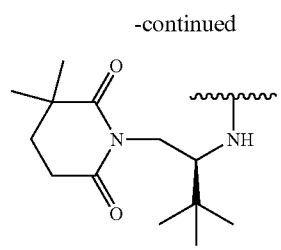 and 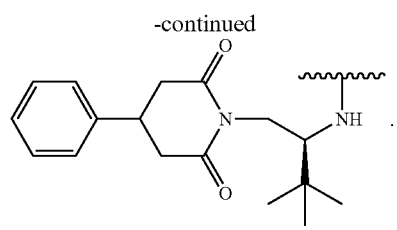
Yet another embodiment of the invention discloses compounds shown in Table 1.
TABLE 1
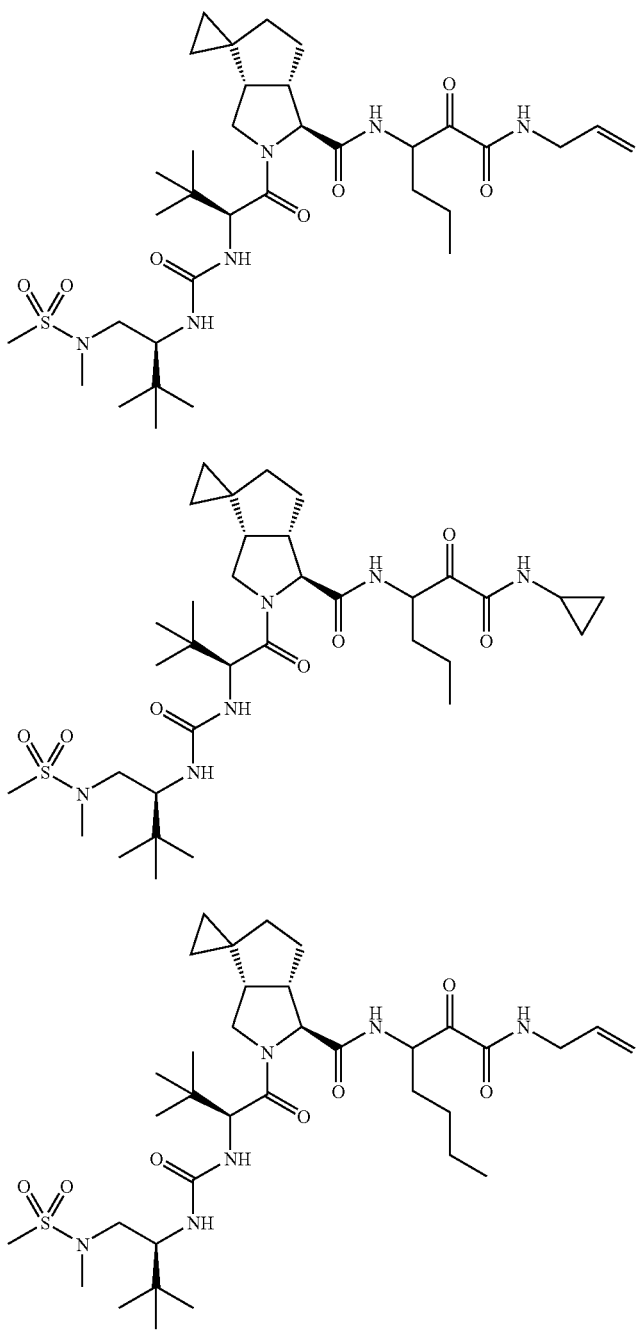

TABLE 1-continued
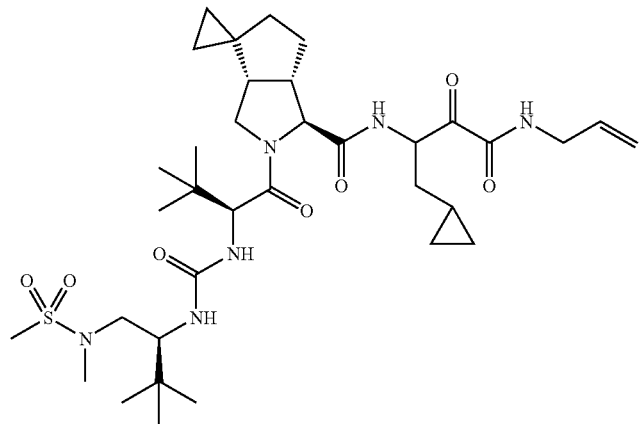
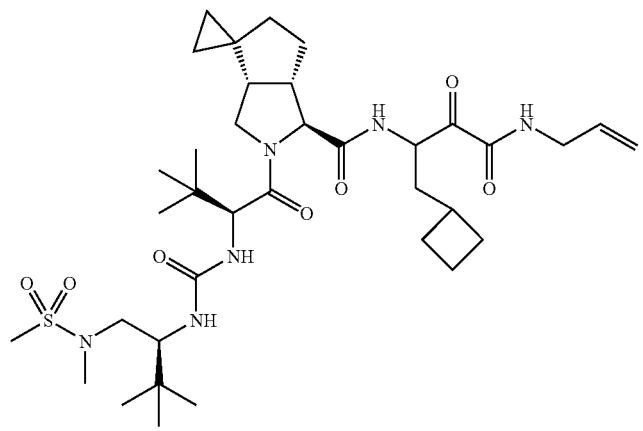
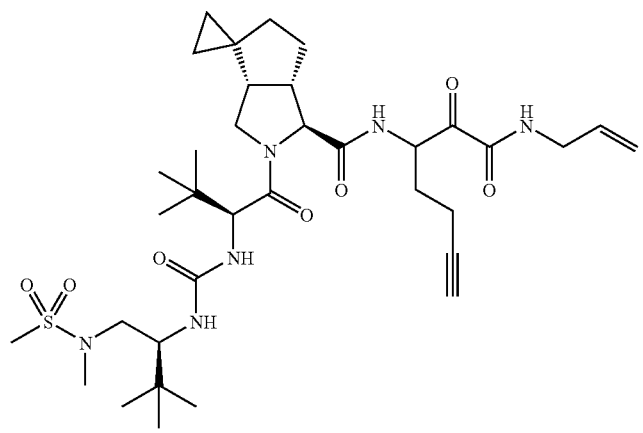

TABLE 1-continued
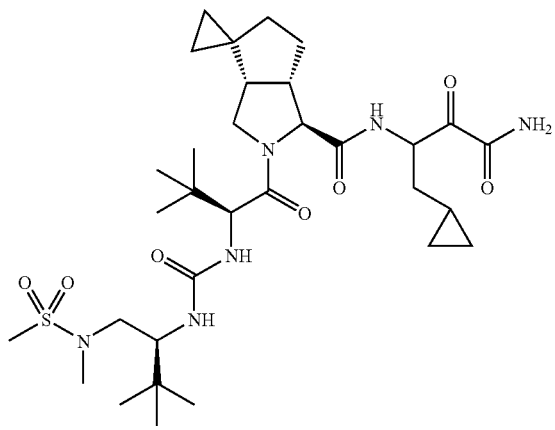
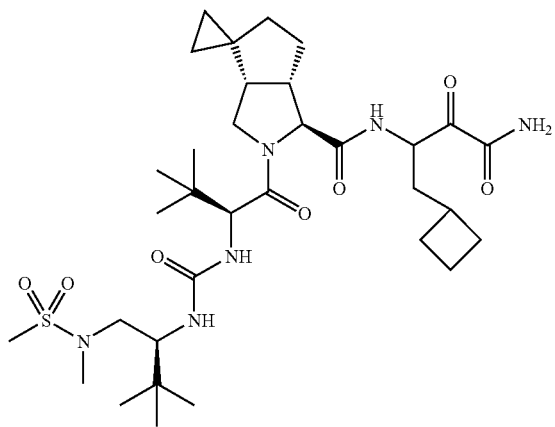
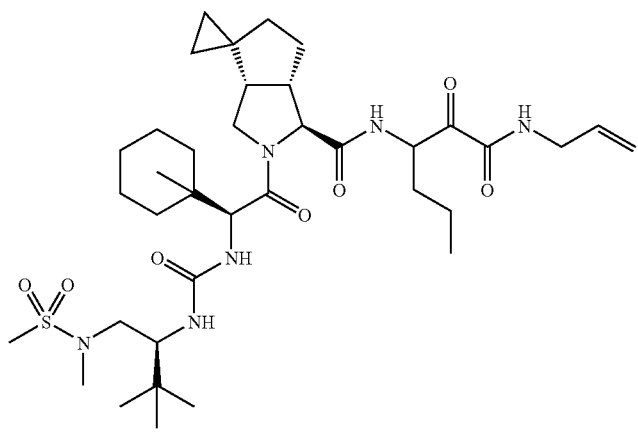

TABLE 1-continued
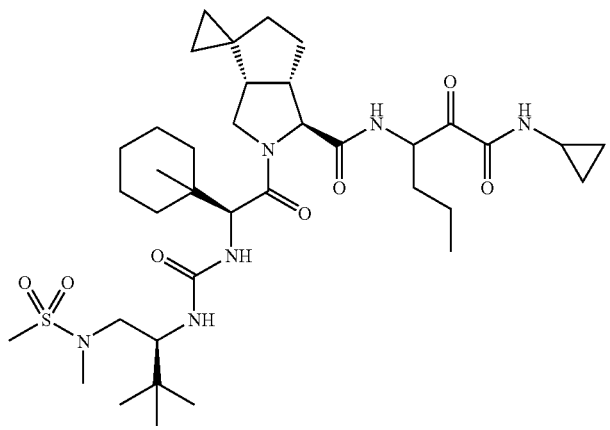
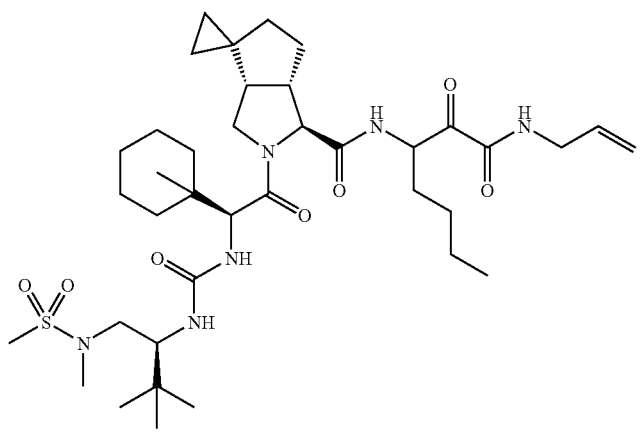
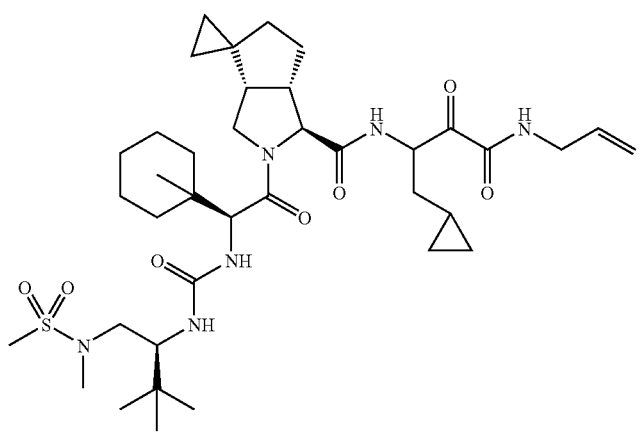

TABLE 1-continued
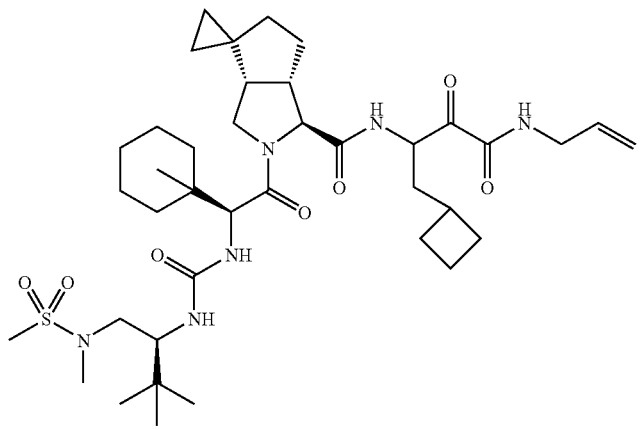
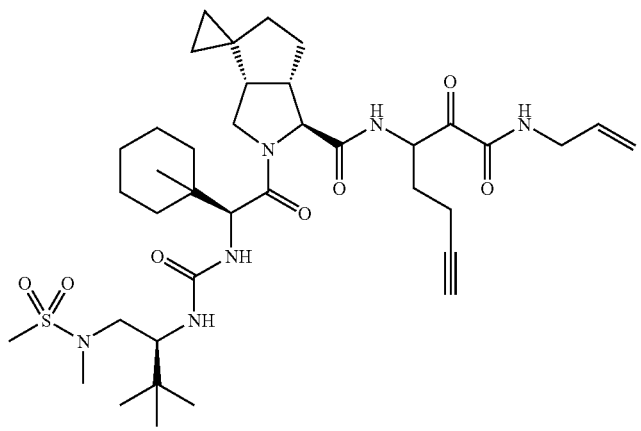
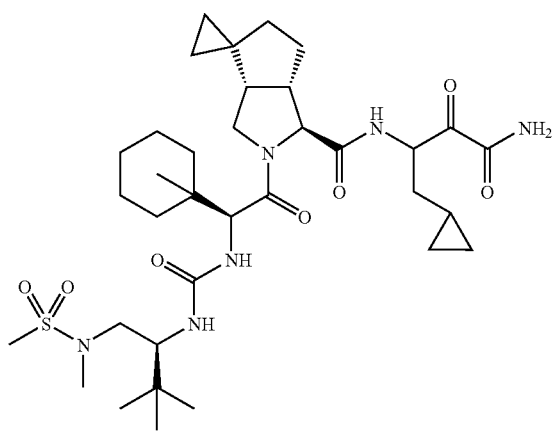

TABLE 1-continued
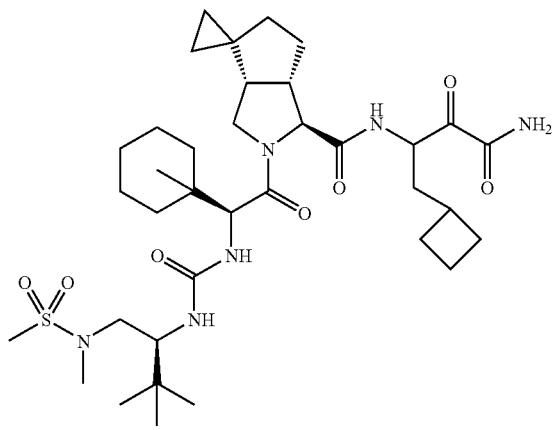
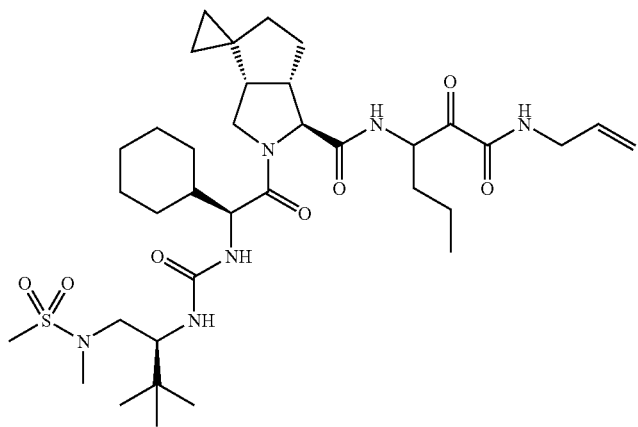
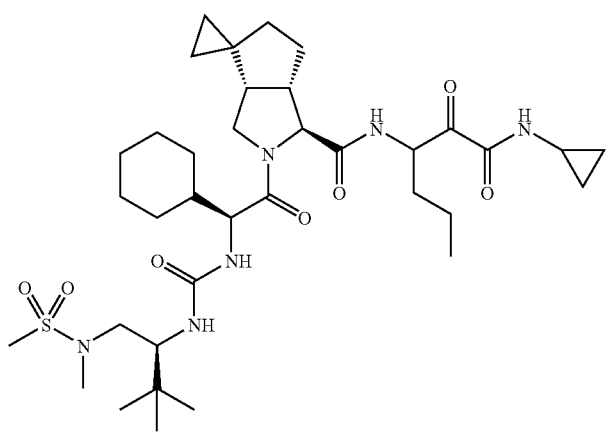

TABLE 1-continued
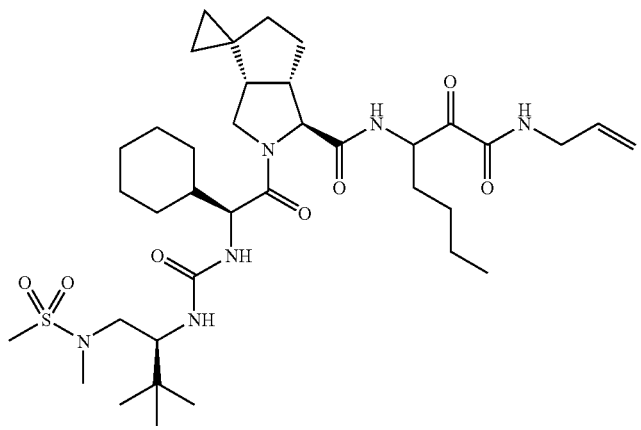
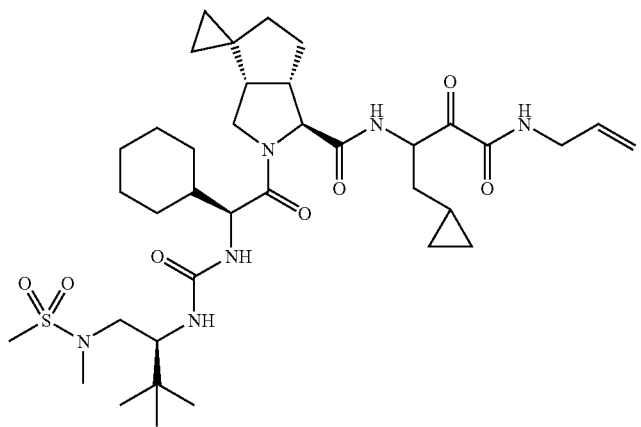
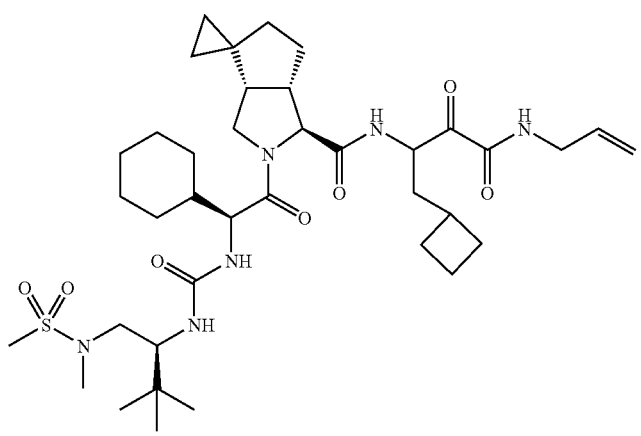

TABLE 1-continued
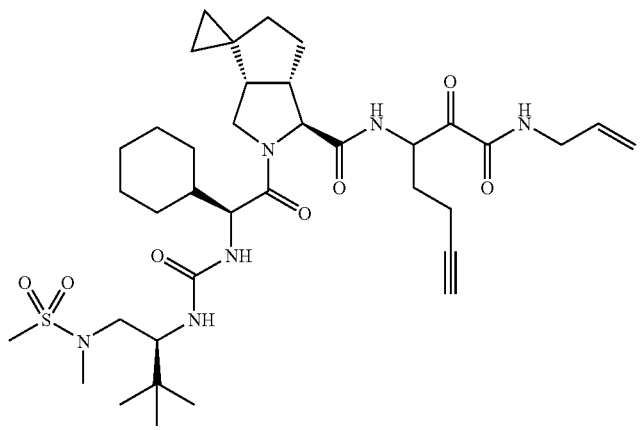
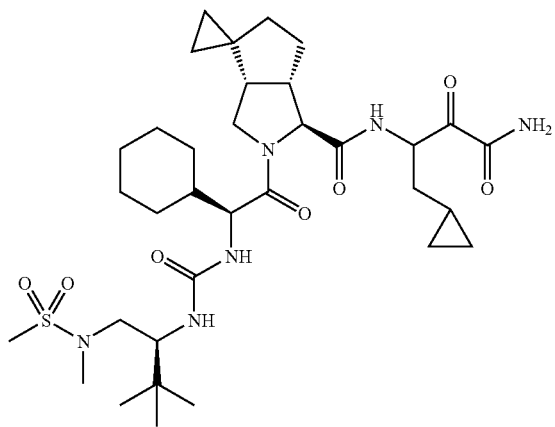
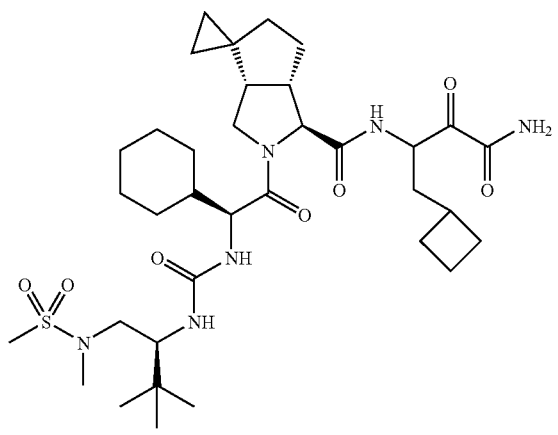

TABLE 1-continued
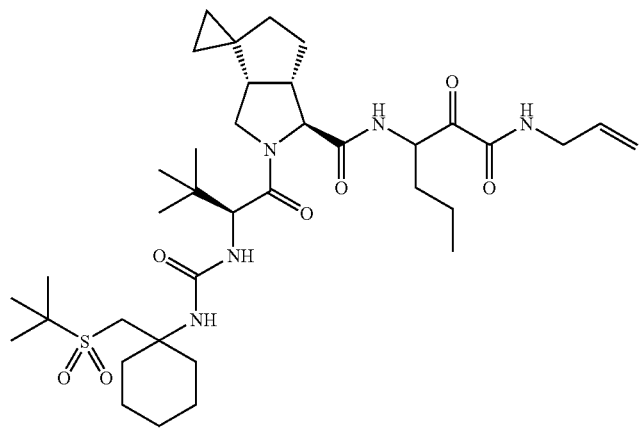
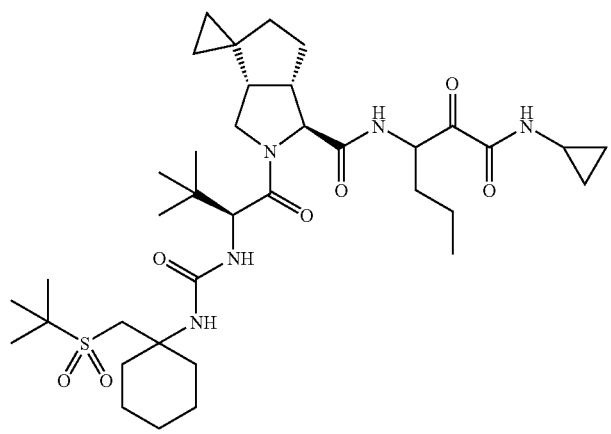
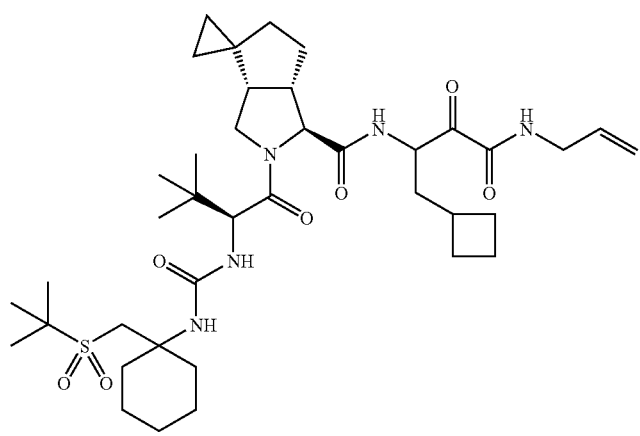

TABLE 1-continued
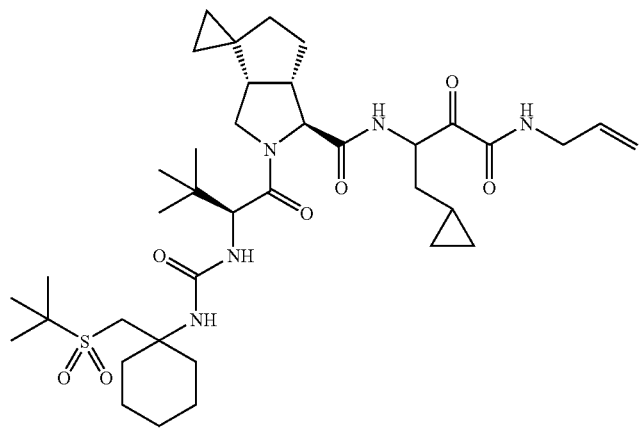
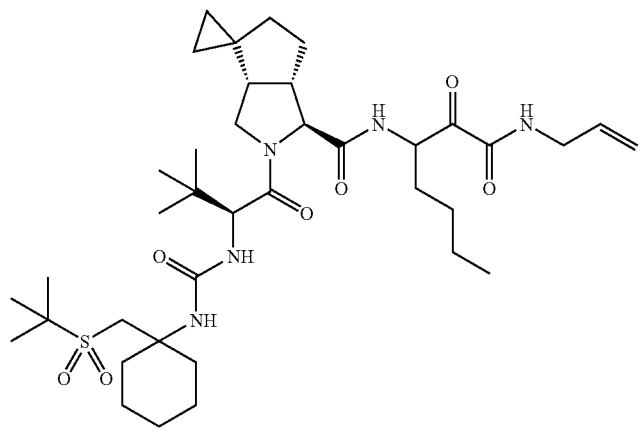
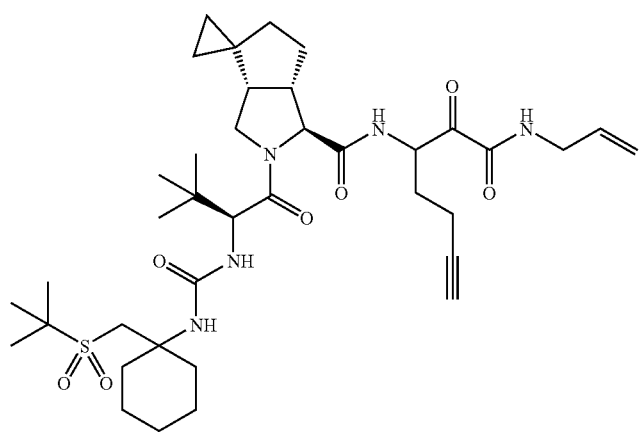

TABLE 1-continued
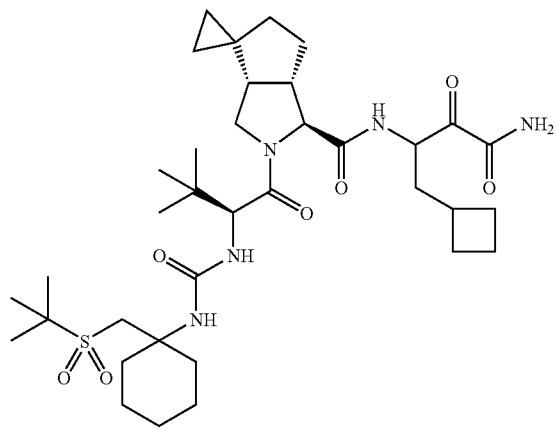
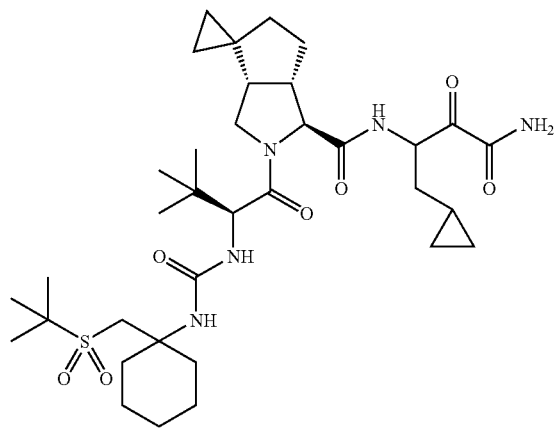
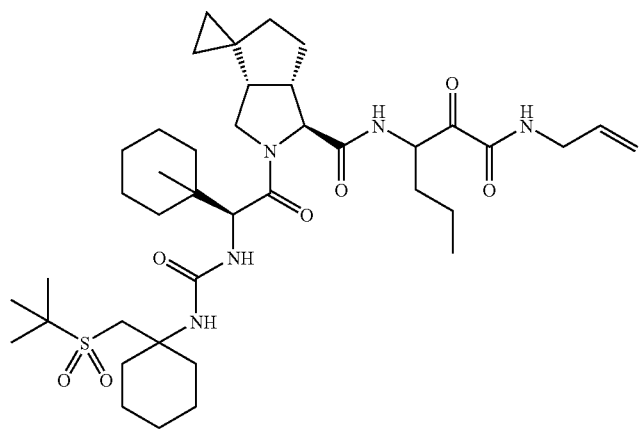

TABLE 1-continued
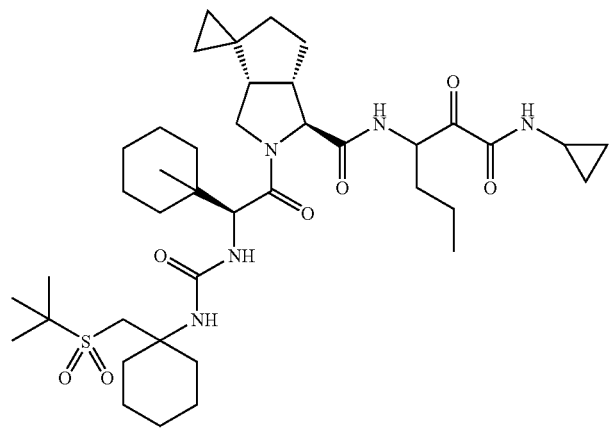
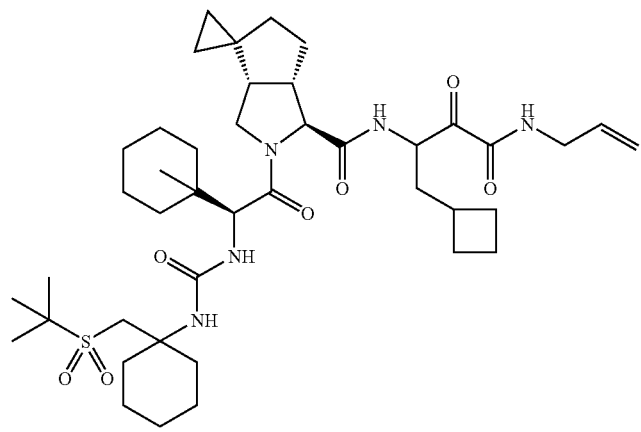
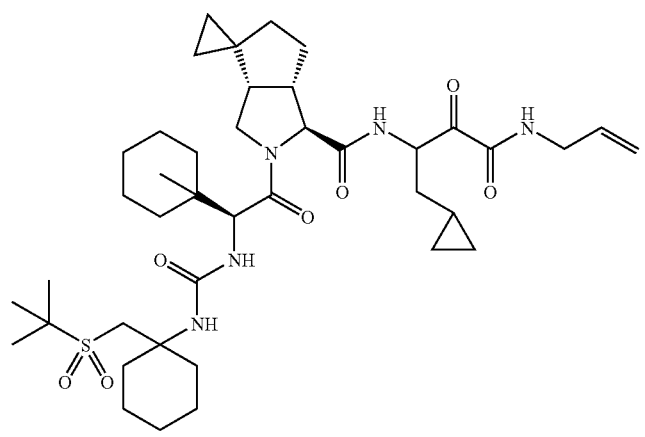

TABLE 1-continued
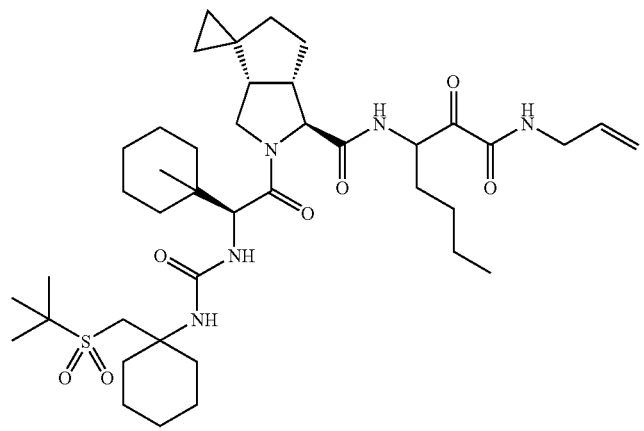
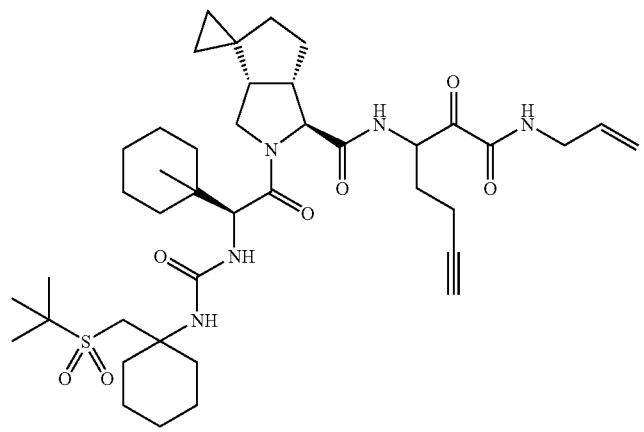
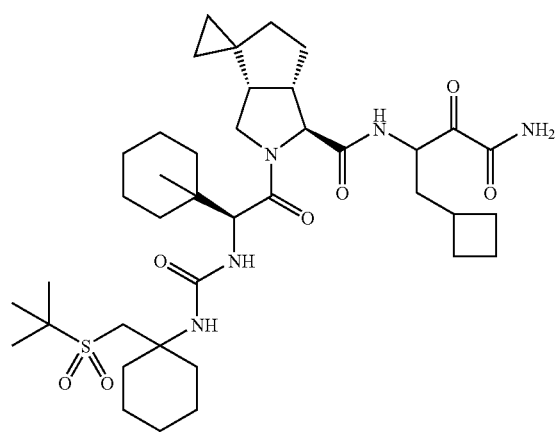

TABLE 1-continued
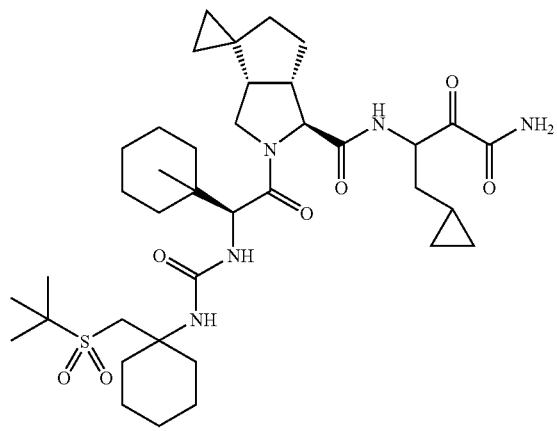
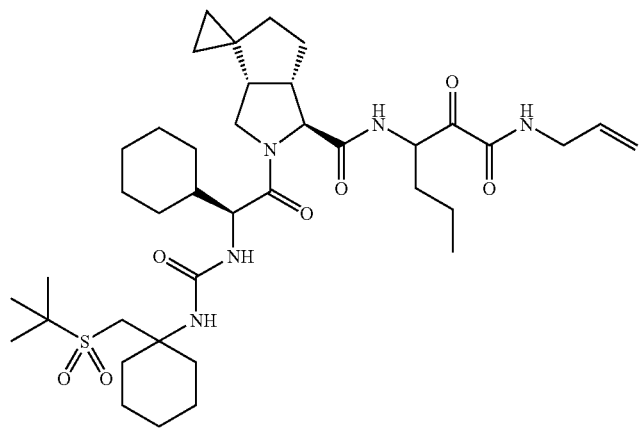
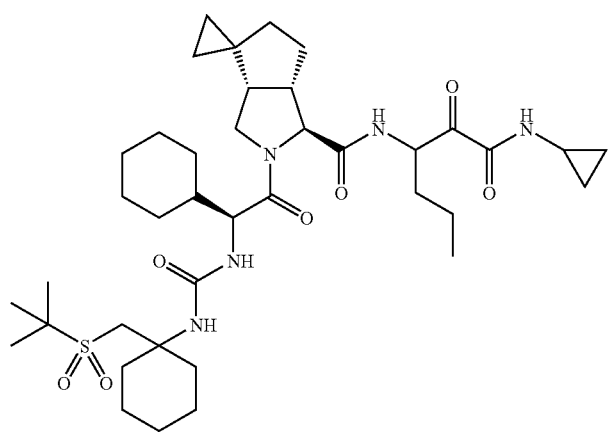

TABLE 1-continued
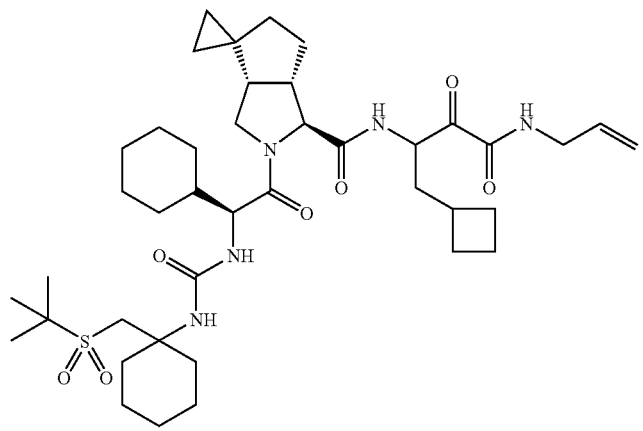
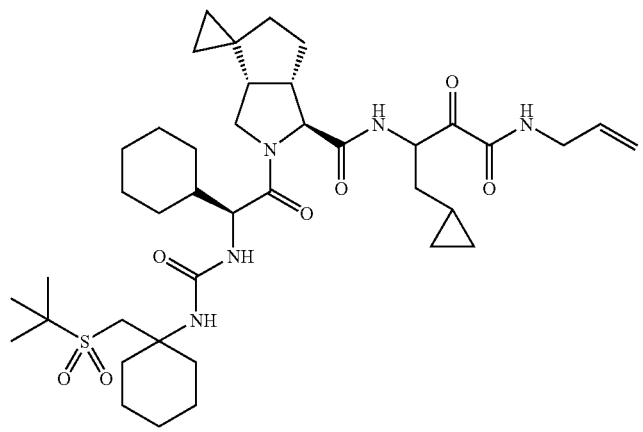
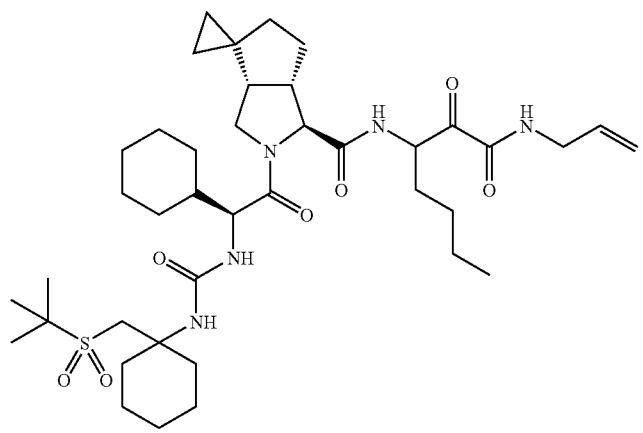

TABLE 1-continued
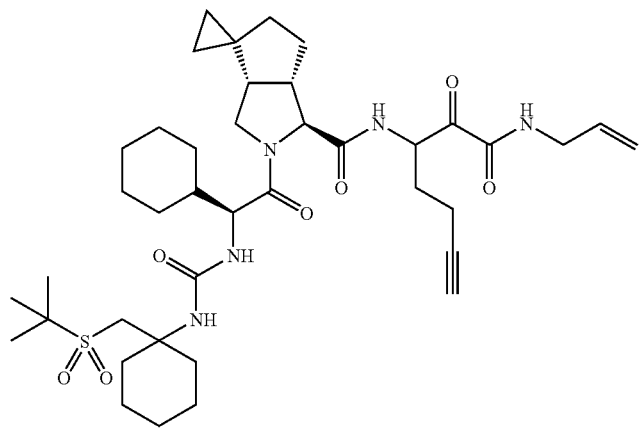
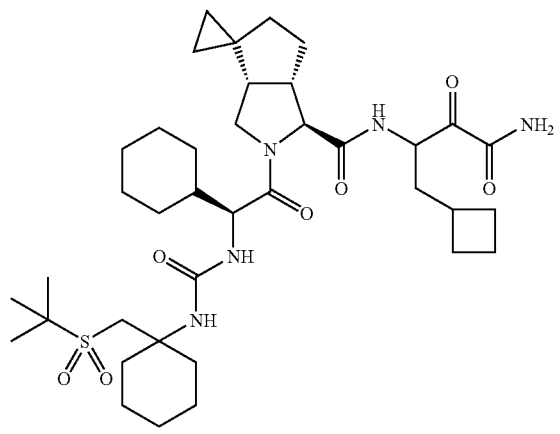
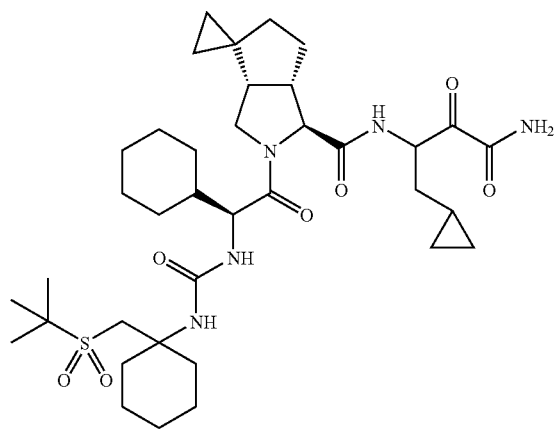

TABLE 1-continued
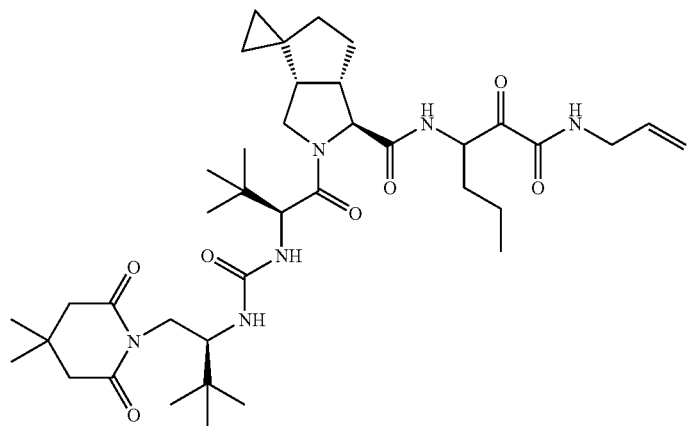
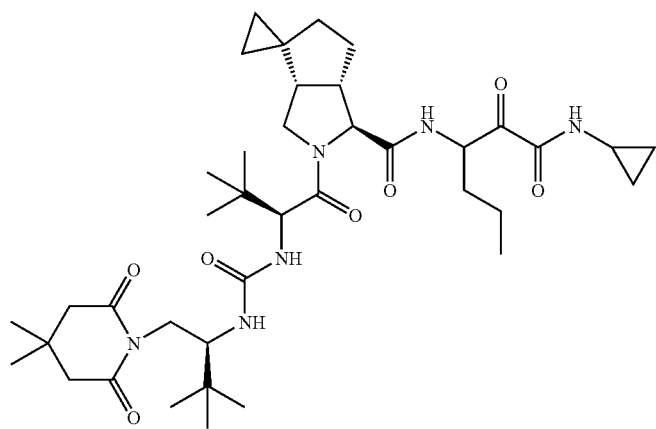
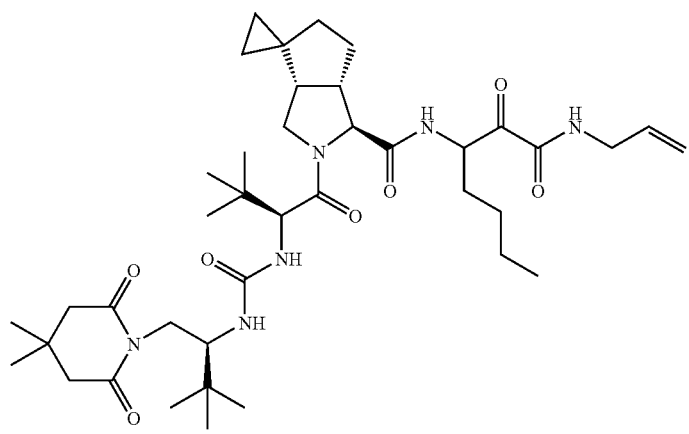

TABLE 1-continued
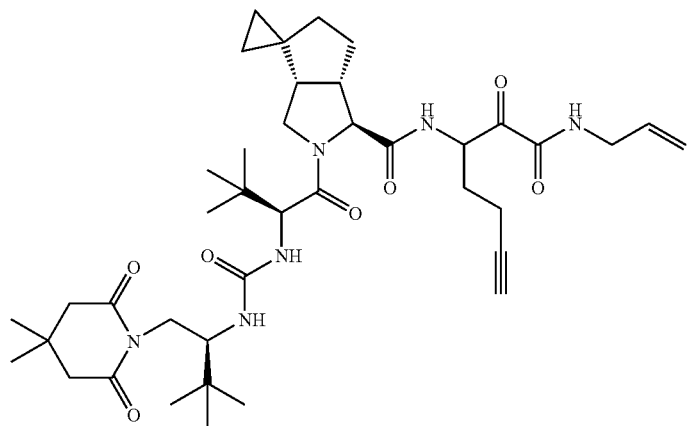
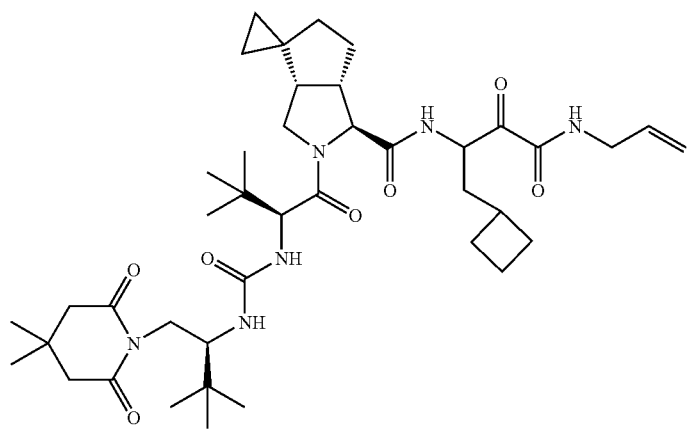
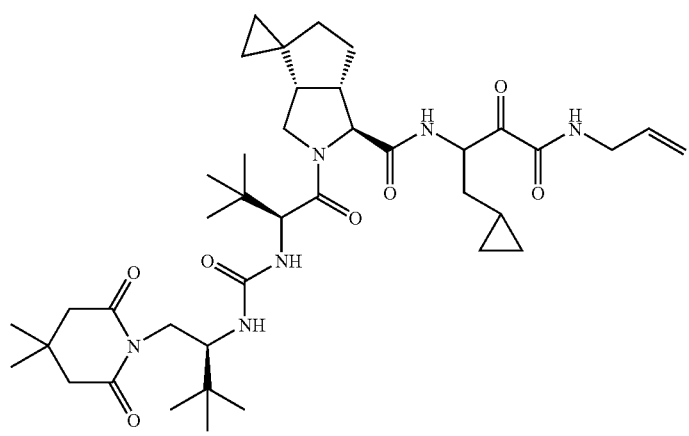

TABLE 1-continued
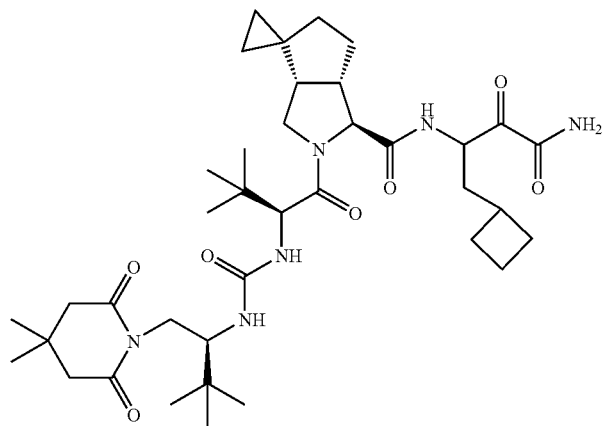
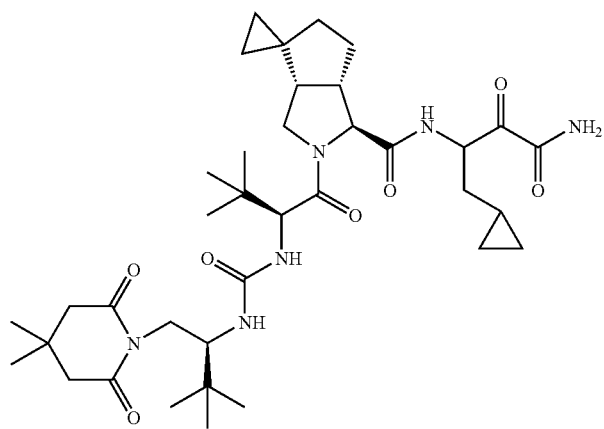
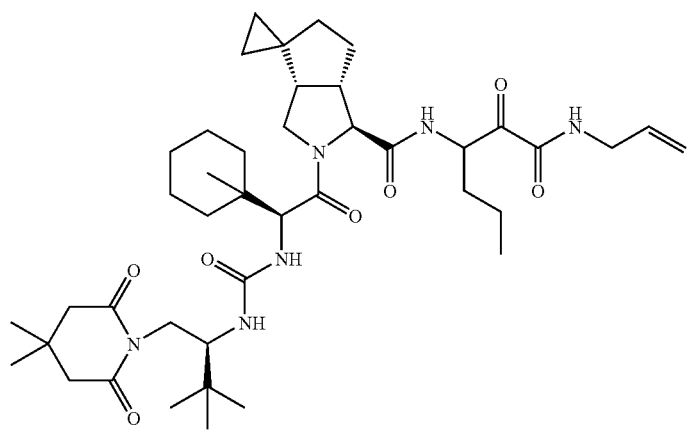

TABLE 1-continued
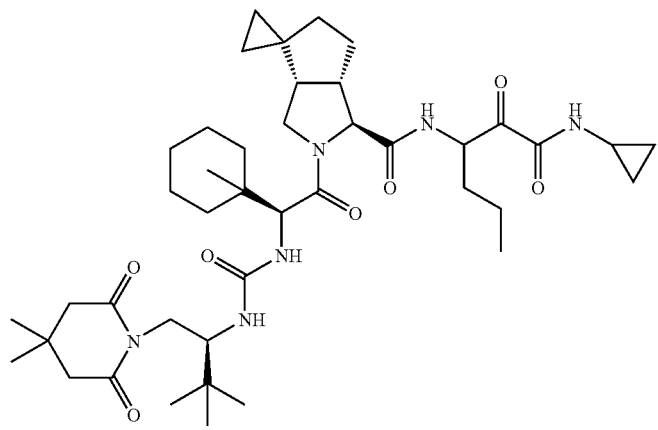
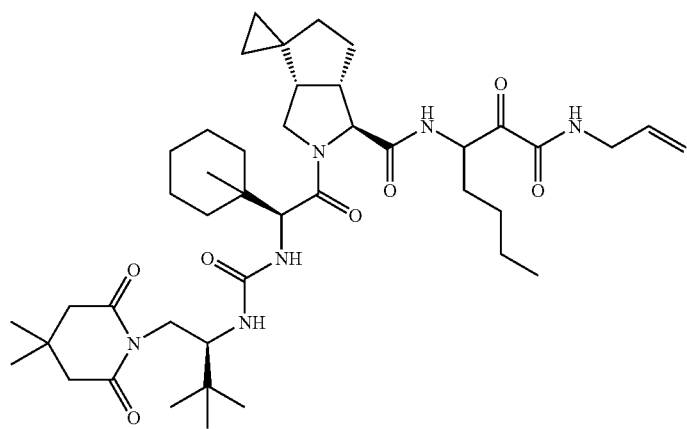
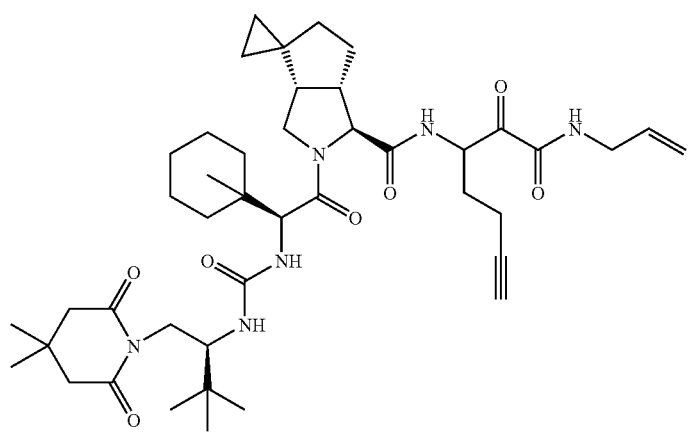

TABLE 1-continued
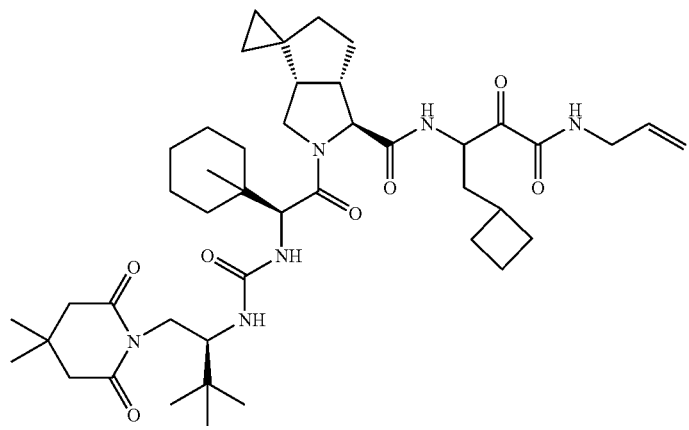
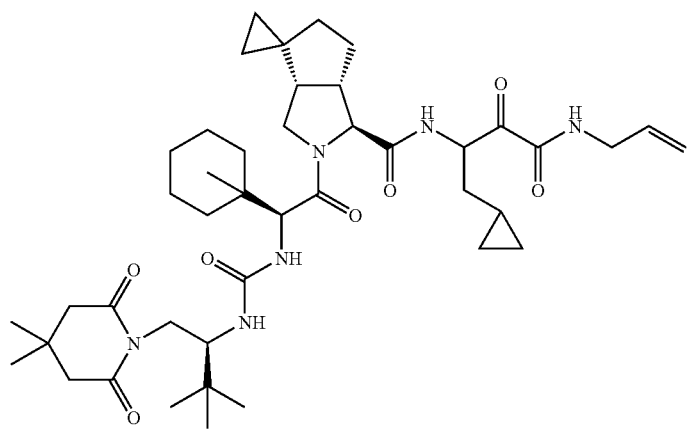
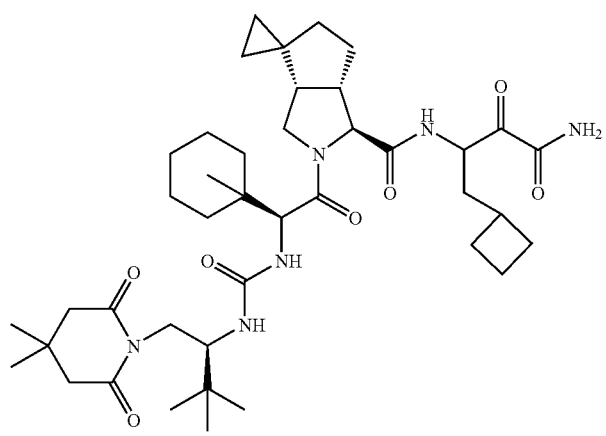

TABLE 1-continued
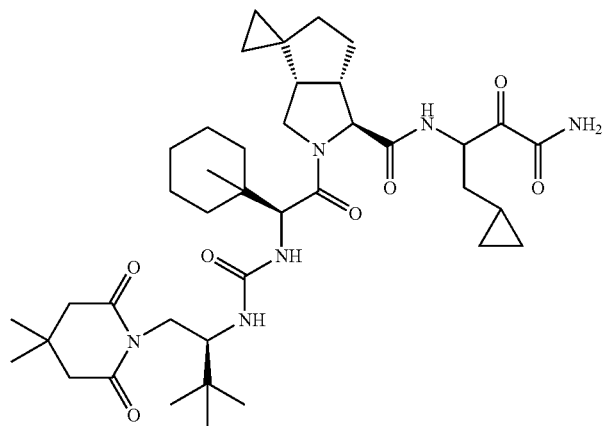
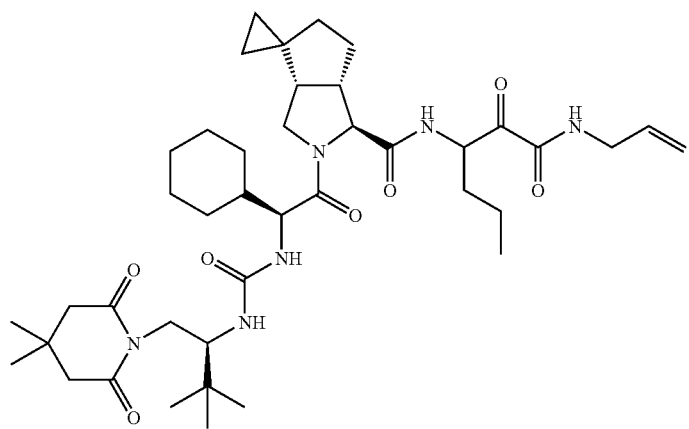
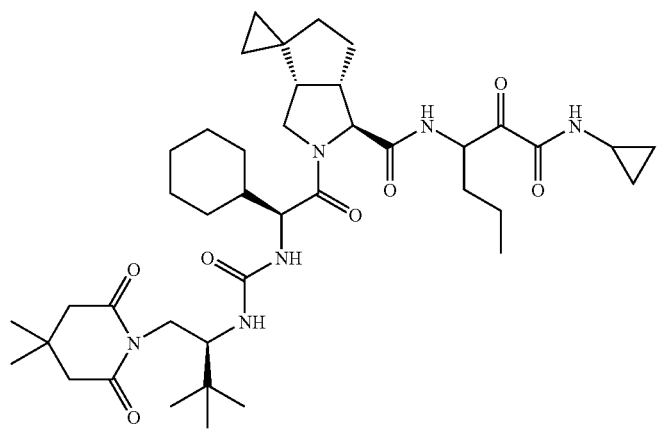

TABLE 1-continued
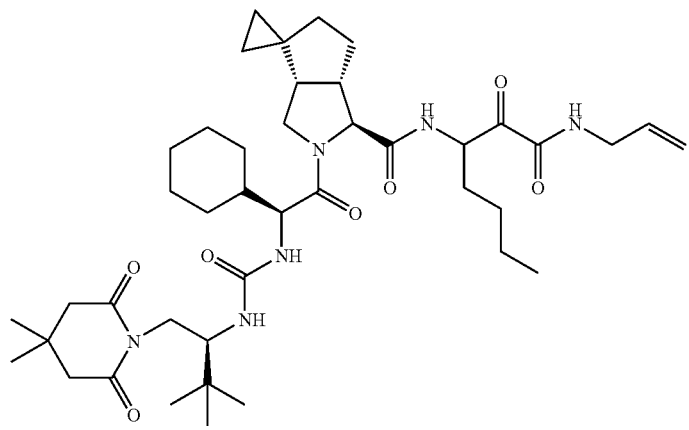
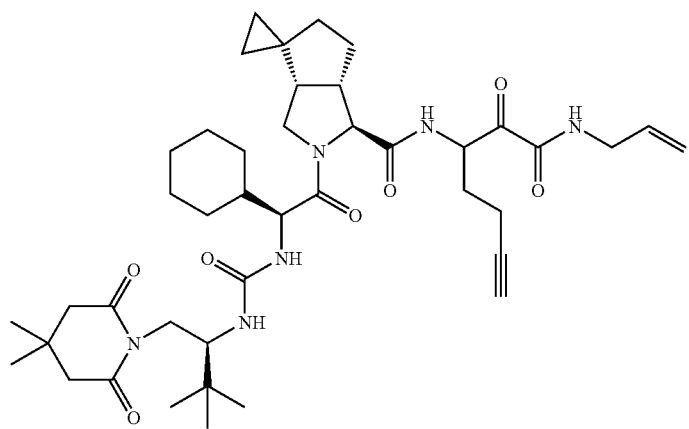
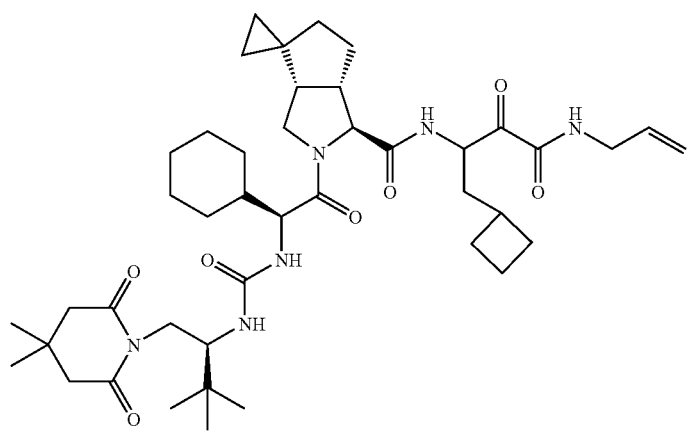

TABLE 1-continued
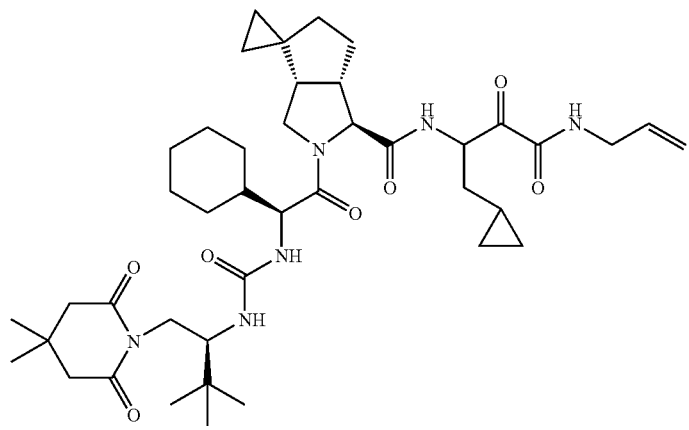
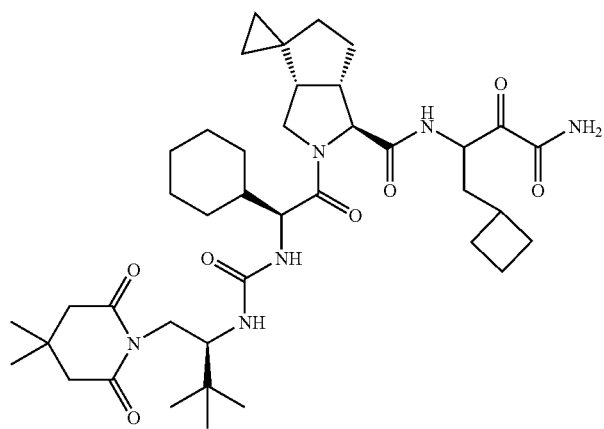
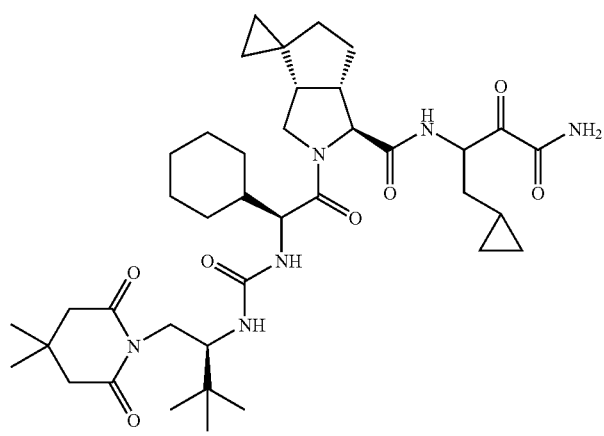

TABLE 1-continued
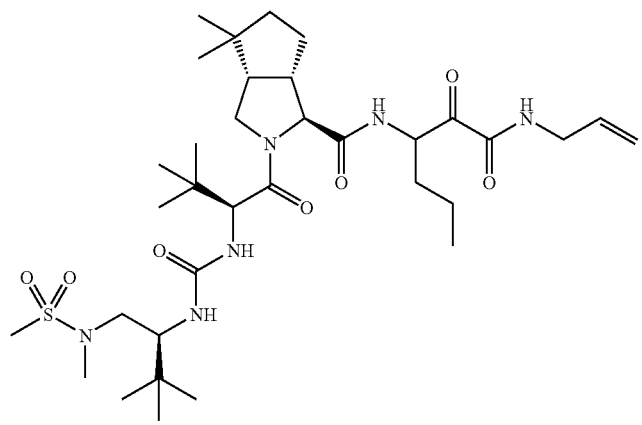
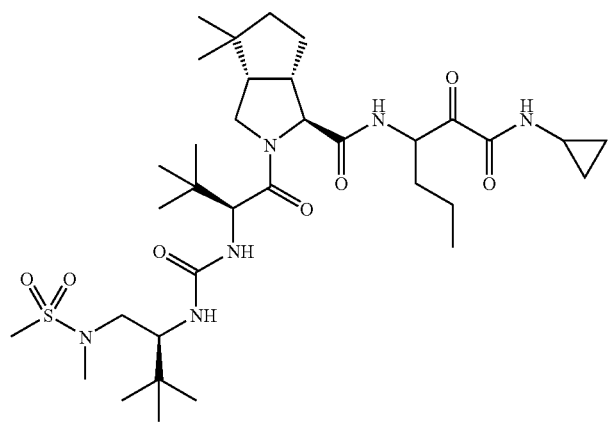
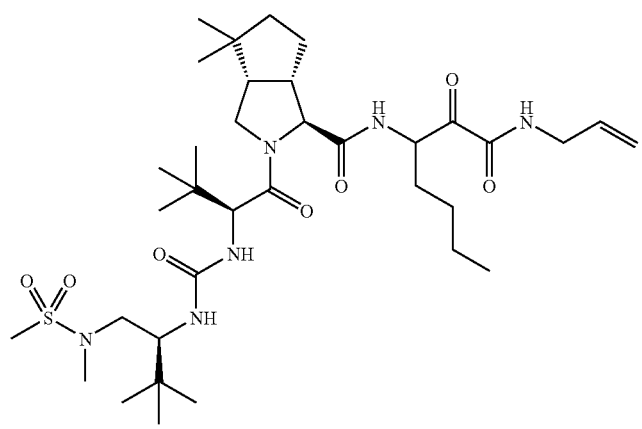

TABLE 1-continued
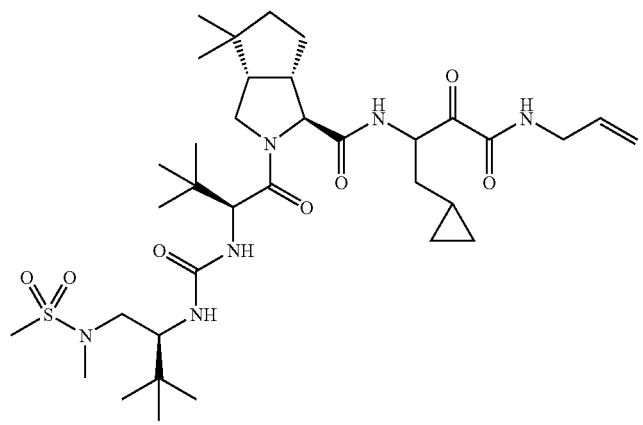
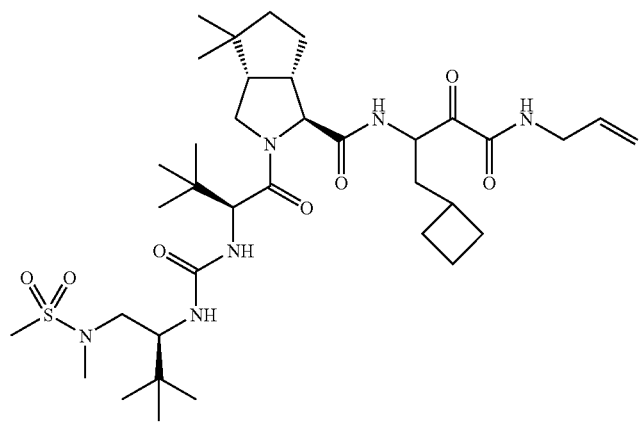
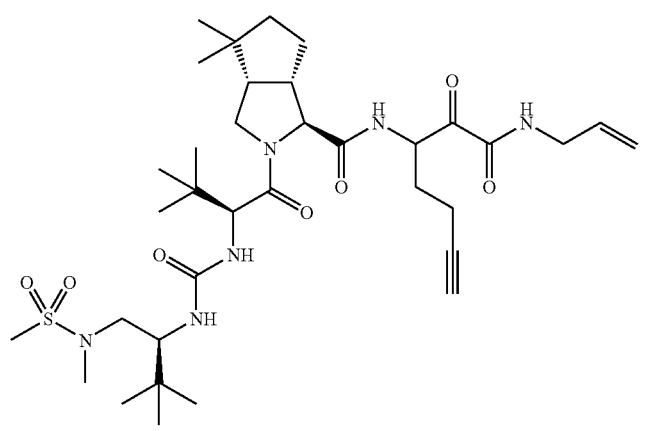

TABLE 1-continued
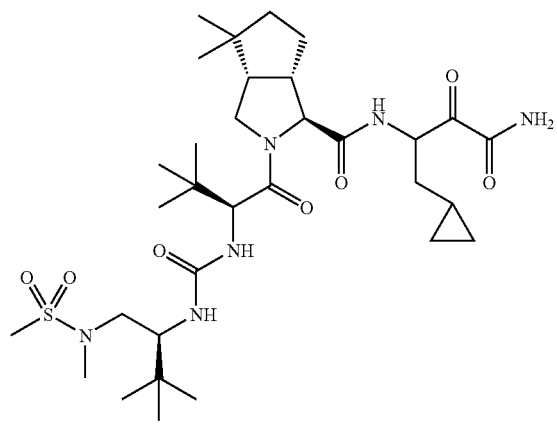
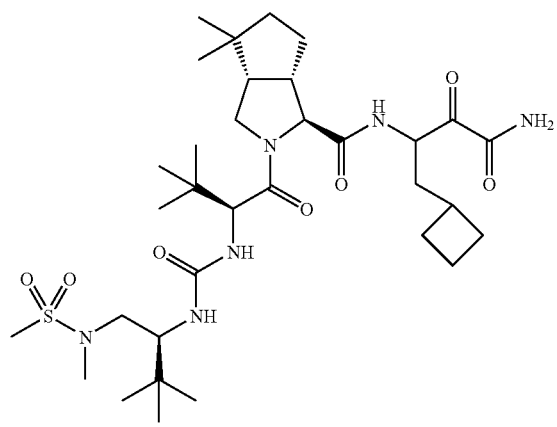
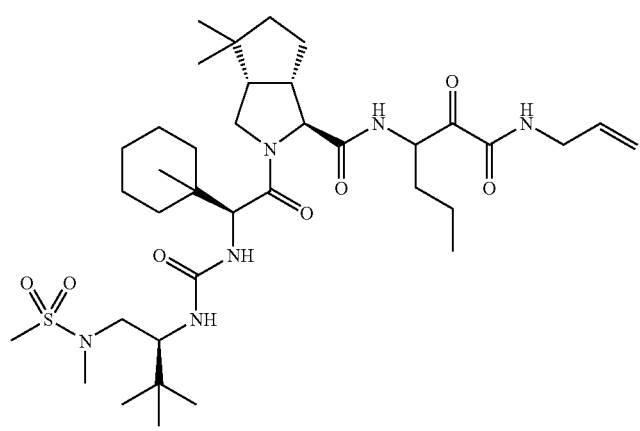

TABLE 1-continued
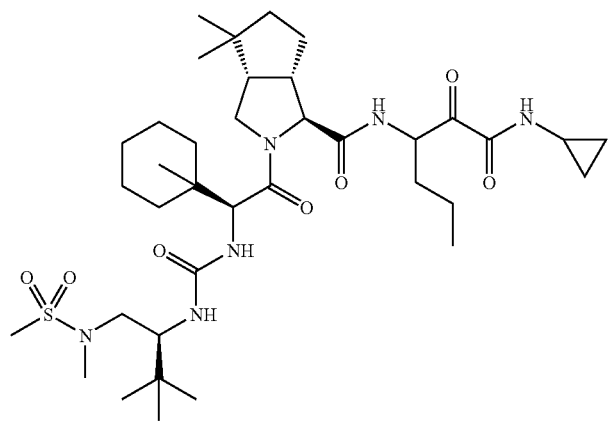
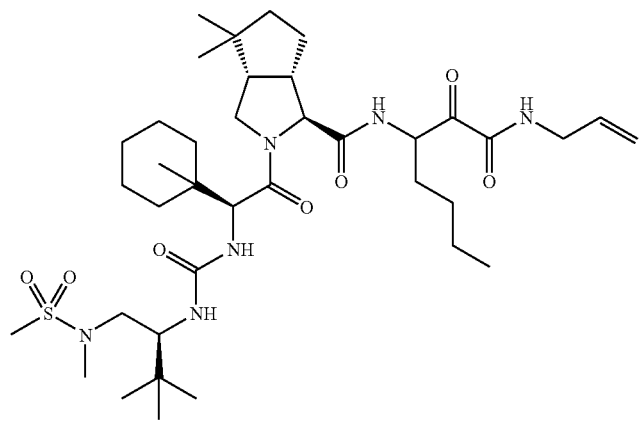
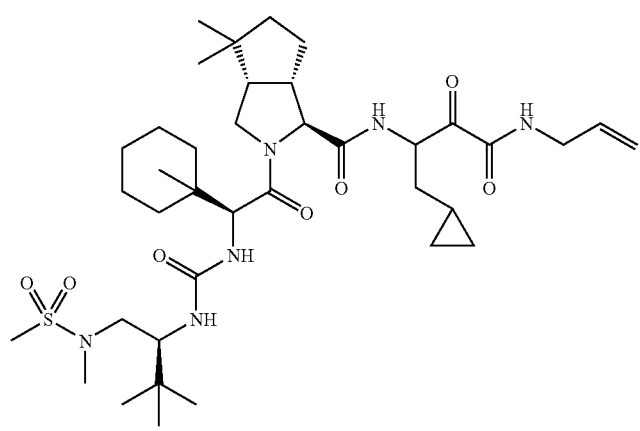

TABLE 1-continued
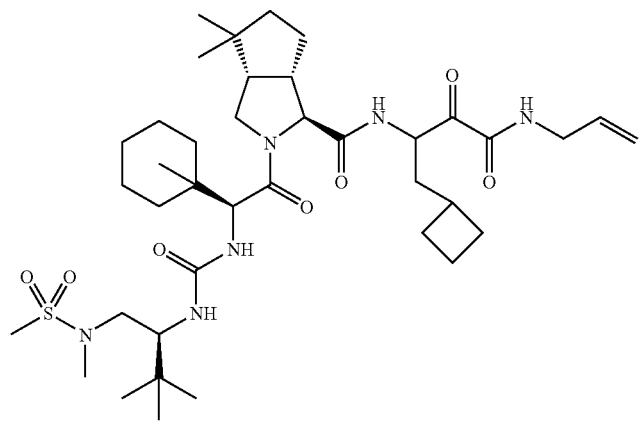
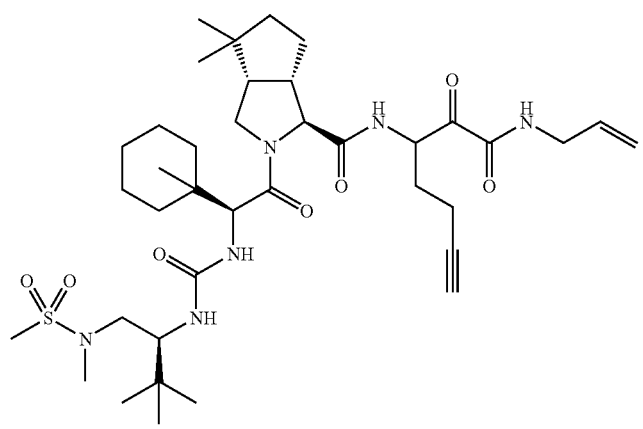
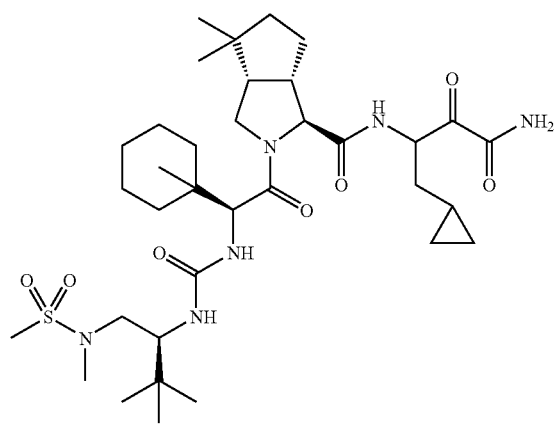

TABLE 1-continued
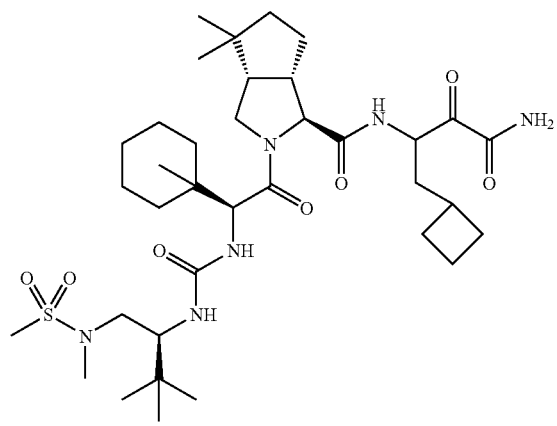
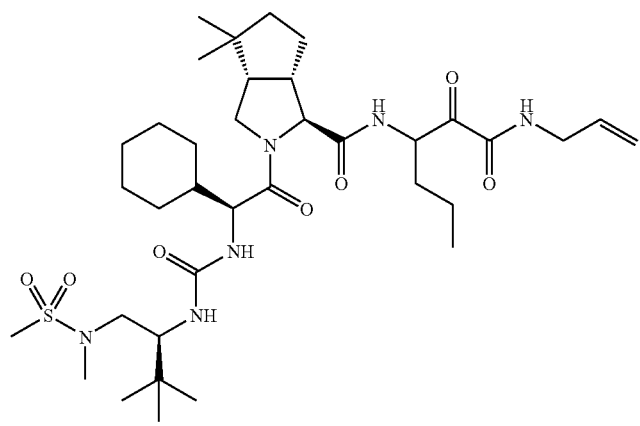
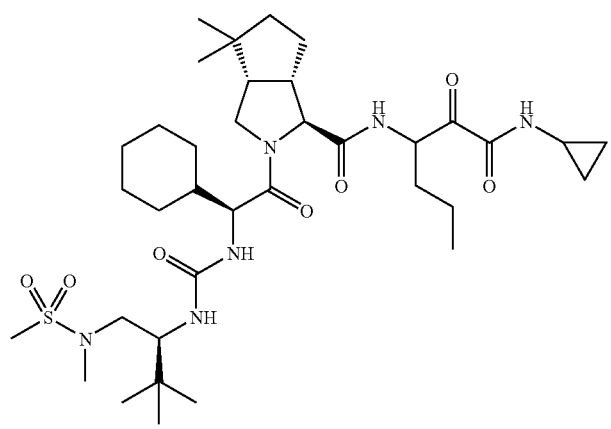

TABLE 1-continued
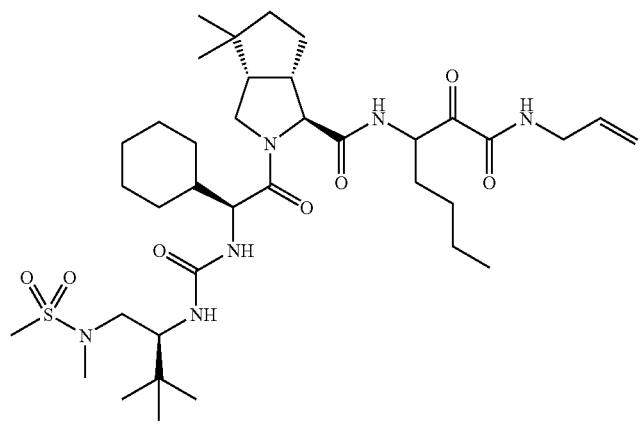
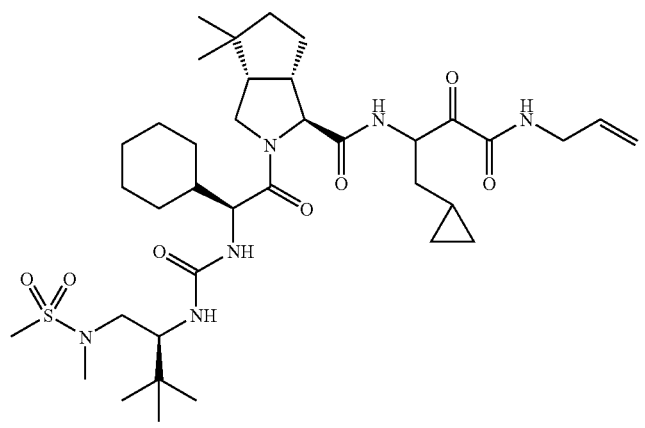
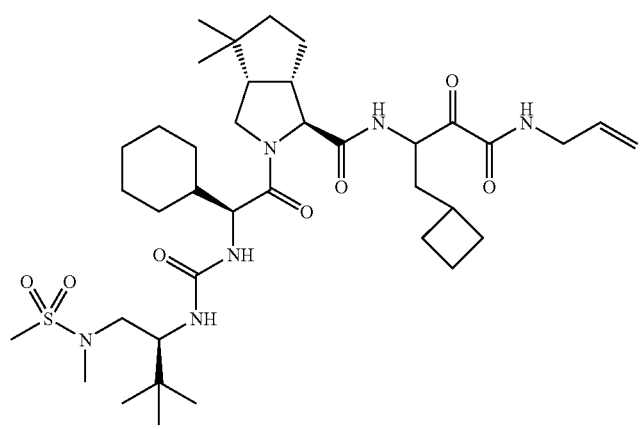

TABLE 1-continued
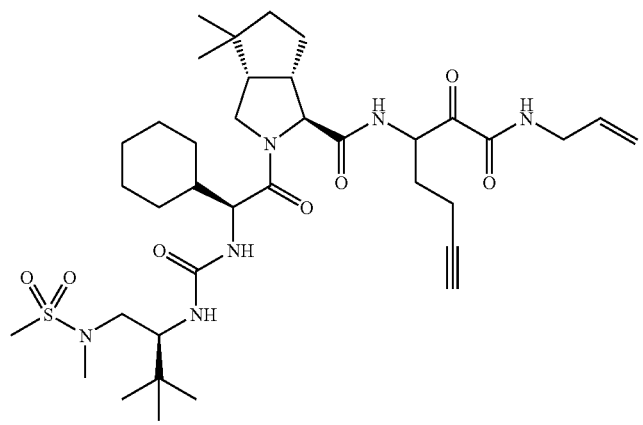
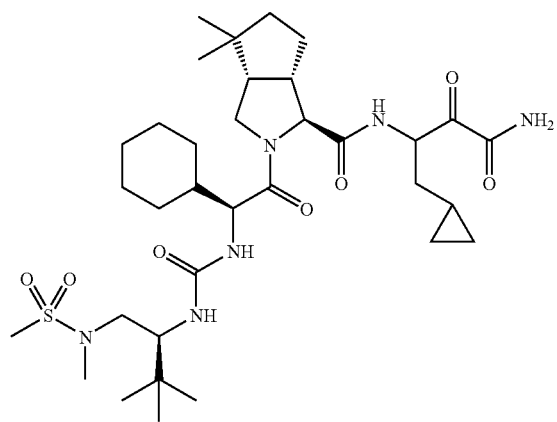
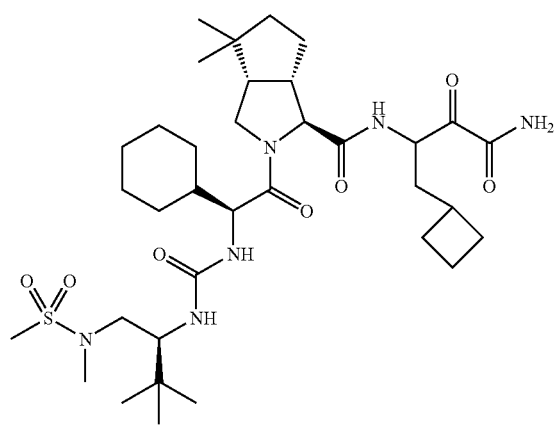

TABLE 1-continued
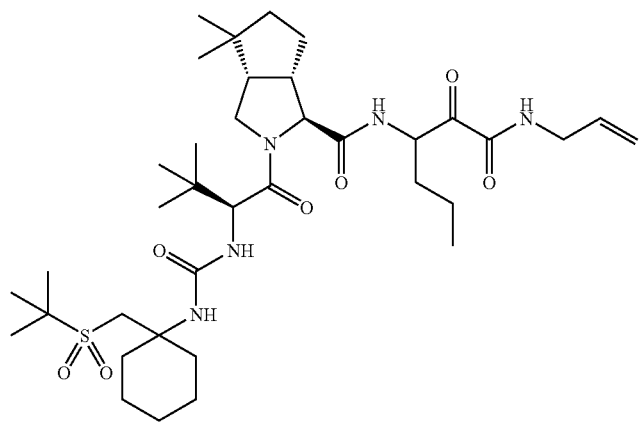
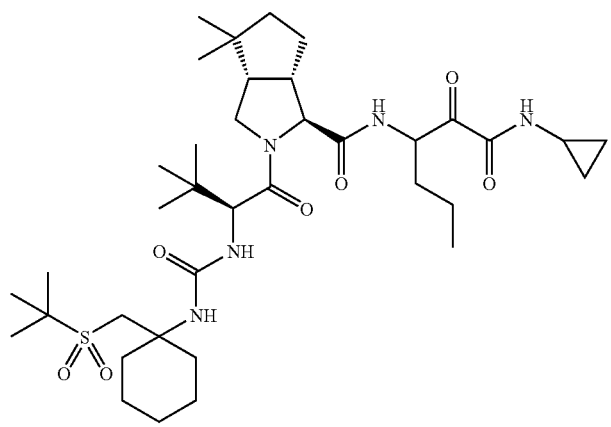
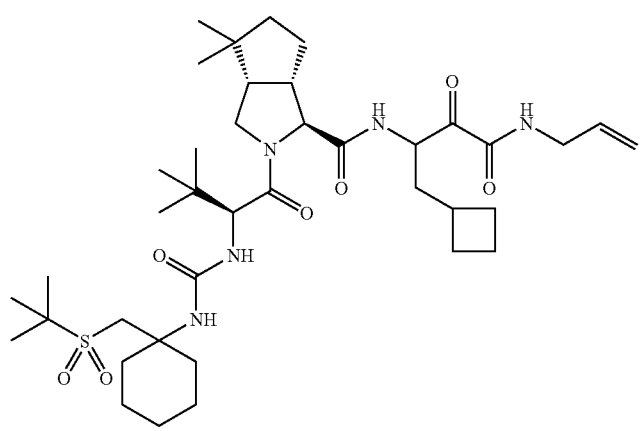

TABLE 1-continued
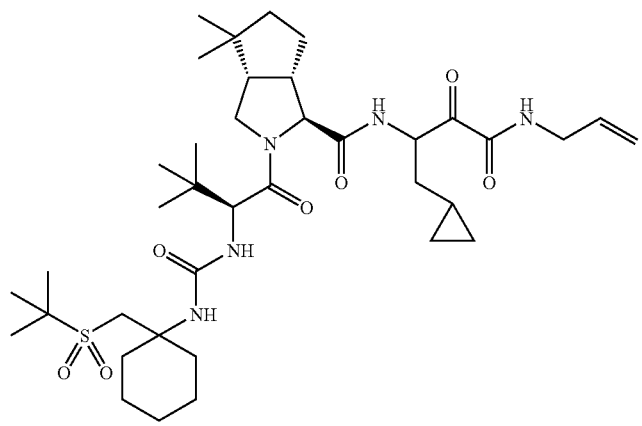
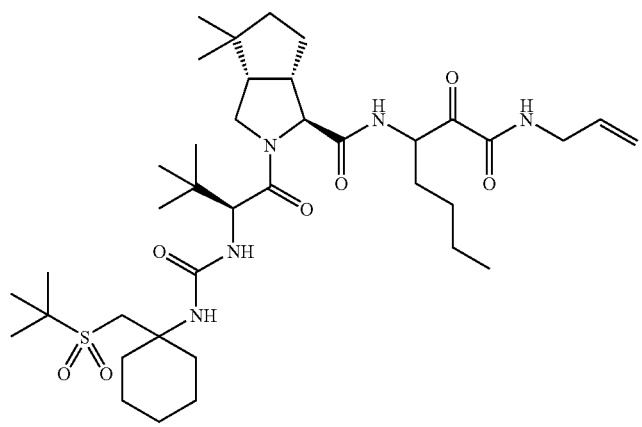
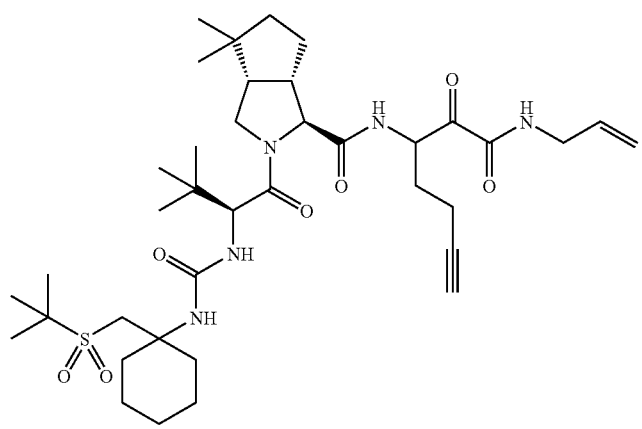

TABLE 1-continued
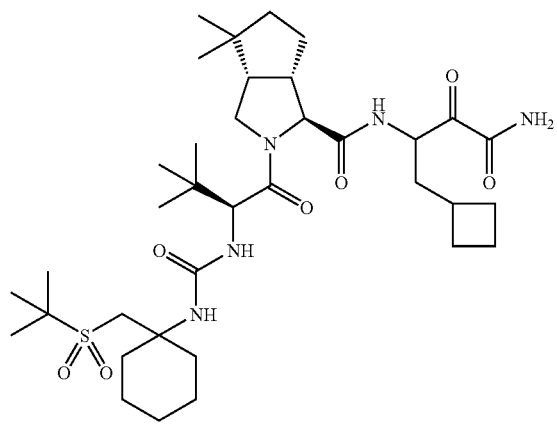
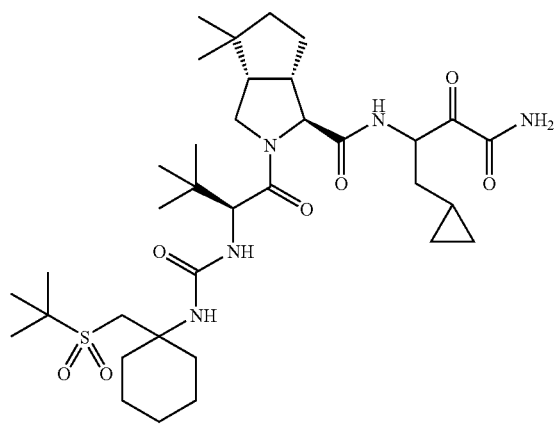
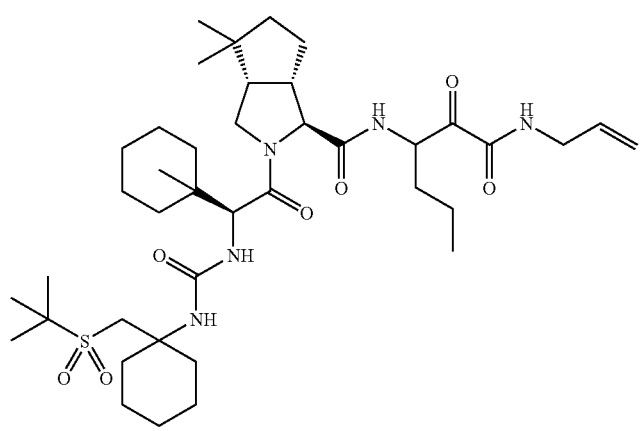

TABLE 1-continued
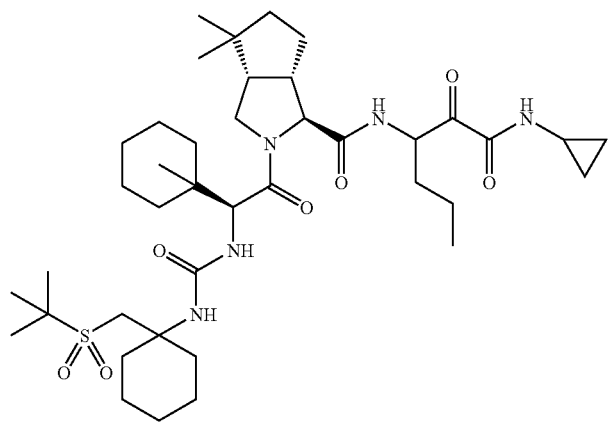
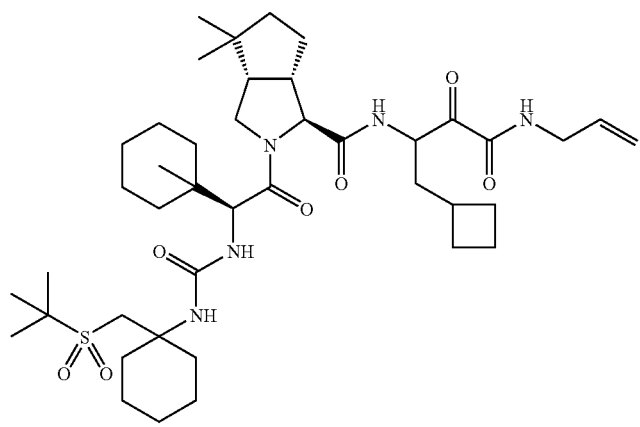
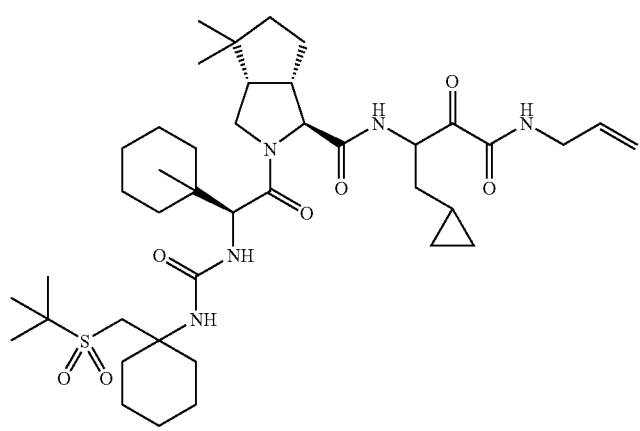

TABLE 1-continued
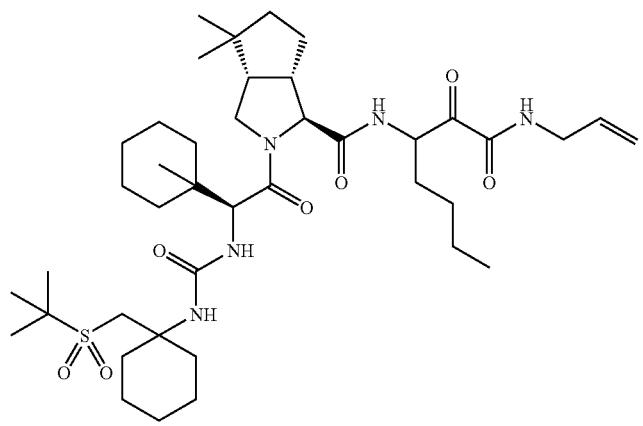
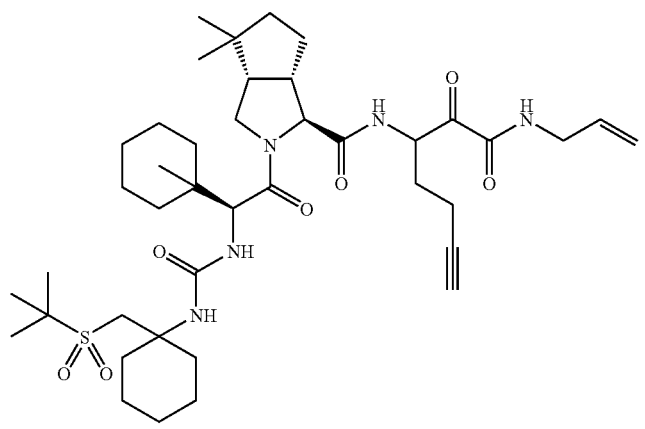
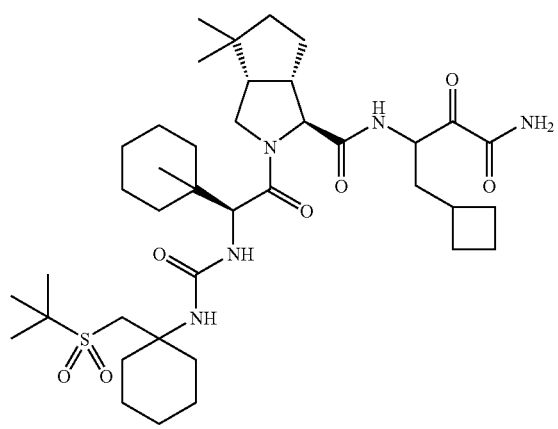

TABLE 1-continued
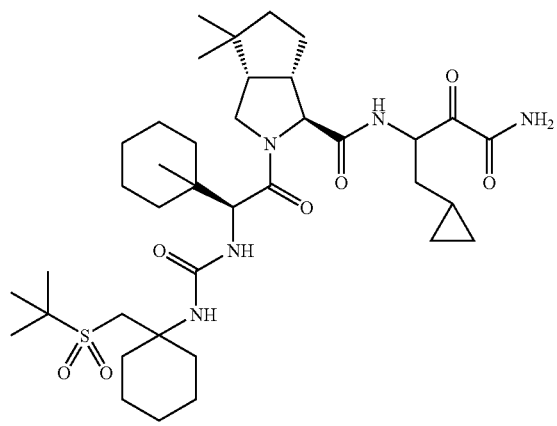
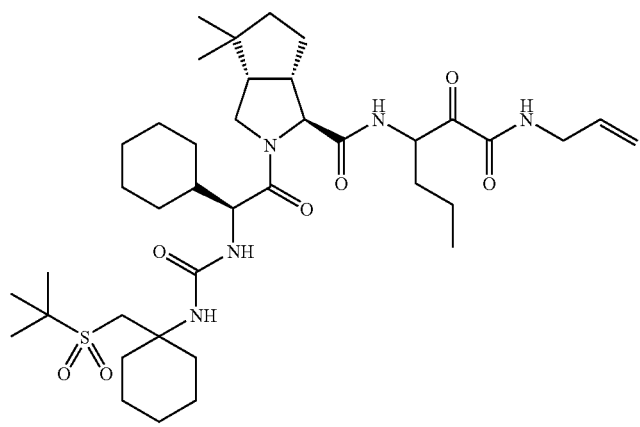
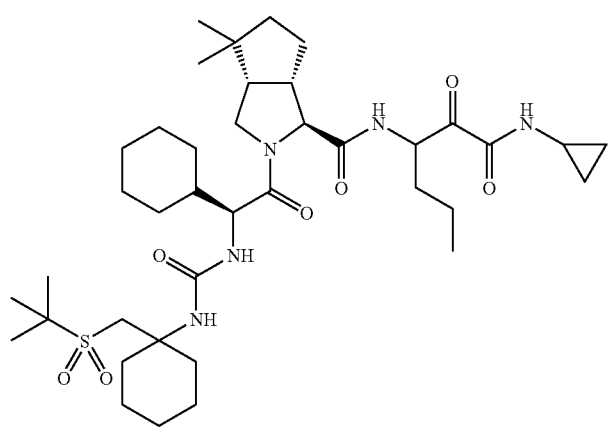

TABLE 1-continued
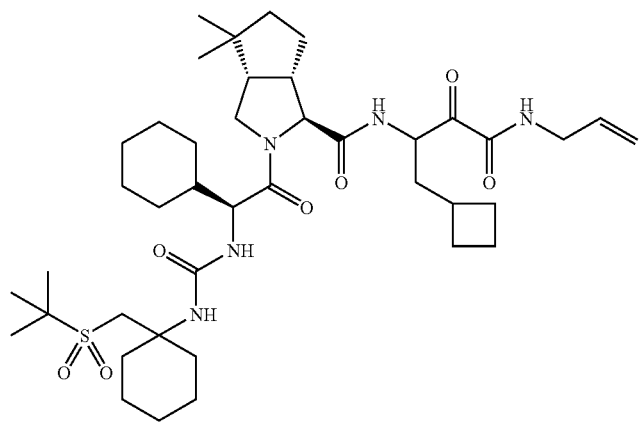
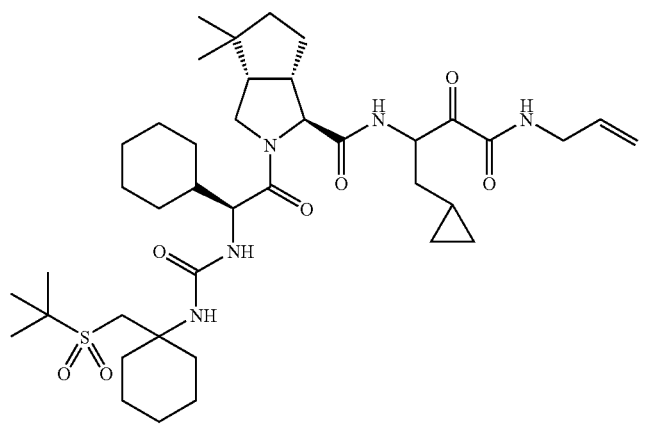
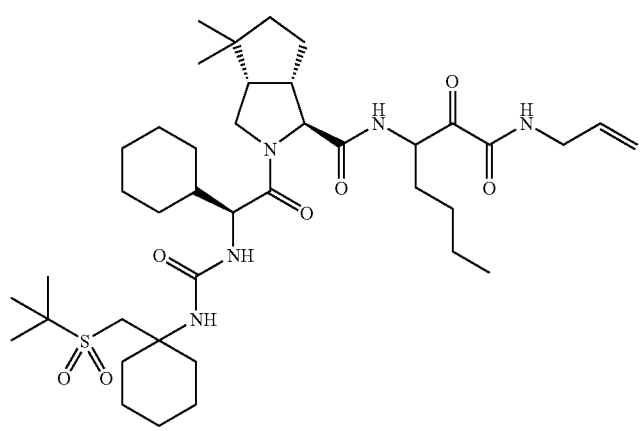

TABLE 1-continued
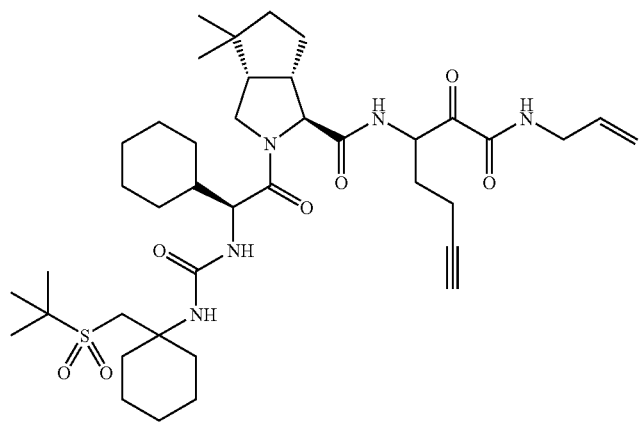
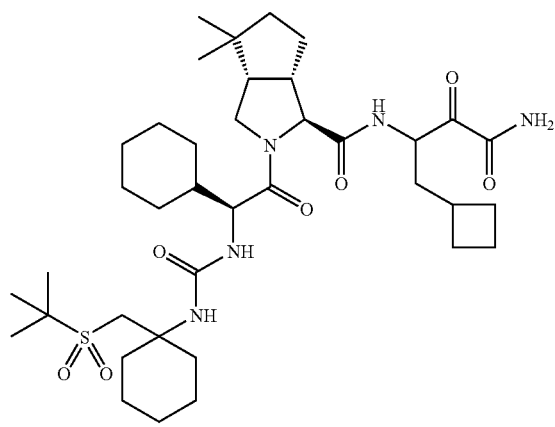
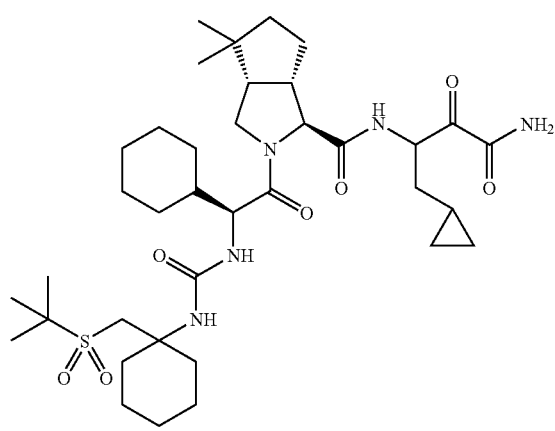

TABLE 1-continued
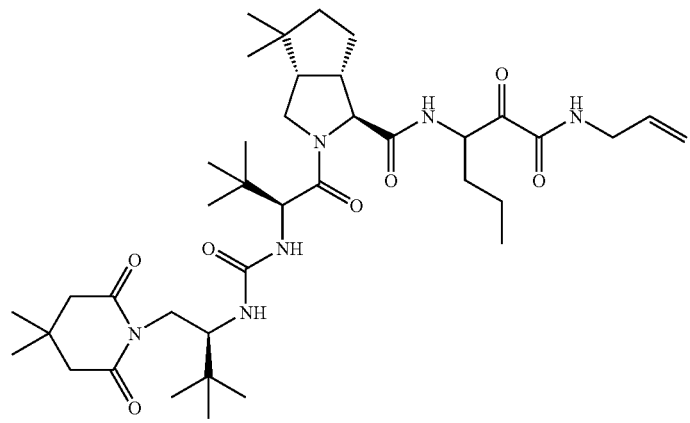
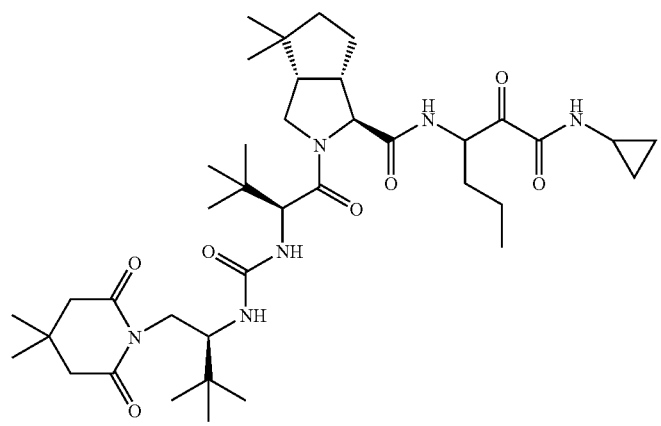
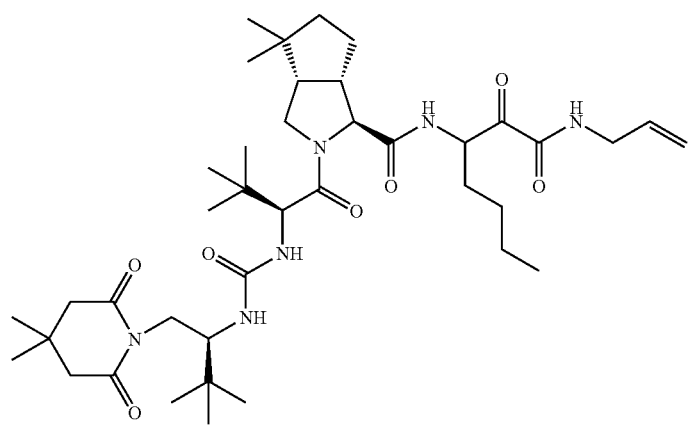

TABLE 1-continued
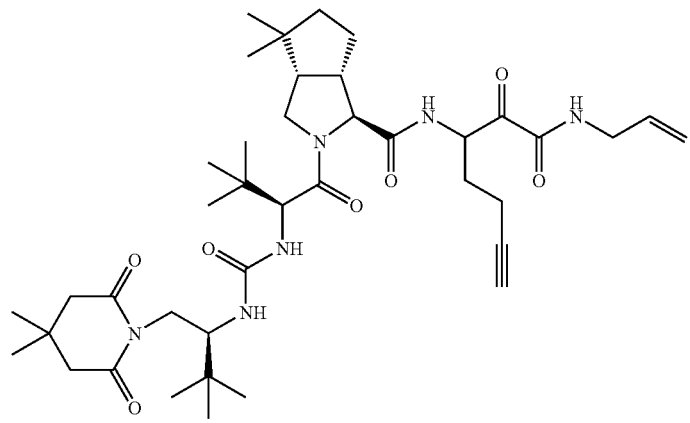
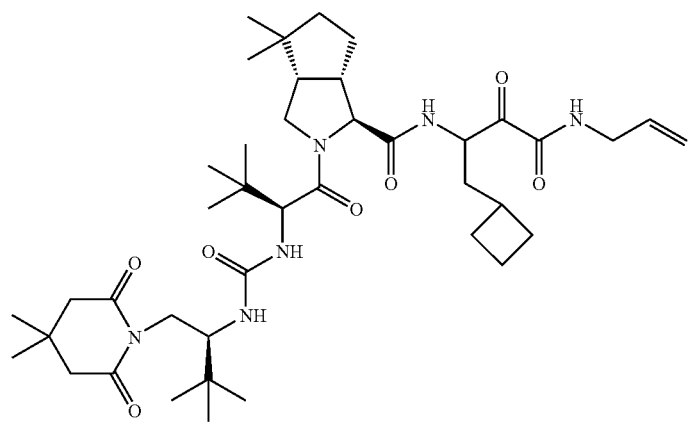
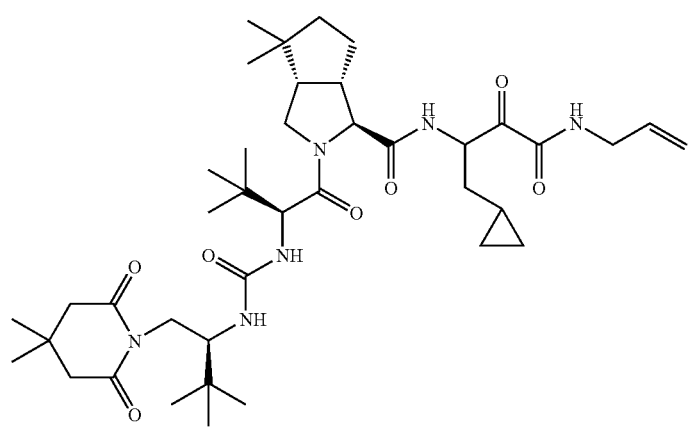

TABLE 1-continued
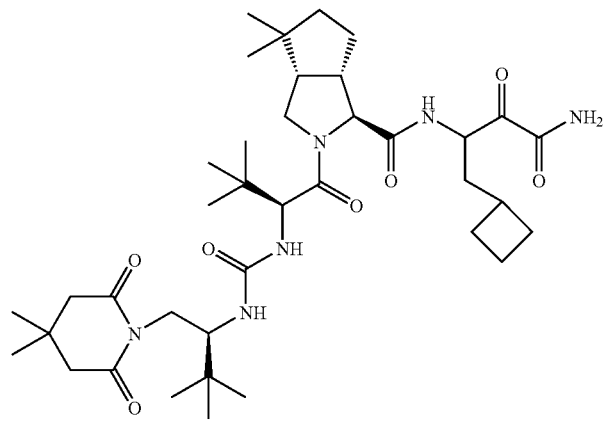
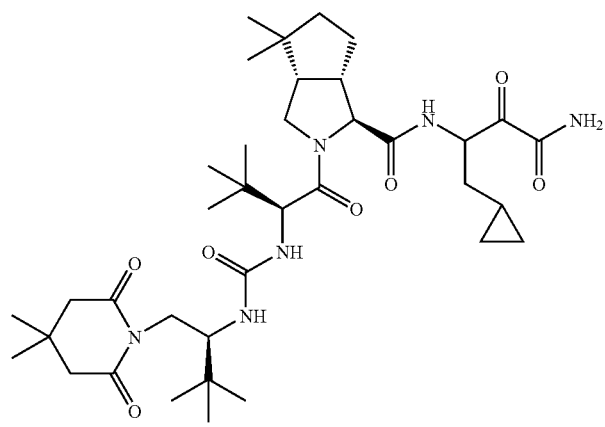
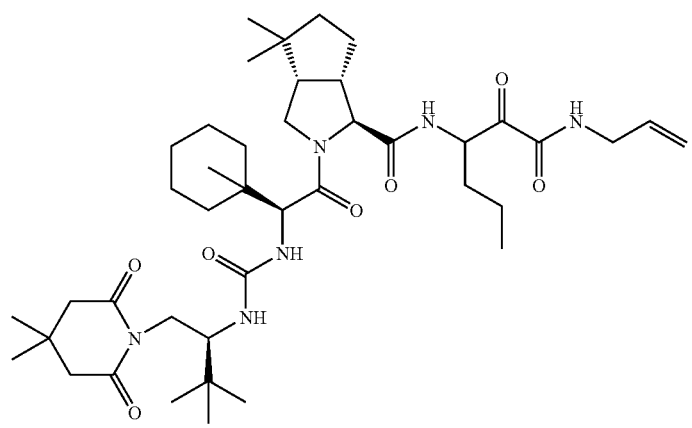

TABLE 1-continued
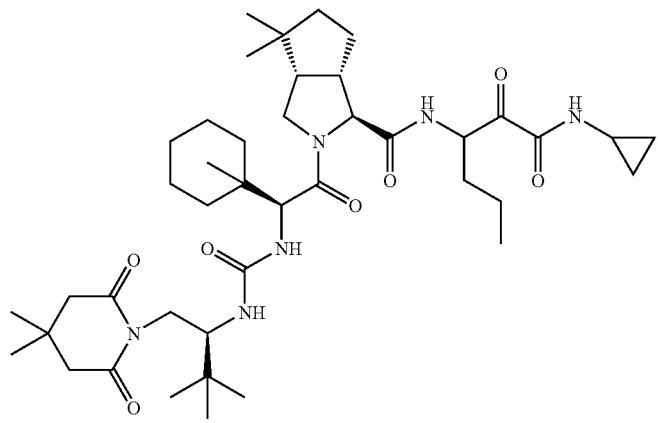
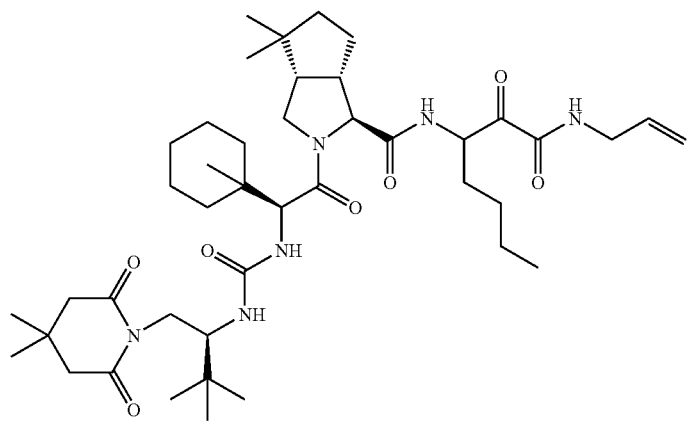
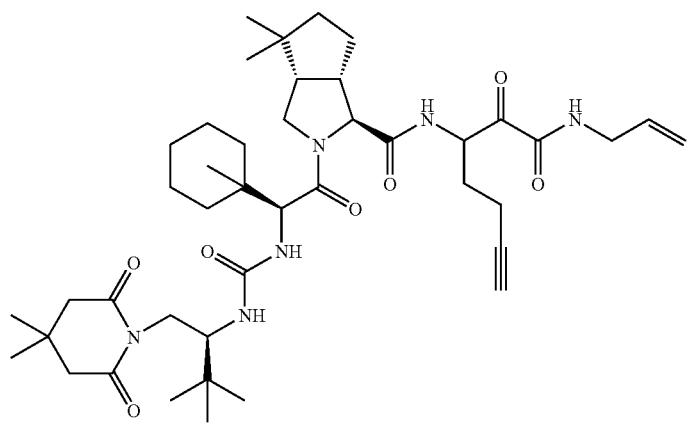

TABLE 1-continued
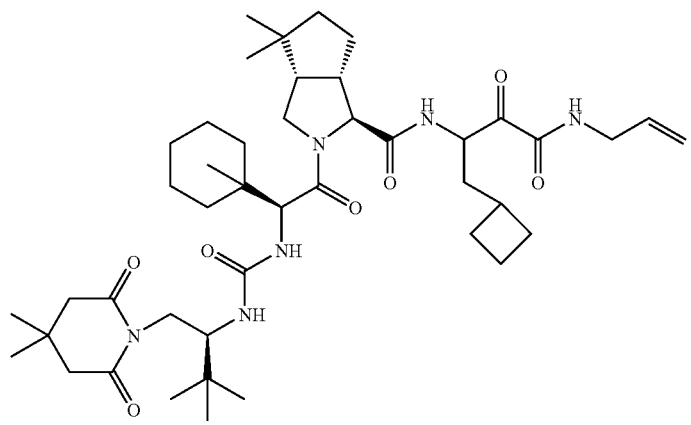
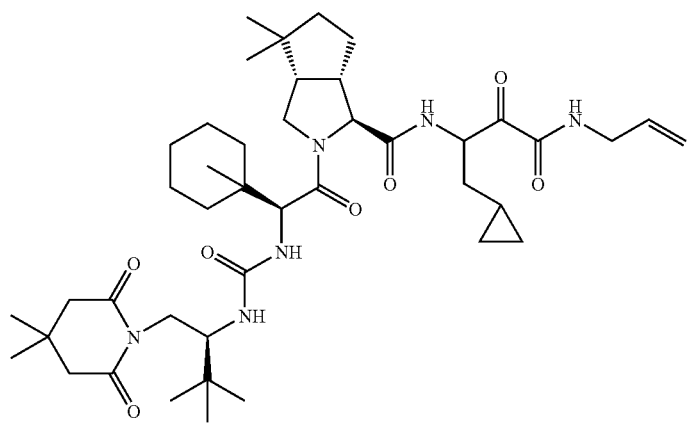
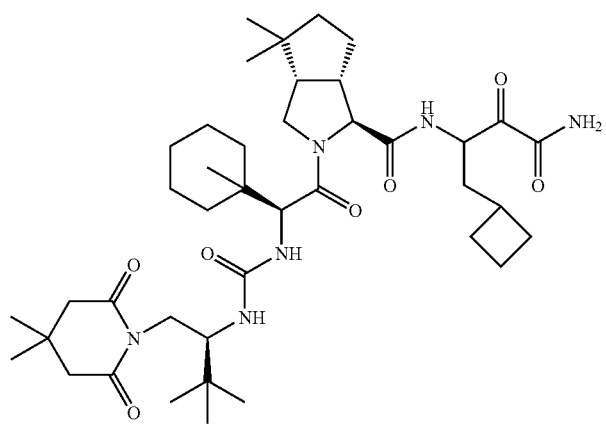

TABLE 1-continued
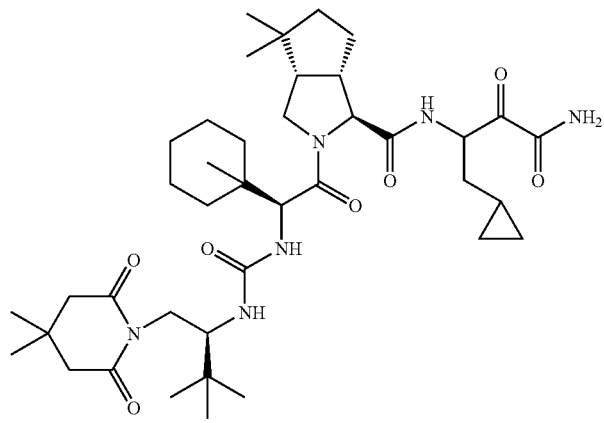
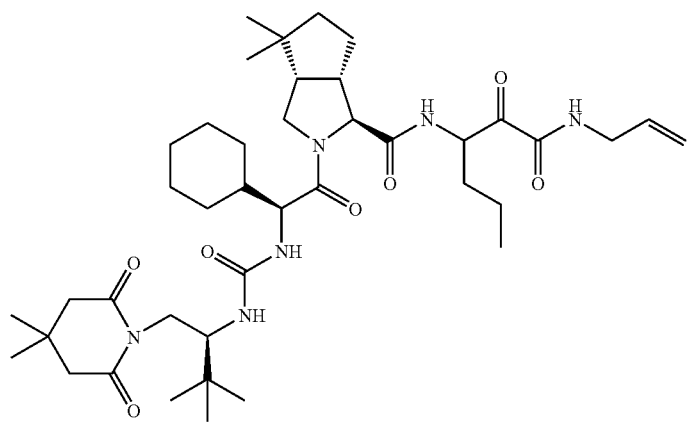
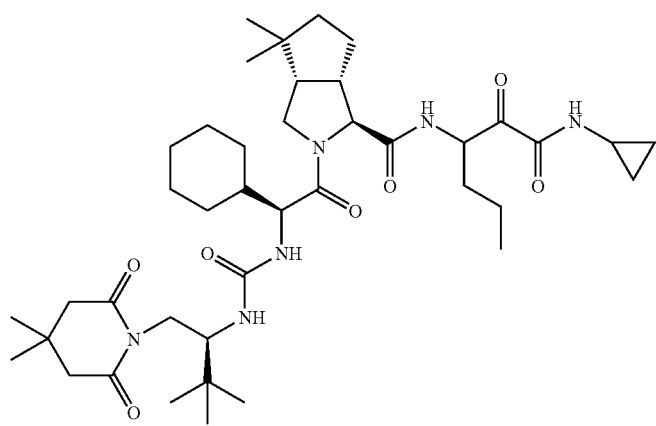

TABLE 1-continued
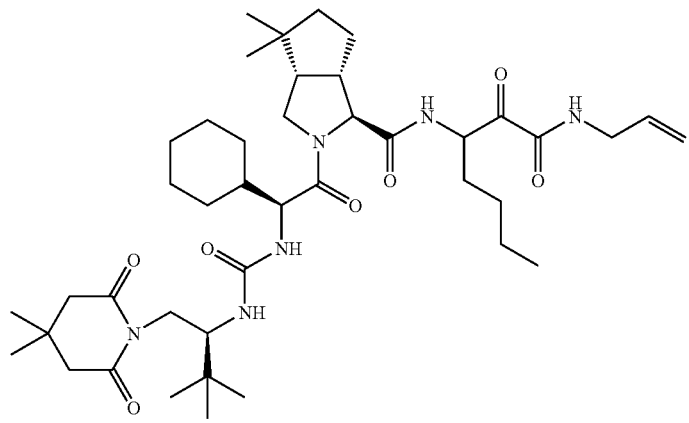
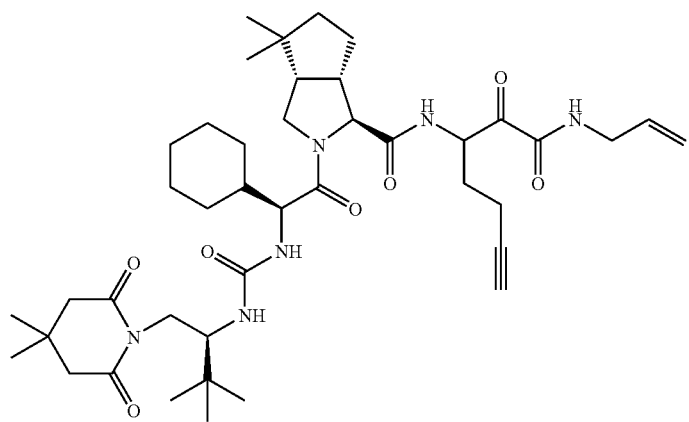
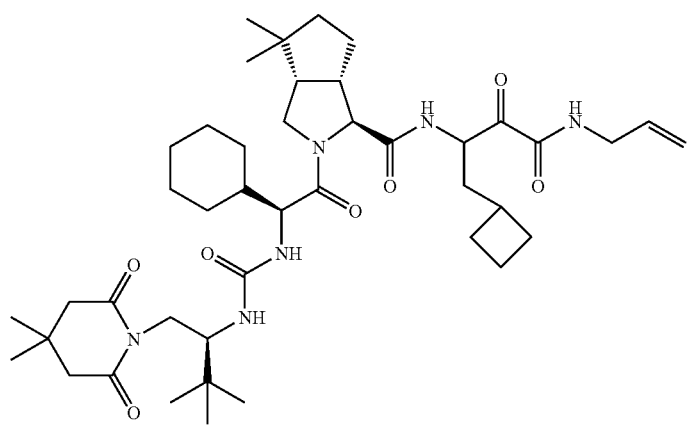

TABLE 1-continued
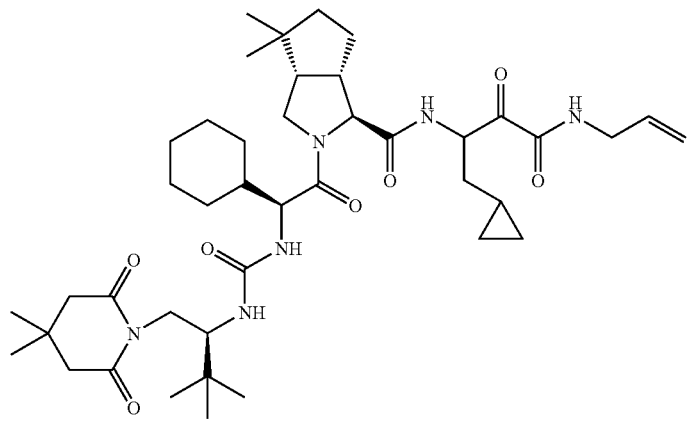
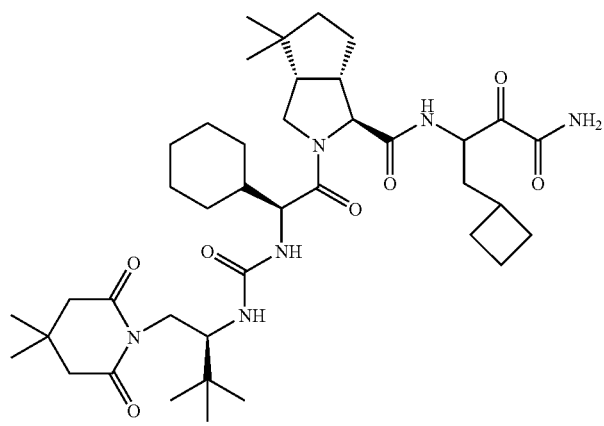
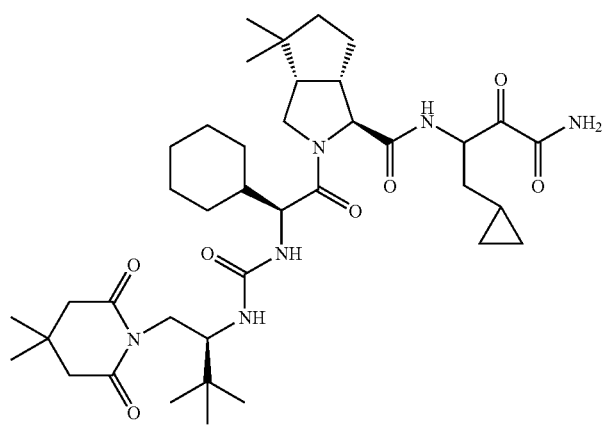

TABLE 1-continued
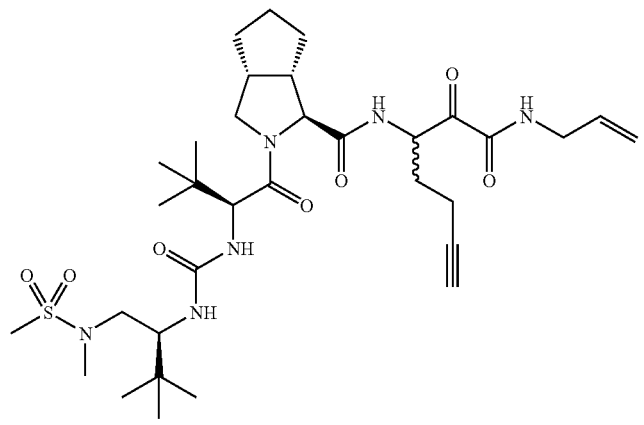
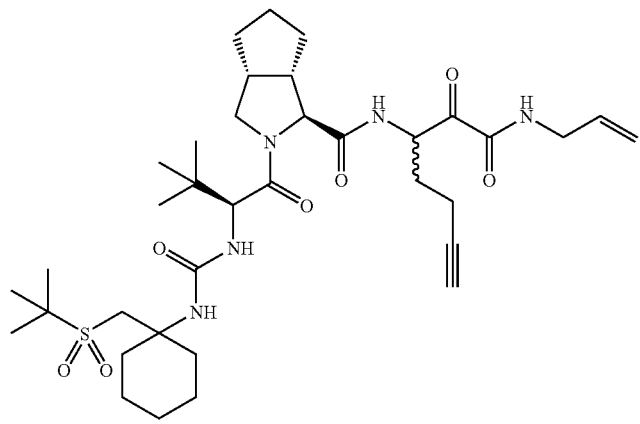
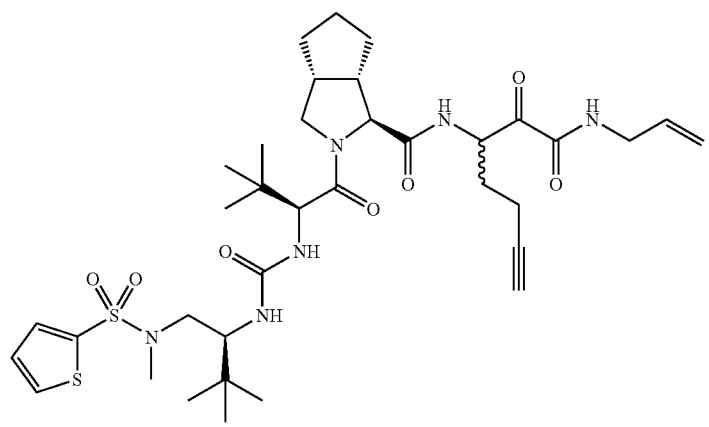

TABLE 1-continued
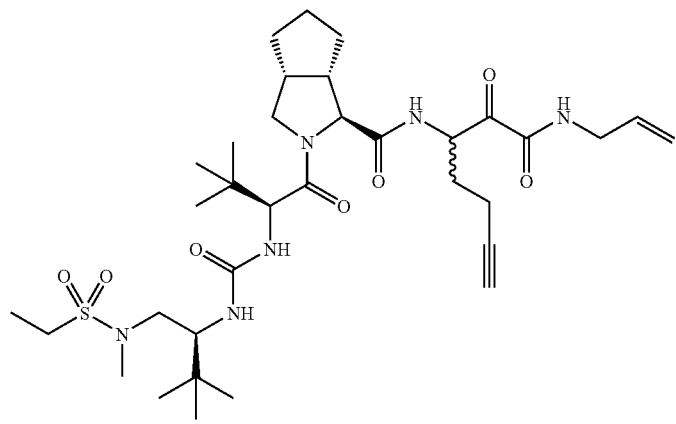
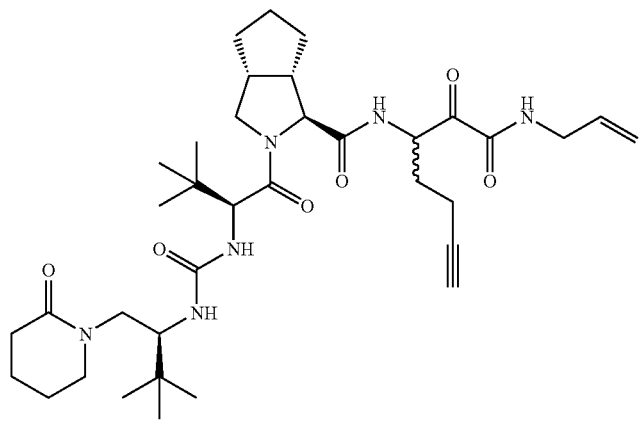
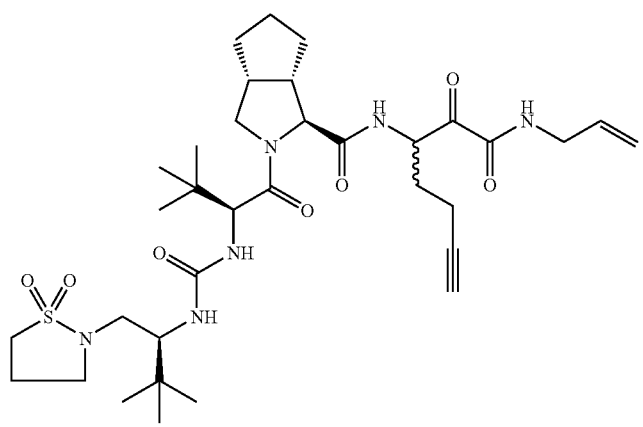

TABLE 1-continued
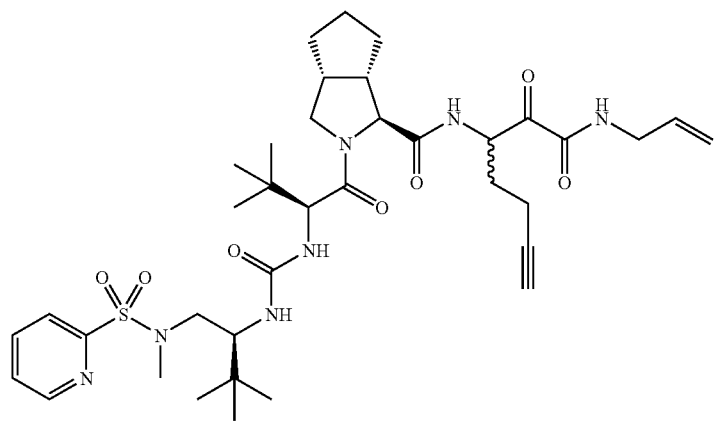
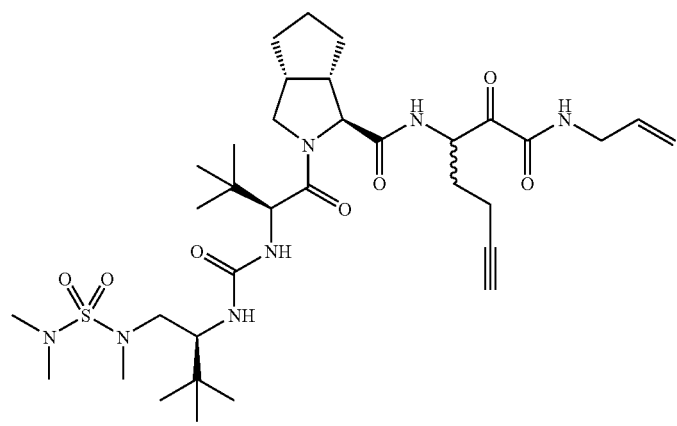
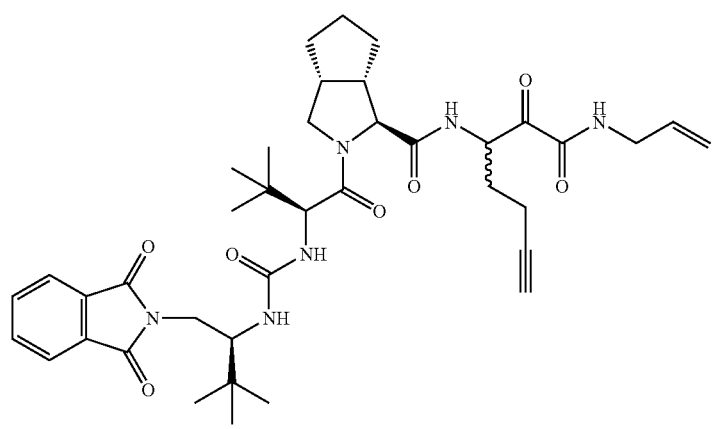

TABLE 1-continued
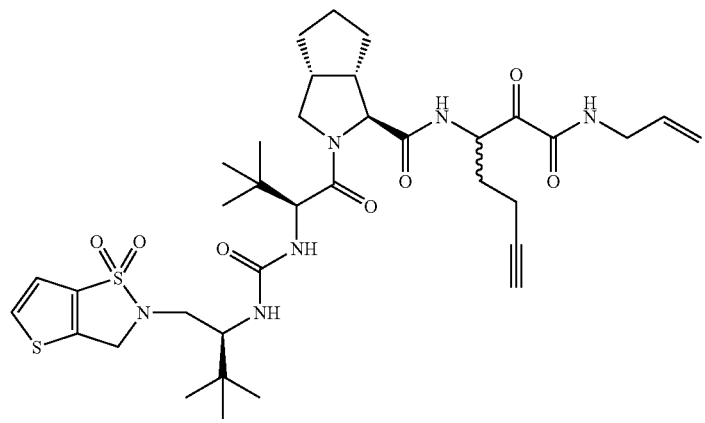
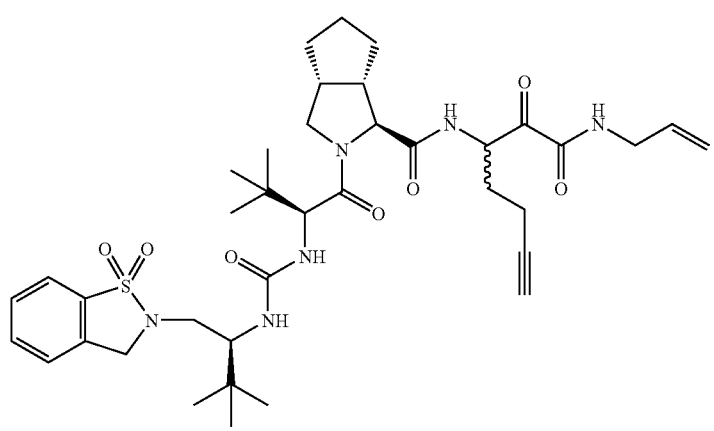
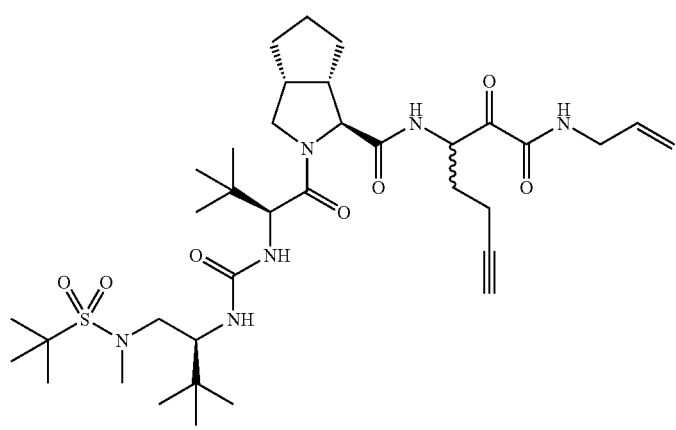

TABLE 1-continued
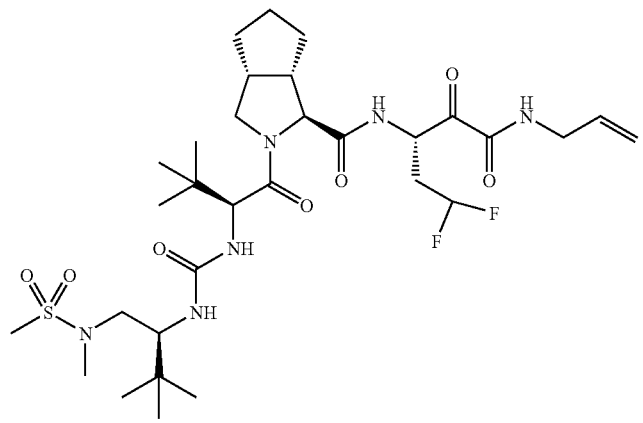
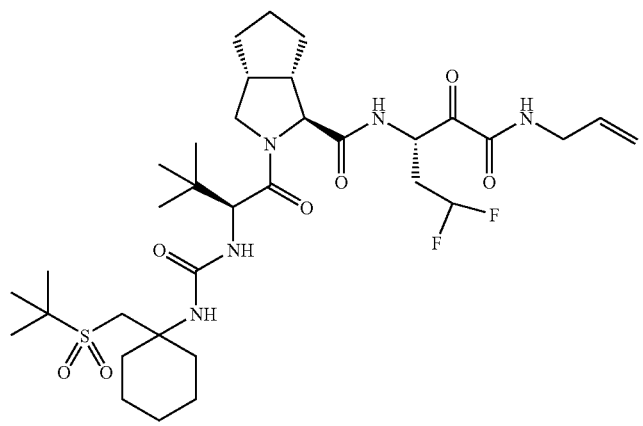
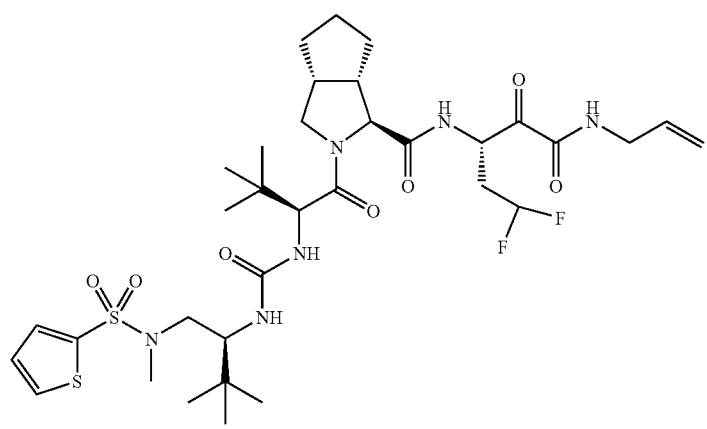

TABLE 1-continued
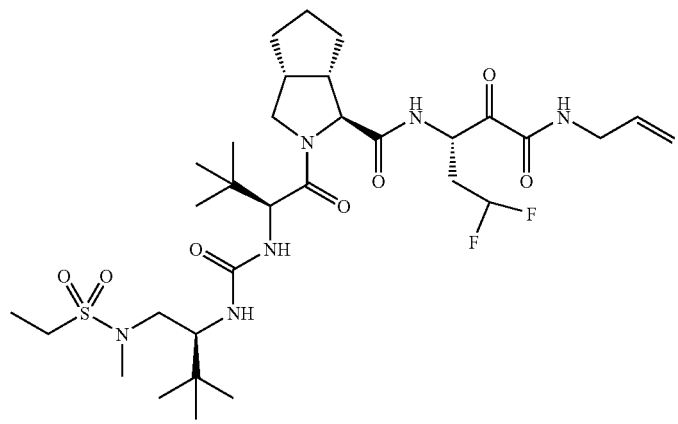
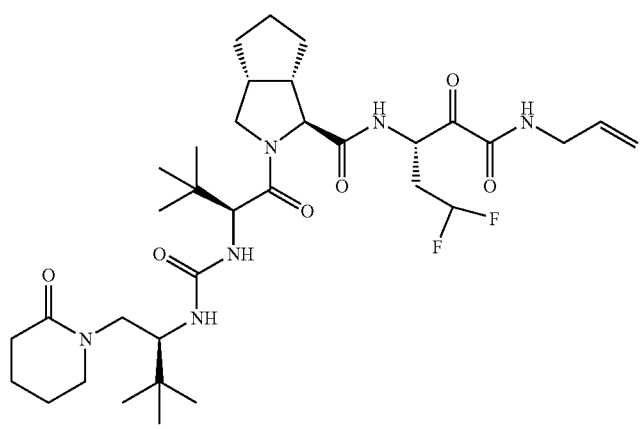
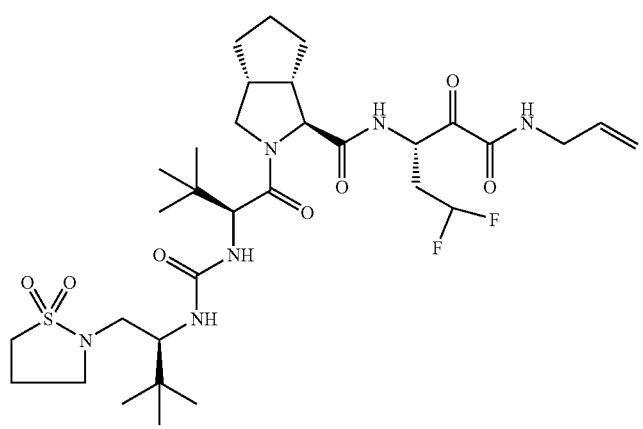

TABLE 1-continued
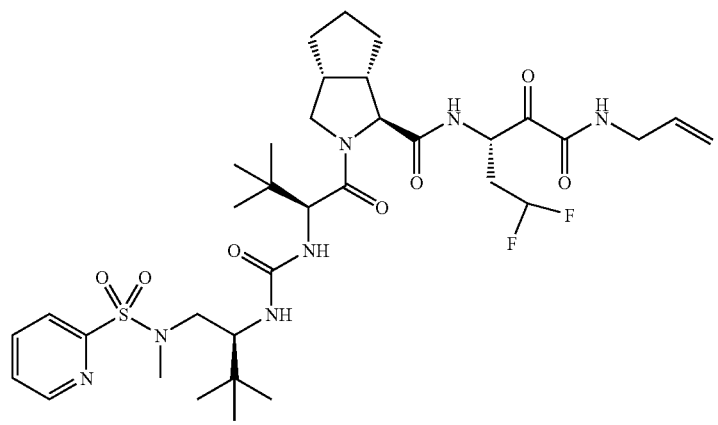
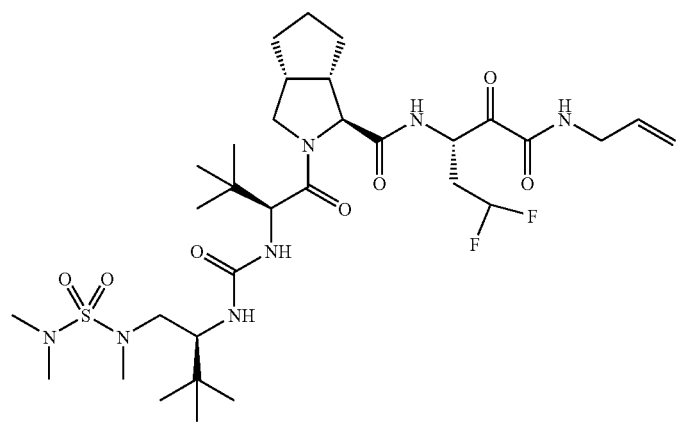
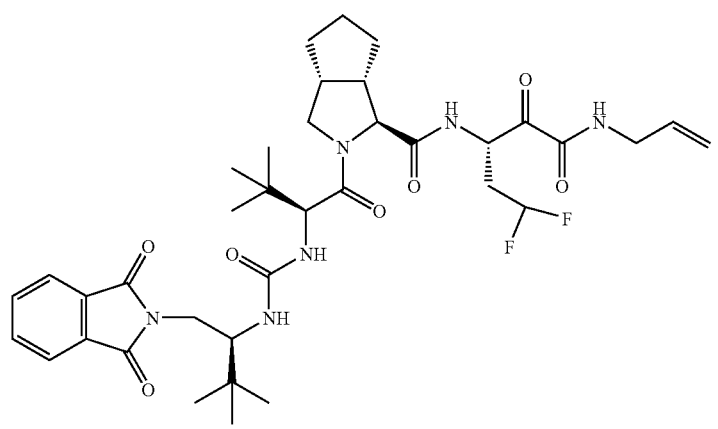

TABLE 1-continued
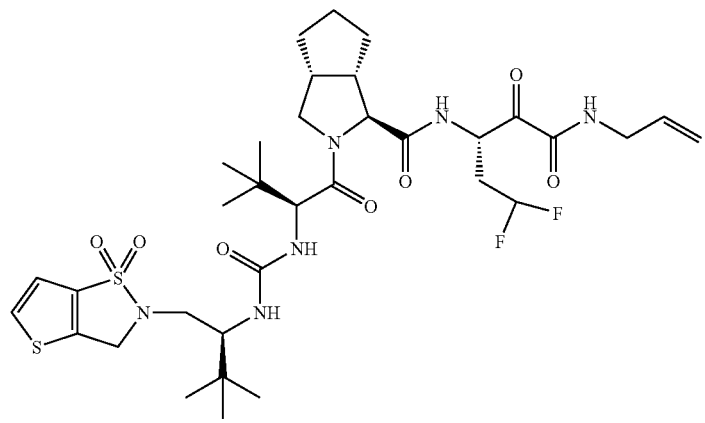
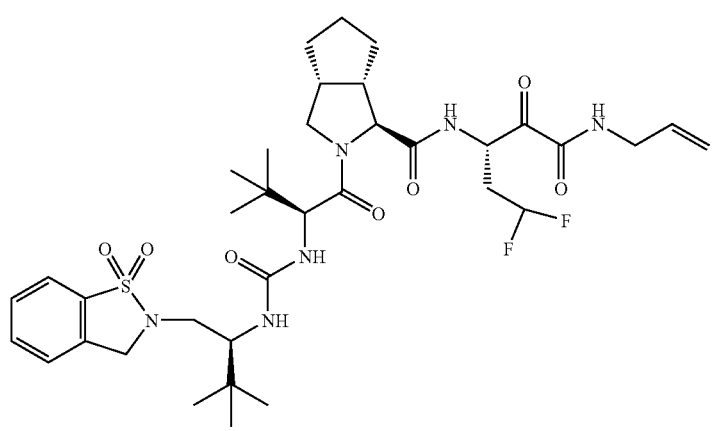
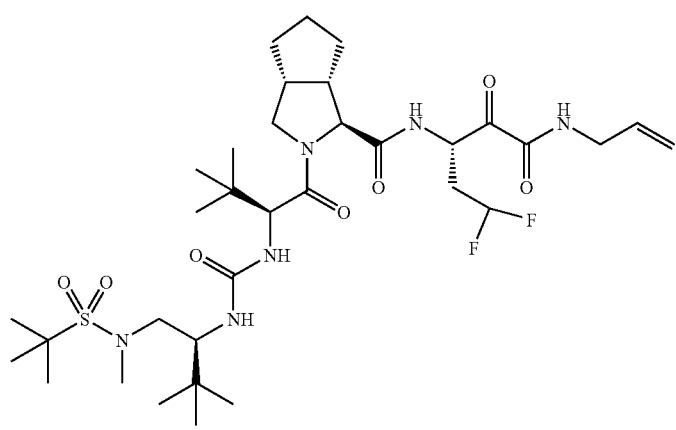

TABLE 1-continued
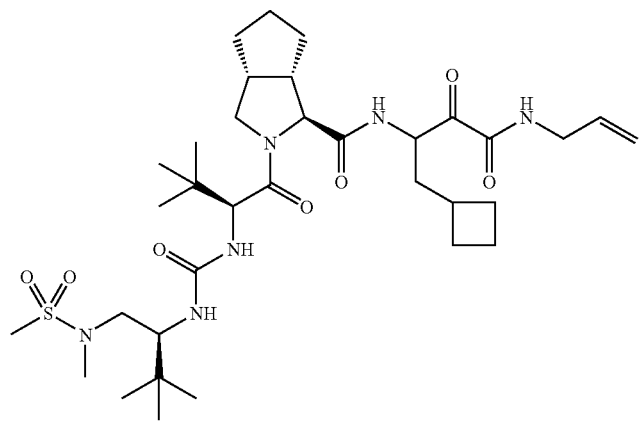
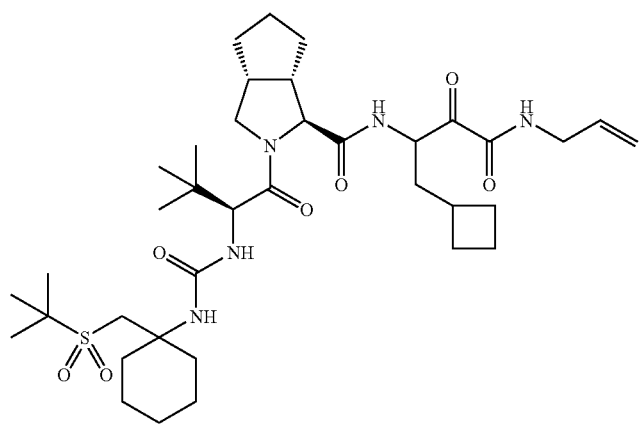
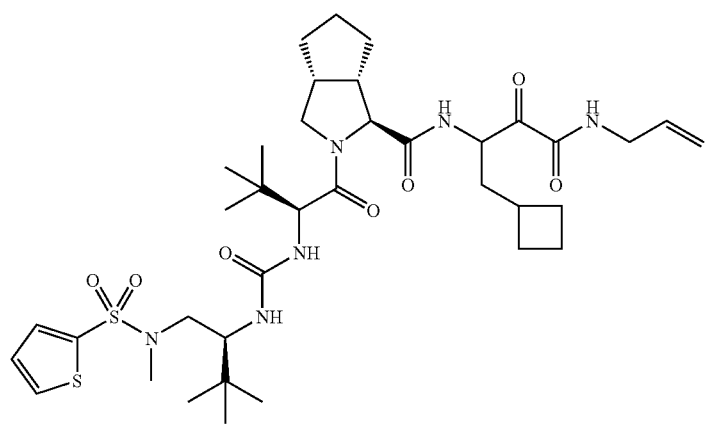

TABLE 1-continued
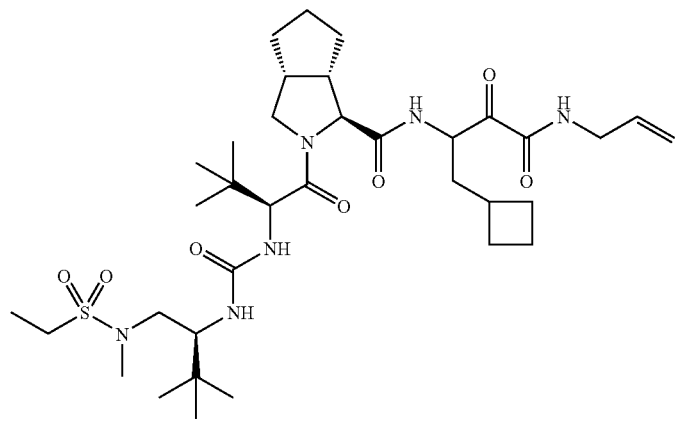
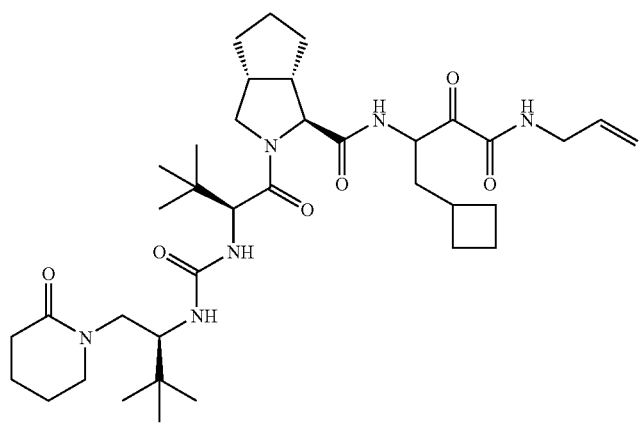
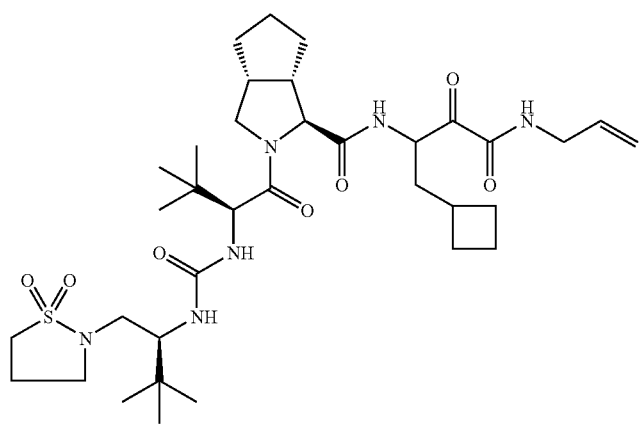

TABLE 1-continued
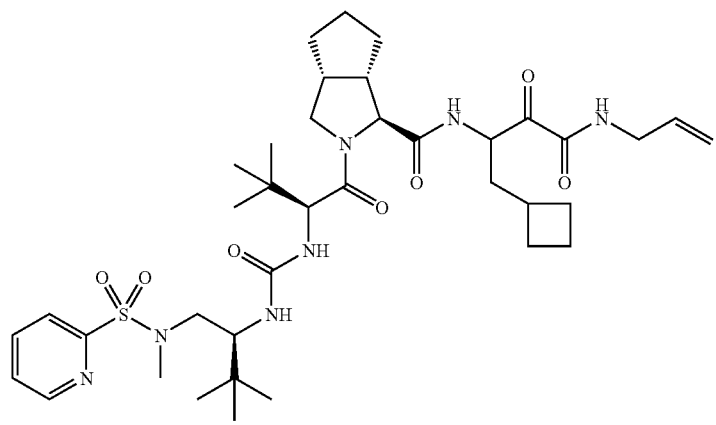
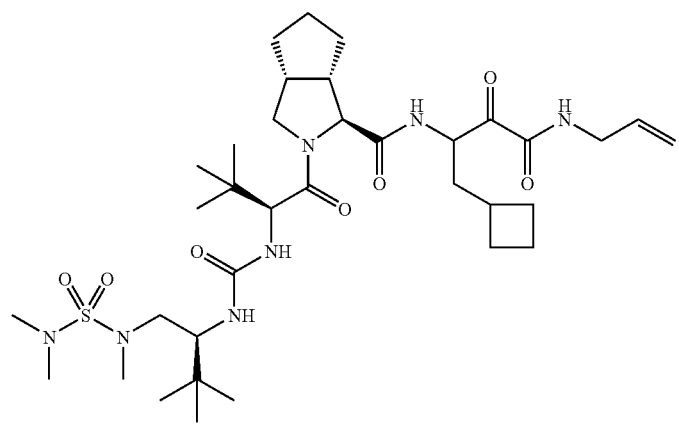
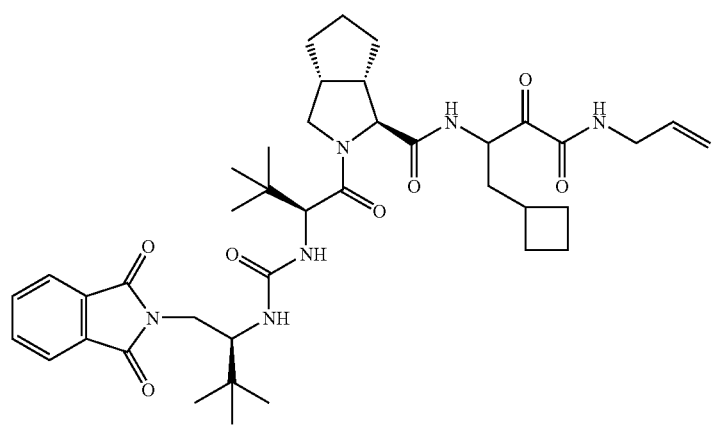

TABLE 1-continued
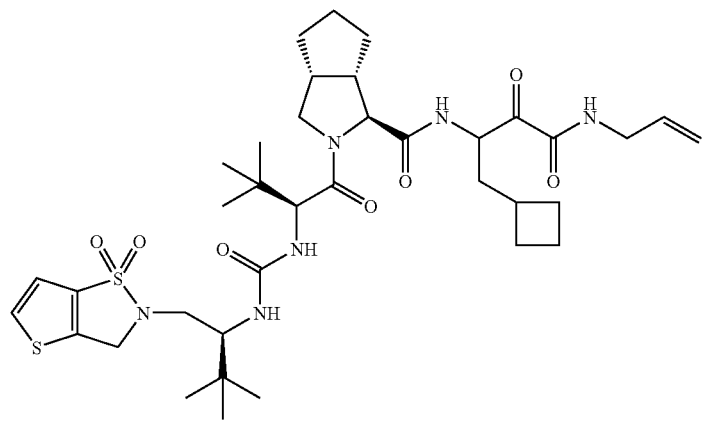
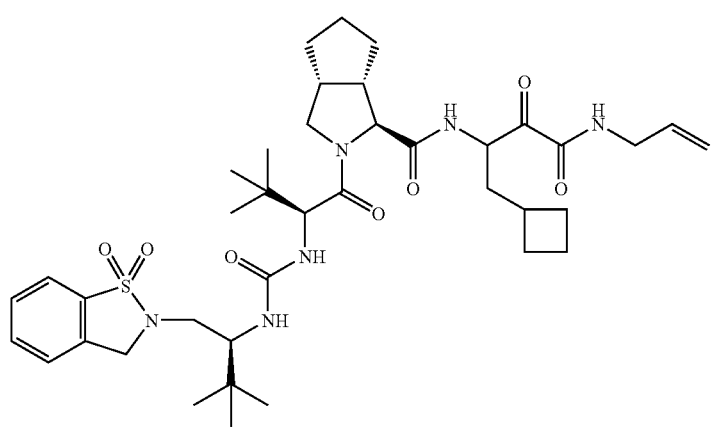
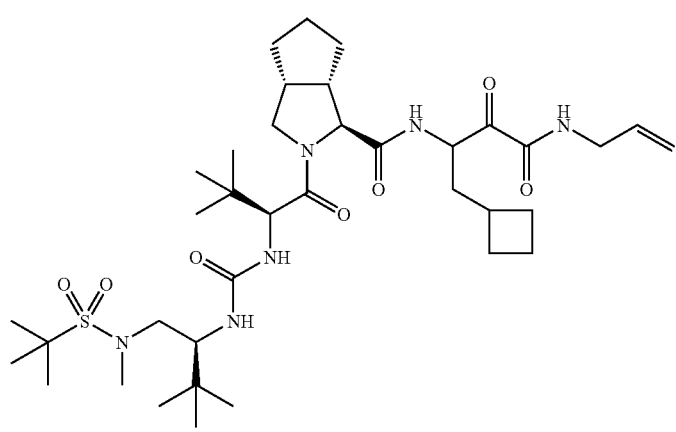

TABLE 1-continued
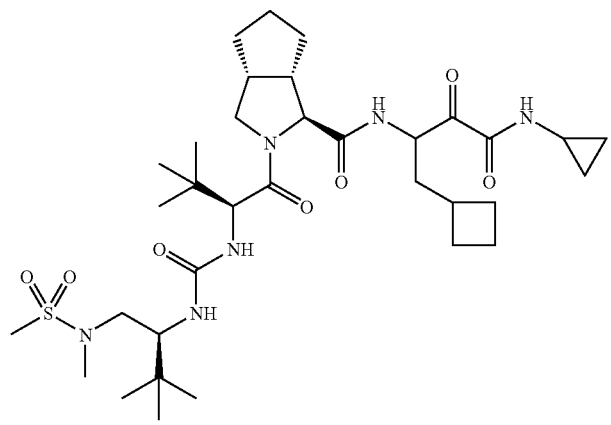
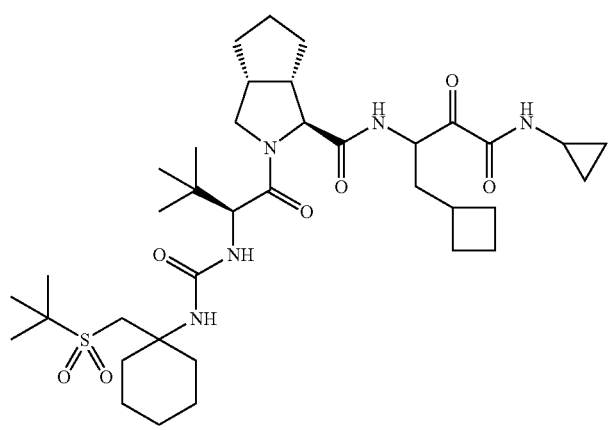
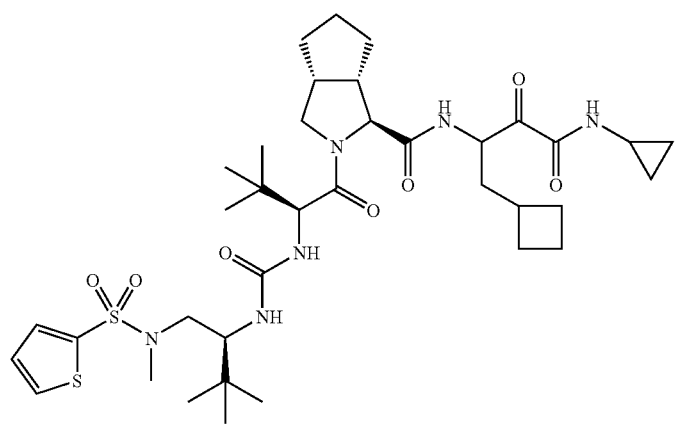

TABLE 1-continued
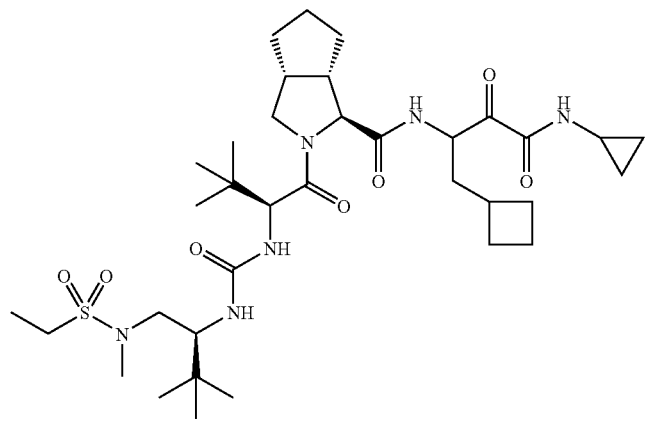
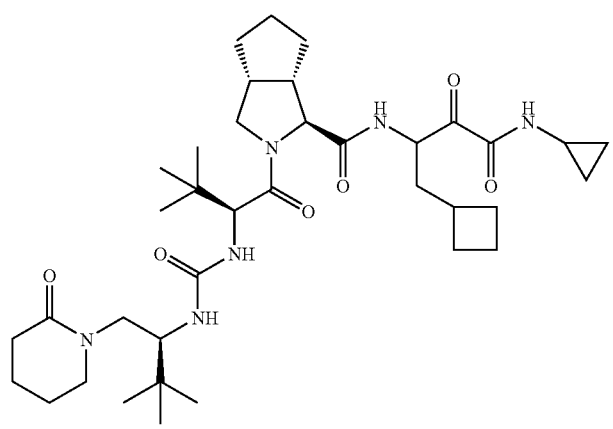
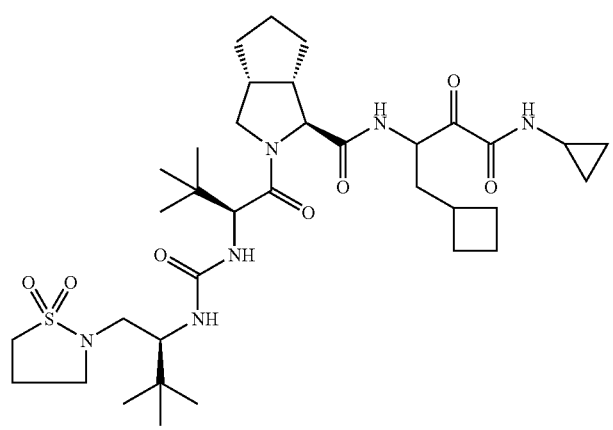

TABLE 1-continued
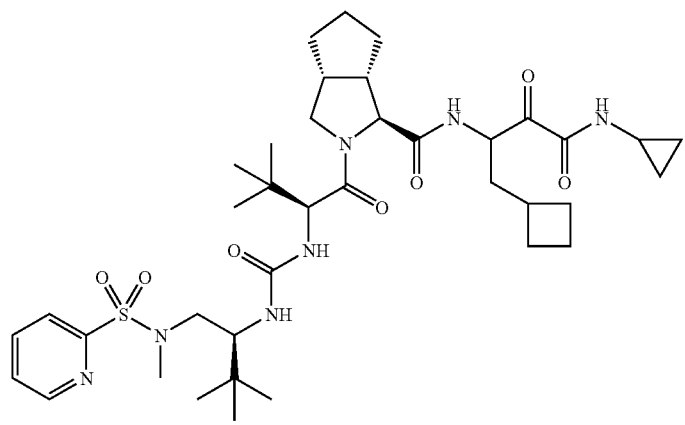
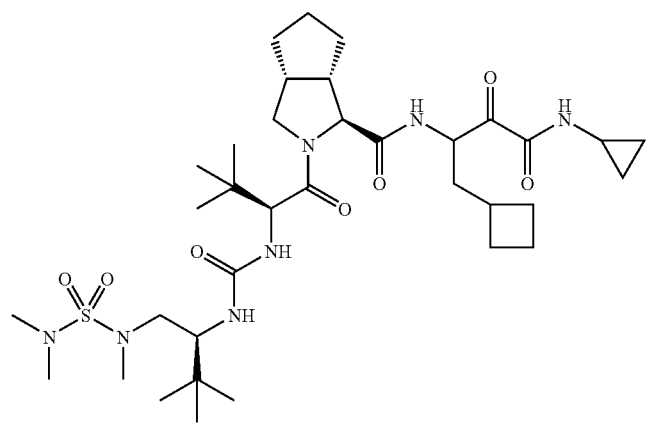
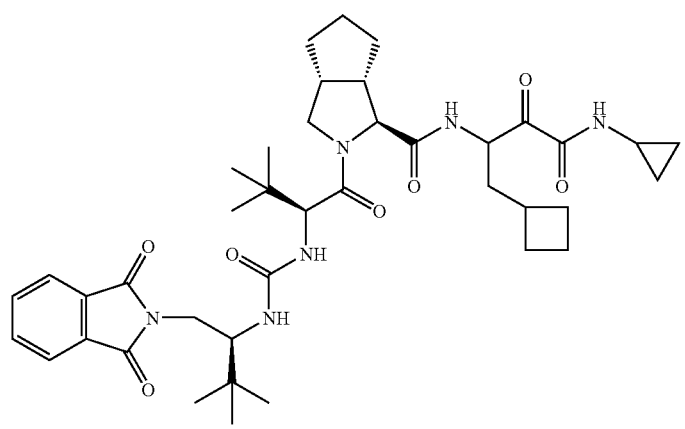

TABLE 1-continued
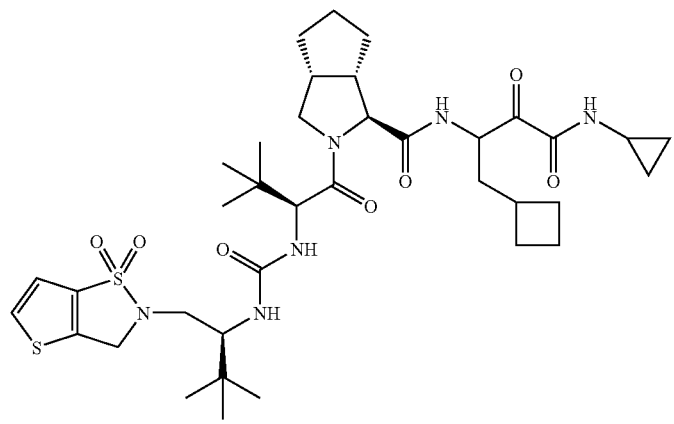
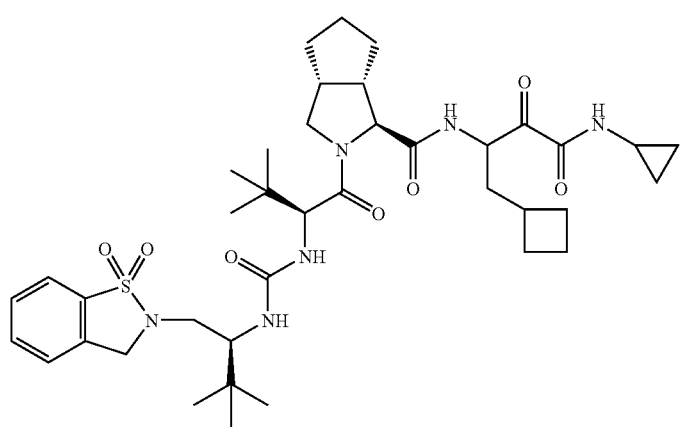
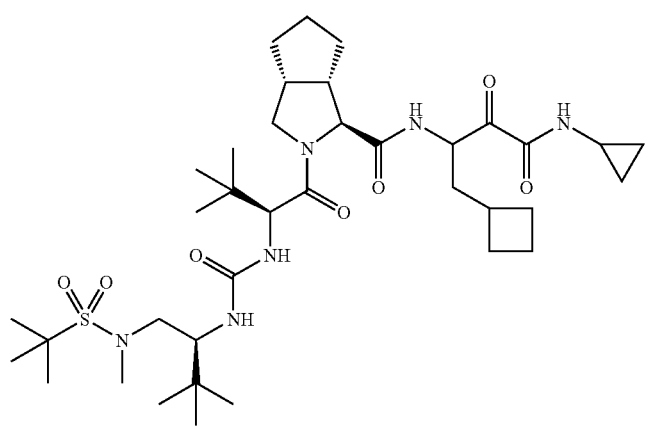

TABLE 1-continued
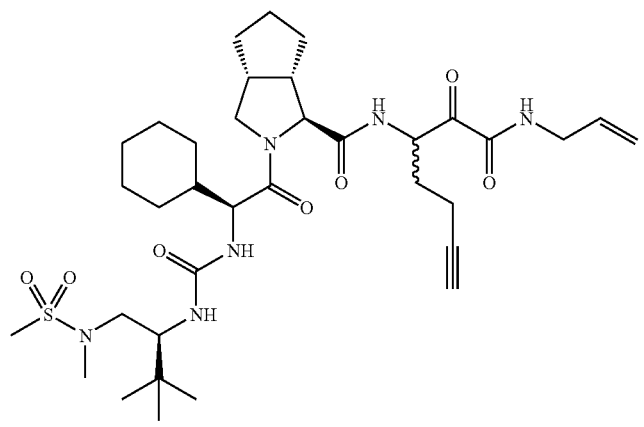
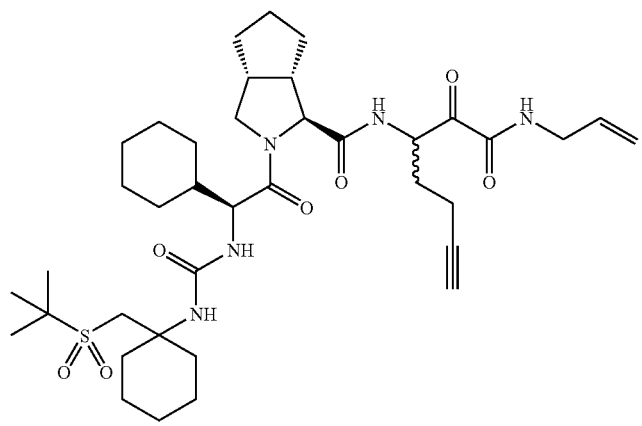
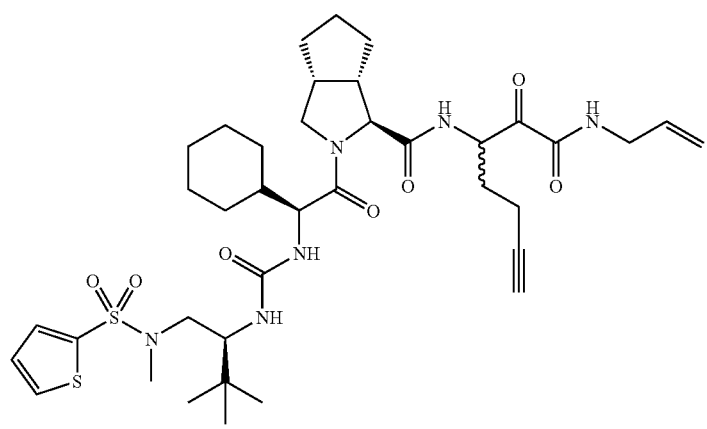

TABLE 1-continued
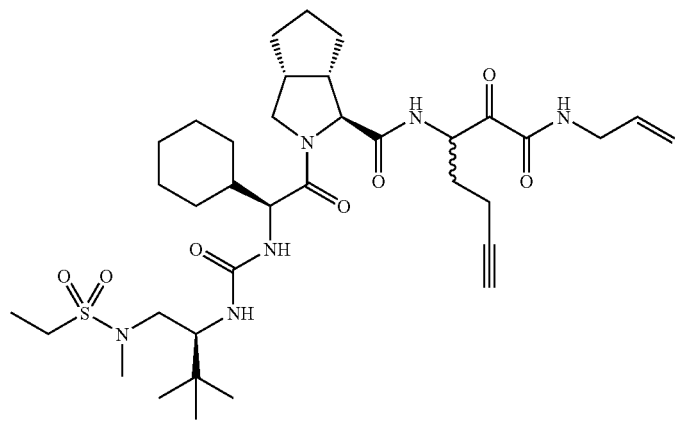
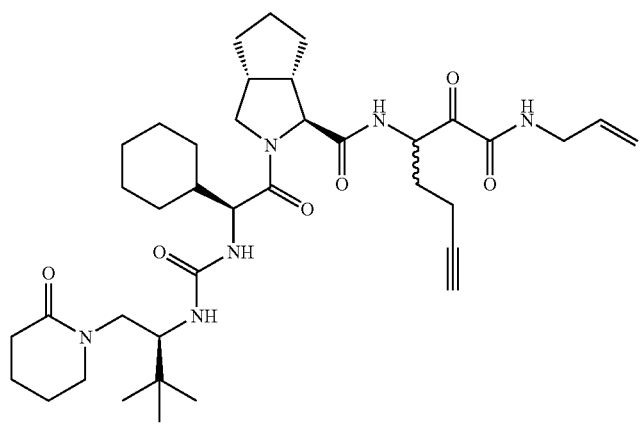
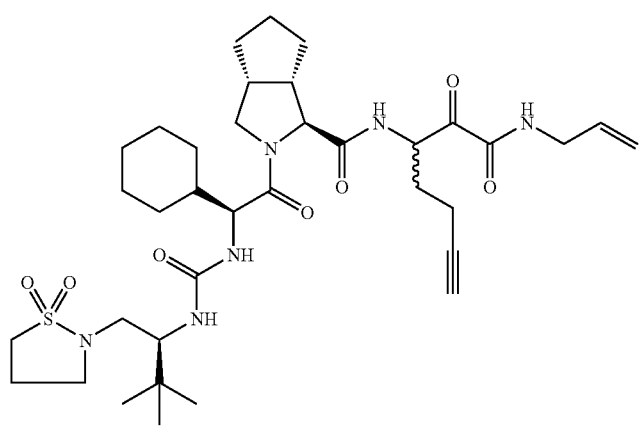

TABLE 1-continued
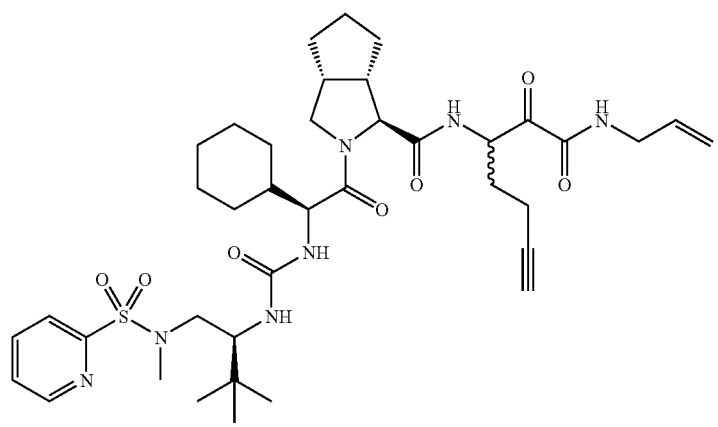
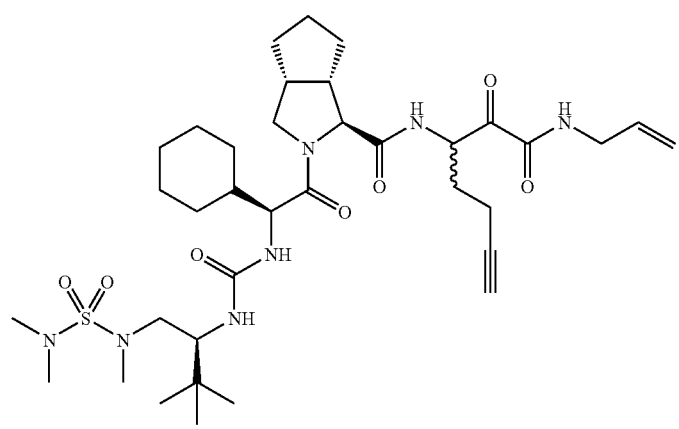
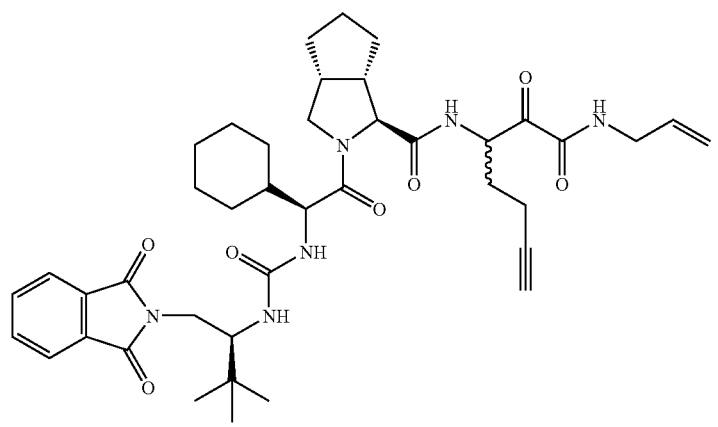

TABLE 1-continued
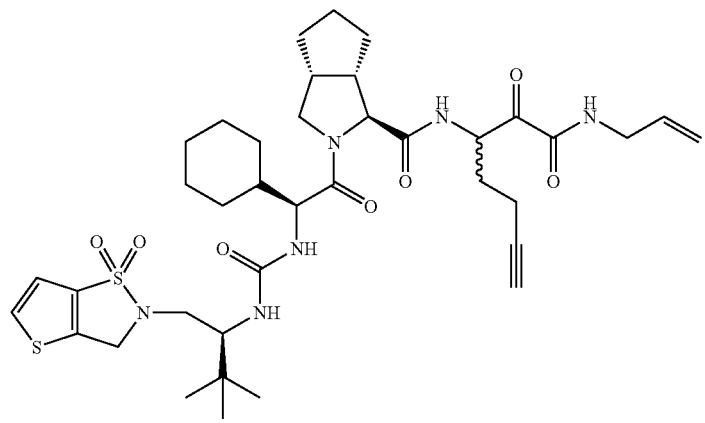
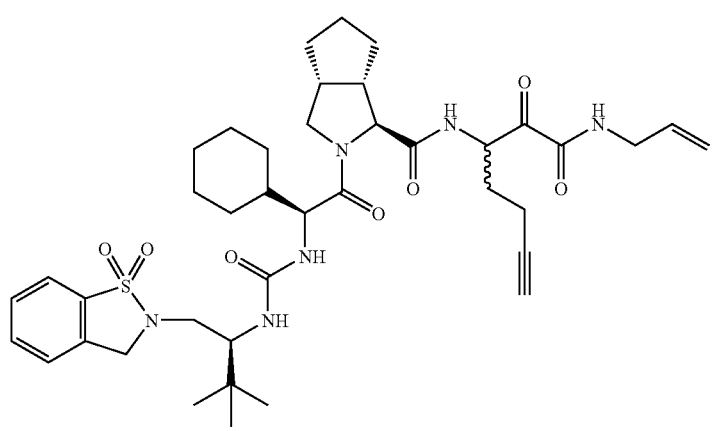
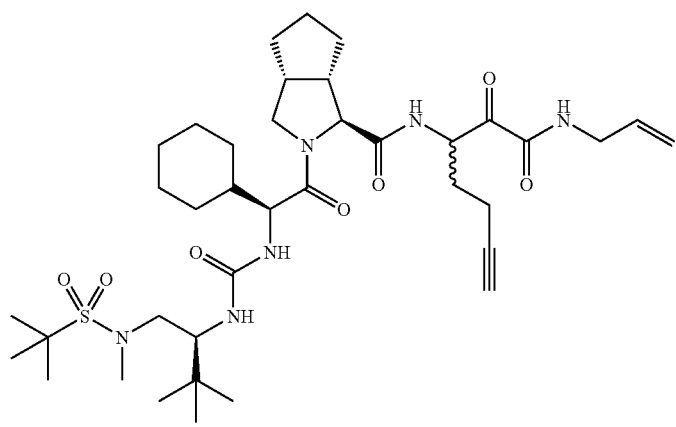

TABLE 1-continued
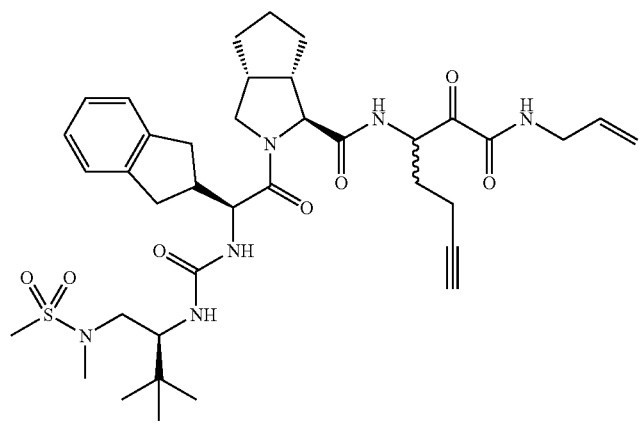
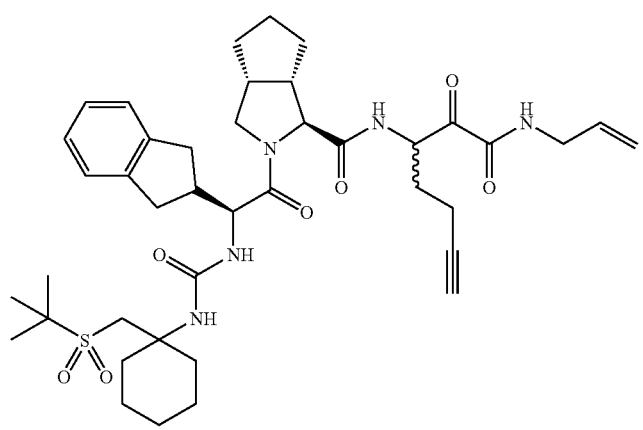
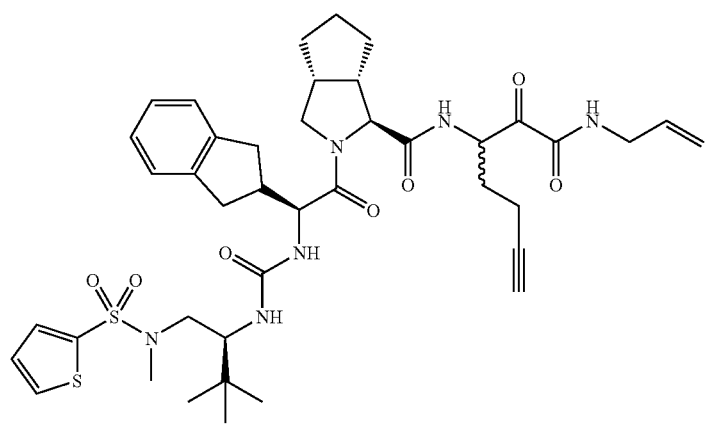

TABLE 1-continued
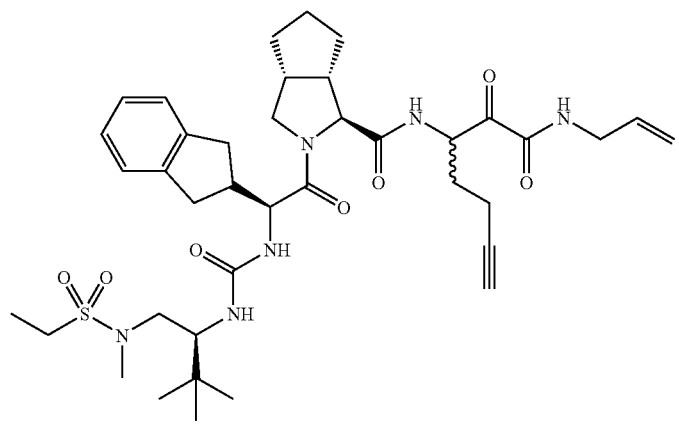
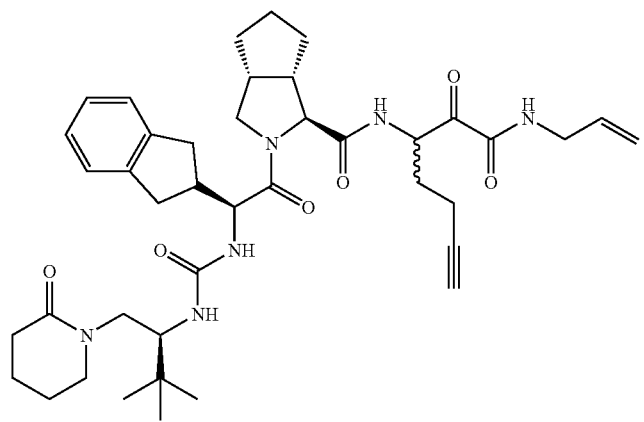
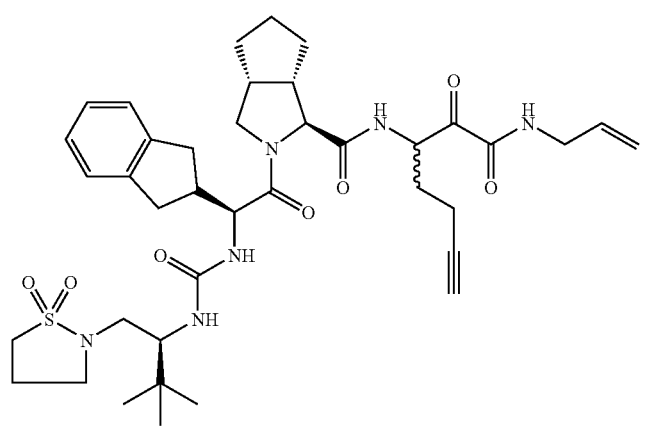

TABLE 1-continued
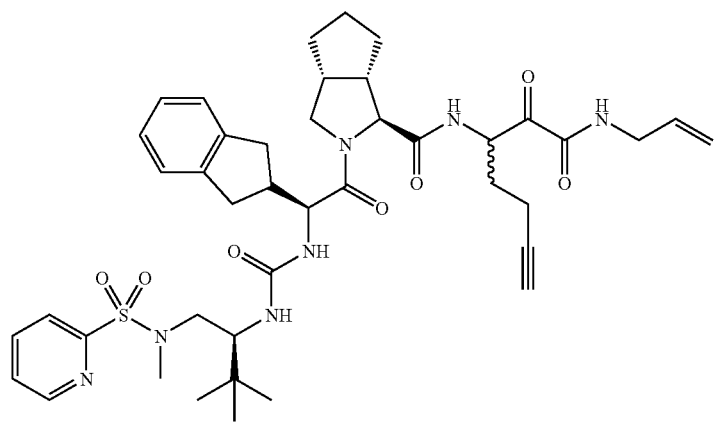
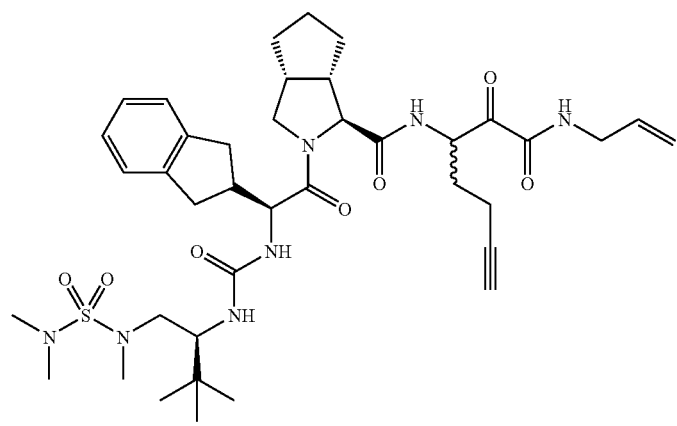
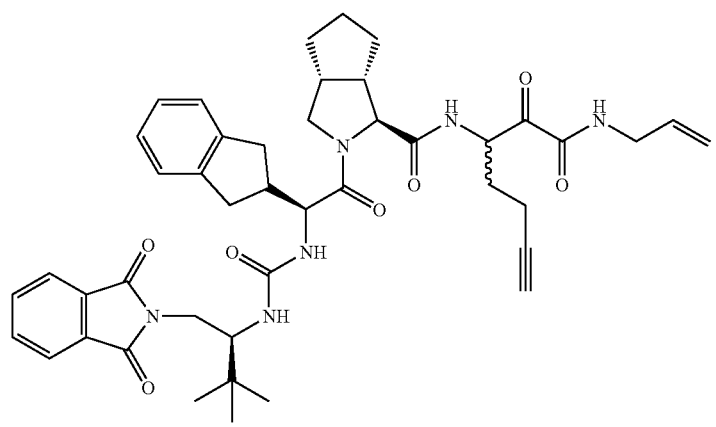

TABLE 1-continued
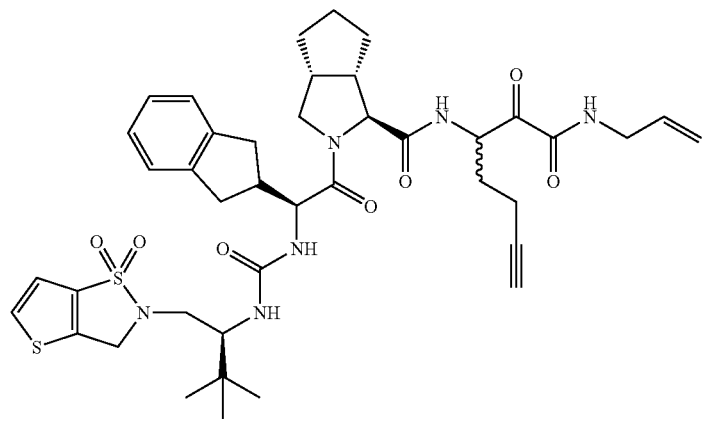
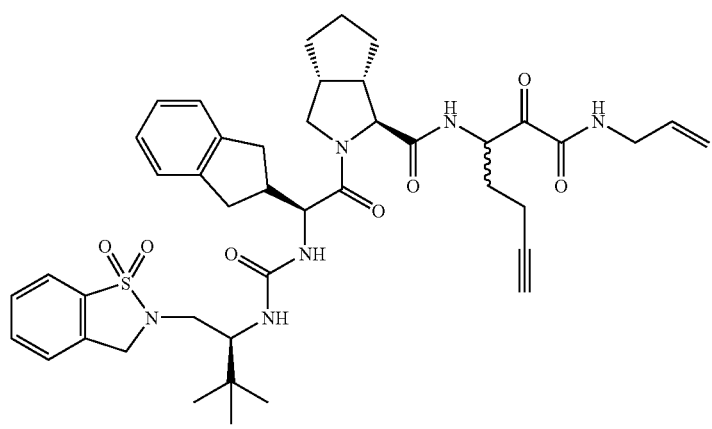
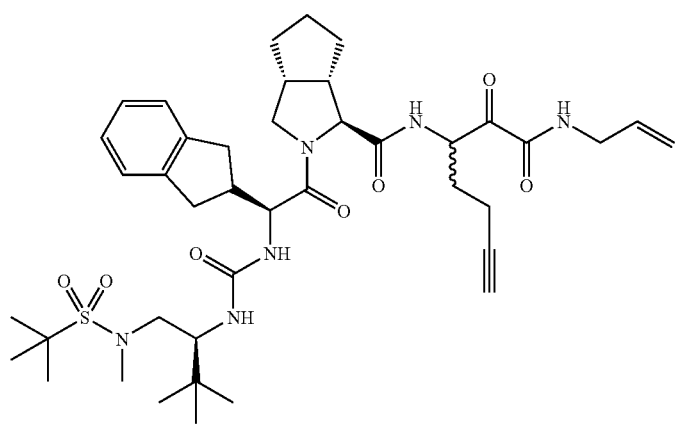

TABLE 1-continued
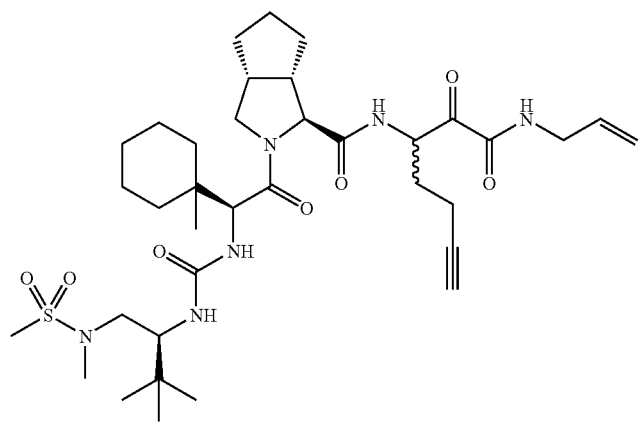
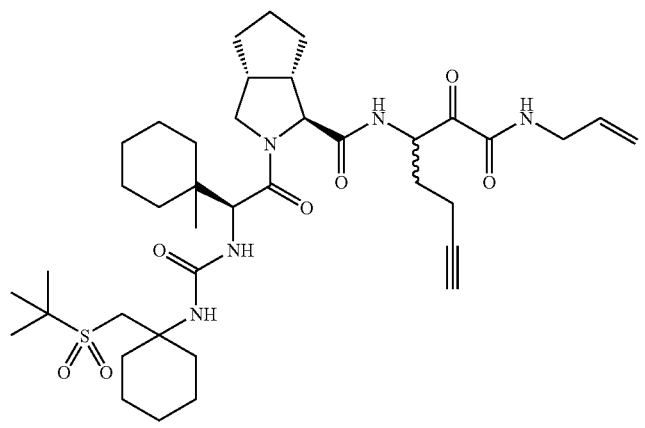
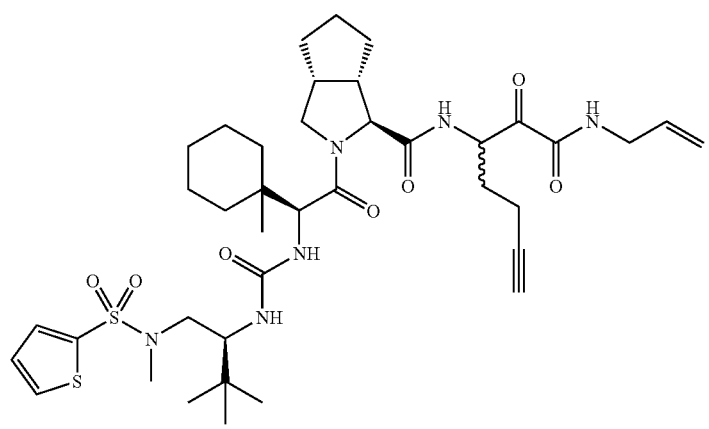

TABLE 1-continued
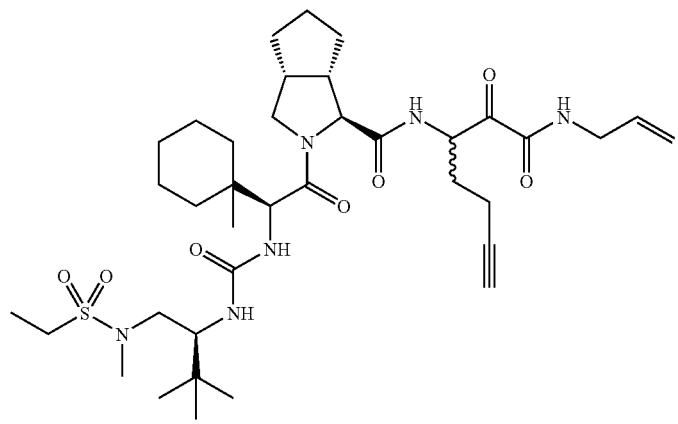
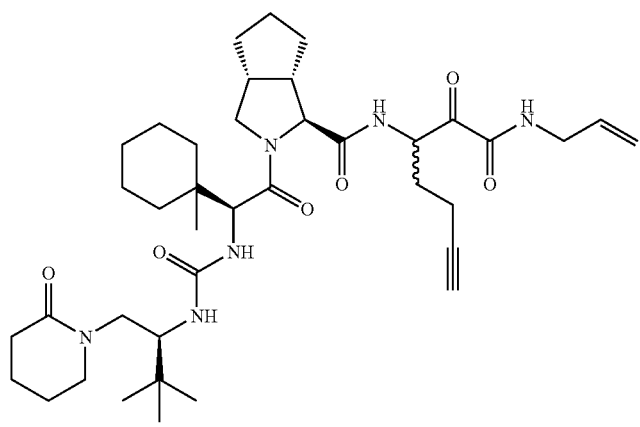
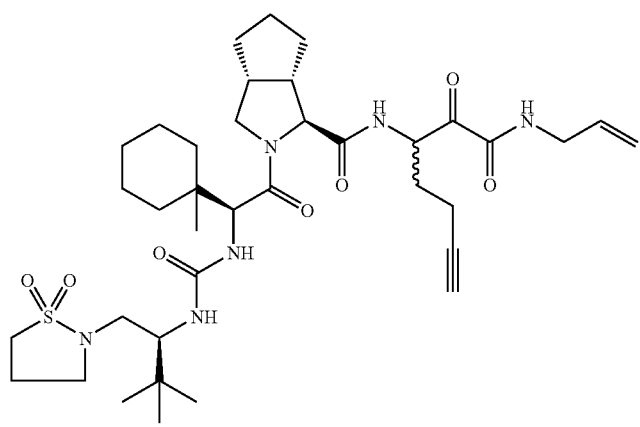

TABLE 1-continued
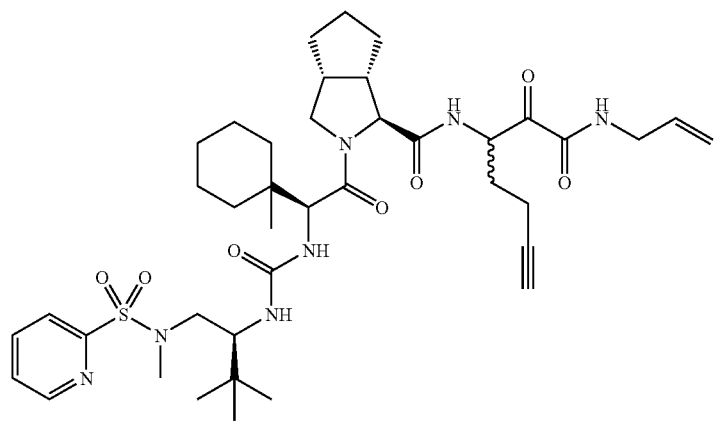
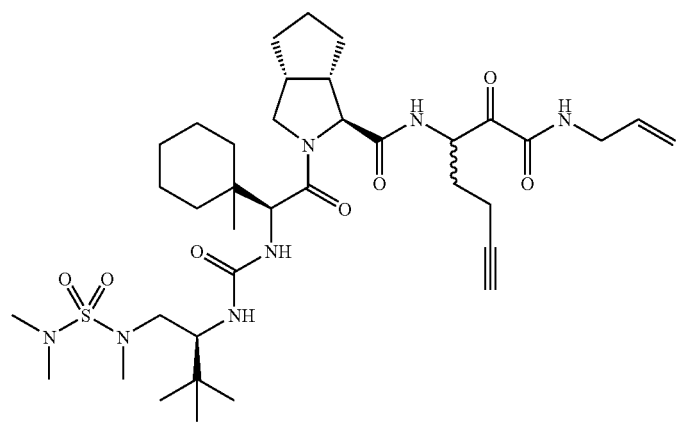
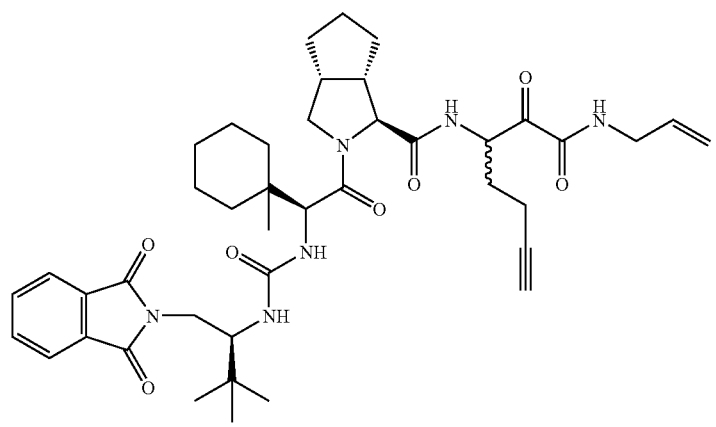

TABLE 1-continued
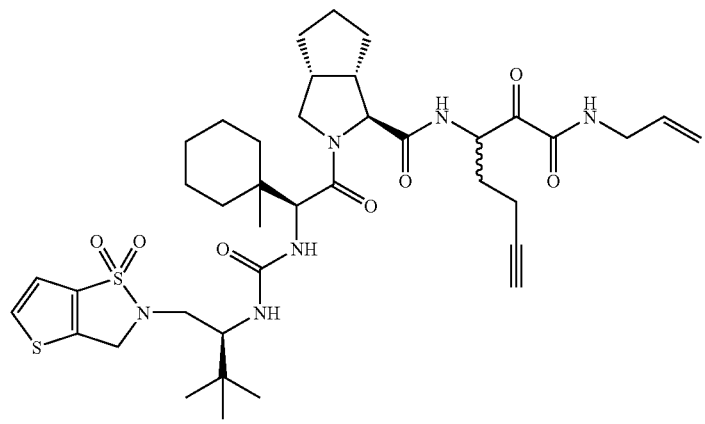
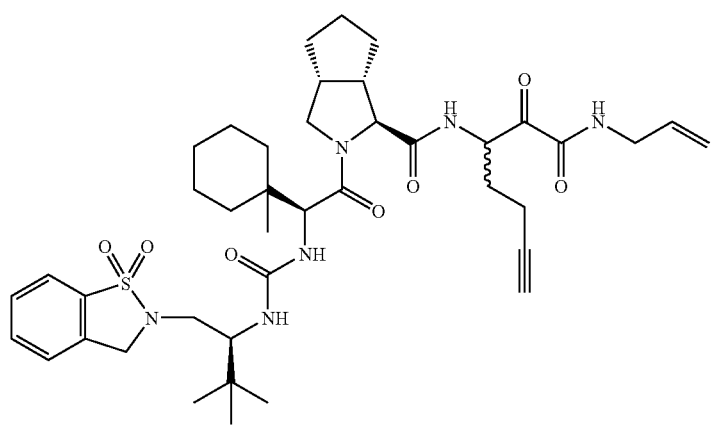
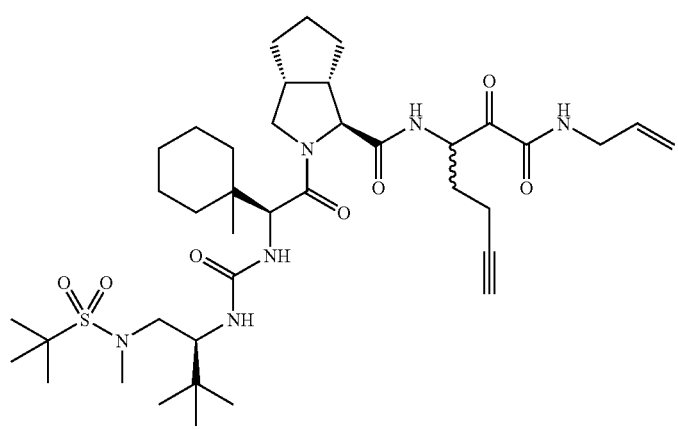

Also presented in Table 1A are additional compounds according to the present invention:
TABLE 1A
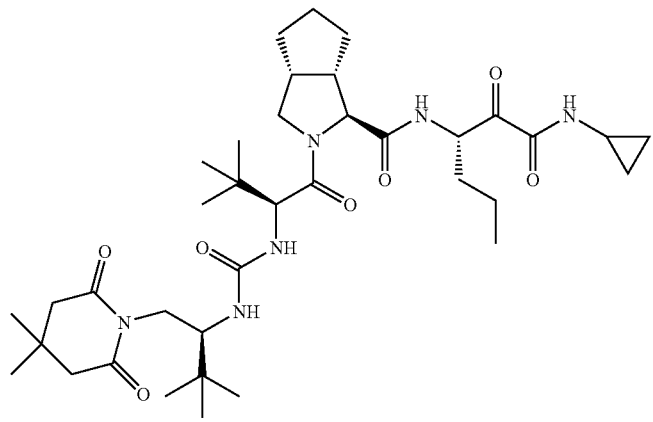
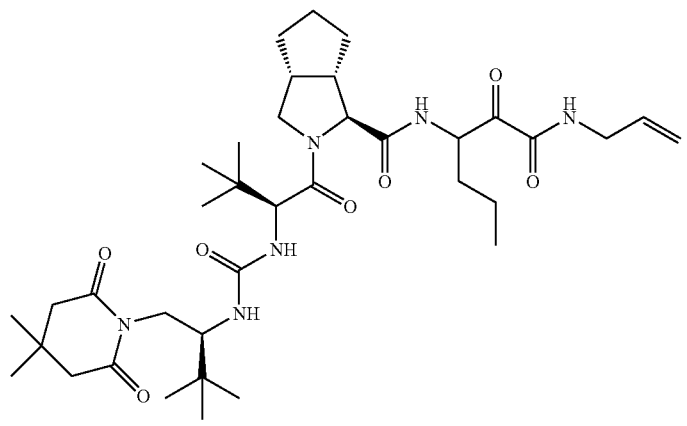
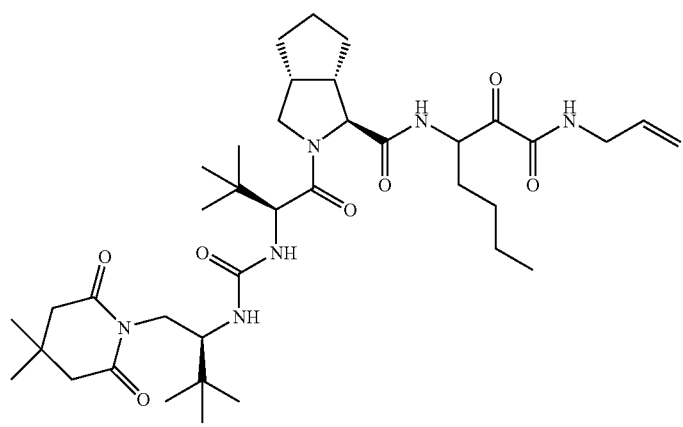

TABLE 1A-continued
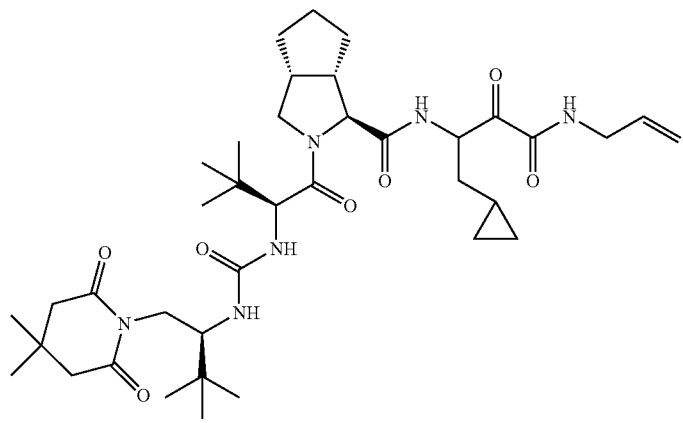
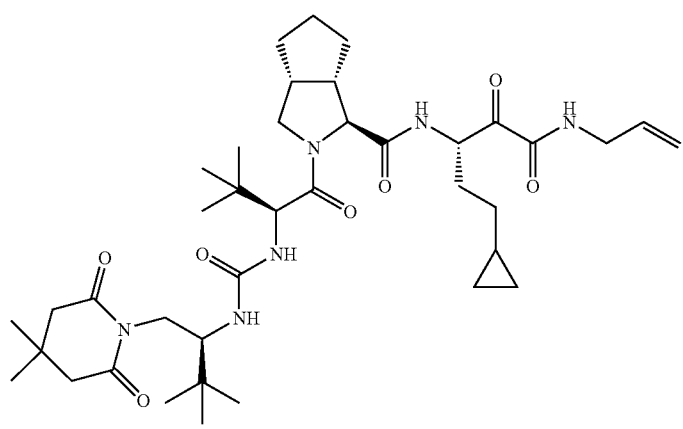
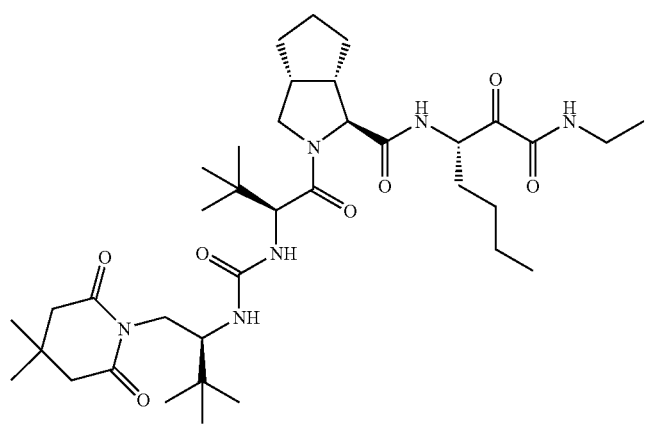

TABLE 1A-continued
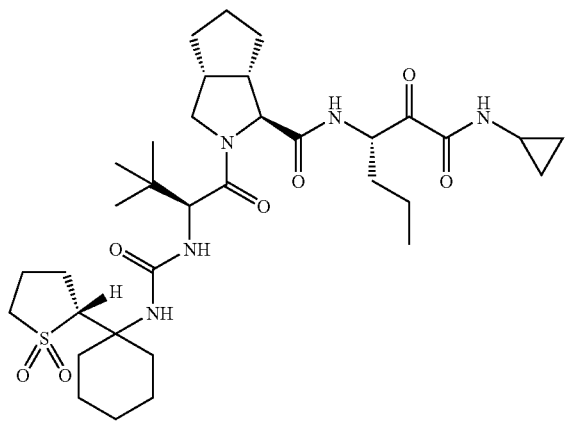
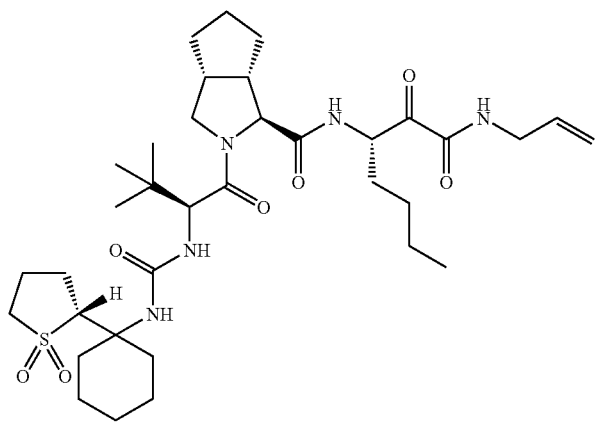
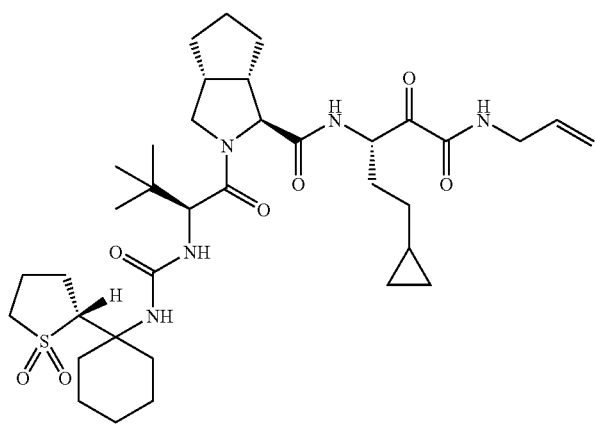

TABLE 1A-continued
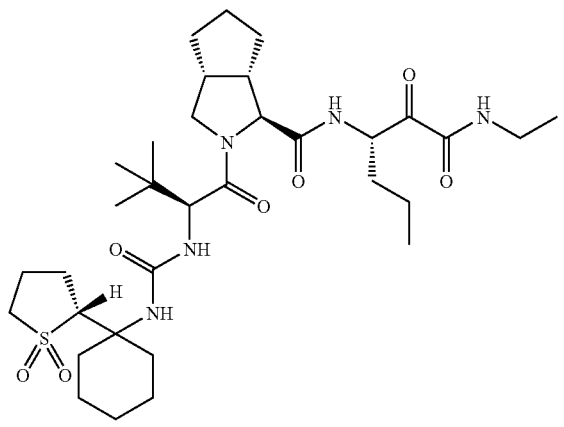
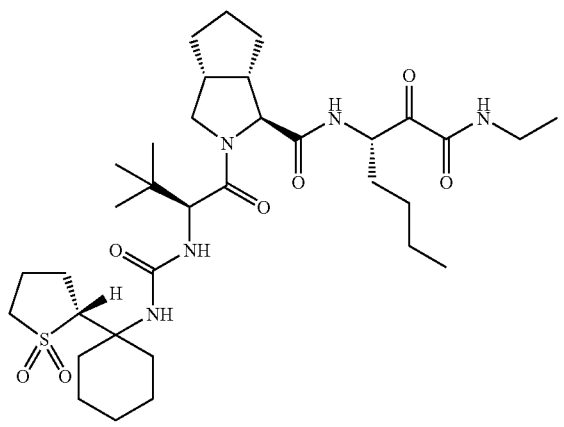
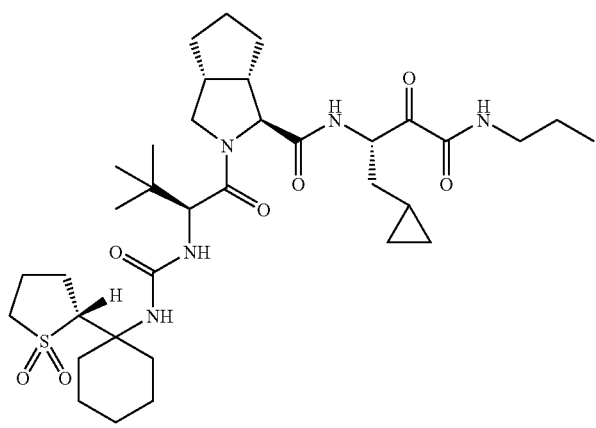

TABLE 1A-continued
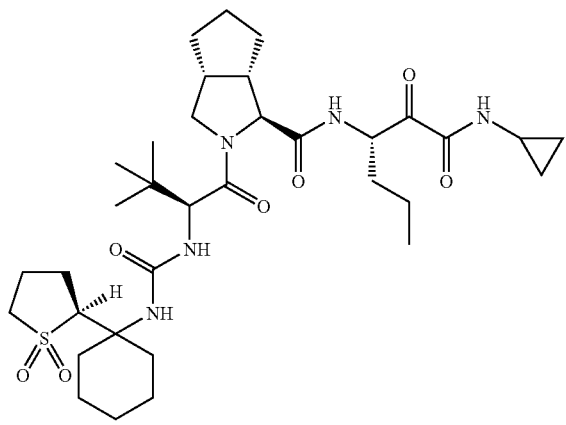
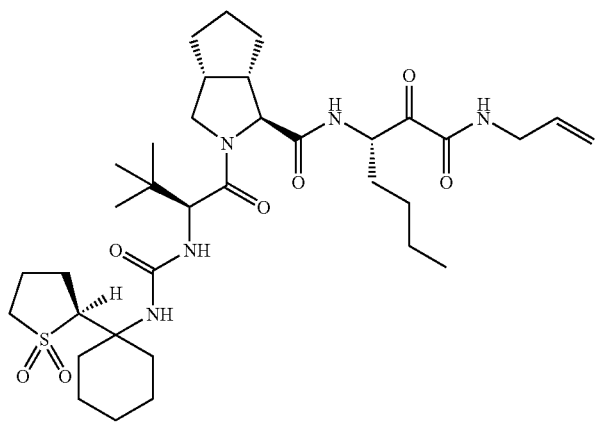
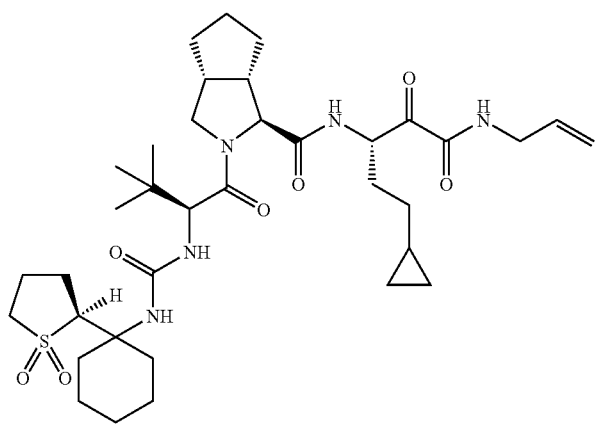

TABLE 1A-continued
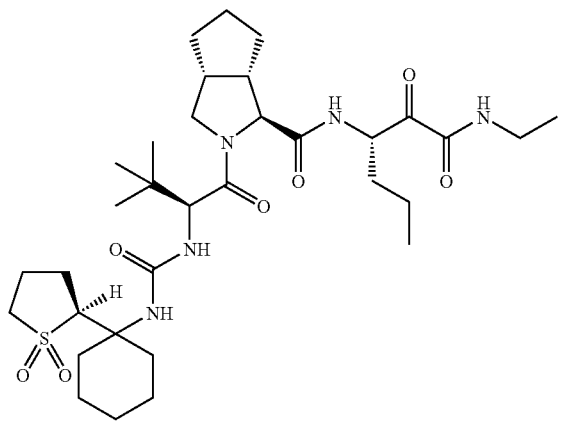
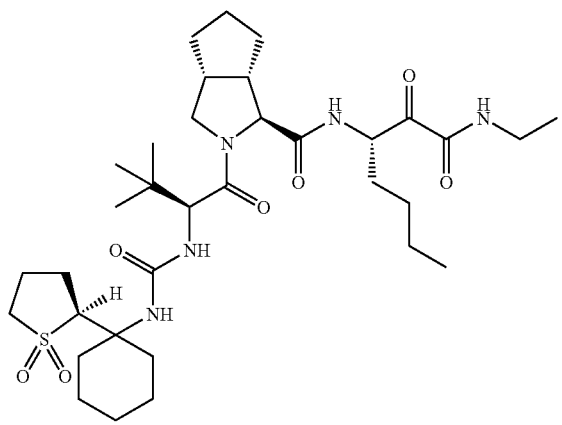
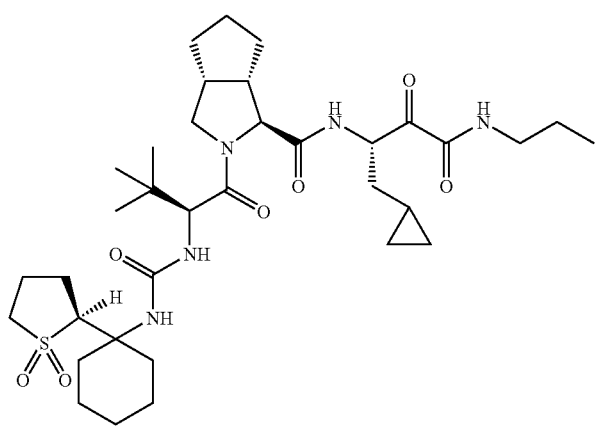

TABLE 1A-continued
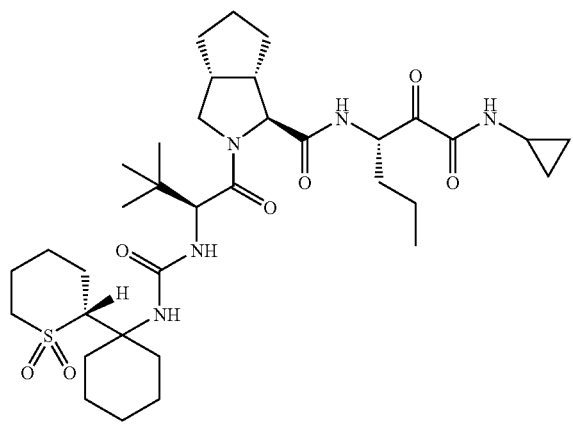
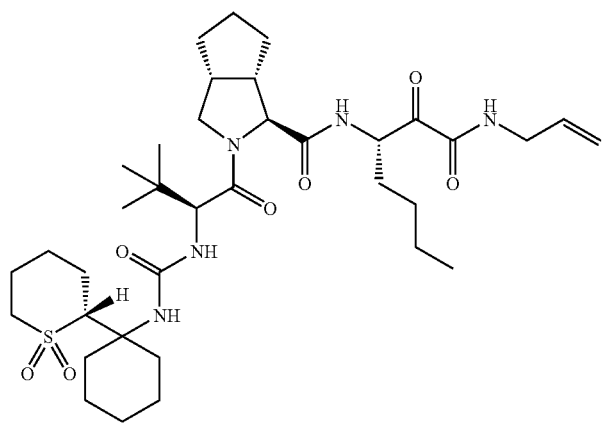
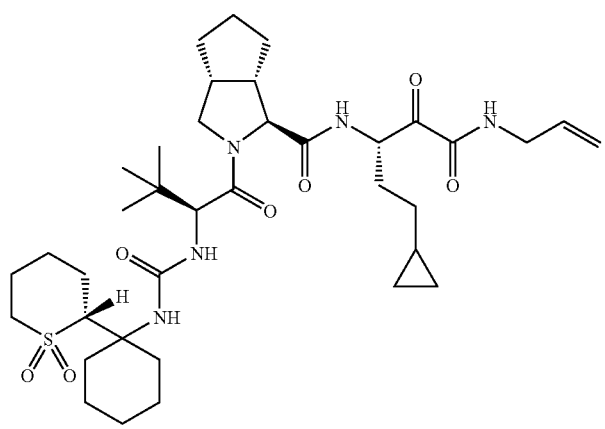

TABLE 1A-continued
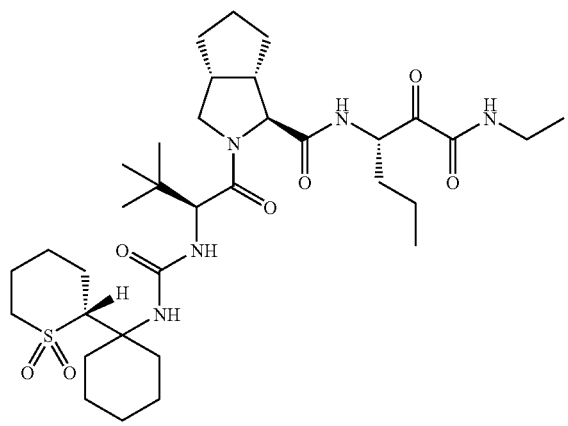
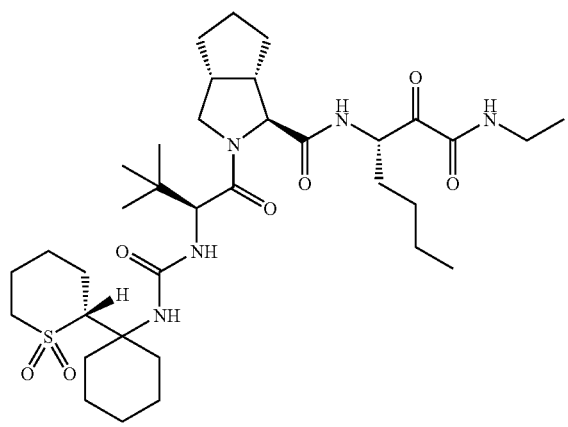
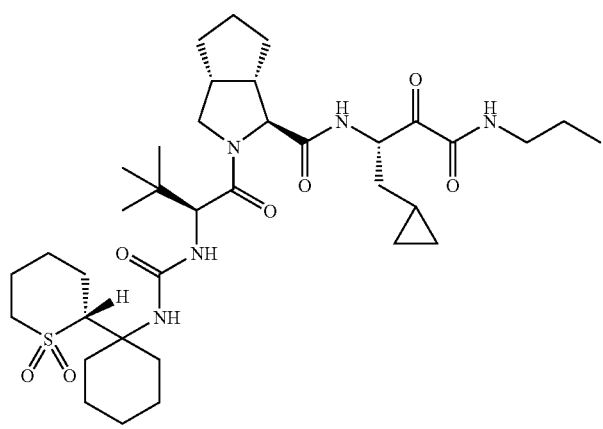

TABLE 1A-continued
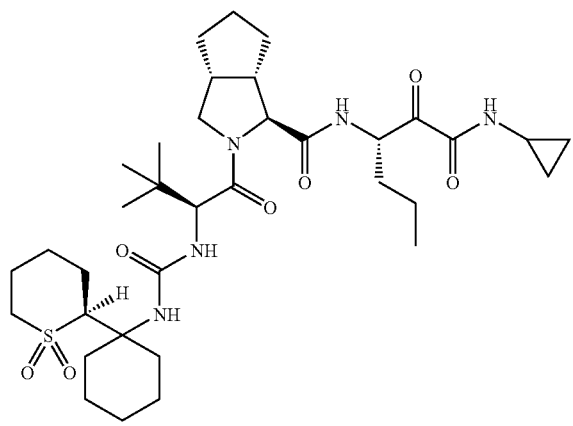
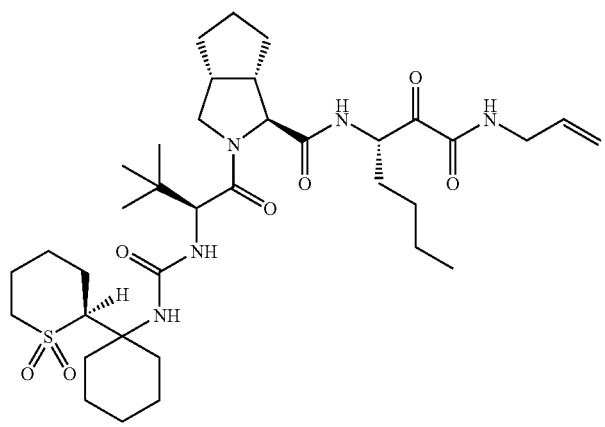
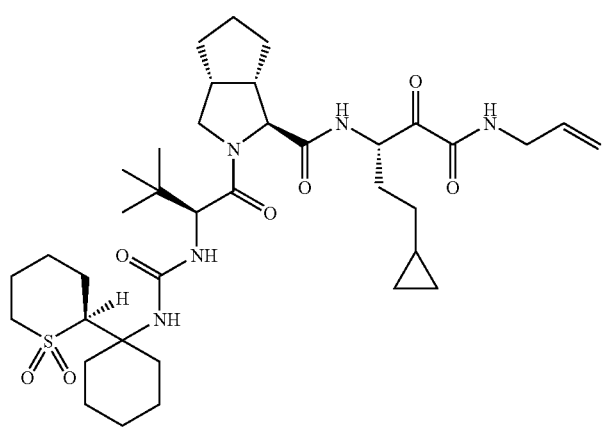

TABLE 1A-continued
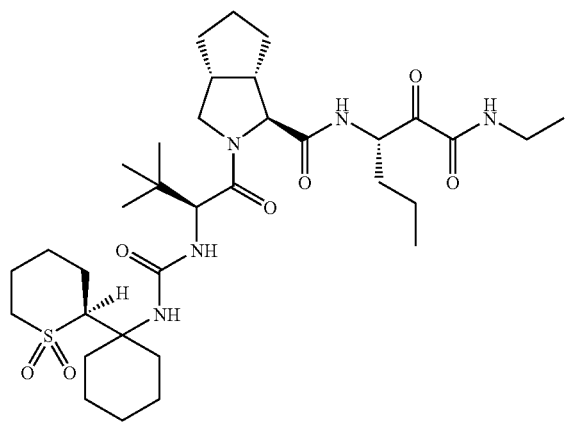
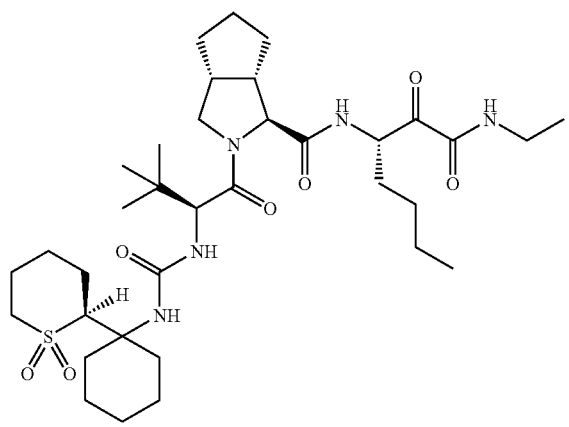
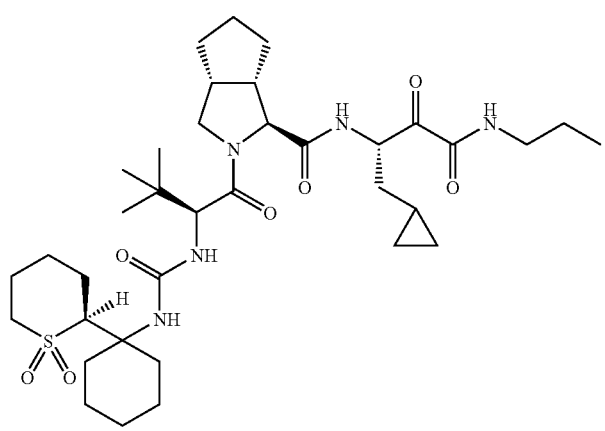

TABLE 1A-continued
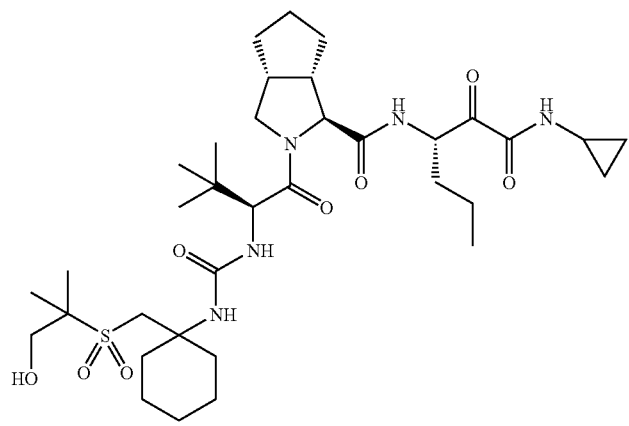
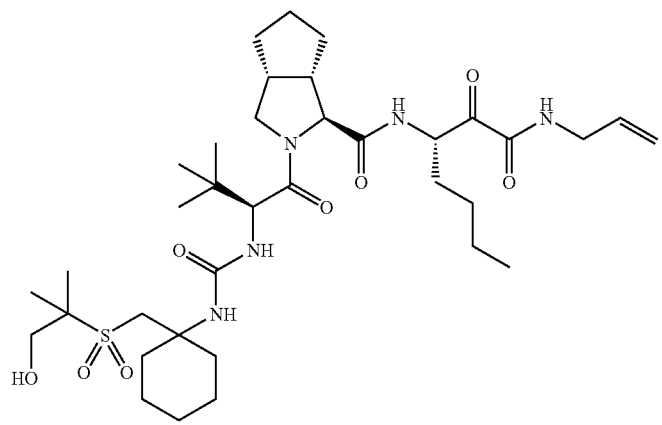
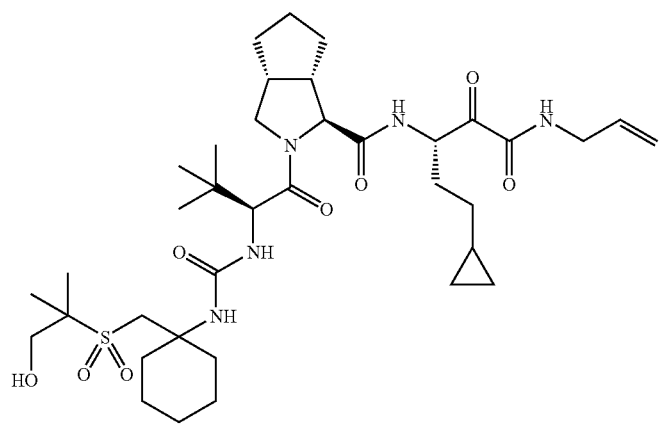

TABLE 1A-continued
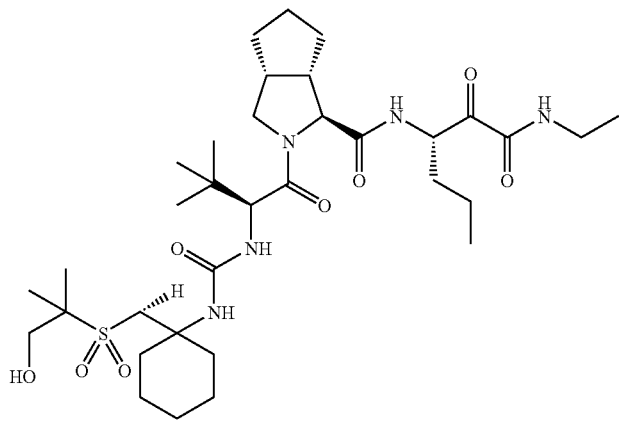
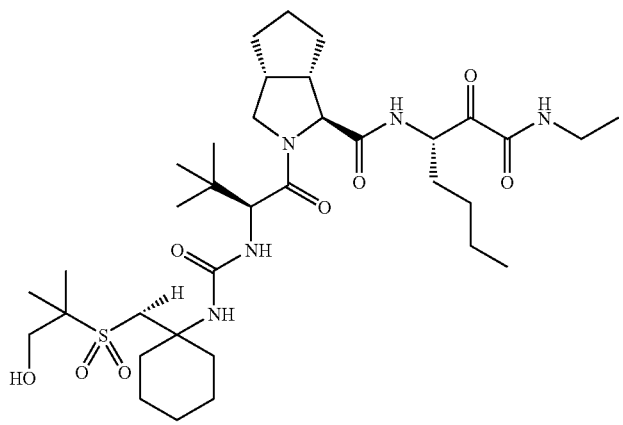
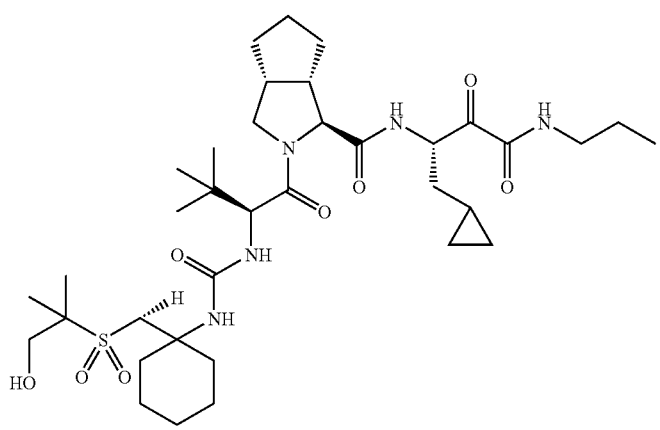

TABLE 1A-continued
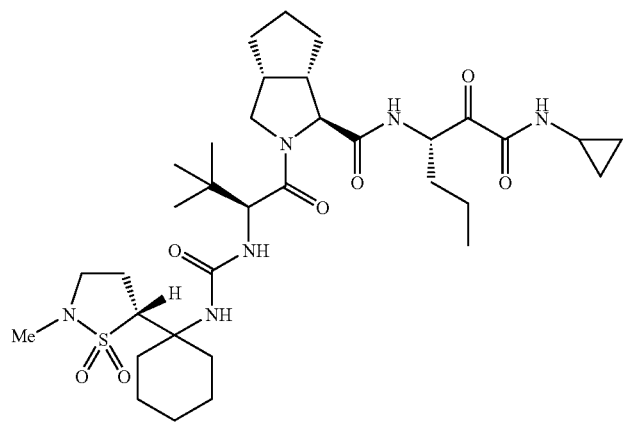
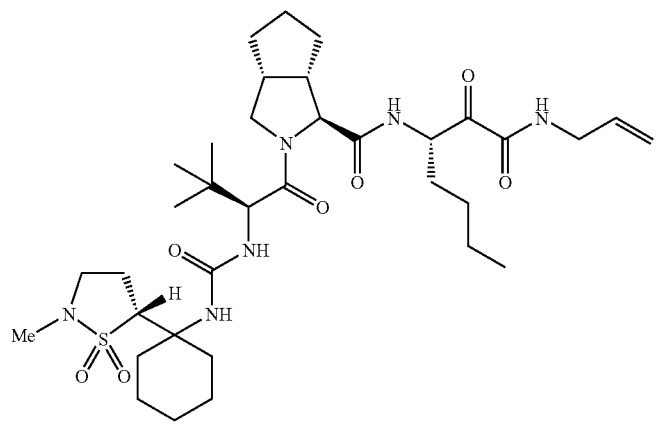
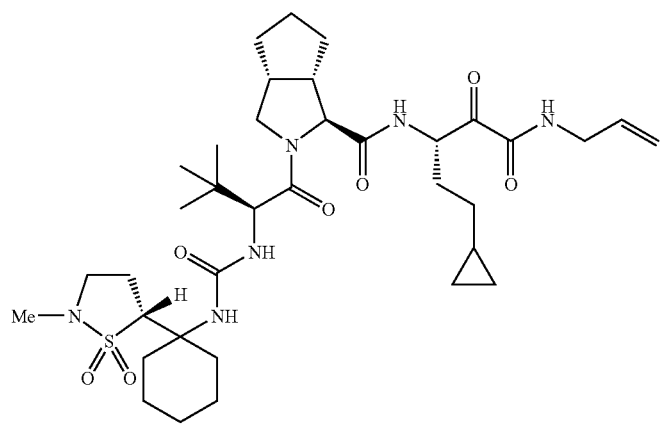

TABLE 1A-continued
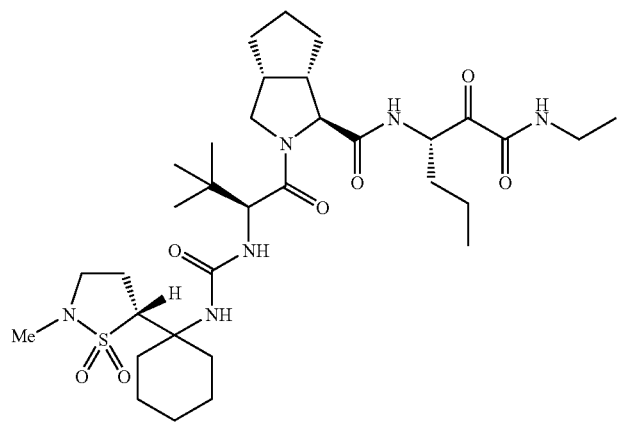
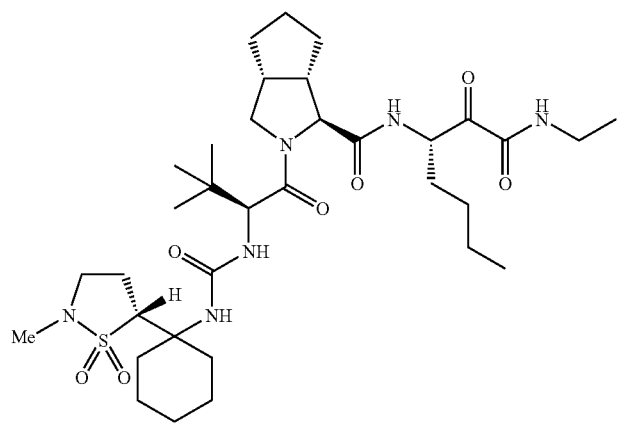
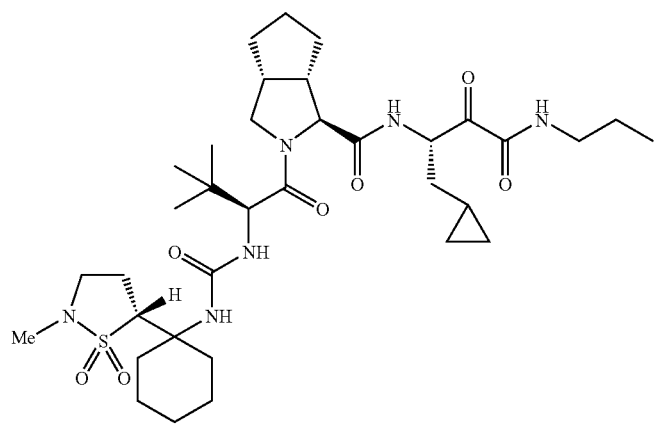

TABLE 1A-continued
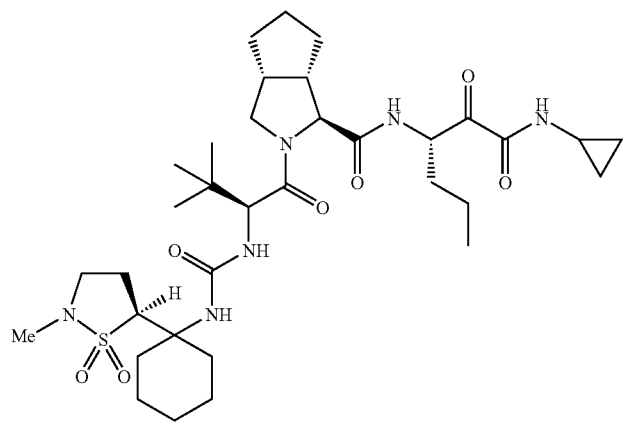
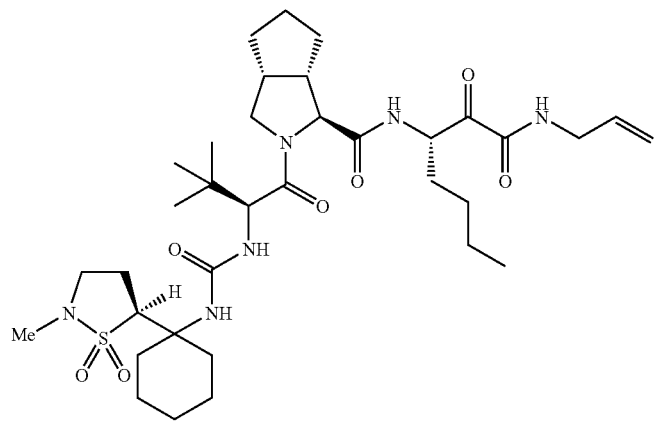
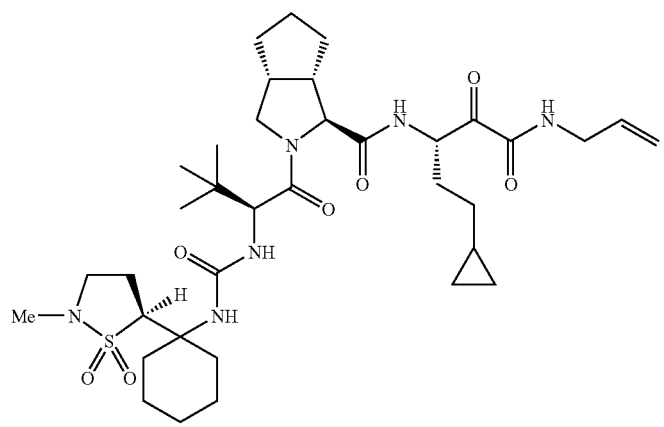

TABLE 1A-continued
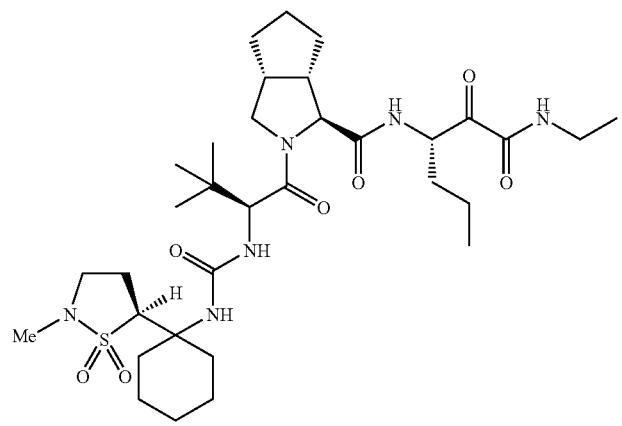
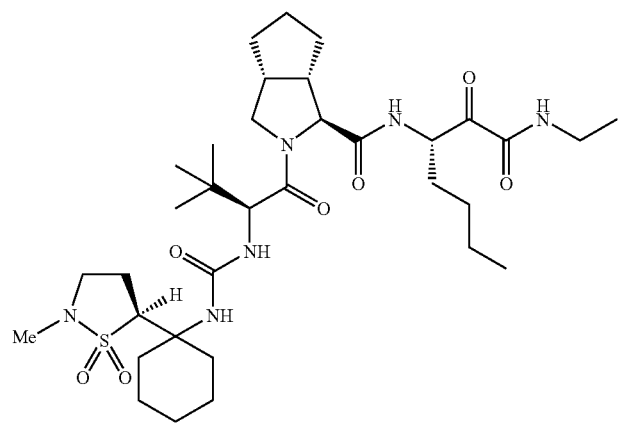
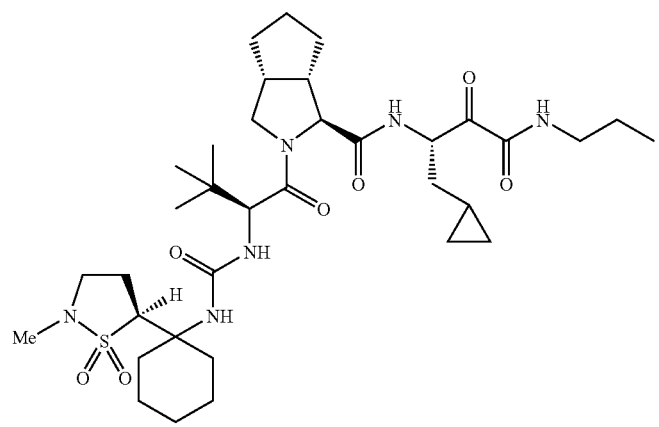

TABLE 1A-continued
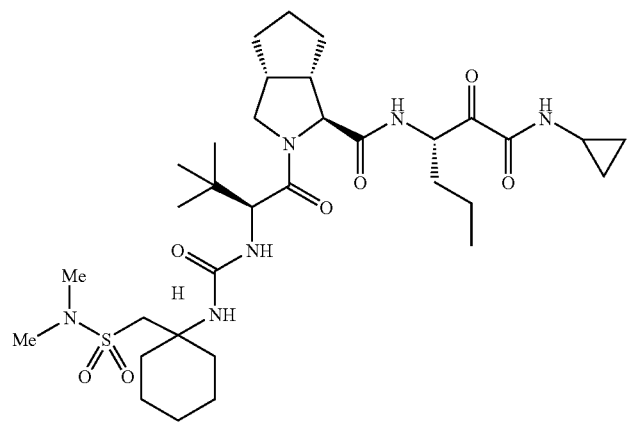
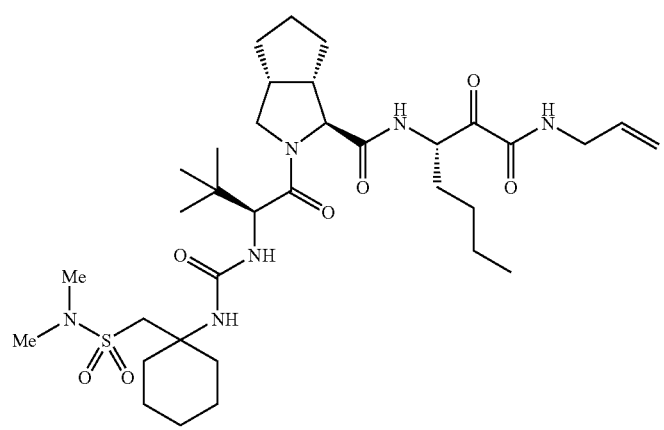
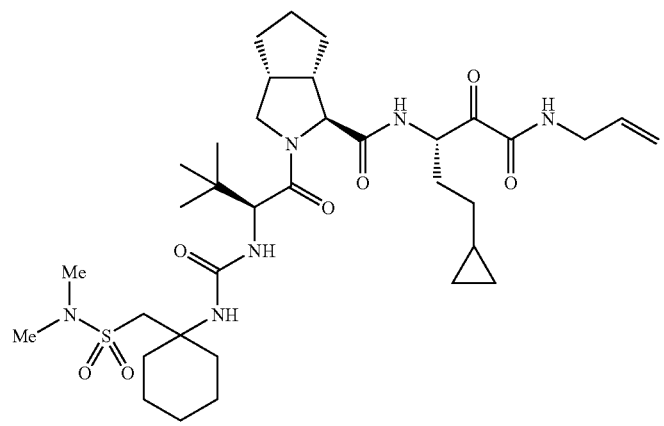

TABLE 1A-continued

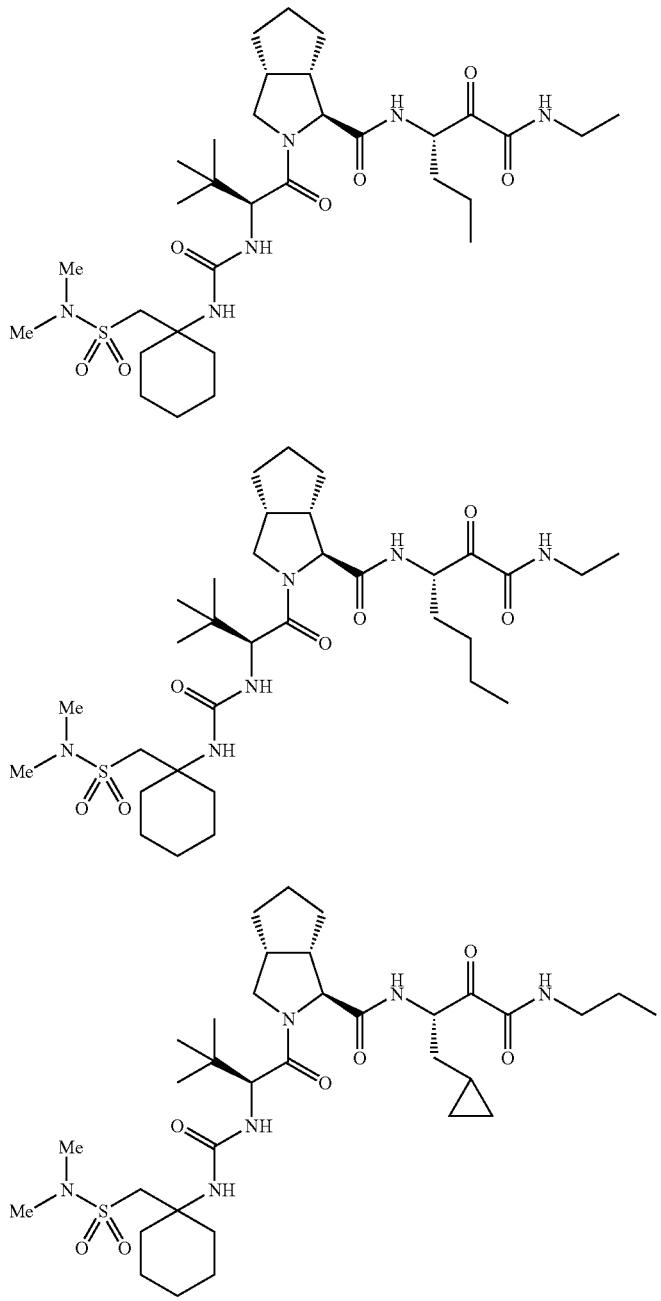

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofu razanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

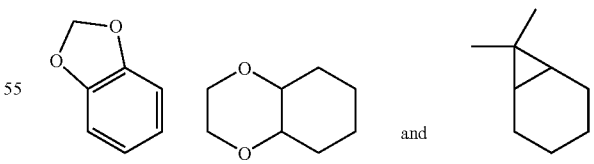

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

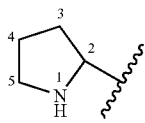

there is no —OH attached directly to carbons marked 2 and 5.

It should also be noted that tautomeric forms such as, for example, the moieties:

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "one or more" or "at least one", when indicating the number of substituents, compounds, combination agents and the like, refers to at least one, and up to the maximum number of chemically and physically permissible, substituents, compounds, combination agents and the like, that are present or added, depending on the context. Such techniques and knowledge are well known within the skills of the concerned artisan.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon or heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula 1, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula 1 can form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1)1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$) acyl glycerol.

Compounds of Formula 1, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

It is to be understood that the utility of the compounds of Formula 1 for the therapeutic applications discussed herein is applicable to each compound by itself or to the combination or combinations of one or more compounds of Formula 1 as illustrated, for example, in the next immediate paragraph. The same understanding also applies to pharmaceutical composition(s) comprising such compound or compounds and method(s) of treatment involving such compound or compounds.

The compounds according to the invention can have pharmacological properties; in particular, the compounds of Formula 1 can be inhibitors of HCV protease, each compound by itself or one or more compounds of Formula 1 can be combined with one or more compounds selected from within Formula 1. The compound(s) can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C.

The compounds of Formula 1 may be used for the manufacture of a medicament to treat disorders associated with the HCV protease, for example, the method comprising bringing into intimate contact a compound of Formula 1 and a pharmaceutically acceptable carrier.

In another embodiment, this invention provides pharmaceutical compositions comprising the inventive compound or compounds as an active ingredient. The pharmaceutical compositions generally additionally comprise at least one pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions.

As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing.

The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the inventive compounds or pharmaceutical compositions disclosed above for treatment of diseases such as, for example, hepatitis C and the like. The method comprises administering a therapeutically effective amount of the inventive compound or pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

ABBREVIATIONS

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin4(3H)-one EDCI: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyidienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)
LIHMDS: Lithium Hexamethyldisilazide or Lithium bis(trimethylsilylamide)
10% Pd/C: 10% Palladium on carbon (by weight).
TG: Thioglycerol

EXAMPLES

Synthesis of Intermediates:

Synthesis of Ethyl Ester 1a:

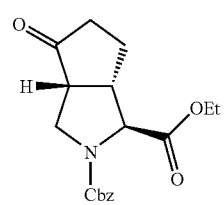

1a

The ethyl ester 1a was synthesized according to the procedure described by Monn and Valli (*J. Org. Chem.* 1994, 59, 2773-2778).

Synthesis of Intermediate 1:

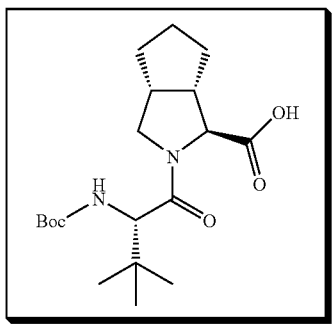

Step A

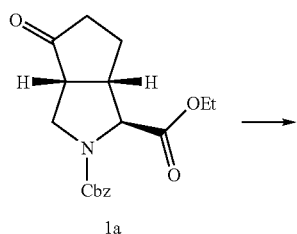
1a

Sodium borohydride (924.5 mg) was added in small portions to a heterogeneous mixture of bicyclic ketone 1a in ethanol (50 mL) at 0° C. Reaction was stirred for 30 min. and TLC analysis (ethyl acetate/hexanes; 1:1) showed that all the starting material had been consumed. The reaction was quenched by the addition of AcOH (3 mL). The mixture was diluted with 250 mL of ethyl acetate and washed with aqueous saturated solution of sodium bicarbonate (2×50 mL) and brine (1×40 mL). The organic layer was dried over magnesium sulfate, filtered, and concentrated under reduced pressure. The residue was purified by column chromatography to afford the product in 92% yield.

Step B

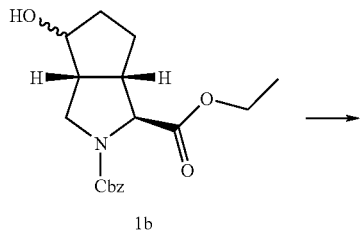
1b

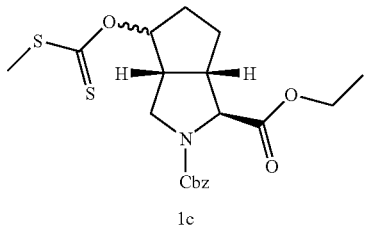
1c

A solution of cyclopentanol 1b in 130 mL of dry tetrahydrofuran at 0° C. was treated with 1.08 g of 60% suspension of NaH. The cooling bath was removed and the resulting yellow solution was stirred for 30 min. Carbon disulfide (16.2 mL) was added and reaction was stirred for 45 min. Then, iodomethane (16.8 mL) was added dropwise and the mixture was stirred for further 1 h. Reaction was quenched by careful addition of aqueous saturated ammonium chloride solution (30 mL). The mixture was extracted with 80 mL of ether and layers were separated. The aqueous layer was back extracted with ether (2×80 mL). The combined organic layers were washed with water (30 mL), brine (30 mL), dried over magnesium sulfate, and concentrated under reduced pressure. The residue was chromatographed on silica gel (gradient: hexane to 30% acetone in hexane) to afford the xanthate product as yellow oil in 63% yield.

Step C

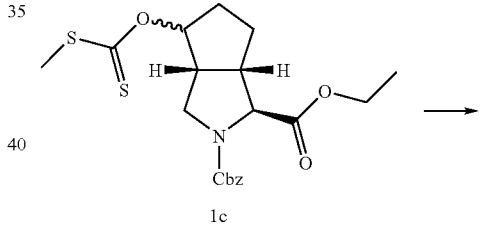
1c

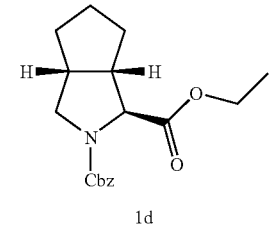
1d

A solution of xanthate 1c in 90 mL of toluene was degassed with dry nitrogen. AIBN (150.4 mg) and tri-n-butyltin hydride (3.7 mL) were added. The reaction mixture was degassed again and stirred at 95° C. for 1 h. TLC analysis (acetone/hexanes; 1:9) showed that all the starting material had been consumed. All the volatiles were removed under reduced pressure and the residue was dissolved in 250 mL of ether and washed with aqueous saturated potassium fluoride solution (2×30 mL). The organic layer was dried over magnesium sulfate, filtered, and concentrated under reduced pressure. The residue was purified by column chromatography on silica gel (gradient: hexanes to 20% ethyl acetate in hexanes) to give the product in 98% yield.

Step D

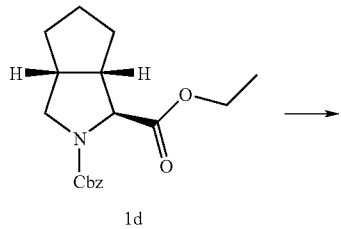
1d

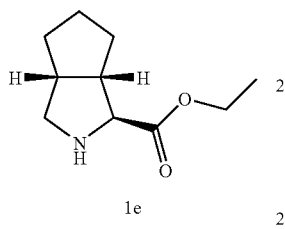
1e

The N-Cbz starting material 1d (2.5 g) was dissolved in 80 mL of trifluoroacetic acid at 0° C. followed by addition of 20 mL of dimethyl sulfide. The reaction mixture was stirred at 0° C. for 5 min and the cooling bath was removed. Reaction was stirred for further 5 h. All the volatiles were removed under reduced pressure and the residue was partitioned between dichloromethane (250 mL) and aqueous 1 N NaOH (50 mL). The aqueous layer was back extracted with dichloromethane (2×80 mL). The combined organic layers were dried over magnesium sulfate, filtered and concentrated. No further purification was done for the product (1.46 g, 97% yield).

Step E

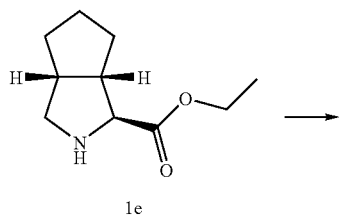
1e

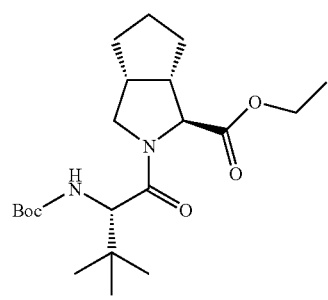
1f

+

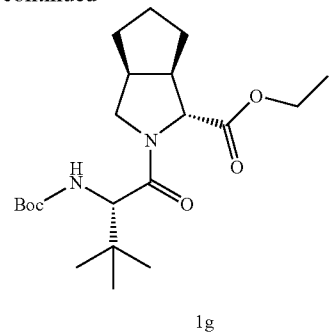
1g

A solution of N-Boc-t-butyl leucine (1.46 g) in 80 mL of dry dichloromethane and 60 mL of dry dimethyl formamide was stirred at 0° C. and treated with HATU (3.26 g). The racemic amine 1e (1.42 g) in dichloromethane (10 mL) was added dropwise followed by addition of N-methylmorpholine (2.7 mL). The mixture was gradually warmed to room temp and stirred overnight. All the volatiles were removed under reduced pressure (high vacuum) and the residue was dissolved in 350 mL of ethyl ether. The organic layer was washed with aqueous 1 N HCL (30 mL), aqueous saturated NaHCO$_3$ (30 mL), water (30 mL), and brine (30 mL). The organic layer was dried over magnesium sulfate and concentrated under reduced pressure. The residue was chromatographed on silica gel (gradient: ether/hexanes; 1:9 to 5:5) to afford the diastereomeric products 1f and 1g in 72% yield.

Step F

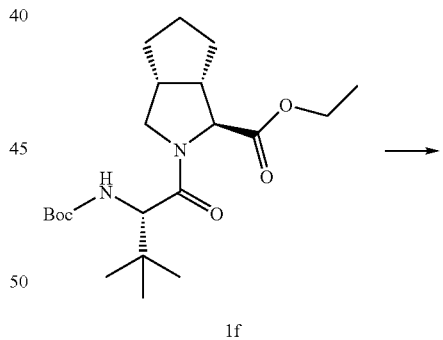
1f

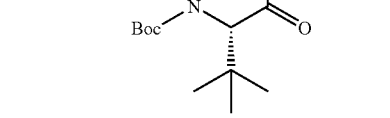
1

Lithium hydroxide monohydrate (79 mg) was added to a solution of 300 mg of ester 1f in 15 mL of a tetrahydrofuran/water/methanol (1:1:1) solution. The reaction was stirred at room temperature for about 3 h until no more starting material was detected by TLC analysis (ether/hexanes; 4:6). The mixture was concentrated under reduced pressure and the residue was partitioned between dichloromethane (100 mL) and aqueous 1 N HCl (20 mL). The aqueous layer was back extracted with dichloromethane (2×20 mL). The combined organic layers were dried over magnesium sulfate, filtered, and concentrated under reduced pressure. No further purification was done for the product 1 which was obtained as a white solid in 91% yield.

Synthesis of Intermediate 2:

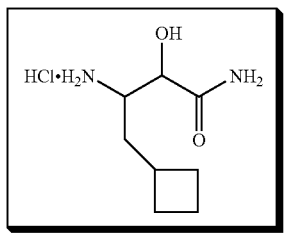

2

Step A

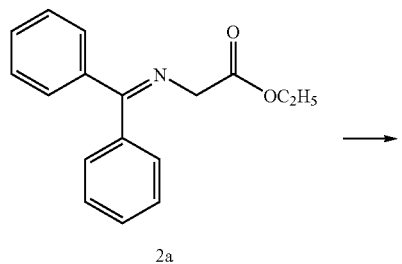

2a

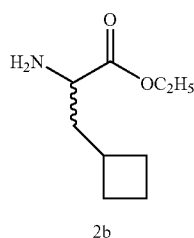

2b

A stirred solution of ketimine 2a (50 g, 187.1 mmol) under $N_2$ in dry THF (400 mL) was cooled to −78° C. and treated with 1 M solution of K-$^t$BuO (220 mL, 1.15 equiv.) in THF. The reaction mixture was warmed to 0° C. and stirred for 1 h and treated with bromomethyl cyclobutane (28 mL, 249 mmol). The reaction mixture was stirred at room temperature for 48 h and concentrated in vacuo. The residue was dissolved in $Et_2O$ (300 mL) and treated with aq. HCl (2 M, 300 mL) The resulting solution was stirred at room temperature for 5 h and extracted with $Et_2O$ (1 L). The aqueous layer was made basic to pH ~12-14 with NaOH (50% aq.) and extracted with $CH_2Cl_2$ (3×300 mL). The combined organic layers were dried ($MgSO_4$), filtered, and concentrated to give the pure amine (2b, 18 g) as a colorless oil.

Step B

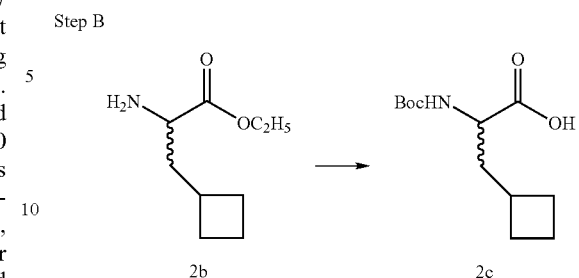

2b  2c

A solution of the amine 2b (18 g, 105.2 mmol) at 0° C. in $CH_2Cl_2$ (350 mL) was treated with di-tert-butyldicarbonate (23 g, 105.4 mmol) and stirred at rt. for 12 h. After the completion of the reaction (TLC), the reaction mixture was concentrated in vacuo and the residue was dissolved in $THF/H_2O$(200 ml, 1:1) and treated with $LiOH.H_2O$ (6.5 g, 158.5 mmol) and stirred at room temperature for 3 h. The reaction mixture was concentrated and the basic aqueous layer was extracted with $Et_2O$. The aqueous layer was acidified with conc. HCl to pH~1-2 and extracted with $CH_2Cl_2$. The combined organic layers were dried ($MgSO_4$), filtered, and concentrated in vacuo to yield 2c as a colorless viscous oil which was used for the next step without any further purification.

Step C

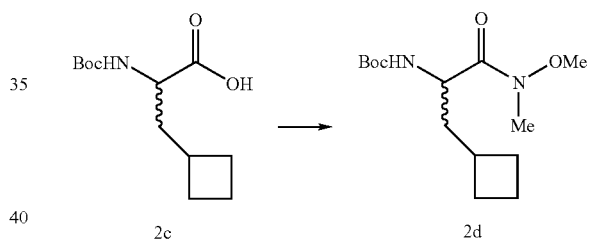

2c  2d

A solution of the acid 2c (15.0 g, 62 mmol) in $CH_2Cl_2$ (250 mL) was treated with BOP reagent (41.1 g, 93 mmol), N-methyl morpholine (27 mL), N,O-dimethyl hydroxylamine hydrochloride (9.07 g, 93 mmol) and stirred overnight at rt. The reaction mixture was diluted with 1 N aq. HCl (250 mL), and the layers were separated and the aqueous layer was extracted with $CH_2Cl_2$ (3×300 ml). The combined organic layers were dried ($MgSO_4$), filtered and concentrated in vacuo and purified by chromatography ($SiO_2$, EtOAc/Hex 2:3) to yield the amide 2d (15.0 g) as a colorless solid.

Step D

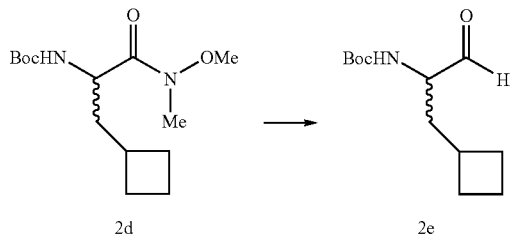

2d  2e

A solution of the amide 2d (15 g, 52.1 mmol) in dry THF (200 mL) was treated dropwise with a solution of LiAlH$_4$ (1M, 93 mL, 93 mmol) at 0° C. The reaction mixture was stirred at room temperature for 1 h and carefully quenched at 0° C. with a solution of KHSO$_4$ (10% aq.) and stirred for 0.5 h. The reaction mixture was diluted with aq. HCl (1 M, 150 mL) and extracted with CH$_2$Cl$_2$ (3×200 mL), The combined organic layers were washed with aq. HCl (1 M), saturated NaHCO$_3$, brine, and dried (MgSO$_4$). The mixture was filtered and concentrated in vacuo to yield 2e as a viscous colorless oil (14 g).

Step E

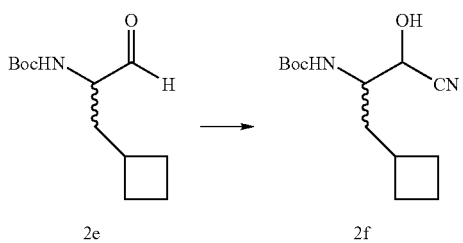

2e            2f

A solution of the aldehyde 2e (14 g, 61.6 mmol) in CH$_2$Cl$_2$ (50 mL), was treated with Et$_3$N (10.73 mL, 74.4 mmol), and acetone cyanohydrin (10.86 g, 127.57 mmol) and stirred at room temperature for 24 hrs. The reaction mixture was concentrated in vacuo and diluted with aq. HCl (1 M, 200 mL) and extracted into CH$_2$Cl$_2$ (3×200 mL). The combined organic layer were washed with H$_2$O, brine, dried (MgSO$_4$), filtered, concentrated in vacuo and purified by chromatography (SiO$_2$, EtOAc/Hex 1:4) to yield 2f (10.3 g) as a colorless liquid.

Step F

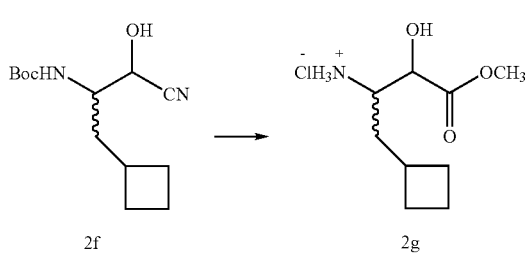

2f            2g

Methanol saturated with HCl*, prepared by bubbling HCl gas through CH$_3$OH (700 ml) at 0° C., was treated with the cyanohydrin 2f and heated to reflux for 24 h. The reaction was concentrated in vacuo to yield 2g, which was used in the next step without purification.

* Alternatively 6M HCl prepared by addition of AcCl to dry methanol can also be used.

Step G

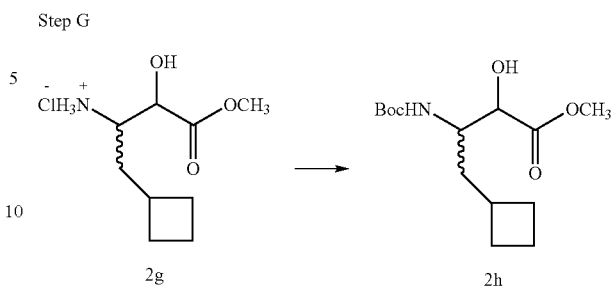

2g            2h

A solution of the amine hydrochloride 2g in CH$_2$C$_2$ (200 mL) was treated with Et$_3$N (45.0 mL, 315 mmol) and Boc$_2$O (45.7 g, 209 mmol) at −78° C. The reaction mixture was then stirred at room temperature overnight and diluted with HCl (2 M, 200 mL) and extracted into CH$_2$Cl$_2$. The combined organic layer were dried (MgSO$_4$) filtered, concentrated in vacuo and purified by chromatography (EtOAc/Hex 1:4) to yield hydroxy ester 2h.

Step H

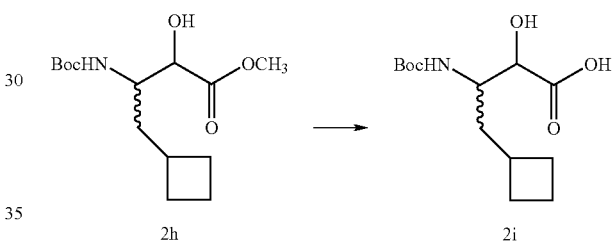

2h            2i

A solution of methyl ester 2h (3 g, 10.5 mmol ) in THF/H$_2$O (1:1) was treated with LiOH.H$_2$O (645 mg, 15.75 mmol) and stirred at rt. for 2 h. The reaction mixture was acidified with aq HCl (1 M, 15 mL) and concentrated in vacuo. The residue was dried in vacuum to afford 2i in quantitative yield.

Step I

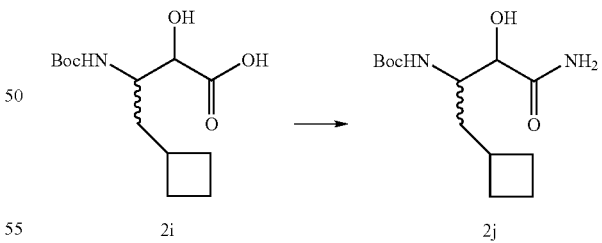

2i            2j

A solution of the acid 2i (from above) in CH$_2$Cl$_2$ (50 mL) and DMF (25 mL) was treated with NH$_4$Cl (2.94 g, 55.5 mmol), EDCl (3.15 g, 16.5 mmol), HOOBt (2.69 g, 16.5 mmol), and NMM (4.4 g, 44 mmol). The reaction mixture was stirred at room temperature for 3 d. The solvents were removed under vacuo and the residue was diluted with aq. HCl (250 mL) and extracted with CH$_2$Cl$_2$. The combined organic layers were washed with aq. Sat'd. NaHCO$_3$, dried (MgSO$_4$) filtered concentrated in vacuo to obtain 2j, which was used as it was in the following steps. (Alternatively 2j can also be obtained directly by the reaction of 2f (4.5 g, 17.7 mmol) with aq. H₂O₂ (10 mL), LiOH.H₂O (820 mg, 20.8 mmol) at 0° C. in 50 mL of CH₃OH for 0.5 h).

Step J

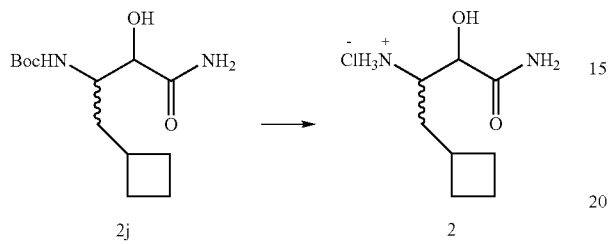

2j → 2

A solution of 2j obtained in the previous step was dissolved in 4N HCl in dioxane and stirred at rt. for 2 h. The reaction mixture was concentrated in vacuo to give the intermediate 2 as a solid, which was used without further purification.

Synthesis of Intermediate 3:

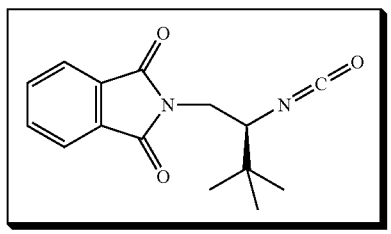

3

Step A

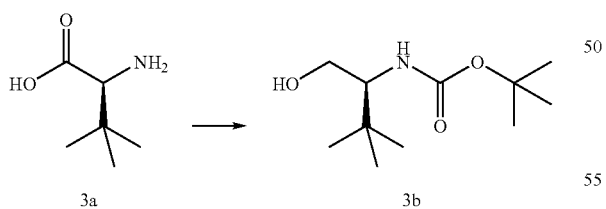

3a → 3b

L-tert-Leucine (1 eq, 10 g) was slowly added to a suspension of lithium aluminum hydride (150 mmol, 1M solution in THF). The reaction mixture was refluxed for 6 h. The mixture was cooled to 0° C. and quenched by addition of 10 mL of aqueous 10% NaOH and 10 mL of water. The mixture was stirred at room temperature for 10 minutes and then treated with di-tert-butylcarbonate (1.1 eq, 18.22 g) and the mixture was stirred at 60° C. overnight. The reaction mixture was filtered through magnesium sulfate. The filtrate was concentrated and the residue was chromatographed on silica gel to give the product 3b in 62% yield.

Step B

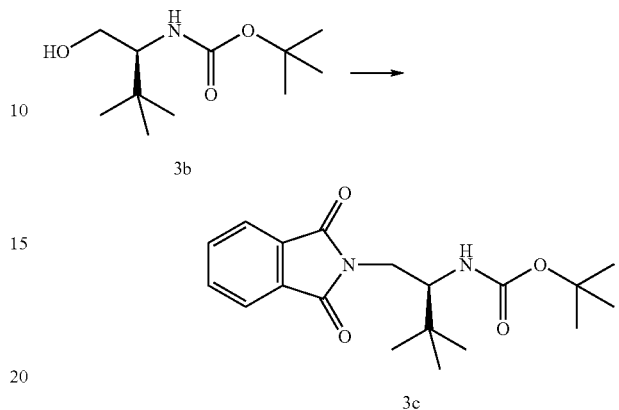

3b → 3c

To a solution of phthalimide (1.01 g) in 50 mL of dry THF was added triphenylphosphine (3 eq) and alcohol 3b (1 eq). The mixture was cooled in an ice-water bath and diisopropyl azodicarboxylate (2.5 eq) was added dropwise. The resulting mixture was stirred at 0° C. for 10 min and warmed to room temp and stirred for approximately 2.5 h until no more starting material was detected by TLC (ethyl acetate/hexanes; 3:7). The mixture was concentrated under reduced pressure. The residue was resuspended in 80 mL of dichloromethane. The solids were filtered off. The filtrate was concentrated to half its volume and hexanes (30 mL) were added. The solids were filtered off. The filtrate was concentrated under reduced pressure and the residue was chromatographed on silica gel (gradient: ethyl acetate/hexanes; 1:9 to 4:6) to give the product 3c.

Step C

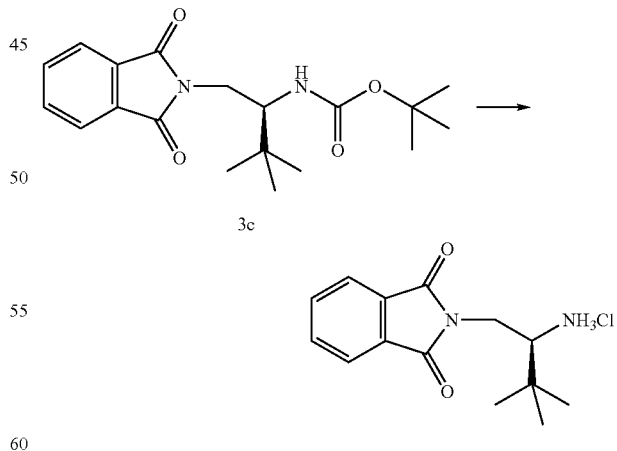

3c → 3d

The N-Boc protected amine 3c (1.4 g) was dissolved in 20 mL of 4M HCl solution in dioxane. The mixture was stirred for about 2 h. All the volatiles were removed under vacuum. No further purification was done for the product 3d.

Step D

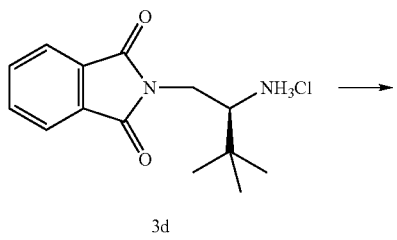

3d

A mixture of amine hydrochloride 3d (1.14 g) in 20 mL of dichloromethane and 20 mL of aqueous saturated NaHCO3 solution at 0° C. was treated with phosgene (10 mL, 15% solution in toluene) and stirred for 2 h. The reaction mixture was diluted with 100 mL of dichloromethane and washed with 30 mL of cold aqueous saturated NaHCO3 solution. The organic layer was dried over magnesium sulfate, filtered, and further diluted with 10 mL of toluene. The mixture was concentrated and the product 3 was kept as a 0.2M solution in toluene.

Synthesis of Intermediate 4:

4

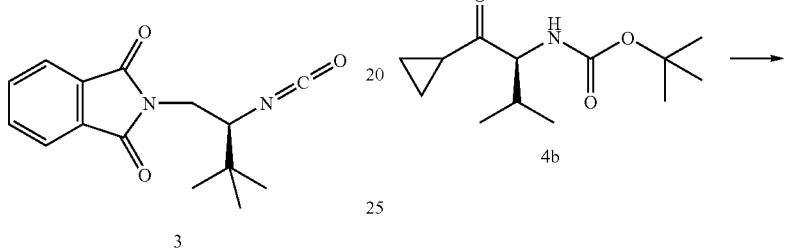

Step A

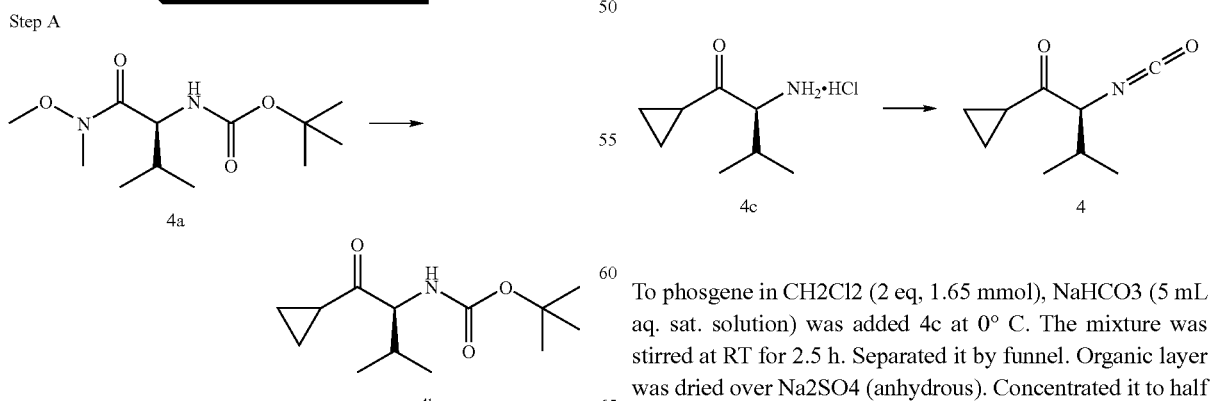

To amide 4a (0.5 g, 1 eq) in THF was added cyclopropylmagnesium bromide (4 eq, 7.68 mmol) at 0° C. The reaction was warmed up to RT after 15 min and the reaction was stirred at RT for 5 hrs, then it was quenched by the addition of 1 N HCl. Reaction was diluted with EtOAc and washed with brine. The organic layer was dried over MgSO4, purified by column chromatography with 10% EtOAc in hexane to get 0.2 g of product 4b. Yield 43.1%.

Step B

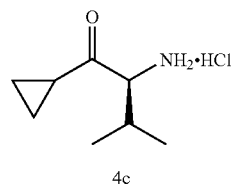

To N-Boc protected amine 4b (0.2 g) was added 4M HCl (in Dioxane). The reaction was stirred at RT for 50 min which TLC indicated the reaction had been completed. The mixture was concentrated to dryness to get 0.162 g of product 4c.

Step C

To phosgene in CH2Cl2 (2 eq, 1.65 mmol), NaHCO3 (5 mL aq. sat. solution) was added 4c at 0° C. The mixture was stirred at RT for 2.5 h. Separated it by funnel. Organic layer was dried over Na2SO4 (anhydrous). Concentrated it to half volume with cooling bath. Diluted it to 10 mL to get desired isocyanate 4 as a 0.083M solution in dichloromethane.

Synthesis of Intermediate 5:

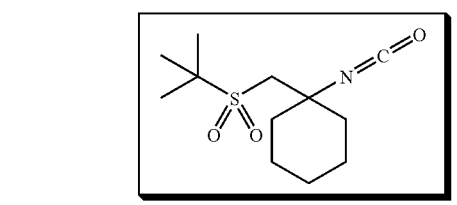

Step A

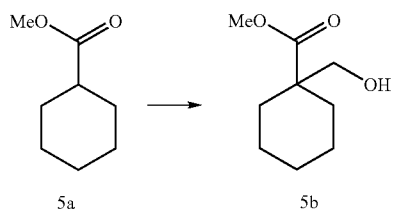

KHMDS (200ml of a 0.5M solution in toluene) was added, dropwise to a stirred solution of Methyl cyclohexanecarboxylate 5a (11.1 g; 78 mmol) in anhydrous THF (200 ml), at −78° C. under an atmosphere of nitrogen. When the addition was complete the reaction was maintained at this temperature for a further 0.5 h. before the addition of Benzyl chloromethyl ether (18.6 ml; 134 mmol). The reaction was allowed to warm to room temperature overnight and water (100 ml) was added. Aqueous work-up provided a residue which was purified by silica gel column chromatography using EtOAc; hexanes (1:10) as eluent to give the desired, impure, intermediate ether (14.98 g) as a colorless oil.

A black suspension of 10% Pd/C (0.5 g) and the aforementioned crude ether (4.1 g) in MeOH (80 ml) was exposed to an atmosphere of nitrogen (balloon) at room temp., overnight. The reaction was filtered through a pad of celite and the solid was washed thoroughly with methanol. The combined filtrate was concentrated under reduced pressure and the crude product was purified by silica gel column chromatography using EtOAc; hexanes (1:5) to give the primary alcohol (5b; 0.62 g), a colorless oil.

Step B

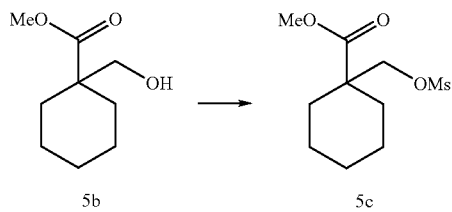

Methanesulfonyl Chloride (0.31 ml) followed by triethylamine (0.75 ml) were added to a stirred solution of the primary alcohol (5b; 0.62 g) at 0° C., under an atmosphere of nitrogen. The resulting mixture was stirred at this temperature for 0.5 h. The reaction mixture was extracted into EtOAc and washed with 1M HCl, sat. aq. NaHCO3, water, dried (MgSO4) and concentrated. The residue (mesylate 5c; 0.74 g), was obtained as a yellow oil, which was used in subsequent steps without purification.

Step C

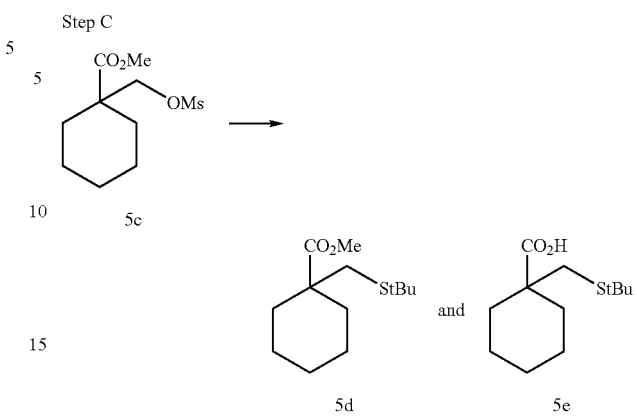

Dimethylformamide (20 ml; anhydrous; Aldrich) was added to sodium hydride (0.56 g; Aldrich) and tert-butyl mercaptan was added to the suspension while cooled in an ice bath under an atmosphere of nitrogen. Once the addition was complete the mesylate (5c; prepared as above from 2.00 g of alcohol; 5b) was added and the resulting mixture was stirred overnight at room temperature. The reaction was partitioned between EtOAc and water and the organic phase was separated, dried (MgSO4). Column chromatography on silica gel using EtOAc-Hexanes (2:98) provided the methyl ester-sulfide (5d; 1.75 g). EtOAc was added to the aqueous phase and 10% aq. HCl was added until the water layer pH=1. The organic layer was separated, washed with water, dried and concentrated under reduced pressure to give the sulfide-carboxylic acid (5e; 0.747 g) as a white solid.

Step D

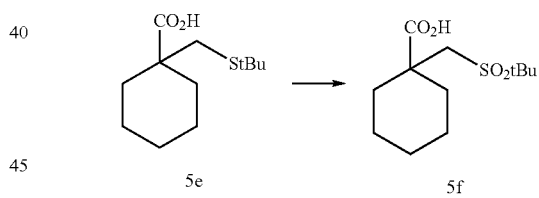

To the sulfide (5e; 2.287 g) in methanol (75 ml) was added a solution of oxone (18.00 g; Aldrich) and the resulting white suspension was stirred overnight at room temperature. The volatiles were removed under reduced pressure and the white solid partitioned between EtOAc and water. The organic phase was separated, dried and concentrated to provide the sulfone (5f; 2.52 g; contains some solvent).

Step E

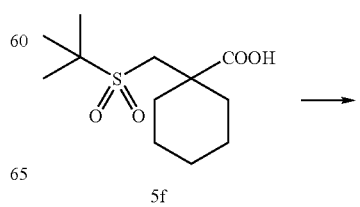

-continued

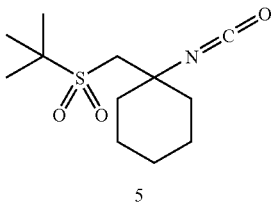

5

A solution of acid 5f (1.61 g) in 50 mL of toluene was treated with DPPA (1 eq, 1.33 mL, d 1.270) and triethylamine (1 eq, 0.85 mL, d 0.726). The mixture was heated to 100° C. for 2 h. The reaction mixture was diluted with aq sat NaHCO3 and extracted with dichloromethane (2×100 mL). The combined organic layers were washed with aq sat NaHCO3 and brine. The organic layer was dried over MgSO4, filtered and concentrated under reduced pressure until approximately 20 mL of solvent were left. The solution of the product 5 was adjusted to 0.2M concentration of isocyanate using toluene.

Synthesis of Intermediate 6:

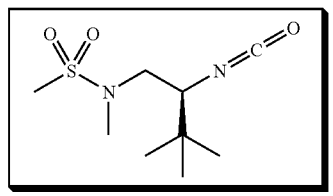

6

Step A

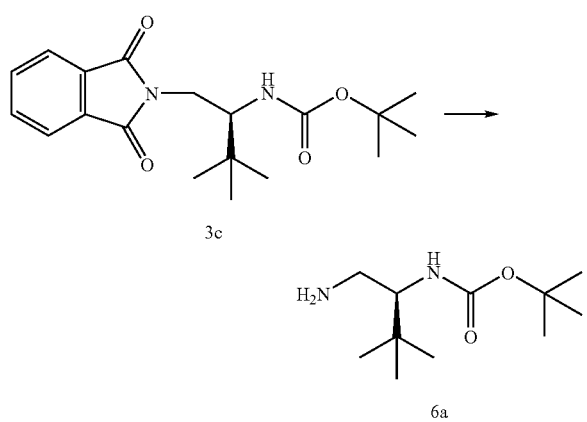

3c

6a

To a solution of phthalimide 3c (7 g) in 100 mL of MeOH was added hydrazine (0.9 mL, 28.68 mmol, 1.4 eq) and the mixture was refluxed (under N2) for 6 h. TLC showed some starting material present and more hydrazine was added (0.45 mL) and stirring was continued at room temperature overnight. A white precipitate was formed. The solids were filtered off and the filtrate was concentrated to yield the product 6a (4.48 g) as a white solid.

Step B

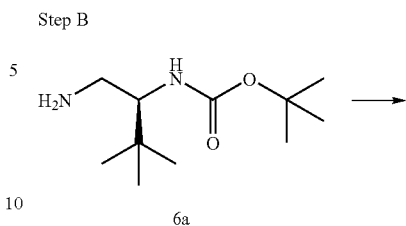

6a

6b

A solution of amine 6a (2.16 g, 10 mmol) in 100 mL of dichloromethane was cooled to 0° C. and treated with triethylamine (2 eq, 2.8 mL). Methanesulfonyl chloride (1.2 eq, 0.93 mL) was added dropwise. The heterogeneous mixture was stirred overnight (temp 0 to 25° C.). The solids were filtered off and the filtrate was washed with aqueous saturated ammonium chloride solution (100 mL), and brine (100 mL). The organic layer was dried over sodium sulfate, filtered and concentrated. The residue was taken in minimum amount of dichloromethane/ethyl acetate (approx 10 mL) and the insoluble white solid was filtered off. The filtrate was purified by column chromatography on silica gel to give the product 6b (2.7 g) as a thick semisolid.

Step C

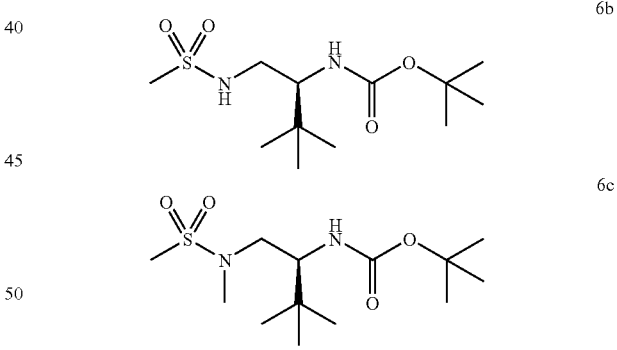

6b

6c

A solution of sulfonamide 6b (2.2 g, 7.5 mmol) in 50 mL of dry DMF was cooled to 0° C. and treated with cesium carbonate (3 eq, 7.34 g). Iodomethane (5 eq, 2.34 mL) was added dropwise and the mixture was stirred for 45 min. The cooling bath was removed and the mixture was stirred for further 4 h. The reaction was quenched by addition of aqueous saturated ammonium chloride solution (100 mL) and extracted with ethyl acetate (2×100 mL). The combined organic layers were washed with water (200 mL), brine (200 mL) and dried over sodium sulfate. The organic layer was filtered and concentrated. The residue was chromatographed on silica gel to afford the product 6c (2.16 g).

Step D

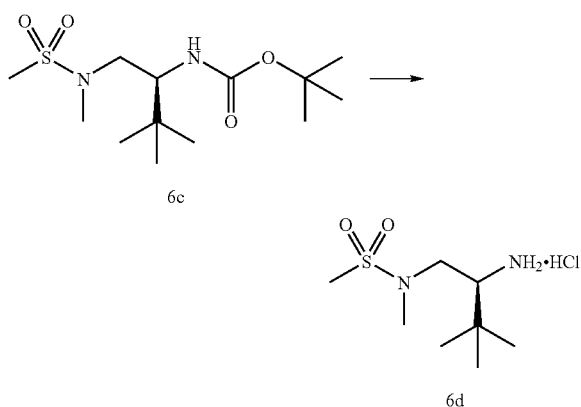

The N-Boc protected amine 6c (2.1 g, 6.82 mmol) was dissolved in 20 mL of 4M HCl in dioxane at room temperature. The reaction mixture was stirred for 1 h and then all the volatiles were removed under reduced pressure to afford the product 6d in quantitative yield.

Step E

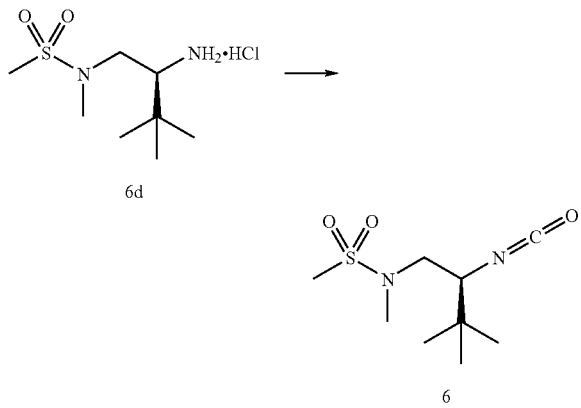

A mixture of amine hydrochloride 6d in dichloromethane and aqueous saturated NaHCO3 solution at 0° C. was treated with phosgene (15% solution in toluene) and stirred for 2 h. The reaction mixture was diluted with dichloromethane and washed with cold aqueous saturated NaHCO3 solution. The organic layer was dried over magnesium sulfate, filtered, and further diluted with toluene. The mixture was concentrated and the product 6 was adjusted and kept as a 0.2M solution in toluene.

Synthesis of Intermediate 7:

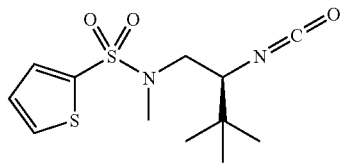

The isocyanate 7 was prepared according to the procedure described for isocyanate 6. 2-Thiophenesulfonyl chloride was used instead of methanesulfonyl chloride in the sulfonamide synthesis step.

Synthesis of Intermediate 8:

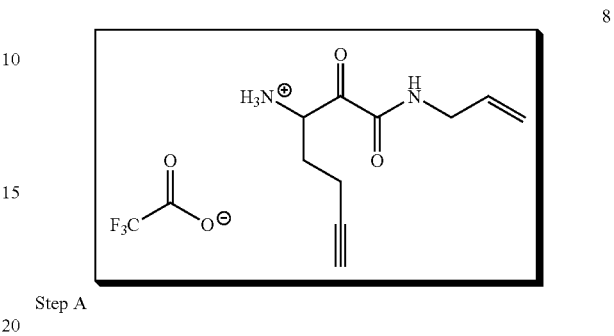

Step A

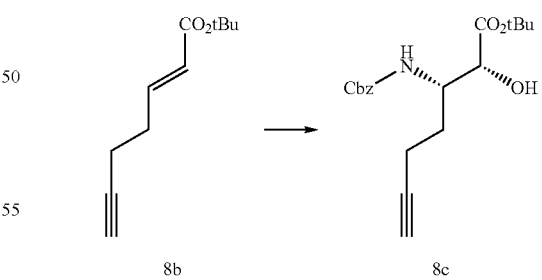

To a solution of 4-pentyn-1-ol, 8a (4.15 g; Aldrich) was added Dess-Martin periodinane (30.25 g; Aldrich) and the resulting mixture was stirred for 45 min. before the addition of (tert-Butoxycarbonylmethylene)triphenylphosphorane (26.75 g; Aldrich). The resulting dark reaction was stirred overnight, diluted with ethyl acetate), washed with aqueous sodium sulfite, saturated aqueous sodium bicarbonate, water, brine and dried. The volatiles were removed under reduced pressure and the residue was purified by silica gel column chromatography using 1% ethyl acetate in hexanes as eluent to give the desired compound 8b (3.92 g). Some impure fractions were also obtained but set aside at this time.

Step B

Using the alkene 8b (1.9 g) in n-propanol (20 mL; Aldrich)), benzyl carbamate (4.95 g; Aldrich) in n-propanol (40 mL), NaOH (1.29 g) in water (79 ml), tert-butyl hypochlorite (3.7 ml), (DHQ)2PHAL (0.423 g; Aldrich)) in n-propanol (37.5 ml), and potassium osmate:dehydrate (0.1544 g; Aldrich) and the procedure set forth in *Angew. Chem. Int. Ed. Engl* (1998), 35, (23/24), pp. 2813-7 gave a crude product which was purified by silica gel column chromatography using EtOAc:Hexanes (1:5) to give the desired amino alcohol 8c (1.37 g, 37%) as a white solid.

Step C

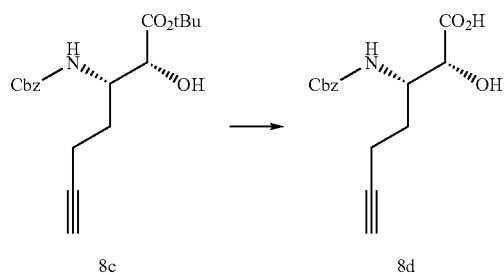

To the ester 8c (0.700 g) was added 4M HCl in dioxane (20 ml; Aldrich) and the resulting mixture was allowed to stand at room temperature overnight. The volatiles were removed under reduced pressure to give the acid 8d (0.621 g) as a white solid.

Step D

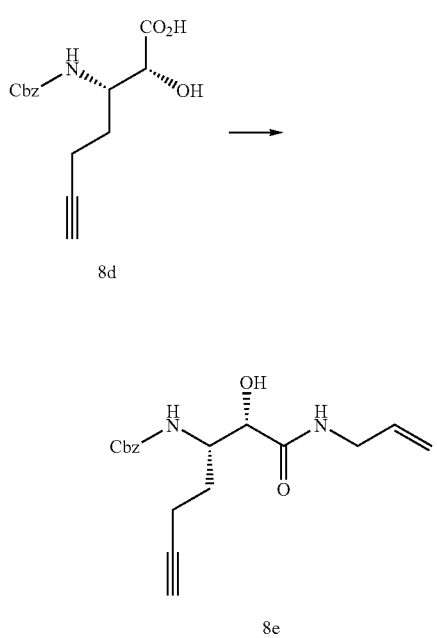

BOP reagent (3.65 g; Sigma) followed by triethylamine (3.45 ml) were added to a dichloromethane (20 ml) solution of the carboxylic acid 8d (2.00 g) and allyl amine (0.616 ml) at room temperature and the resulting mixture was stirred overnight. The reaction mixture was partitioned between EtOAc and 10% aqueous HCl. The organic phase was separated, washed with saturated aqueous sodium bicarbonate, water, dried (magnesium sulfate). The crude reaction product was purified by silica gel column chromatography using (EtOAc:Hexanes; 70:30) as eluent to provide the desired amide 8e (1.73 g) as a viscous yellow oil.

Step E

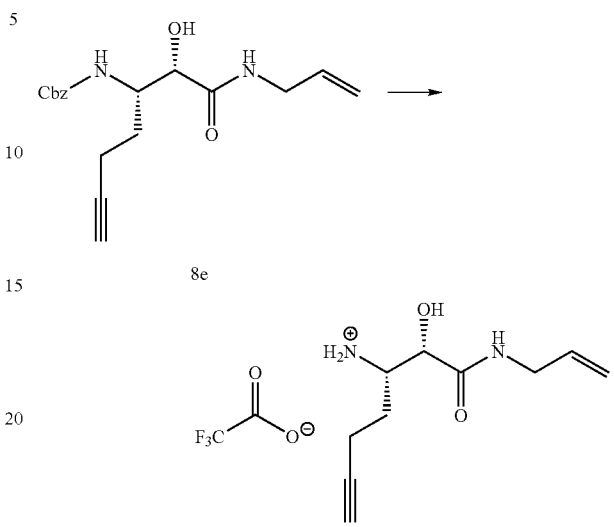

A solution of N-Cbz amine 8e (85.8 mg) in 5 mL of a 4:1 mixture of trifluoroacetic acid/methyl sulfide was stirred at room temperature for about 3 h. All the volatiles were removed under reduced pressure. The product 8 was placed under high vacuum for about 3 h and used without further purification.

Synthesis of Intermediate 9:

Step 1

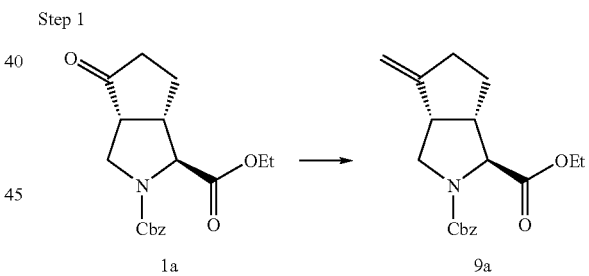

To a solution of 1a (13.24 g, 40 mmol, prepared as described by Monn and Valli, *J. Org. Chem.*, 1994, 59, 2773-2778) in THF (200 mL) was added zinc dust (21 g, 320 mmol), zirconecene dichloride (14.04 g, 48 mmol) and finally dibromomethane (6.18 mL, 44 mmol) dropwise. The reaction mixture was heated to reflux for 5 hr. Then it was cooled to room temperature and then to 0° C. using an ice bath. Water was added dropwise (caution: exothermic) till gas evolution ceased. The diethyl ether (400 mL) was added and the mixture was filtered through a pad of celite. The filter cake was rinsed with ether (200 mL) and the combined filtrate was washed with water (2×500 mL), aq. 1 N HCl (500 mL), water (500 mL), brine (500 mL), dried (Na$_2$SO$_4$), filtered and concentrated. The crude material was purified by flash chromatography using 10/90 to 20/80 of EtOAc/hexanes which afforded 6.82 g of 9a as a pale yellow oil.

Step 2

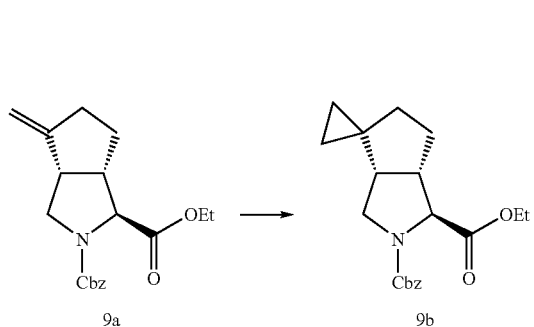

Diethyl zinc (1M in heptanes, 73 mL, 73 mmol) was added to dichloromethane (100 mL) at 0° C. under nitrogen atmosphere. Trifluoroacetic acid (5.6 mL, 73 mmol) was added dropwise over 30 min. Maintained the temperature for additional 15-20 min. Diiodomethane (5.9 mL, 73 mmol) was then added dropwise over 20 min and temperature was maintained for additional 15-20 min. Finally a solution of 9a (4.8 g, 14.6 mmol) was added in dichloromethane (20 mL) was added dropwise. The reaction mixture was warmed to room temperature over 16 hr. Then the reaction mixture was cooled to 0° C. and quenched by slow addition of saturated ammonium chloride solution (200 mL). The aqueous layer was separated and extracted with dichloromethane (125 mL). The combined organic layer was washed with saturated sodium bicarbonate, brine, dried ($Na_2SO_4$), filtered and concentrated. The crude material was purified by flash chromatography using 15/85 of EtOAc/hexanes which afforded 2.89 g of 9b.

Step 3

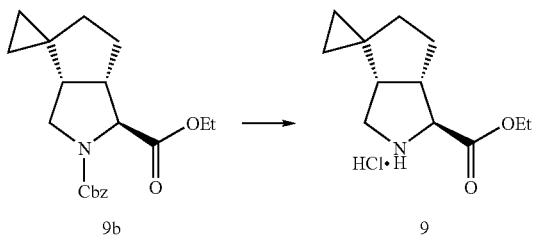

To a well-stirred solution of 9b (2.41 g, 7.03 mmol) in ethanol (100 mL) was added 4M HCl in dioxane (2 mL) and catalytic amount of 10% palladium on carbon. The mixture was hydrogenated using a balloon filled with hydrogen gas at room temperature for 5 hr. At this time another portion of the catalyst was added and the mixture was hydrogenated over 16 hr. The reaction was stopped, filtered through a pad of celite, rinsed with ethanol, and the filtrate was concentrated to afford 1.74 g of 9, which was used without further purification.

Synthesis of Intermediate 10

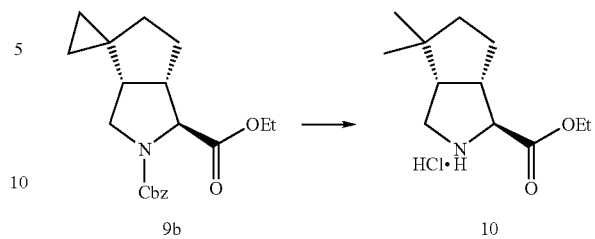

Compound 9b will be converted to the required material 10 using the above hydrogenation procedure (Step 3) using Platinum (IV) oxide instead of 10% palladium on carbon.

Synthesis of:

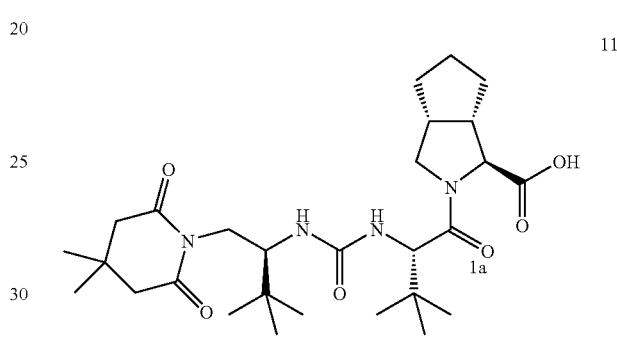

Step A

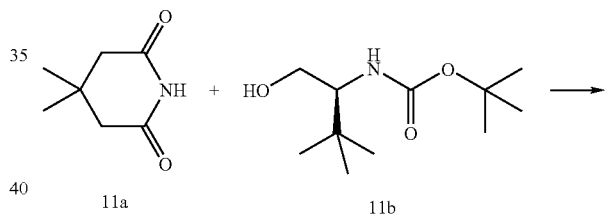

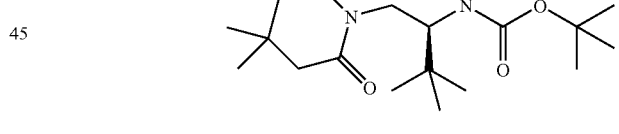

A solution of 4,4-dimethylglutarimide 11a (1.5 eq, 4.86 g, Aldrich) in 200 mL of dry THF was cooled to 0° C. and treated with triphenylphosphine (3 eq, 18.07 g) and S-Boc-tert-butylglycinol 11b (5 g, Aldrich). Diisopropylazodicarboxylate (2.5 eq, 11.3 mL, d 1.027) was added dropwise and the resulting solution was stirred at 0° C. After 10 min, the mixture became a slurry and stirring was continued overnight (0 to 25° C.). The mixture was concentrated under reduced pressure and the residue was dissolved in 80 mL of ether. Hexanes (100 mL) was added and the precipitated solids were filtered off. The filtrate was concentrated to half its volume and hexanes (100 mL) was added again. The solids were filtered off. The filtrate was concentrated under reduced pressure. The residue was chromatographed on silica gel (ethyl acetate/hexanes; 2:8) to afford the product 11c (4.0 g; 51%) as a white solid.

Step B

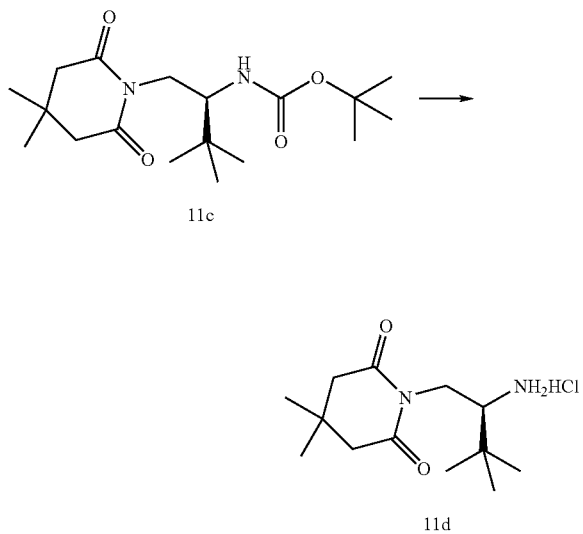

The N-Boc protected amine 11c (3 g) was dissolved in 50 mL of 4M HCl solution in dioxanes. The reaction mixture was stirred for about 1 h until all the starting material had been consumed as determined by TLC analysis (ethyl acetate/hexanes; 2:8). All the volatiles were removed under reduced pressure to afford the product 11d (2.4 g; 98%) as a white solid.

Step C

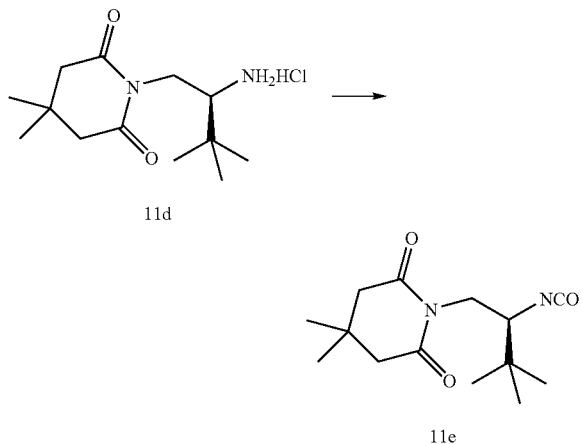

A solution of amine hydrochloride 11d (1.0 g) in 40 mL of dichloromethane was treated with 40 mL of aqueous saturated sodium bicarbonate solution and stirred vigorously for 10 min at 0° C. Stirring was stopped and layers were allowed to separate. Phosgene (10 mL of 20% soln in toluene) was added through a needle to the organic layer (lower layer) in one portion. The mixture was vigorously stirred immediately after addition for 10 min at 0° C. and further stirred at room temp for 2.5 h. The mixture was diluted with 100 mL of dichloromethane and layers were separated. The organic layer was washed with 30 mL of cold aqueous saturated sodium bicarbonate solution and dried over magnesium sulfate. The organic layer was filtered and the filtrate was diluted with 50 mL of toluene. The resulting solution was concentrated and the product 11e was kept as a 0.241M solution.

Step D

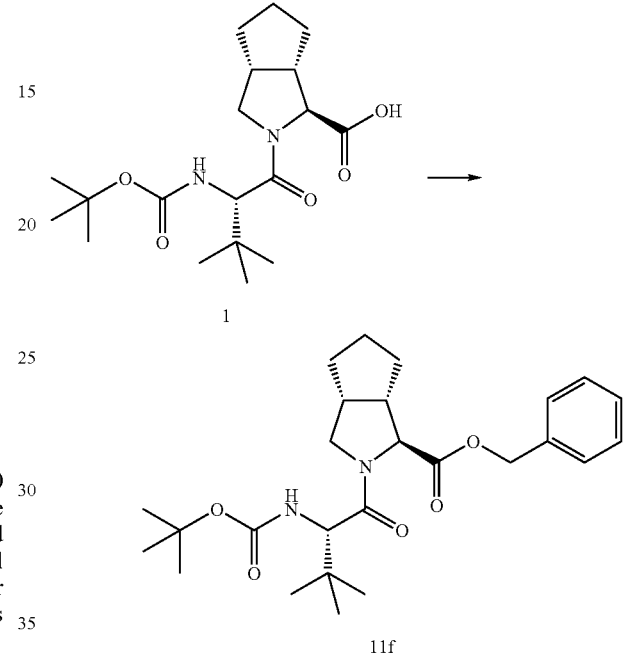

A solution of acid 1 (2.19 g) in 40 mL of dry DMF was cooled to 0° C. and treated with cesium carbonate (1.2 eq, 1.22 g) followed by addition of benzyl bromide (1.2 eq, 0.85 mL, d 1.438). The reaction mixture was stirred for 24 h (temp: 0 to 25° C.). The mixture was diluted with ethyl acetate (350 mL) and washed with water (3×50 mL). The organic layer was dried over magnesium sulfate, filtered and concentrated under reduced pressure. The residue was chromatographed on silica gel (gradient: hexanes to ethyl acetate/hexanes 25:75) to afford the product 11f (2.1 g; 77%) as a clear oil.

Step E

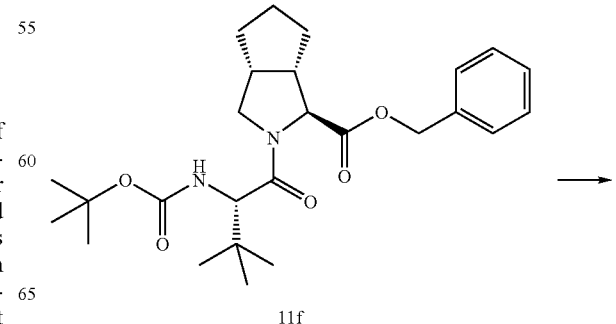

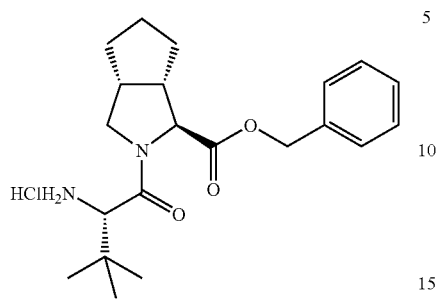
11g
The N-Boc protected amine 11f (2.1 g) was dissolved in 50 mL of 4M HCl solution in dioxane. The resulting solution was stirred at room temperature until all the starting material had been consumed as determined by TLC analysis (ethyl acetate/hexanes; 25:75). After 1 h, all the volatiles were removed under reduced pressure to afford the product 11g (1.8 g; 98%) as a white solid.
Step F
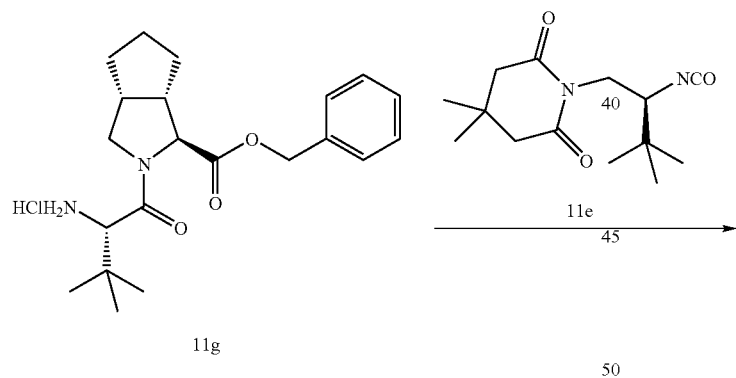
11g    11e
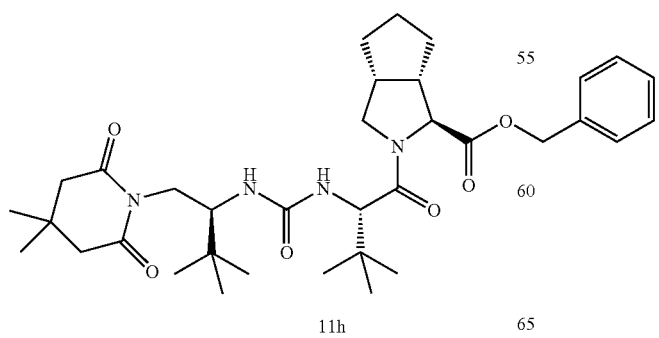
11h A solution of amine hydrochloride 11g in 10 mL of dry dichloromethane was treated with N-methylmorpholine (2.5 eq, 0.7 mL, d 0.920) at 0° C. The resulting solution was stirred for 5 min followed by addition of isocyanate 11e (1.3 eq, 13.6 mL of 0.241M soln in toluene). The reaction mixture was stirred for 5 min and the cooling bath was removed. The mixture was further stirred for 2 h. The mixture was partitioned between dichloromethane (200 mL) and aqueous 1M HCl (50 mL). Layers were separated and the organic layer was washed with aqueous saturated sodium bicarbonate solution (50 mL). The organic layer was dried over magnesium sulfate, filtered and concentrated under reduced pressure. The residue was chromatographed on silica gel (gradient: acetone/hexanes; 5:95 to 35:65) to afford the product 11h (1.33 g; 84%) as a white solid.

Step A

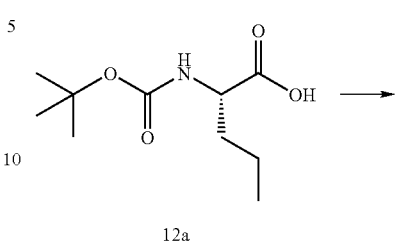

12a

Step G

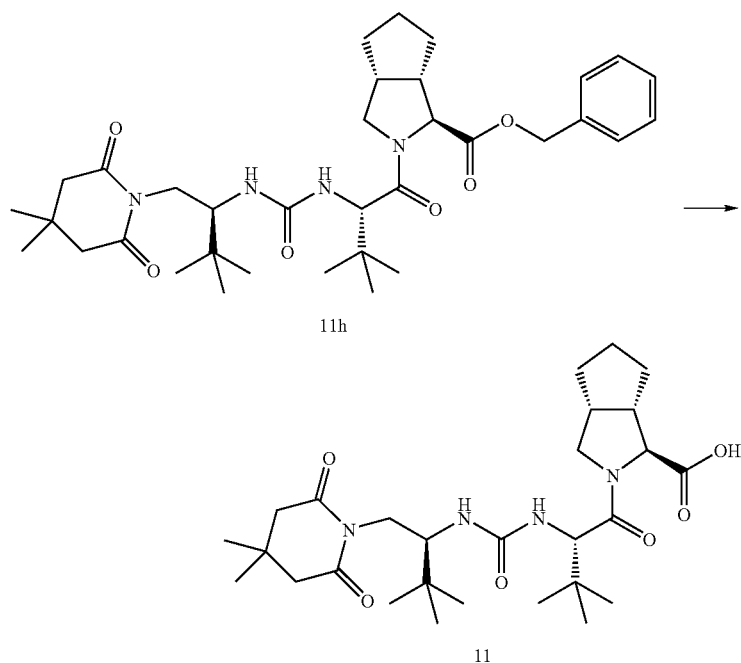

The benzyl ester 11h (1.3 g) was dissolved in 30 mL of ethyl acetate and treated with 20% palladium dihydroxide on carbon (0.1 mol%; 145 mg). The heterogeneous mixture was hydrogenated at 50 psi for 2 h. The mixture was diluted with 200 mL of dichloromethane and filtered thru a short path of celite. The filtrate was concentrated under reduced pressure to afford the product 11 (1.1 g; 98%) as a white solid.

Synthesis of:

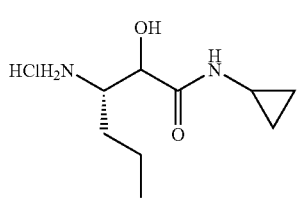

12

-continued

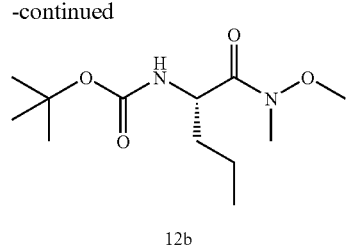

12b

A solution of acid 12a (2 g) in 100 mL of dry dichloromethane and 5 mL of DMF was treated with N,O-dimethylhydroxylamine hydrochloride (1.1 eq, 986 mg), BOP reagent (1.1 eq, 4.47 g), and N-methylmorpholine (3.3 eq, 3.3 mL, d 0.920) in that order. The mixture was heated to 50° C. overnight. The reaction mixture was concentrated to half its volume and diluted with 400 mL of ethyl acetate. The organic layer was washed with water (80 mL), aqueous 1M HCl (80 mL), aqueous saturated sodium bicarbonate solution (80 mL), and brine (80 mL). The organic layer was dried over magnesium sulfate, filtered, and concentrated under reduced pressure. The residue was chromatographed on silica gel (gradient: acetone/hexanes; 5:95 to 3:7) to afford the product 12b as a clear oil.

Step B

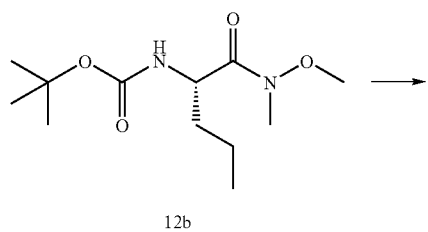

12b

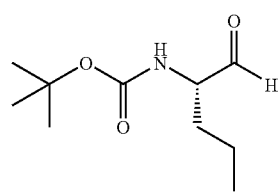

12c

A solution of amide 12b (2.2 g) in 100 mL of dry THF was cooled to 0° C.

Lithium aluminum hydride solution (1.3 eq) was added dropwise. The cooling bath was removed after 5 min and the mixture was allowed to reach room temperature. TLC analysis (ethyl acetate/hexanes; 2:8) showed that all the starting material had been consumed. The excess LAH was carefully quenched by addition of drops of aqueous saturated sodium hydrogen sulfate.

The mixture was diluted with 200 mL of ether and aqueous saturated sodium hydrogen sulfate was added in small portions until a white solid precipitated. The mixture was filtered thru celite and the filtrate was washed with 50 mL of brine. The organic layer was dried over magnesium sulfate, filtered and concentrated. The residue was chromatographed on silica gel (gradient: ethyl acetate/hexanes; 5:95 to 4:6) to afford the aldehyde product 12c as a colorless oil.

Step C

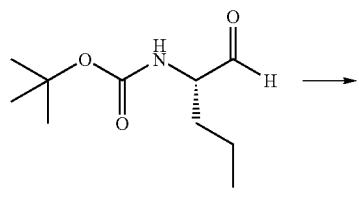

12c

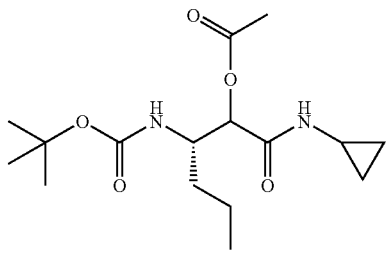

12d

A solution of aldehyde 12c (1.8 g) in 100 mL of dry dichloromethane was treated with isonitrile (1.1 eq, 680 mg) and acetic acid (2 eq, 1.02 mL, d 1.0149). The mixture was stirred overnight. All the volatiles were removed under vacuum and the residue was chromatographed on silica gel (gradient: ethyl acetate/hexanes; 2:8 to 6:4) to afford the product 12d as a white solid.

Step D

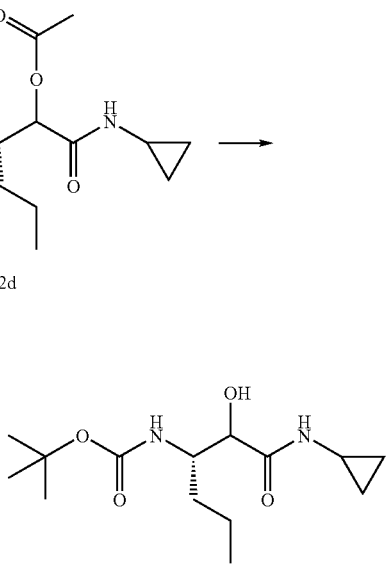

A solution of acetate 12d (1.6 g) in 60 mL of a 1:1:1 mixture of THF/MeOH/water was treated with lithium hydroxide monohydrate and stirred for approximately 1 h until all the starting material had been consumed as determined by TLC analysis (ethyl acetate/hexanes; 1:1). The volatiles were removed in rotavap and the residue was diluted with dichloromethane (150 mL). The layers were separated and the aqueous layer was diluted with 30 mL of aqueous saturated sodium bicarbonate solution and extracted with dichloromethane (3×80 mL). The combined organic layers were dried over magnesium sulfate, filtered and concentrated to afford the product 12e as a white solid.

Step E

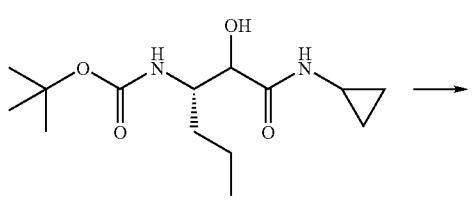

12e

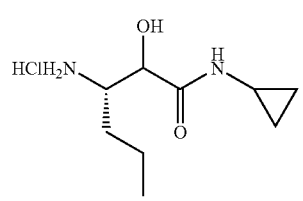

12

The N-Boc protected amine 12e (1.5 g) was dissolved in 20 mL of 4M HCl in dioxane. The reaction mixture was stirred for about 1 h until all the starting material had been consumed. All the volatiles were removed under vacuum to afford the product 12 as a white solid.

Synthesis of:

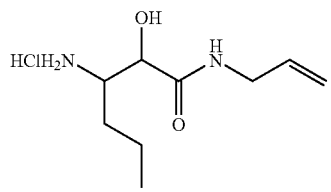

13

The amine hydrochloride 13 will be prepared following the synthetic route described for the preparation of amine hydrochloride 12. The commercially available N-Boc-D,L-norvaline will be used as starting material and allyl isocyanide will be used instead of cyclopropylisocyanide to form the corresponding allyl amide.

Synthesis of:

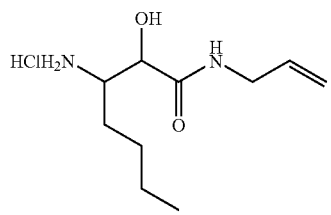

14

The amine hydrochloride 14 will be prepared following the synthetic route described for the preparation of amine hydrochloride 12. N-Boc-D,L-norleucine will be used as starting material and allyl isocyanide will be used instead of cyclopropylisocyanide to form the corresponding allyl amide.

Synthesis of:

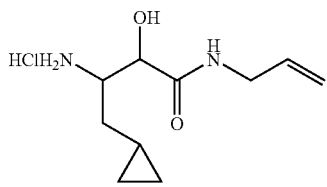

15

The amine hydrochloride 15 will be prepared following the synthetic route described for the preparation of amine hydrochloride 12. N-Boc-beta-cyclopropyl-D,L-alanine will be used as starting material and allyl isocyanide will be used instead of cyclopropylisocyanide to form the corresponding allyl amide.

Synthesis of Inhibitors

Preparative Example A

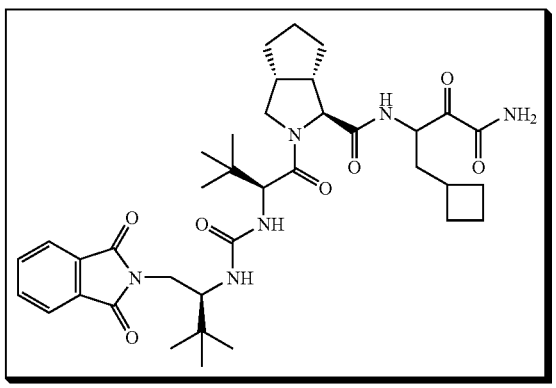

A

Step 1

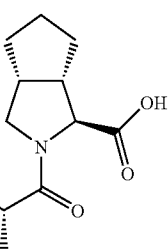

1

+

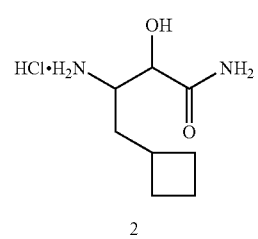

2

-continued

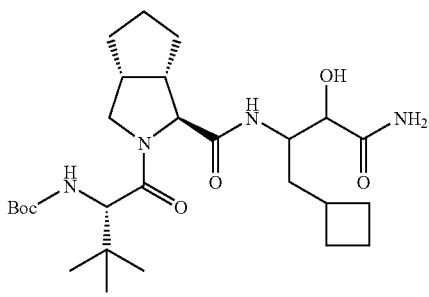

A1

A solution of acid 1 (255 mg) in 5 mL of dry dichloromethane and 5 mL of dry DMF was stirred at 0° C. and treated with HATU (368 mg). The amine hydrochloride 2 (201 mg) was added followed by addition of N-methylmorpholine (0.42 mL). The reaction mixture was gradually warmed to room temperature and stirred overnight. All the volatiles were removed under vacuum and the residue was taken into 100 mL of ethyl acetate. The organic layer was washed with aqueous 1 N HCl (15 mL), aqueous saturated NaHCO3 (15 mL), water (15 mL), brine (15 mL), dried over MgSO4, filtered, and concentrated under reduced pressure to afford the desired product A1. No further purification was carried out for the product.

Step 2

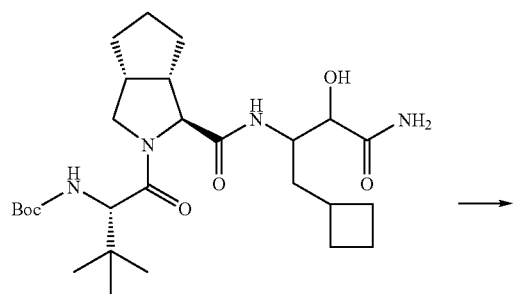

A1

A solution of A1 (360 mg) in 20 mL of a 1:1 mixture of toluene/DMSO was treated with EDCl (1.3 g) and dichloroacetic acid (0.42 mL, d 1.563). Reaction mixture was stirred at room temperature for about 3 h. The reaction mixture was diluted with dichloromethane (100 mL) and washed with aqueous saturated NaHCO₃ (15 mL), aqueous 1N HCl (15 mL), and brine (15 mL). The organic layer was dried over magnesium sulfate, filtrated, and concentrated under reduced pressure. The residue was chromatographed on silica gel (gradient: acetone/hexanes; 2:8 to 5:5) to afford the product A2 in 84% yield.

Step 3

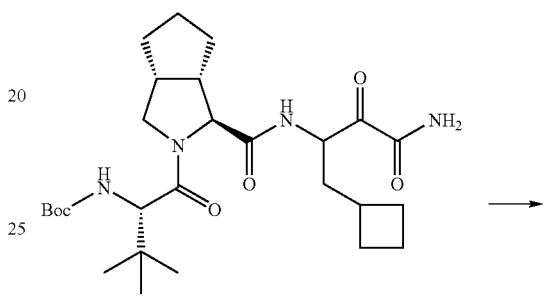

A2

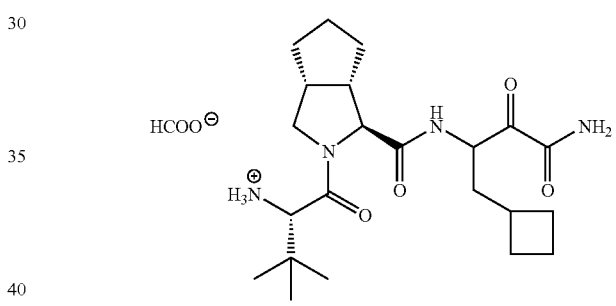

A3

The N-Boc protected amine A2 was treated with 10 mL of formic acid. The resulting solution was stirred for 2 h. All the volatiles were removed under reduced pressure. No further purification was done for the product A3.

Step 4

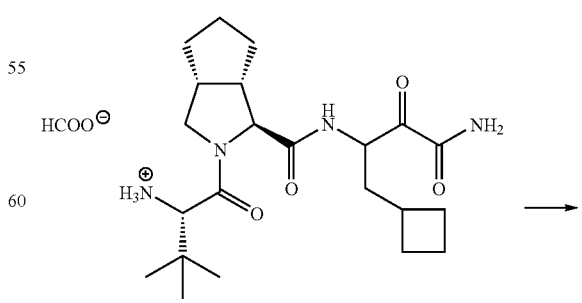

A3

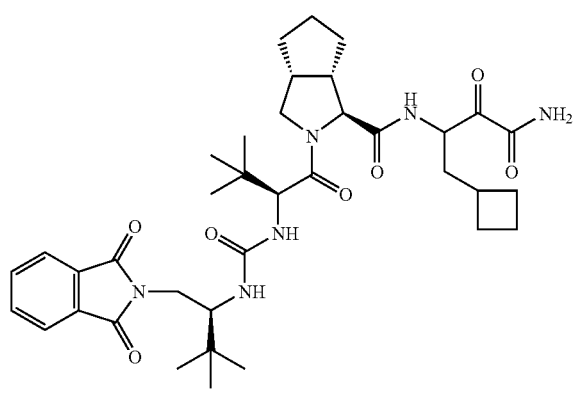

A

To a solution of the amine salt A3 in 1 mL of dry methylene chloride was added N-methylmorpholine (0.037 mL, d 0.920). The resulting solution was cooled in an ice-water bath and a solution of isocyanate in toluene (2.5 mL of a 0.135M soln) was slowly added. The mixture was stirred for 2 h (temp 0 to 25° C.). The reaction mixture was diluted with 60 mL of dichloromethane and washed with 15 mL of aqueous 1 N HCl. Aqueous layer was back extracted with dichloromethane (2×20 mL). Combined organic layers were dried over magnesium sulfate, filtered and concentrated under reduced pressure. The residue was chromatographed on Silica gel (gradient: acetone/hexanes; 1:9 to 6:4) to give the product A (15 mg) as a white solid in 20% yield. HRMS (FAB) calcd for $C_{37}H_{53}N_6O_7$ [M+H] 693.3976; found 693.3987

Preparative Example B

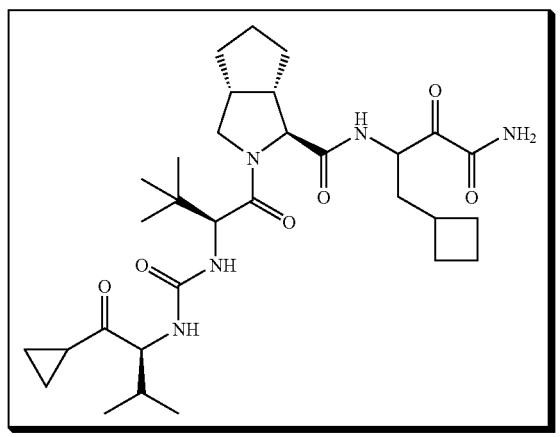

B

Step 1

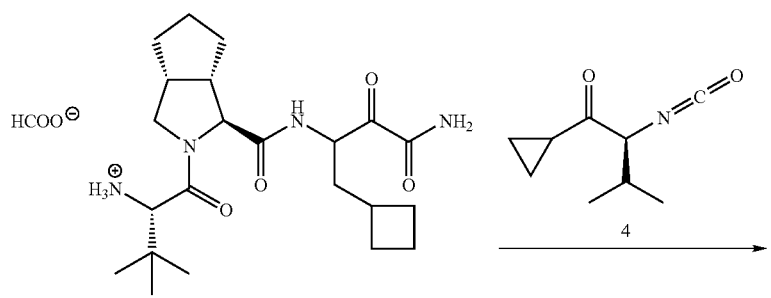

A3

-continued

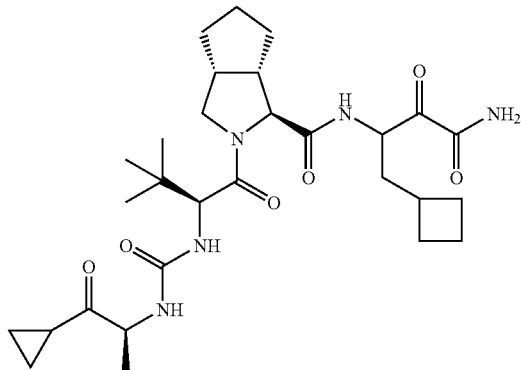

B

To a solution of the amine salt A3 in 1 mL of dry methylene chloride was added N-methylmorpholine (0.037 mL, d 0.920). The resulting solution was cooled in an ice-water bath and a solution of isocyanate 4 in toluene (0.64 mL of a 0.538M soln) was slowly added. The mixture was stirred for 2 h (temp 0 to 25° C.). The reaction mixture was diluted with 60 mL of dichloromethane and washed with 15 mL of aqueous 1 N HCl. Aqueous layer was back extracted with dichloromethane (2×20 mL). Combined organic layers were dried over magnesium sulfate, filtered and concentrated under reduced pressure. The residue was chromatographed on Silica gel (gradient: acetone/hexanes; 1:9 to 6:4) to give the product B (14.6 mg) as a white solid in 22% yield. HRMS (FAB) calcd for $C_{31}H_{50}N_5O_6$ [M+H] 588.3761; found 588.3757.

Preparative Example C

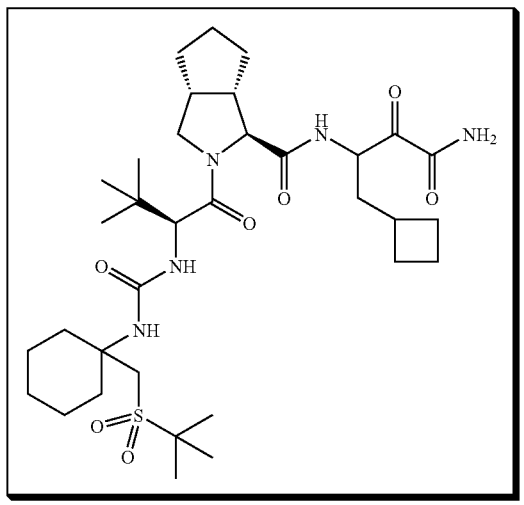

C

Step 1

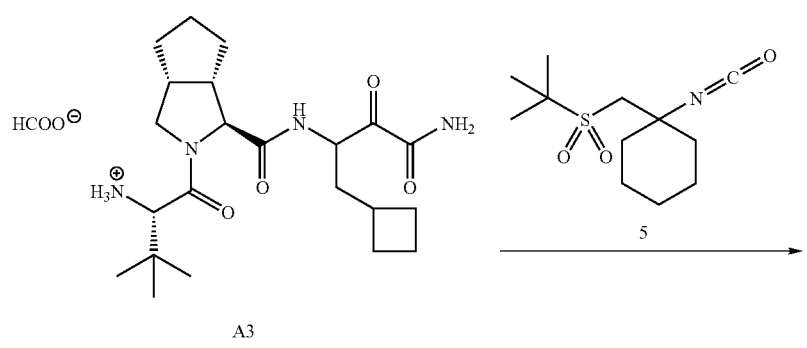

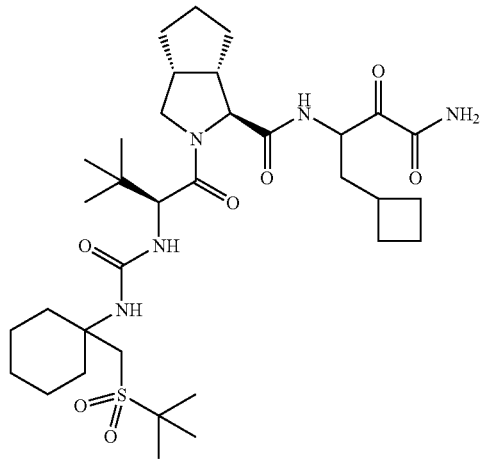

C

To a solution of the amine salt A3 in 1 mL of dry methylene chloride was added N-methylmorpholine (0.037 mL, d 0.920). The resulting solution was cooled in an ice-water bath and a solution of isocyanate 5 in toluene (1.4 mL of a 0.250M soln) was slowly added. The mixture was stirred for 2 h (temp 0 to 25° C.). The reaction mixture was diluted with 60 mL of dichloromethane and washed with 15 mL of aqueous 1 N HCl. Aqueous layer was back extracted with dichloromethane (2×20 mL). Combined organic layers were dried over magnesium sulfate, filtered and concentrated under reduced pressure. The residue was chromatographed on Silica gel (gradient: acetone/hexanes; 1:9 to 6:4) to give the product C (9.7 mg) as a white solid in 13% yield. HRMS (FAB) calcd for $C_{34}H_{58}N_5O_7S$ [M+H] 680.4057; found 680.4066.

Preparative Example D

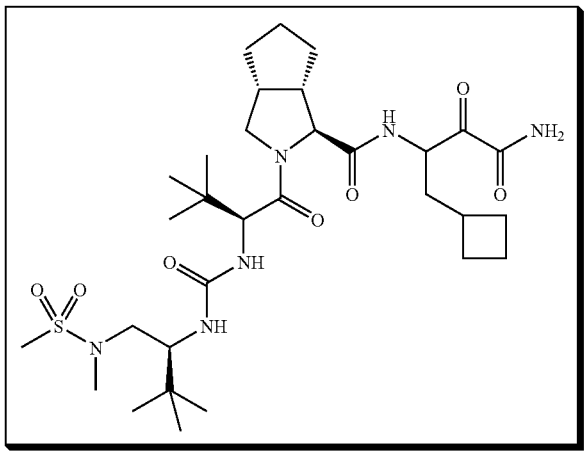

D

Step 1

-continued

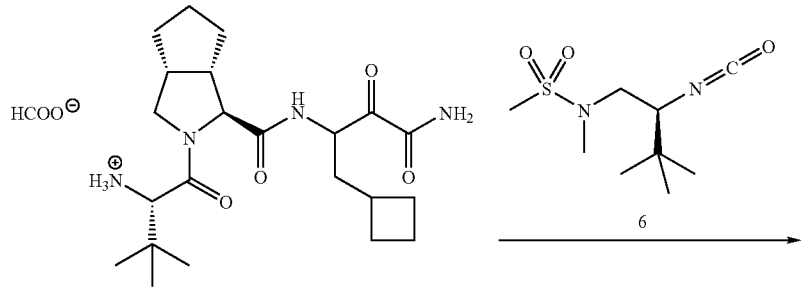

A3

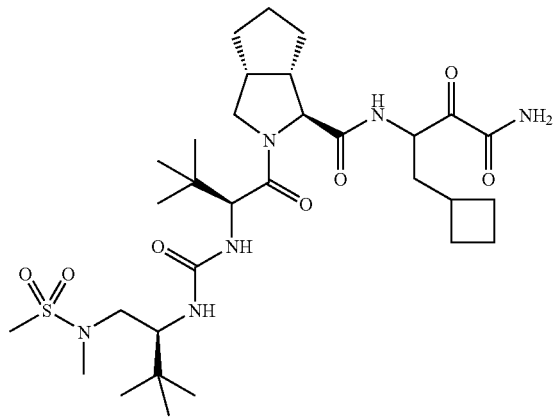

D

To a solution of the amine A3 in 1 mL of dry methylene chloride was added N-methylmorpholine (0.037 mL, d 0.920). The resulting solution was cooled in an ice-water bath and a solution of isocyanate 6 in toluene (1.0 mL of a 0.340M soln) was slowly added. The mixture was stirred for 2 h (temp 0 to 25° C.). The reaction mixture was diluted with 60 mL of dichloromethane and washed with 15 mL of aqueous 1 N HCl. The aqueous layer was back extracted with dichloromethane (2×20 mL). Combined organic layers were dried over magnesium sulfate, filtered and concentrated under reduced pressure. The residue was chromatographed on silica gel (gradient: acetone/hexanes; 1:9 to 6:4) to give the product D (23 mg) as a white solid in 32% yield. HRMS (FAB) calcd for $C_{31}H_{55}N_6O_7S$ [M+H] 655.3853; found 655.3870.

Preparative Example E

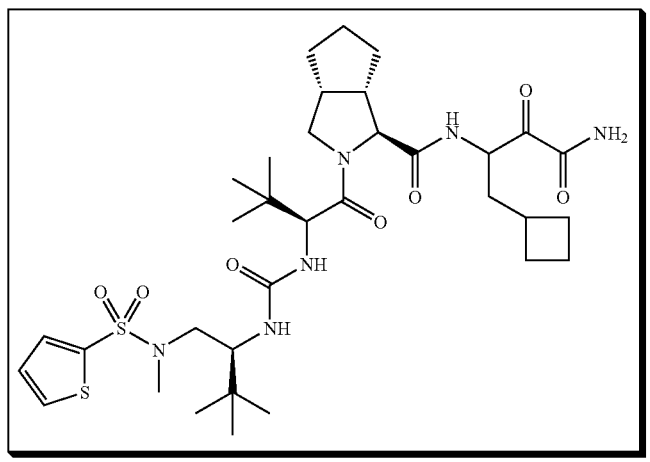

E

Step 1

-continued

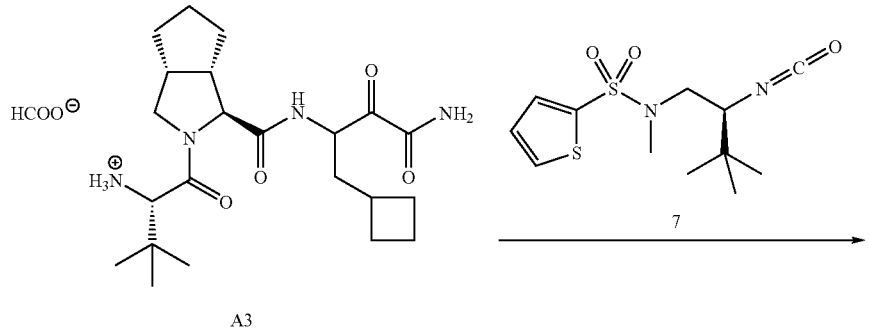

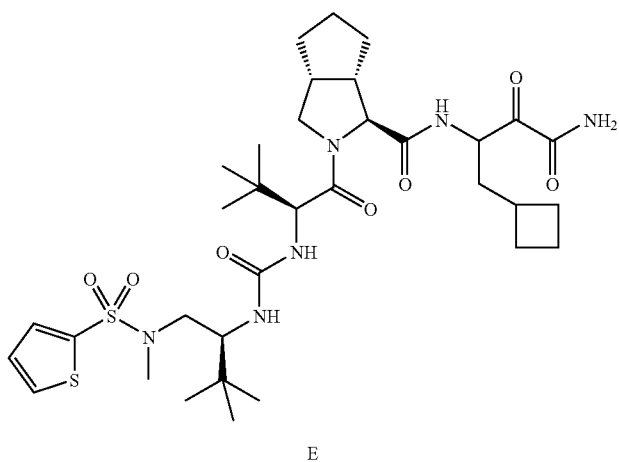

To a solution of the amine A3 in 1 mL of dry methylene chloride was added N-methylmorpholine (0.037 mL, d 0.920). The resulting solution was cooled in an ice-water bath and a solution of isocyanate 7 in toluene (1.4 mL of a 0.250M soln) was slowly added. The mixture was stirred for 2 h (temp 0 to 25° C.). The reaction mixture was diluted with 60 mL of dichloromethane and washed with 15 mL of aqueous 1 N HCl. Aqueous layer was back extracted with dichloromethane (2×20 mL). Combined organic layers were dried over magnesium sulfate, filtered and concentrated under reduced pressure. The residue was chromatographed on Silica gel (gradient: acetone/hexanes; 1:9 to 6:4) to give the product D (11.5 mg) as a white solid in 14% yield. HRMS (FAB) calcd for $C_{34}H_{55}N_6O_7S_2$ [M+H] 723.3574; found 723.3568.

Preparative Example F

F

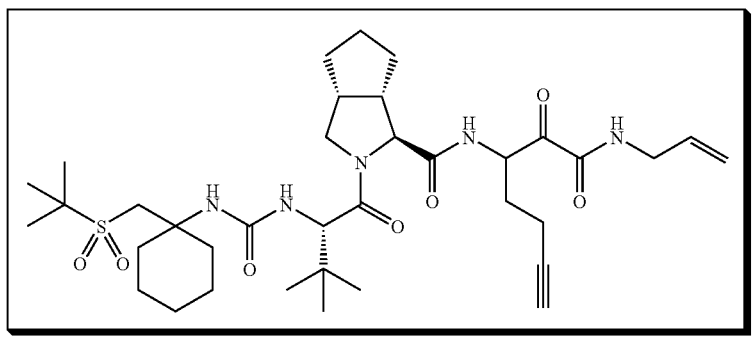

Step 1

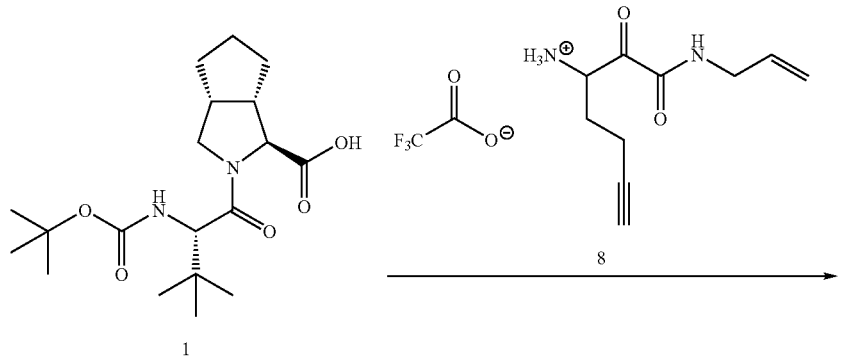

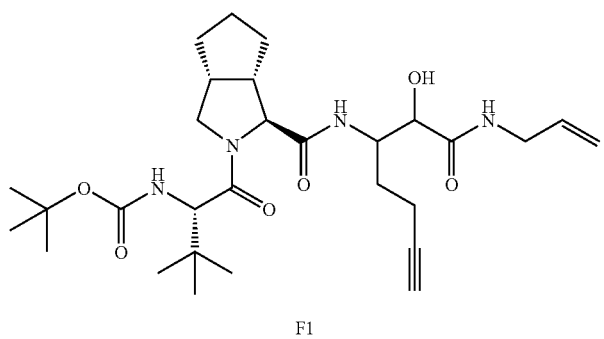

A solution of acid 1 (280 mg) in 10 mL of dry dichloromethane and 10 mL of dry DMF was stirred at 0° C. and treated with HATU (1.4 eq, 405 mg). The amine salt 8 (1.3 eq, 569 mg) was added in dichloromethane. Then, N-methylmorpholine (4 eq, 0.33 mL, d 0.920) was added. The reaction mixture was stirred at −20° C. for 48 h. All the volatiles were removed under vacuum and the residue was dissolved in 200 mL of ethyl acetate. The organic layer was washed with water (30 mL), aqueous 1 N HCl (30 mL), aqueous saturated sodium bicarbonate (30 mL), and brine (30 mL). The organic layer was dried over magnesium sulfate, filtered and concentrated under reduced pressure. The product F1 was used without further purification.

Step 2

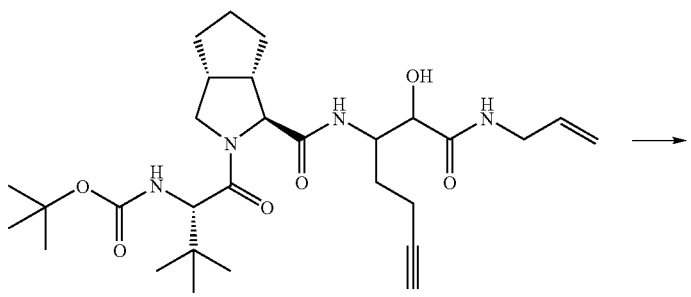

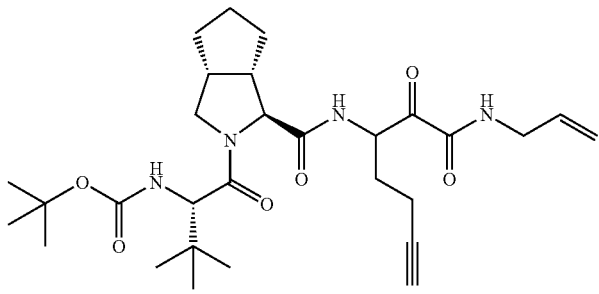

F2

A solution of hydroxyamide F1 (415 mg) in 20 mL of dry dichloromethane was treated with Dess-Martin periodinane (3 eq, 966 mg). Reaction mixture was stirred at room temperature for 45 min. The mixture was treated with aqueous 1M sodium thiosulfate solution (15 mL) and aqueous saturated sodium bicarbonate (15 mL) and stirred for 15 min. The mixture was extracted with dichloromethane (3×50 mL). The combined organic layers were dried over magnesium sulfate, filtered, and concentrated. The residue was chromatographed on silica gel (gradient: acetone/hexanes; 1:9 to 4:6) to afford the product F2 as a colorless oil.

The N-Boc protected amine F2 (155 mg) was dissolved in 5 mL of 4M HCl in dioxane at room temperature. The mixture was stirred until all the starting material had been consumed as determined by TLC analysis (acetone/hexanes; 3:7). After 45 minutes, all the volatiles were removed under vacuum to give the product F3 as a white solid which was used without further purification.

Step 3

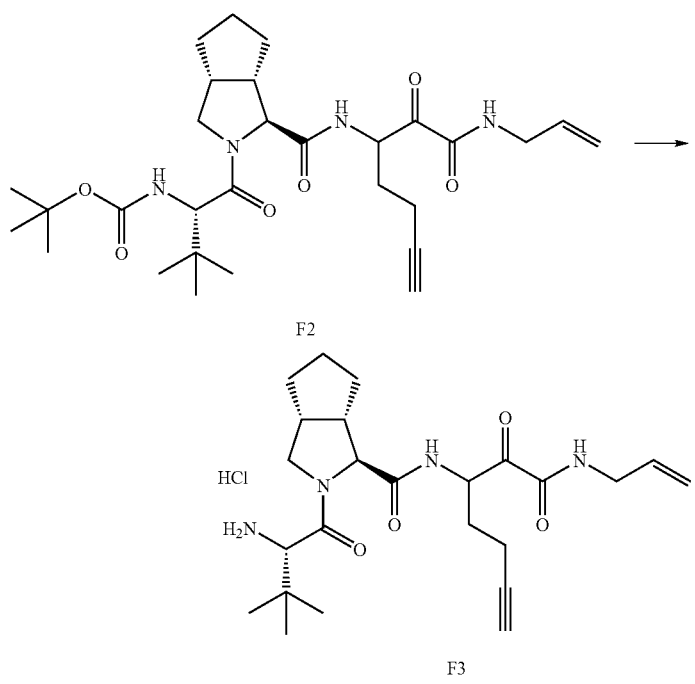

Step 4

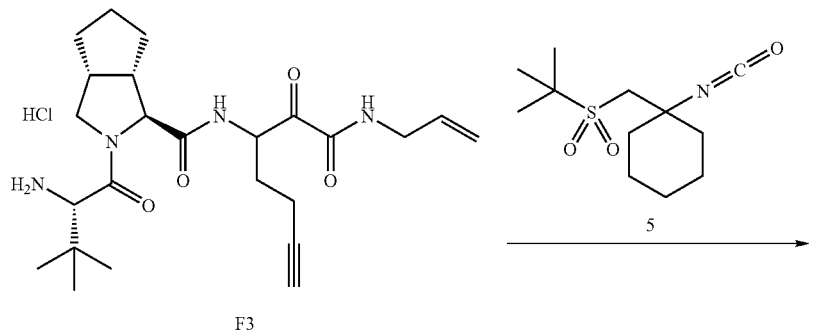

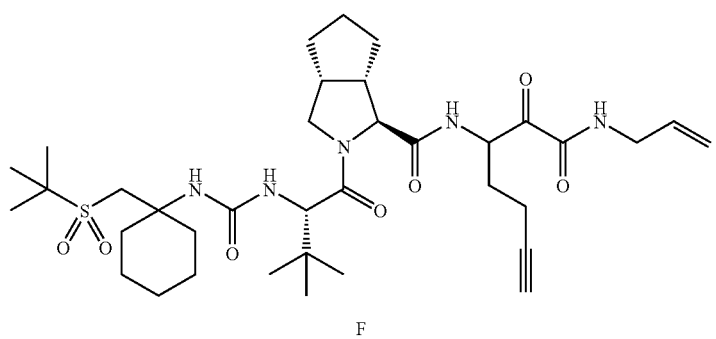

A solution of the amine hydrochloride F3 (67 mg) in 2 mL of dry dichloromethane was treated with N-methylmorpholine (3.7 eq, 0.06 mL, d 0.920) and cooled to 0° C. The isocyanate was added dropwise (0.75 mL of a 0.2M solution in toluene) and the mixture was stirred overnight (temp 0 to 25 ° C.). The reaction mixture was diluted with 50 mL of dichloromethane and washed with 15 mL of aqueous 1M HCl and 15 mL of aqueous saturated sodium bicarbonate solution. The organic layer was dried over magnesium sulfate, filtered and concentrated. The residue was chromatographed on silica gel (gradient: acetone/hexanes; 1:9 to 4:6) to give the product F as a white solid. HRMS (FAB) calcd for $C_{36}H_{58}N_5O_7S$ [M+H] 704.4057; found 704.4071.

Preparative Example G

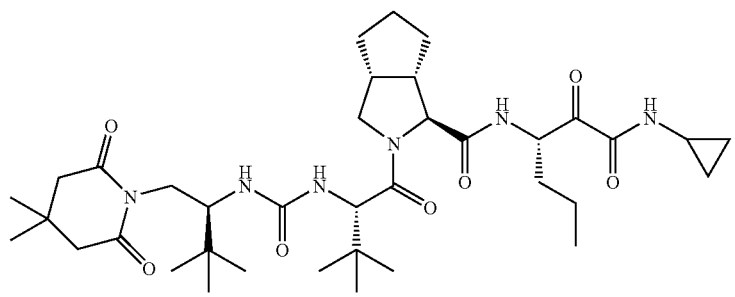

Step 1

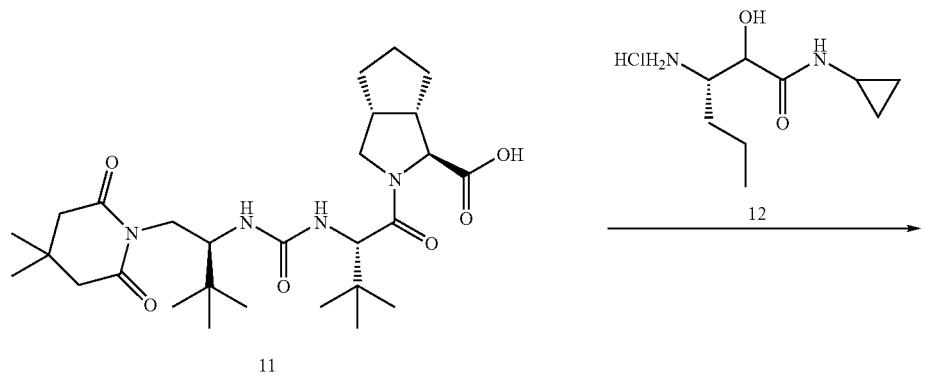

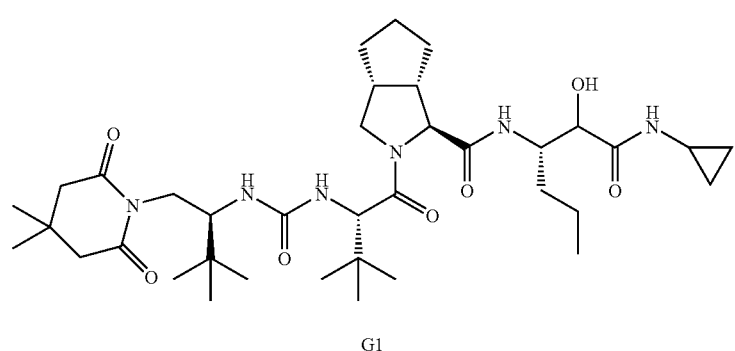

A solution of acid 11 (60 mg) in 2 mL of dry dichloromethane and 1 mL of dry DMF was stirred at 0° C. and treated with HATU (1.4 eq, 60 mg). The amine salt 12 (1.2 eq, 30 mg) was added followed by N-methylmorpholine (4 eq, 0.05 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1M HCl (10 mL), aqueous saturated sodium bicarbonate solution (10 mL), and brine (10 mL). The organic layer was dried over magnesium sulfate, filtered and concentrated under reduced pressure. The product G1 was used without further purification.

Step 1

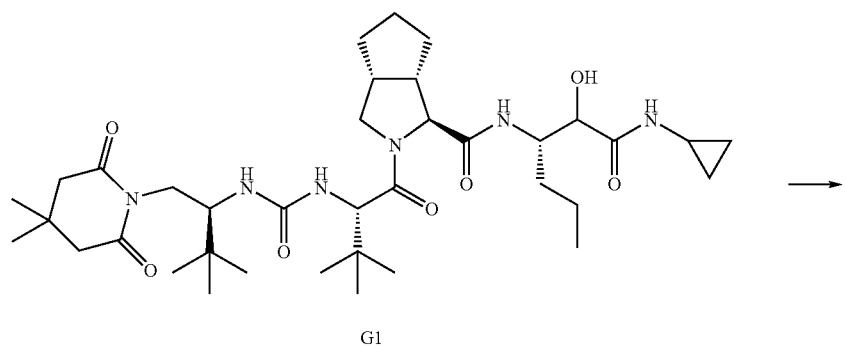

-continued

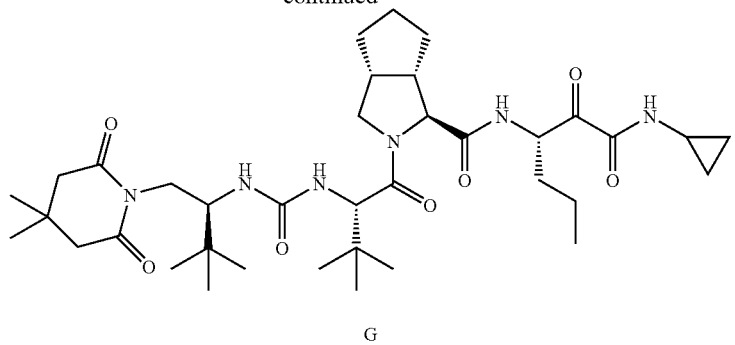

G

A solution of hydroxyamide G1 (0.112 mmol) in 10 mL of dry dichloromethane was treated with Dess-Martin periodinane (2.0 eq, 95 mg). The reaction mixture was stirred at room temperature for 30 min. The mixture was treated with aqueous 1 M sodium thiosulfate solution (10 mL) and stirred for 5 min. Aqueous saturated sodium bicarbonate solution (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 4:6) to afford the product G (63 mg; 80%) as white solid. HRMS (FAB) calcd for $C_{37}H_{61}N_6O_7$ [M+H] 701.4601; found 701.4614.

Preparative Example H

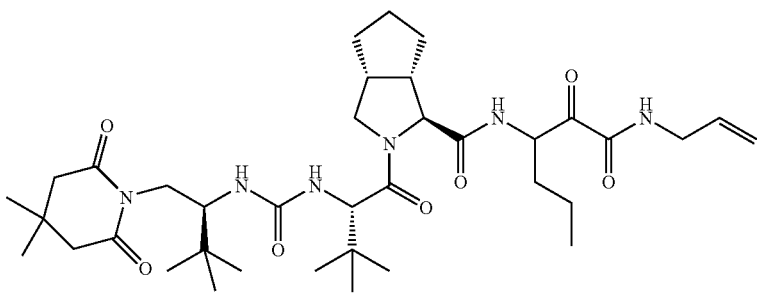

H

Step 1

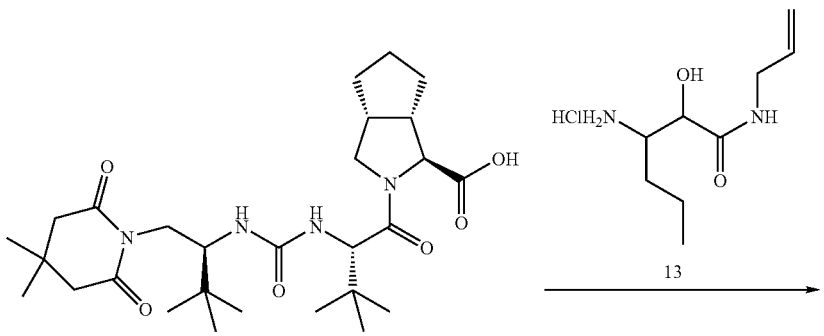

-continued

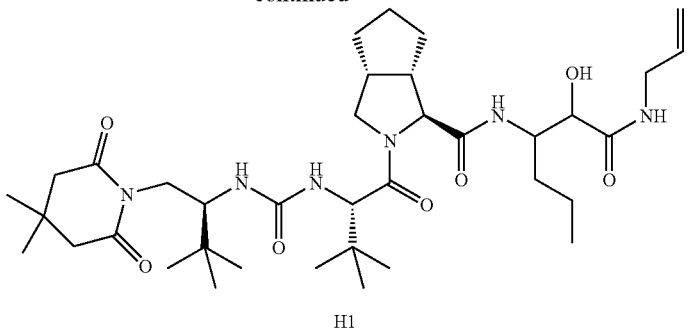

H1

A solution of acid 11 (60 mg) in 2 mL of dry dichloromethane and 1 mL of dry DMF was stirred at 0° C. and treated with HATU (1.4 eq, 60 mg). The amine salt 13 (1.2 eq, 30 mg) was added followed by N-methylmorpholine (4 eq, 0.05 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1M HCl (10 mL), aqueous saturated sodium bicarbonate solution (10 mL), and brine (10 mL). The organic layer was dried over magnesium sulfate, filtered and concentrated under reduced pressure. The product H1 was used without further purification.

A solution of hydroxyamide H1 (0.112 mmol) in 10 mL of dry dichloromethane was treated with Dess-Martin periodinane (2.0 eq, 95 mg). The reaction mixture was stirred at room temperature for 30 min. The mixture was treated with aqueous 1M sodium thiosulfate solution (10 mL) and stirred for 5 min. Aqueous saturated sodium bicarbonate solution (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 45:55) to afford the product H (64

Step 2

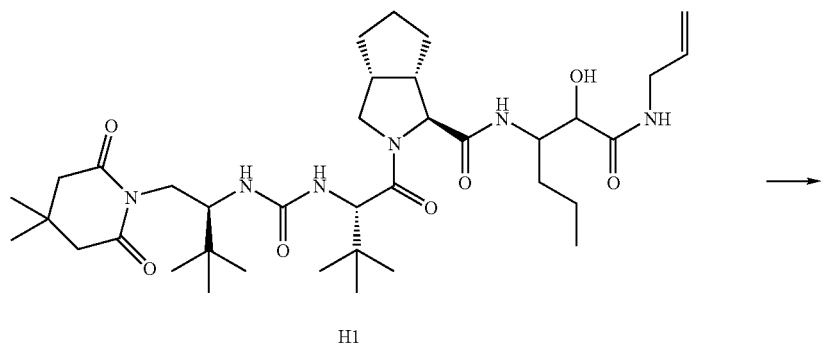

H1

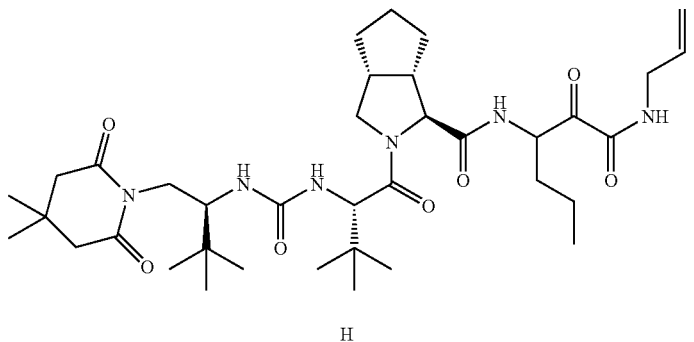

H mg; 82%) as white solid. HRMS (FAB) calcd for C$_{37}$H$_{61}$N$_6$O$_7$ [M+H] 701.4601; found 701.4607.

Preparative Example I

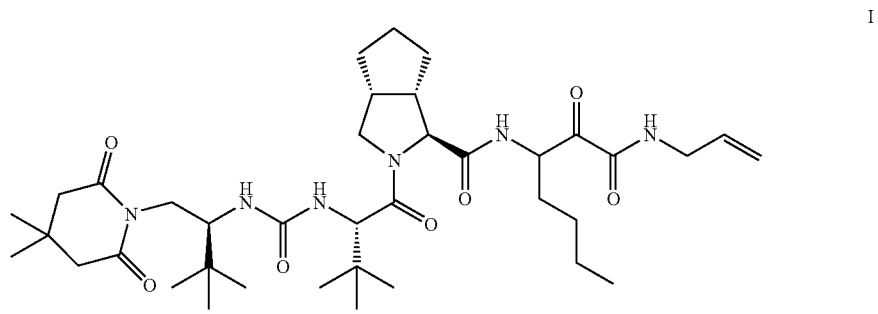

I

Step 1

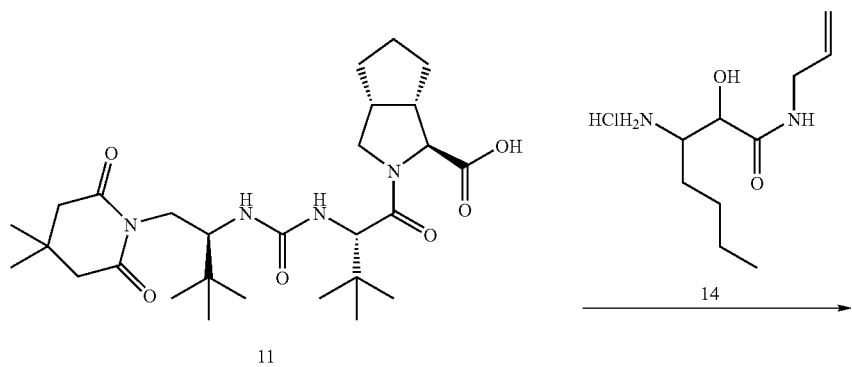

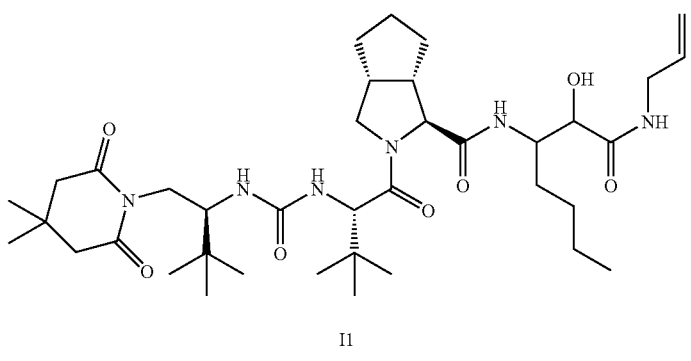

A solution of acid 11 (60 mg) in 2 mL of dry dichloromethane and 1 mL of dry DMF was stirred at 0° C. and treated with HATU (1.4 eq, 60 mg). The amine salt 14 (1.2 eq, 32 mg) was added followed by N-methylmorpholine (4 eq, 0.05 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1M HCl (10 mL), aqueous saturated sodium bicarbonate solution (10 mL), and brine (10 mL). The organic layer was dried over magnesium sulfate, filtered and concentrated under reduced pressure. The product I1 was used without further purification.

Step 2

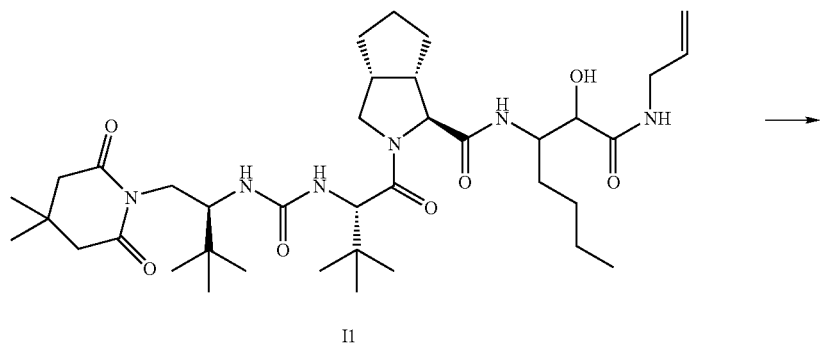

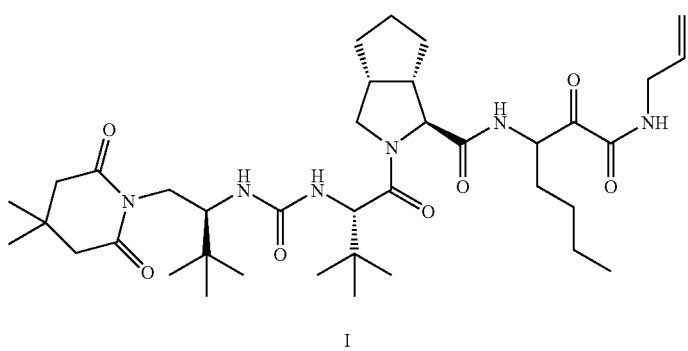

A solution of hydroxyamide I1 (0.112 mmol) in 10 mL of dry dichloromethane was treated with Dess-Martin periodinane (2.0 eq, 95 mg). The reaction mixture was stirred at room temperature for 30 min. The mixture was treated with aqueous 1M sodium thiosulfate solution (10 mL) and stirred for 5 min. Aqueous saturated sodium bicarbonate solution (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 45:55) to afford the product I (64 mg; 80%) as white solid.

Preparative Example J

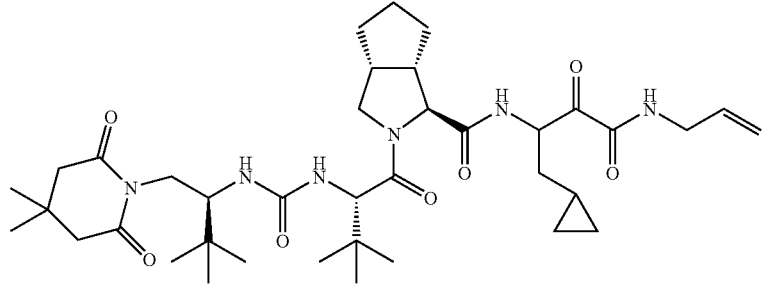

Step 1

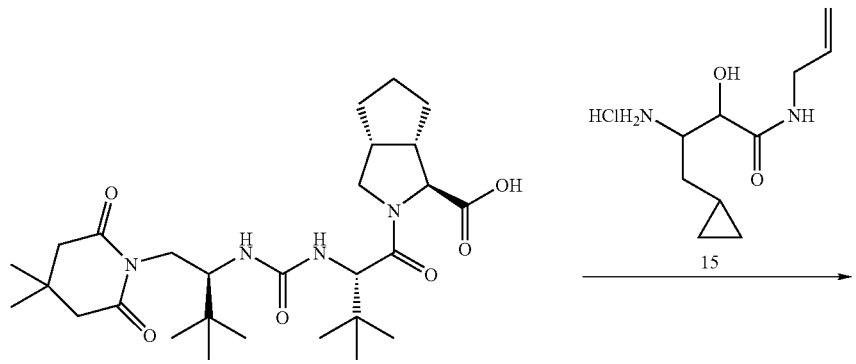

A solution of acid 11 (60 mg) in 2 mL of dry dichloromethane and 1 mL of dry DMF was stirred at 0° C. and treated with HATU (1.4 eq, 60 mg). The amine salt 15 (1.2 eq, 31 mg) was added followed by N-methylmorpholine (4 eq, 0.05 mL, d 0.920). The reaction mixture was stirred overnight (temp 0 to 25 ° C.). All the volatiles were removed under vacuum and the residue was dissolved in 50 mL of ethyl acetate. The organic layer was washed with water (20 mL), aqueous 1M HCl (10 mL), aqueous saturated sodium bicarbonate solution (10 mL), and brine (10 mL). The organic layer was dried over magnesium sulfate, filtered and concentrated under reduced pressure. The product J1 was used without further purification.

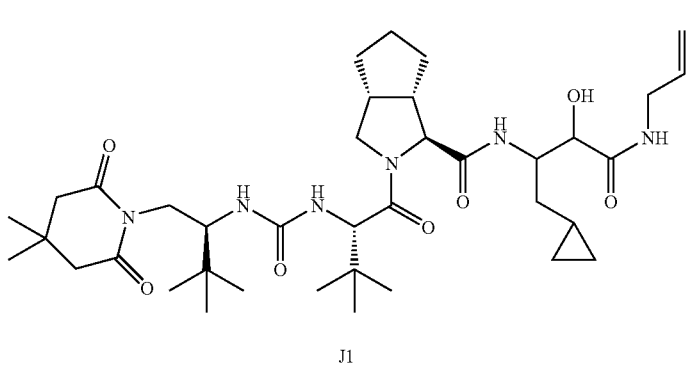

Step 2

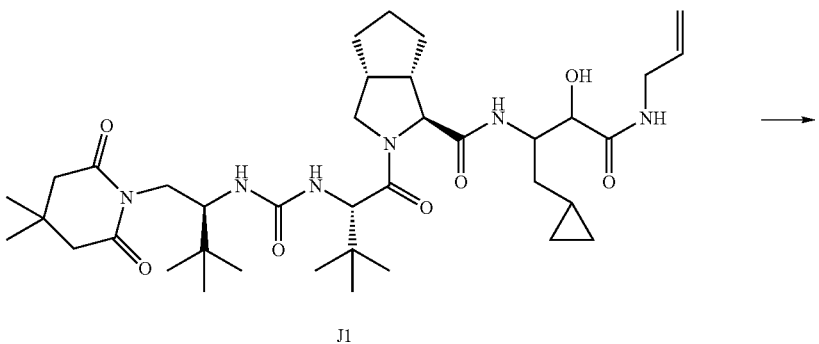

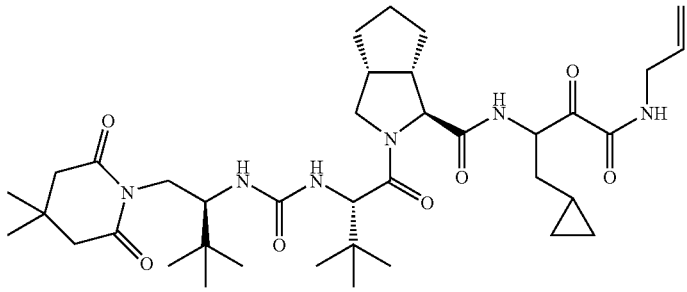

J

A solution of hydroxyamide J1 (0.112 mmol) in 10 mL of dry dichloromethane was treated with Dess-Martin periodinane (2.0 eq, 95 mg). The reaction mixture was stirred at room temperature for 30 min. The mixture was treated with aqueous 1M sodium thiosulfate solution (10 mL) and stirred for 5 min. Aqueous saturated sodium bicarbonate solution (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 45:55) to afford the product J (57 mg; 71%) as white solid. HRMS (FAB) calcd for $C_{38}H_{61}N_6O_7$ [M+H] 713.4601; found 713.4607.

The present invention relates to novel HCV protease inhibitors. This utility can be manifested in their ability to inhibit the HCV NS3/NS4a serine protease. A general procedure for such demonstration is illustrated by the following in vitro assay.

Assay for HCV Protease Inhibitory Activity:

Spectrophotometric Assay: Spectrophotometric assay for the HCV serine protease can be performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates are derived from the P side of the NS5A-NS5B junction sequence (Ac-DTEDWX (Nva), where X=A or P) whose C-terminal carboxyl groups are esterified with one of four different chromophoric alcohols (3- or 4-nitrophenol, 7-hydroxy-4-methyl-coumarin, or 4-phenylazophenol). Illustrated below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers are obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides are synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block can be from USA Scientific (Ocala, Fla.) and the 96-well plate vortexer is from Labline Instruments (Melrose Park, Ill.). A Spectramax Plus microtiter plate reader with monochrometer is obtained from Molecular Devices (Sunnyvale, Calif.).

Enzyme Preparation: Recombinant heterodimeric HCV NS3/NS4A protease (strain 1a) is prepared by using the procedures published previously (D. L. Sali et al, *Biochemistry*, 37 (1998) 3392-3401). Protein concentrations are determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) is exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates is done as reported by R. Zhang et al, (ibid.) and is initiated by anchoring Fmoc-Nva-OH to 2-chlorotrityl chloride resin using a standard protocol (K. Barlos et al, *Int. J. Pept. Protein Res.*, 37 (1991), 513-520). The peptides are subsequently assembled, using Fmoc chemistry, either manually or on an automatic ABI model 431 peptide synthesizer. The N-acetylated and fully protected peptide fragments are cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash is evaporated azeotropically (or repeatedly extracted by aqueous $Na_2CO_3$ solution) to remove the acid used in cleavage. The DCM phase is dried over $Na_2SO_4$ and evaporated.

The ester substrates are assembled using standard acid-alcohol coupling procedures (K. Holmber et al, *Acta Chem. Scand.*, B33 (1979) 410-412). Peptide fragments are dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) is added to initiate the coupling reactions. Product formation is monitored by HPLC and can be found to be complete following 12-72 hour reaction at room temperature. Pyridine solvent is evaporated under vacuum and further removed by azeotropic evaporation with toluene. The peptide ester is deprotected with 95% TFA in DCM for two hours and extracted three times with anhydrous ethyl ether to remove excess chromophore. The deprotected substrate is purified by reversed phase HPLC on a C3 or C8 column with a 30% to 60% acetonitrile gradient (using six column volumes). The overall yield following HPLC purification can be approximately 20-30%. The molecular mass can be confirmed by electrospray ionization mass spectroscopy. The substrates are stored in dry powder form under desiccation.

Spectra of Substrates and Products: Spectra of substrates and the corresponding chromophore products are obtained in the pH 6.5 assay buffer. Extinction coefficients are determined at the optimal off-peak wavelength in 1-cm cuvettes (340 nm for 3-Np and HMC, 370 nm for PAP and 400 nm for 4-Np) using multiple dilutions. The optimal off-peak wavelength is defined as that wavelength yielding the maximum fractional difference in absorbance between substrate and product (product OD−substrate OD)/substrate OD).

Protease Assay: HCV protease assays are performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) are optimized for the NS3/NS4A heterodimer (D. L. Sali et al, ibid.)). Typically, 150 µl mixtures of buffer, substrate and inhibitor are placed in wells (final concentration of DMSO<4% v/v) and allowed to preincubate at 30° C. for approximately 3 minutes. Fifty µls of prewarmed protease (12 nM, 30° C.) in assay buffer, is then used to initiate the reaction (final volume 200 µl).The plates are monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore is monitored at the appropriate wavelength against a no enzyme blank as a control for non-enzymatic hydrolysis. The evaluation of substrate kinetic parameters is performed over a 30-fold substrate concentration range (~6-200 µM). Initial velocities are determined using linear regression and kinetic constants are obtained by fitting the data to the Michaelis-Menten equation using non-linear regression analysis (Mac Curve Fit 1.1, K. Raner). Turnover numbers ($k_{cat}$) are calculated assuming the enzyme is fully active.

Evaluation of Inhibitors and Inactivators: The inhibition constants ($K_i$) for the competitive inhibitors Ac-D-(D-Gla)-L-I-(Cha)-C-OH (27), Ac-DTEDVVA(Nva)-OH and Ac-DTEDWP(Nva)-OH are determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data are fitted using linear regression and the resulting slope, $1/(K_i(1+[S]_o/K_m)$, is used to calculate the $K_i$ value. The obtained Ki* values (in nanoMolar) for some of the inventive compounds are shown below in Table 2.

TABLE 2

| Entry | Compound | Ki* (nM) |
|---|---|---|
| 1 | | 13 |
| 2 | | 40 |

TABLE 2-continued
| Entry | Compound | Ki* (nM) |
|---|---|---|
| 3 | 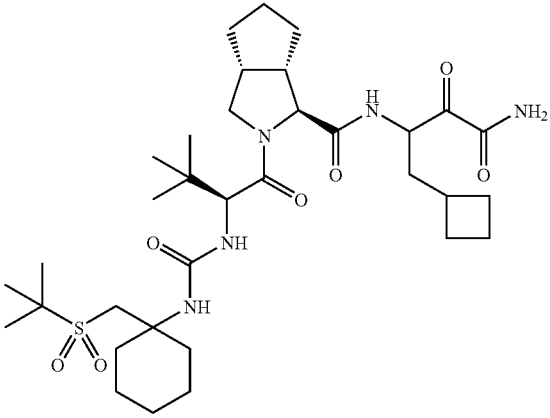 | 30 |
| 4 | 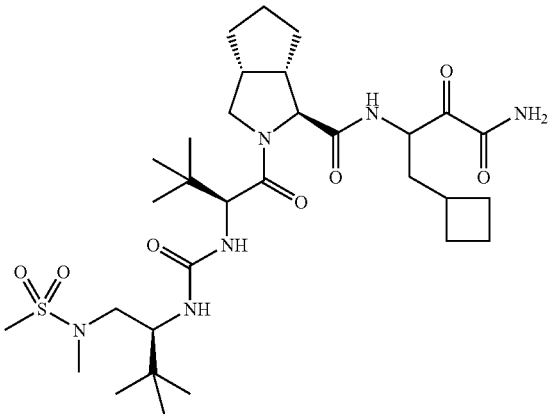 | 15 |
| 5 | 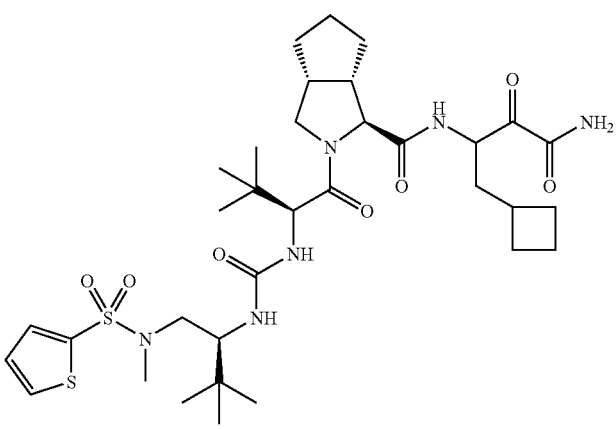 | 19 |

TABLE 2-continued

| Entry | Compound | Ki* (nM) |
|---|---|---|
| 6 | | 27 |

Table 2A lists additional inventive compounds and their activities:

TABLE 2A

| 1 | | C |
|---|---|---|
| 2 | | A |

TABLE 2A-continued
| | | |
|---|---|---|
| 3 | 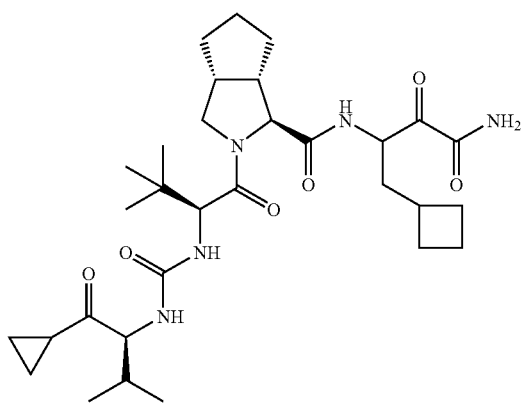 | A |
| 4 | 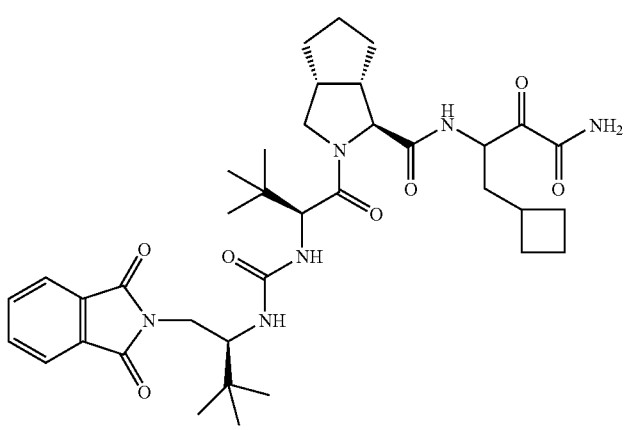 | A |
| 5 | 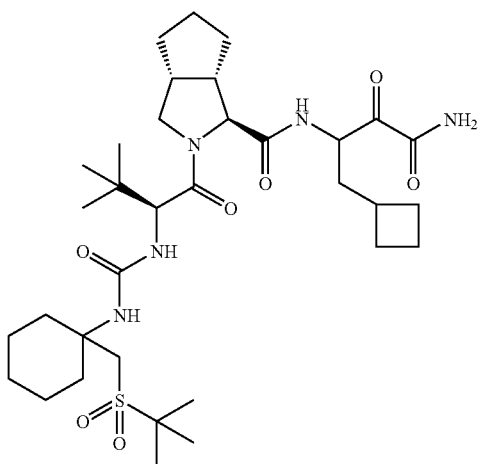 | A |

TABLE 2A-continued
6 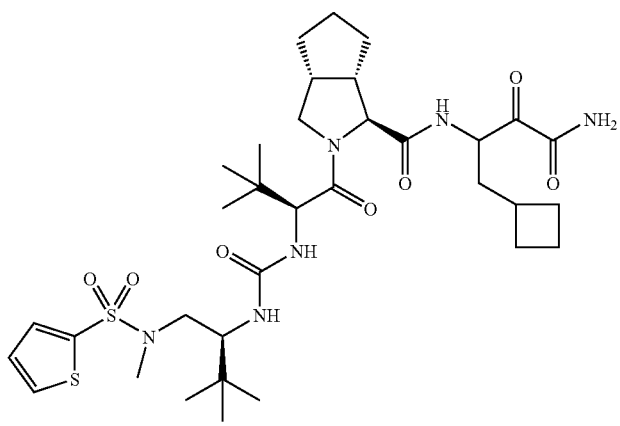 A
7 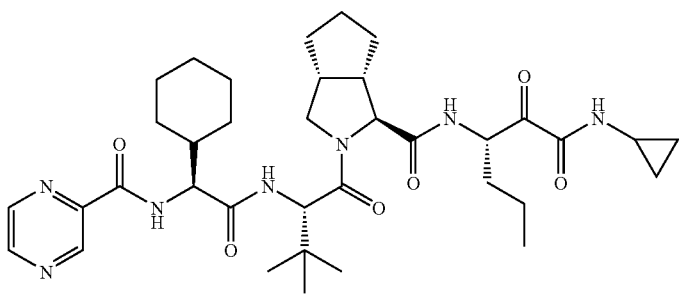 A
8 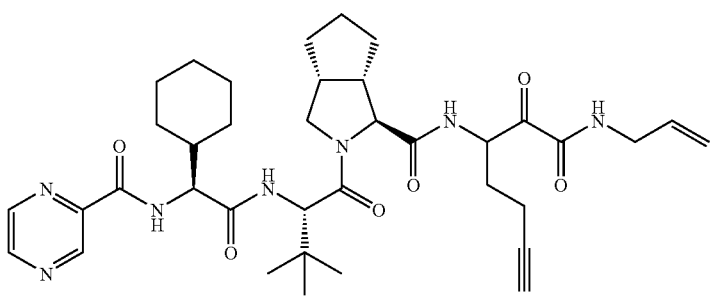 A
9 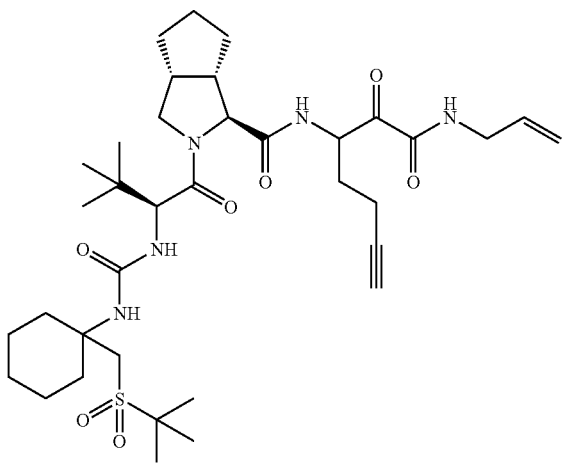 A TABLE 2A-continued
| 10 | 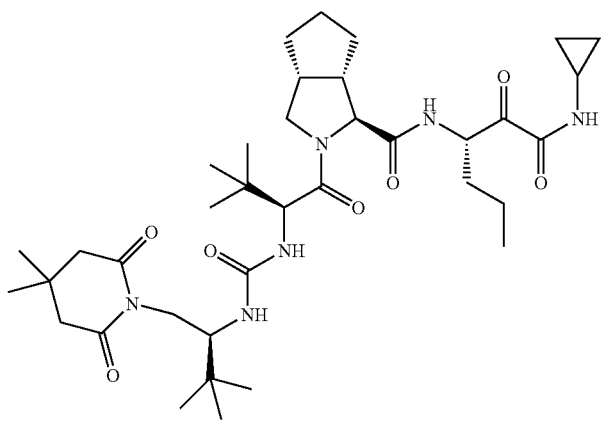 | A |
|---|---|---|
| 11 | 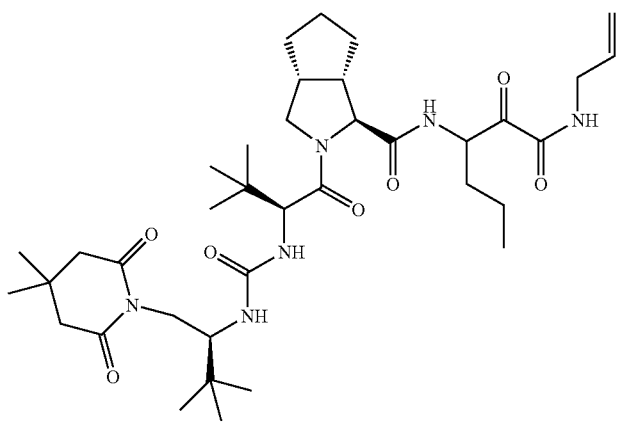 | A |
|---|---|---|
| 12 | 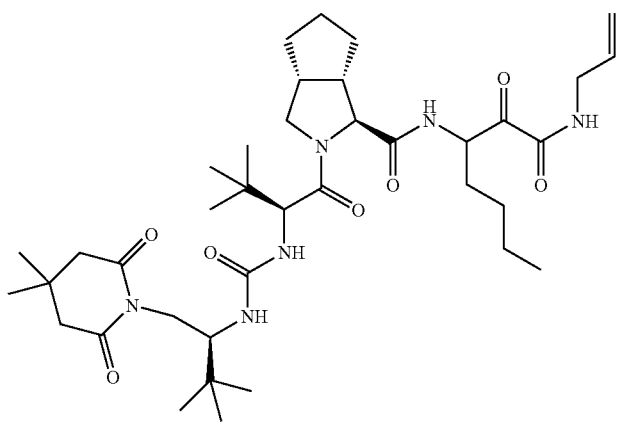 | A |
|---|---|---|

TABLE 2A-continued

| 13 | 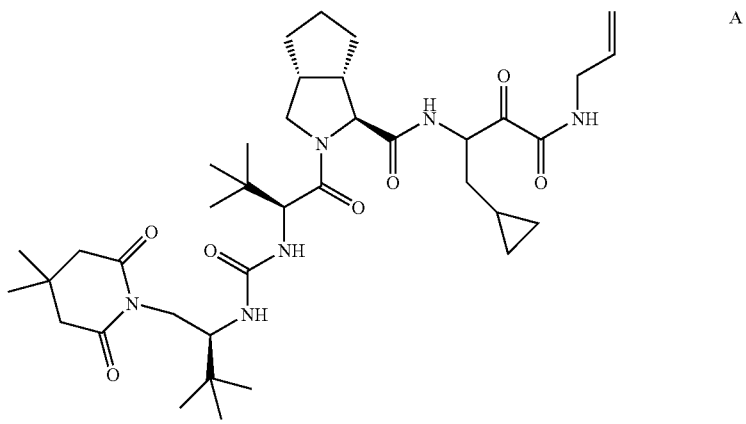 | A |

Range of Ki* indicated A ≦ 75 nM; 75 < B ≦ 250 nM; C > 250 nM.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or enantiomers, stereoisomers, rotamers, tautomers, diastereomers or racemates of said compound, or a pharmaceutically acceptable salt, solvate or ester of said compound, said compound having the general structure shown in Formula I:

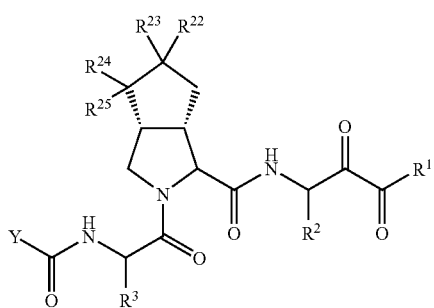

Formula 1 wherein:
- $R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroaryl-, cycloalkyl-, heterocyclyl-, arylalkyl-, and heteroarylalkyl, or alternately $R^9$ and $R^{10}$ in $NR^9R^{10}$ are connected to each other such that $NR^9R^{10}$ forms a four to eight-membered heterocyclyl, and likewise independently alternately $R^9$ and $R^{10}$ in $CHR^9R^{10}$ are connected to each other such that $CHR^9R^{10}$ forms a four to eight-membered cycloalkyl;
- $R^2$ and $R^3$ can be the same or different, each being independently selected from the group consisting of H, alkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

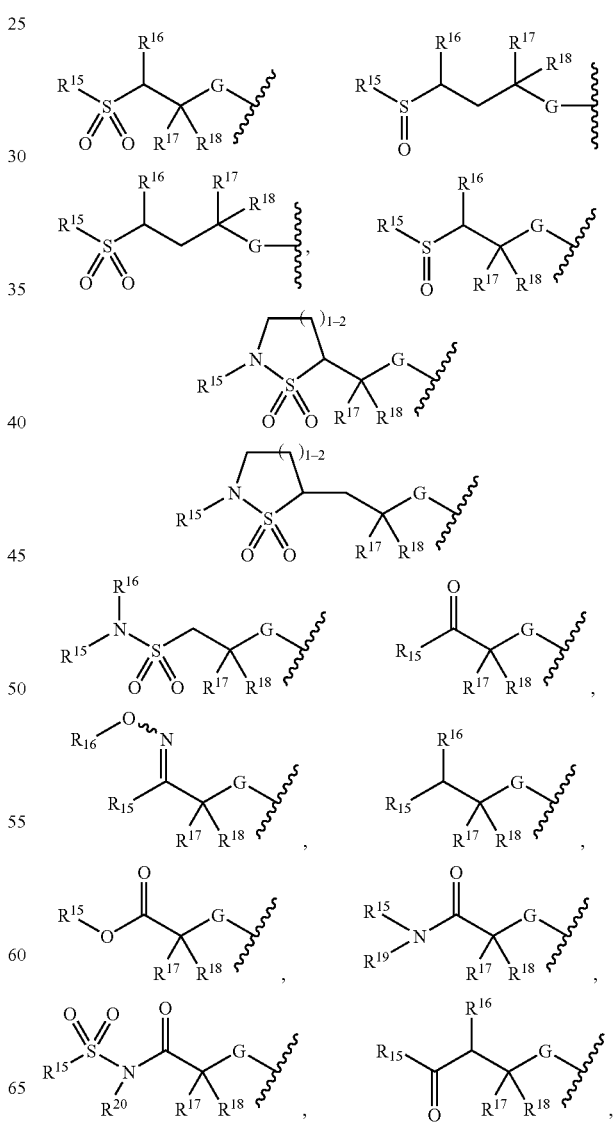

-continued

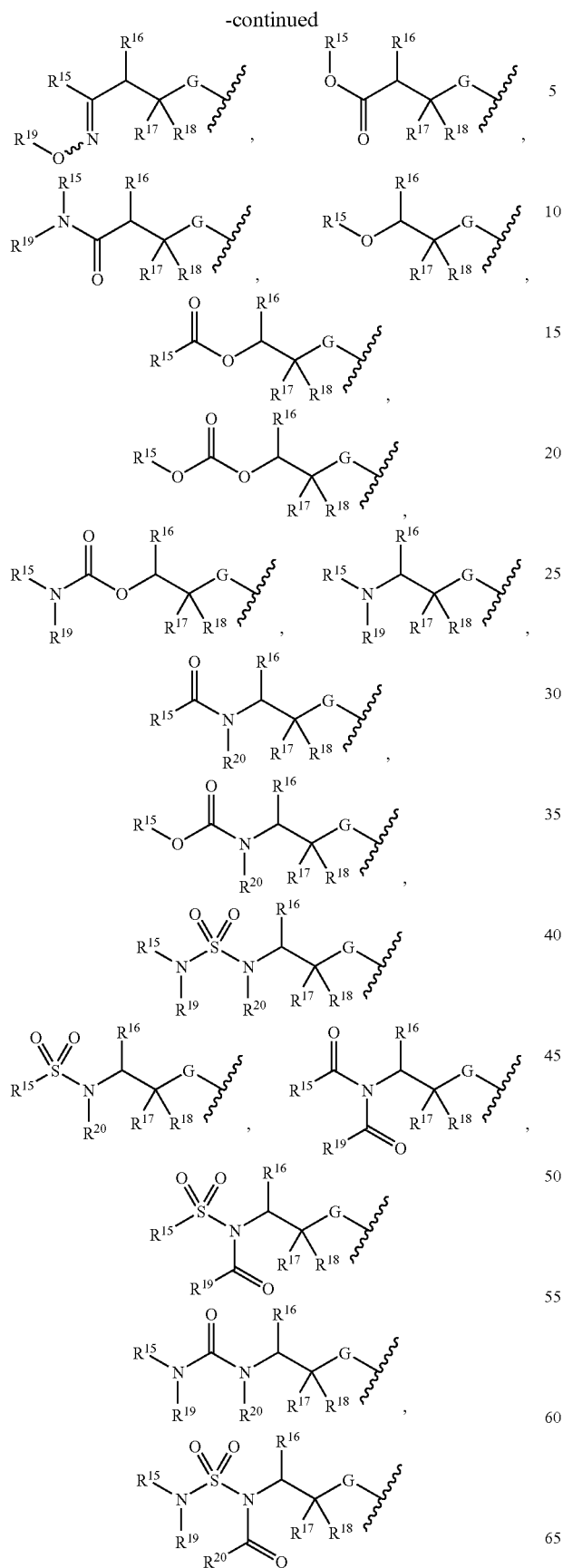

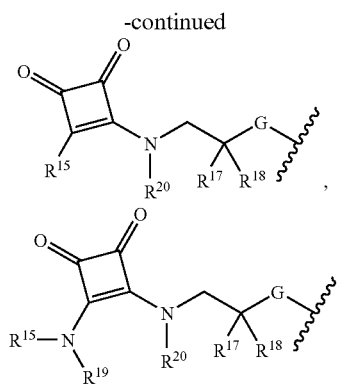

wherein G is NH or O; and $R^{15}$, $R^{16}$, $R^{17}$, $R^{18}$, $R^{19}$, $R^{20}$, $R^{21}$, $R^{22}$, $R^{23}$, $R^{24}$ and $R^{25}$ can be the same or different, each being independently selected from the group consisting of H, alkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; (iv) likewise independently $R^{15}$ and $R^{20}$ are connected to each other to form a four to eight-membered heterocyclyl; (v) likewise independently $R^{22}$ and $R^{23}$ are connected to each other to form a three to eight-membered cycloalkyl or a four to eight-membered heterocyclyl; and (vi) likewise independently $R^{24}$ and $R^{25}$ are connected to each other to form a three to eight-membered cycloalkyl or a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

2. The compound of claim 1, wherein $R^1$ is $NR^9R^{10}$, and $R^9$ is H, $R^{10}$ is H, or $R^{14}$ wherein $R^{14}$ is H, alkyl, aryl, heteroaryl, cycloalkyl, alkyl-aryl, alkyl-heteroaryl, arylalkyl, alkenyl, alkynyl or heteroaryl-alkyl.

3. The compound of claim 2, wherein $R^{14}$ is selected from the group consisting of:

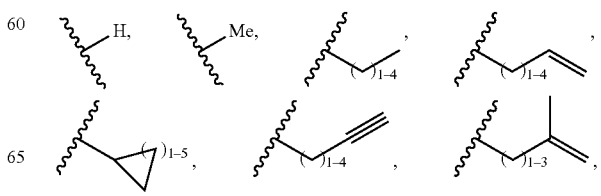

4. The compound of claim 1, wherein R² is selected from the group consisting of the following moieties:

5. The compound of claim 1, wherein $R^3$ is selected from the group consisting of:
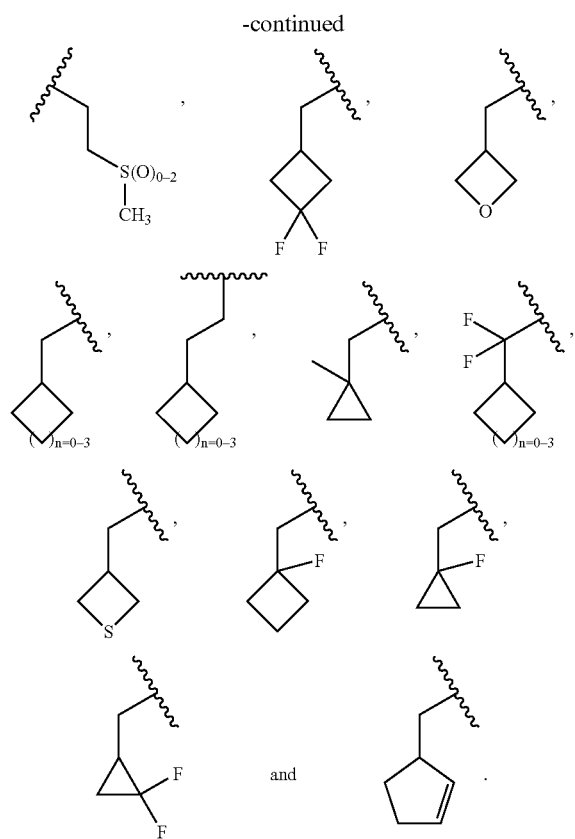
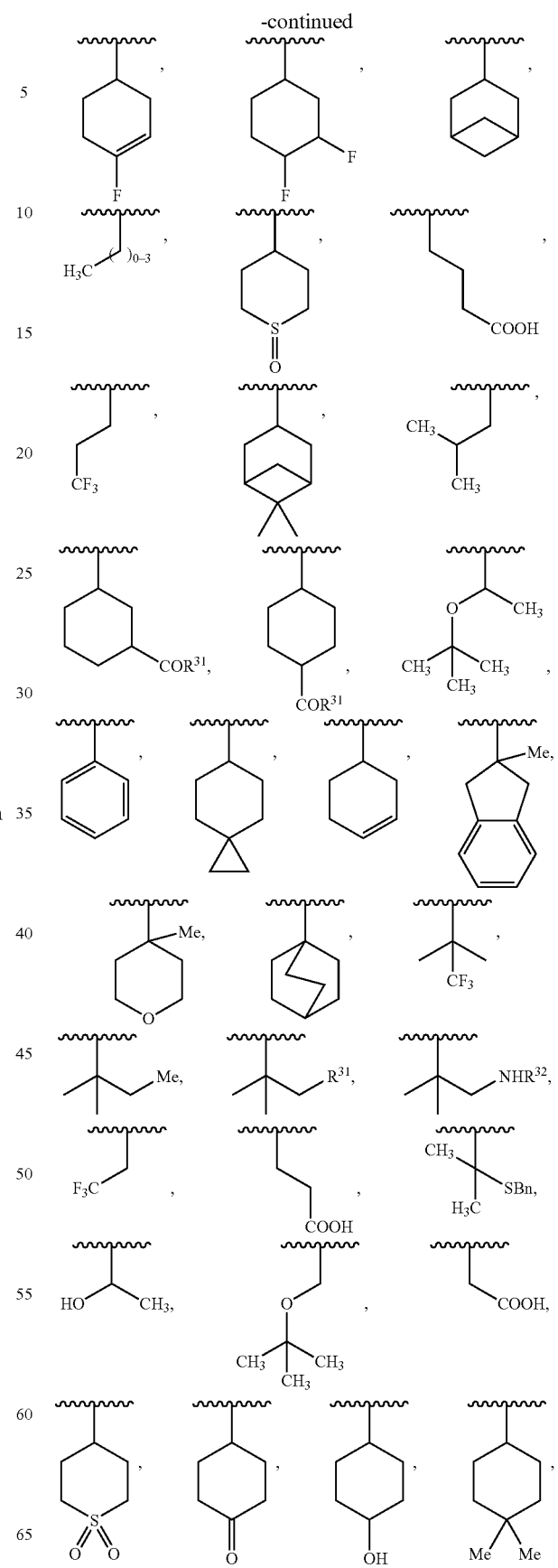
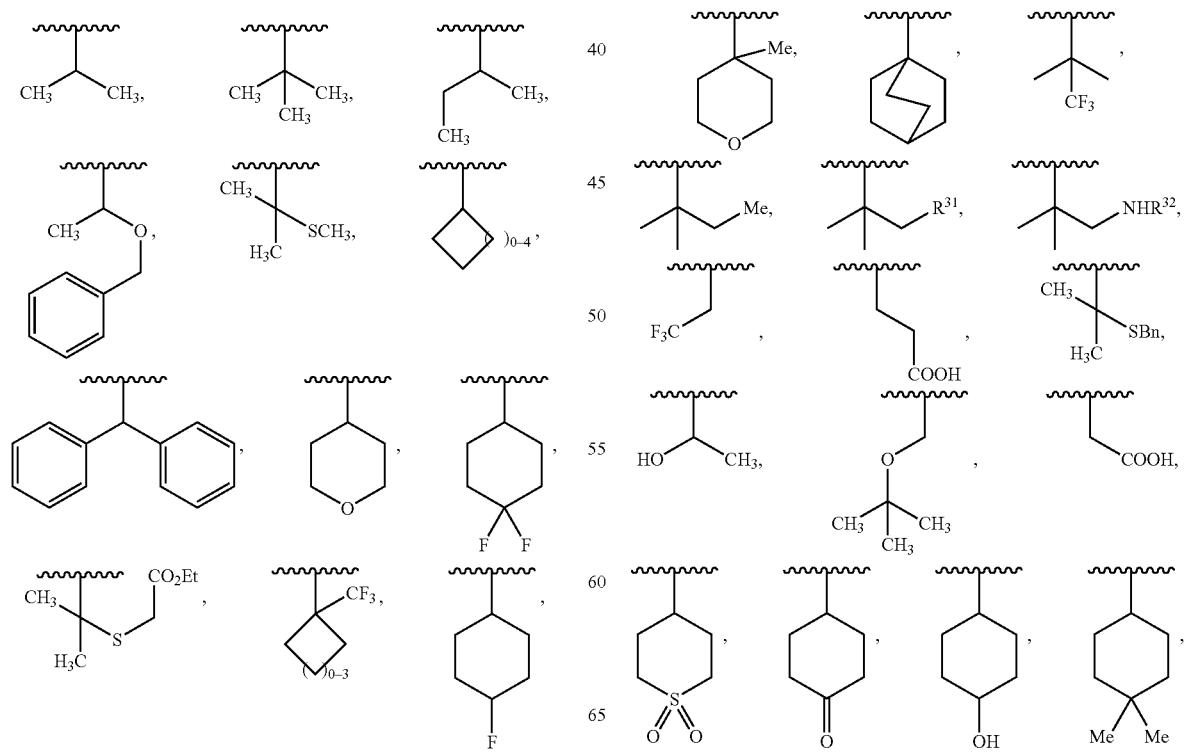

-continued
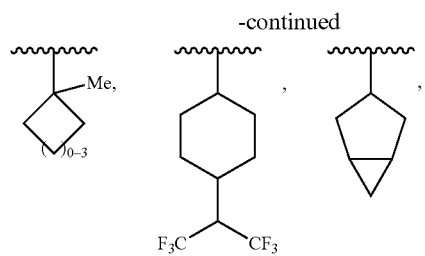
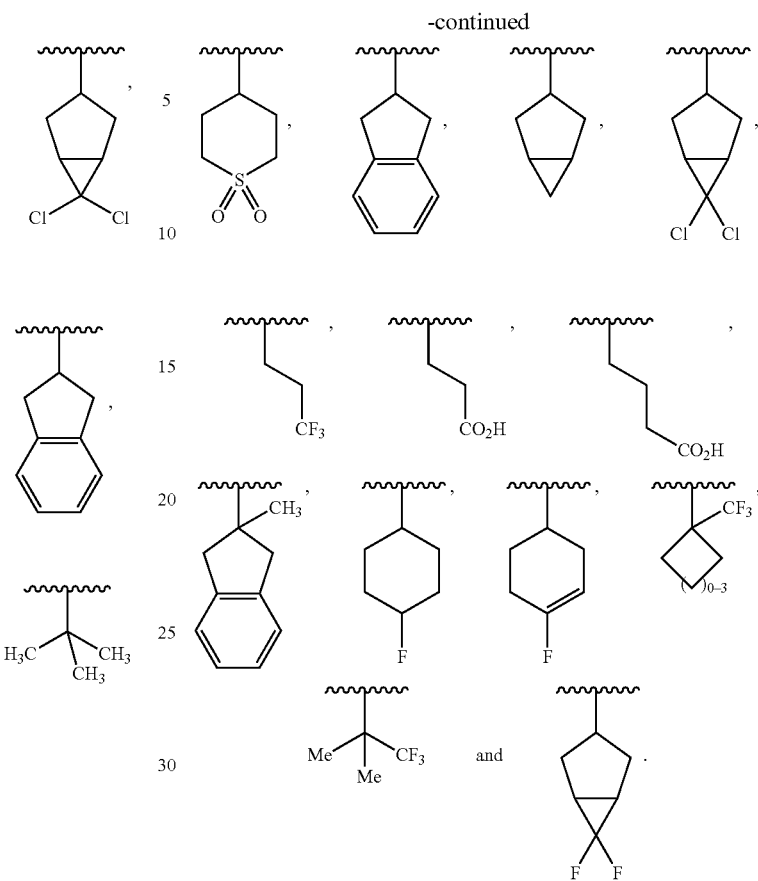
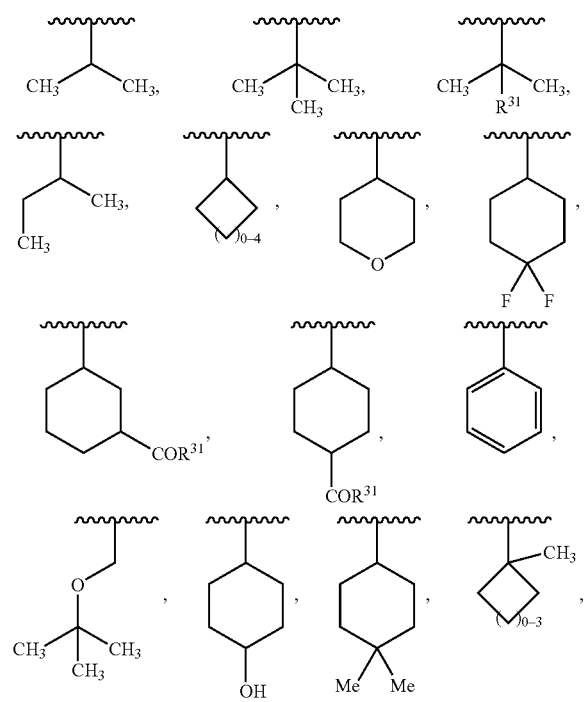
wherein $R^{31}$ is OH or O-alkyl; and
$R^{32}$ is H, C(O)CH$_3$, C(O)OtBu or C(O)N(H)tBu.
6. The compound of claim 5, wherein $R^3$ is selected from the group consisting of the following moieties:
7. The compound of claim 1, wherein G is NH.
8. The compound of claim 7, wherein Y is selected from the following moieties:
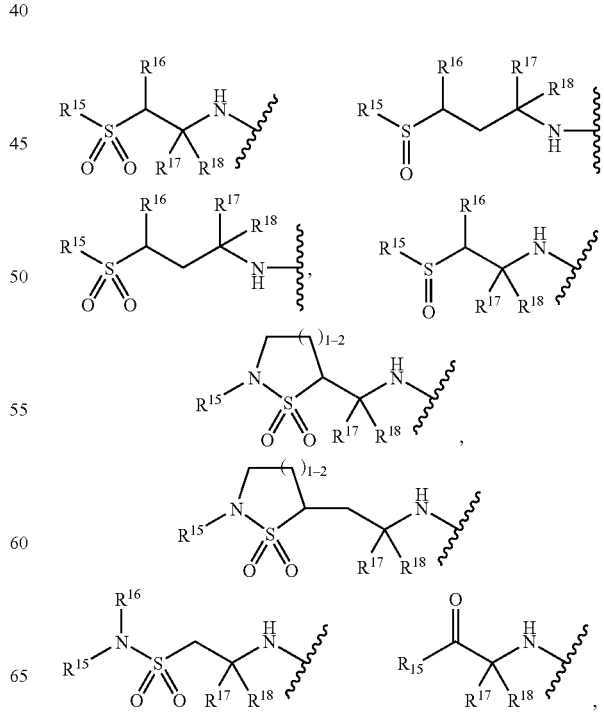

-continued

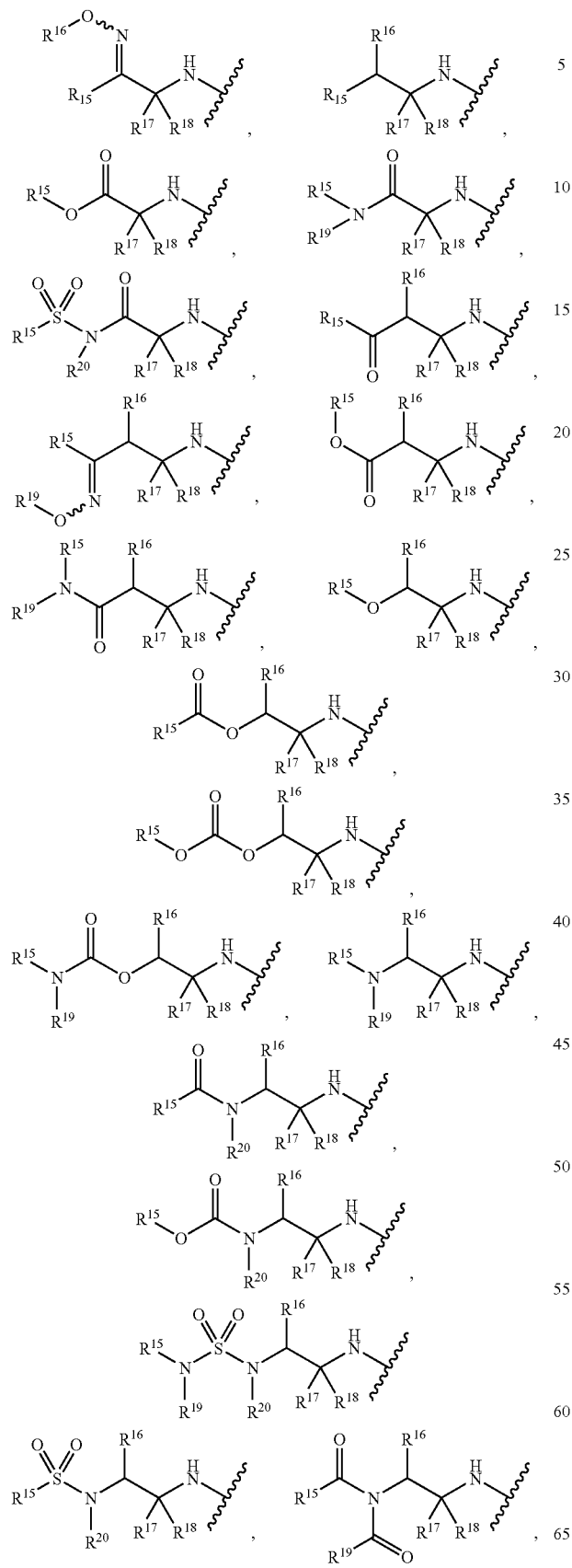

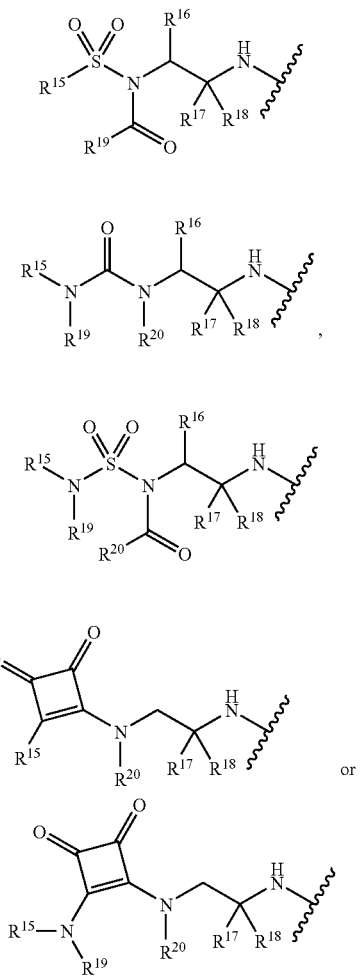

wherein $R^{15}$, $R^{16}$, $R^{17}$, $R^{18}$, $R^{19}$, $R^{20}$, $R^{21}$, $R^{22}$, $R^{23}$, $R^{24}$, and $R^{25}$ each being independently selected from the group consisting of H, alkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to from a three to eight-membered cycloalkyl or heterocyclyl, (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

9. The compound of claim 8, wherein the moiety:
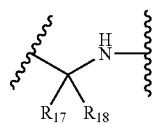
is selected from the following:
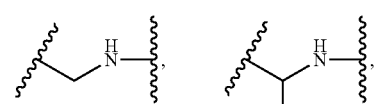
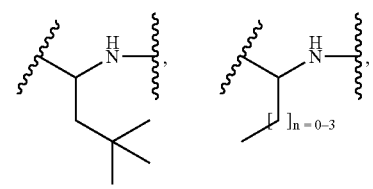
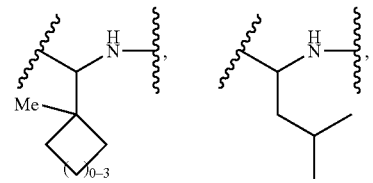
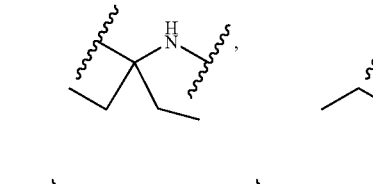
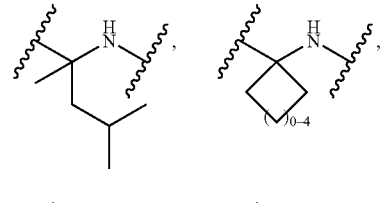
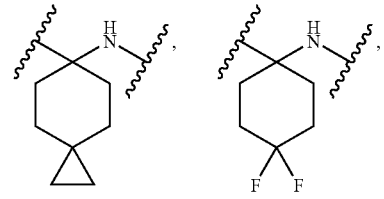
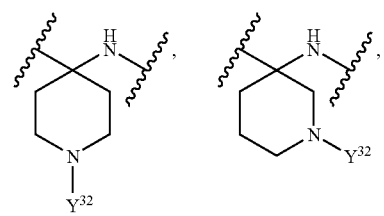
-continued
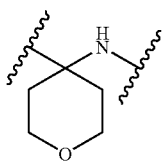 and 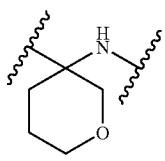
wherein $Y^{32}$ is selected from the group consisting of:
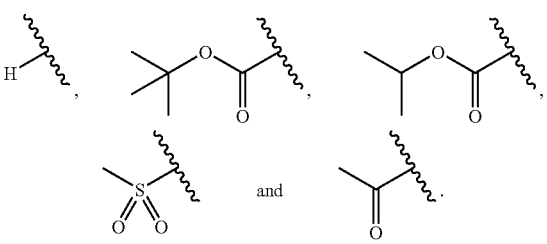
10. The compound of claim 8, wherein Y is selected from:
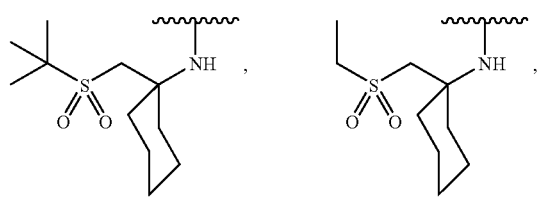
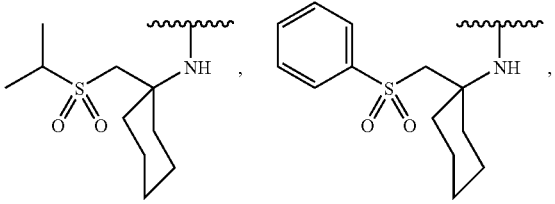
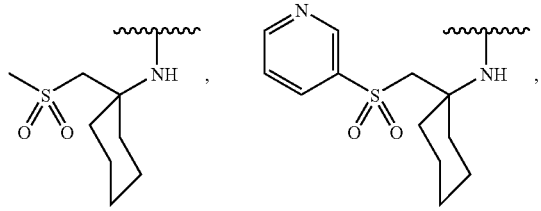
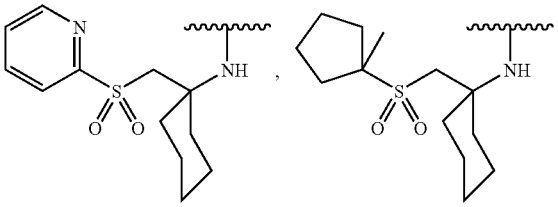
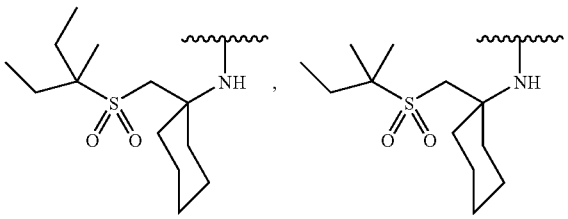

-continued
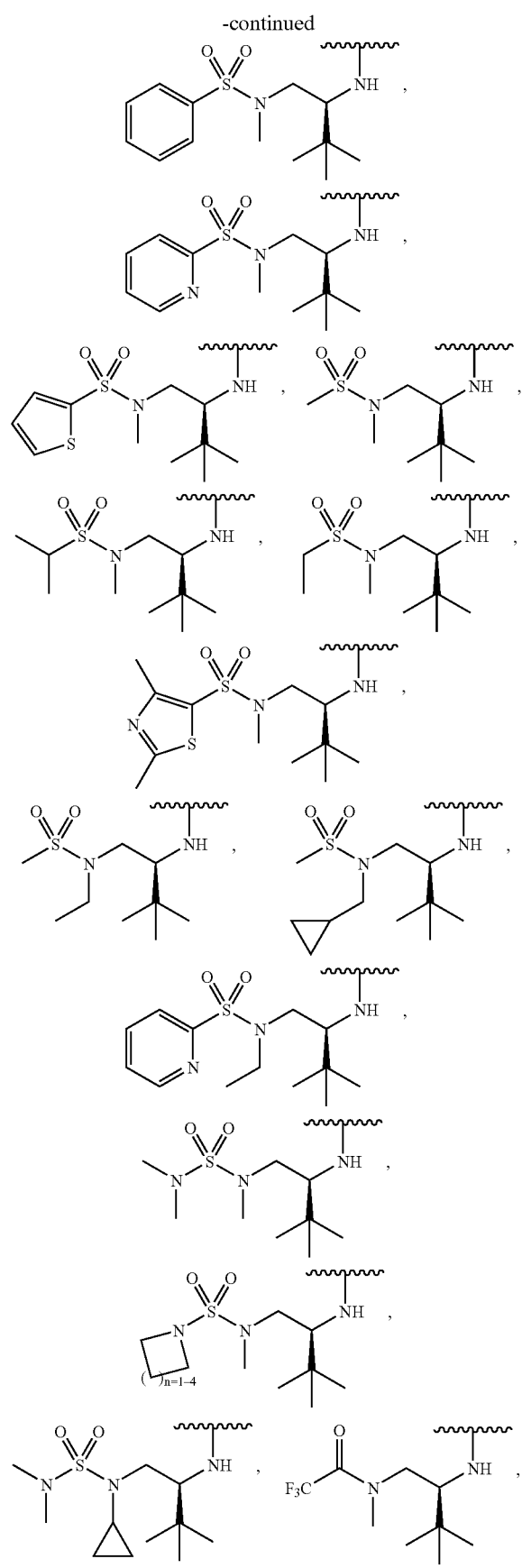
-continued
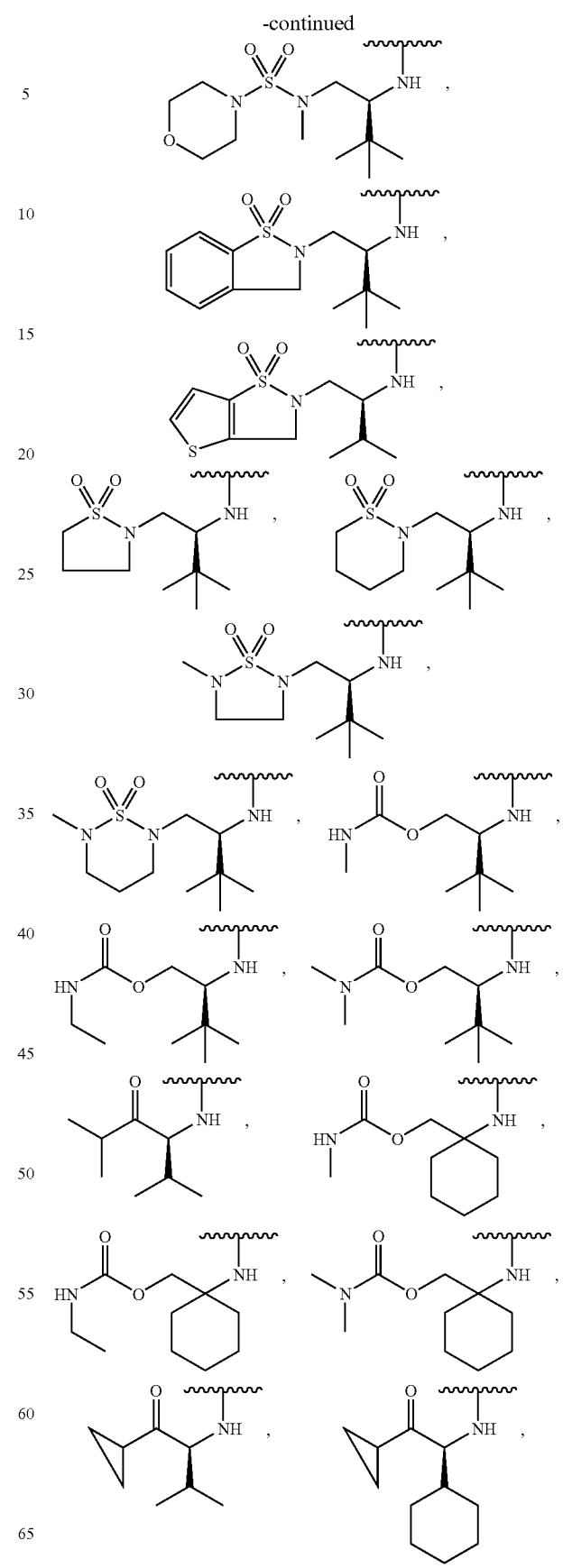

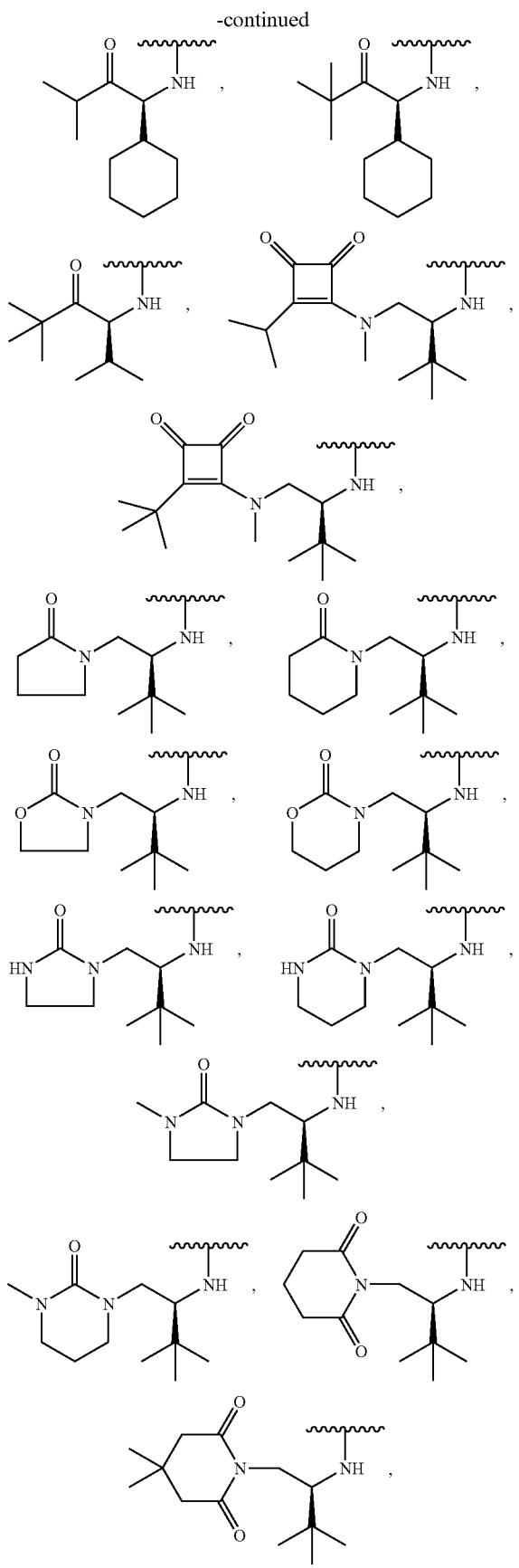
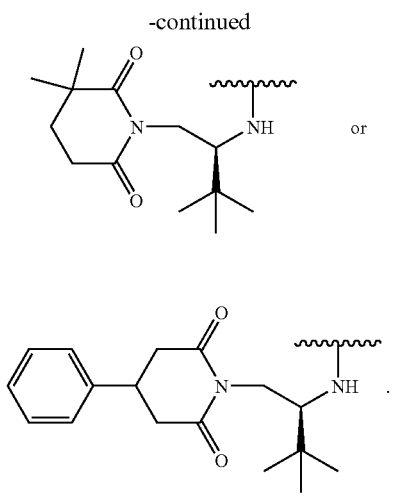
11. The compound of claim 1, wherein the moiety:
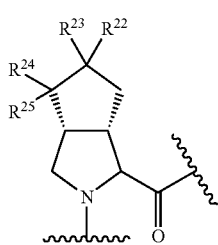
is selected from the following structures:
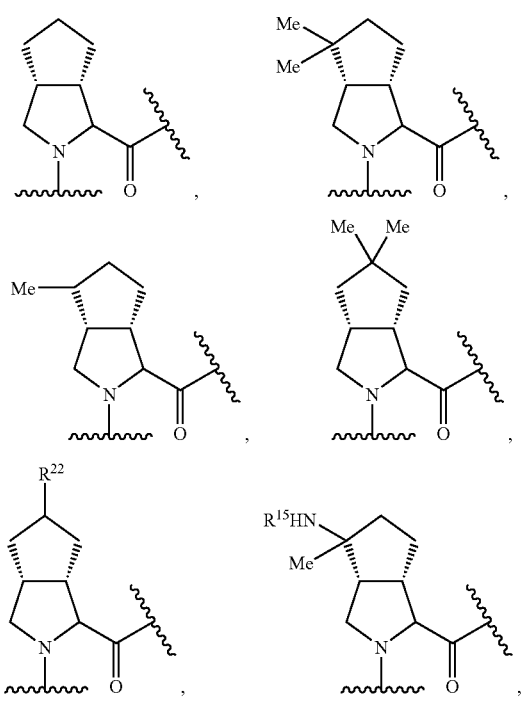

12. The compound of claim 1, wherein $R^1$ is $NHR^{14}$, where $R^{14}$ is selected from the group consisting of:
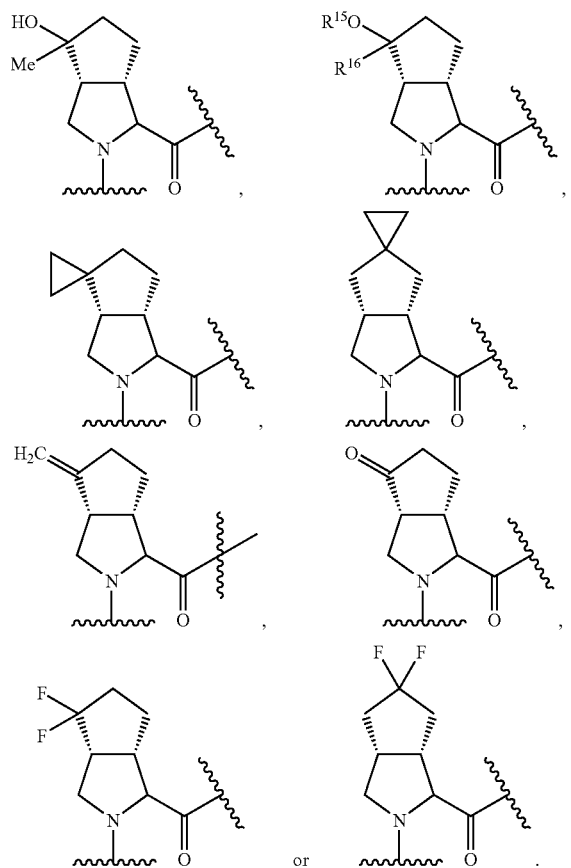
$R^2$ is selected from the group consisting of the following moieties:

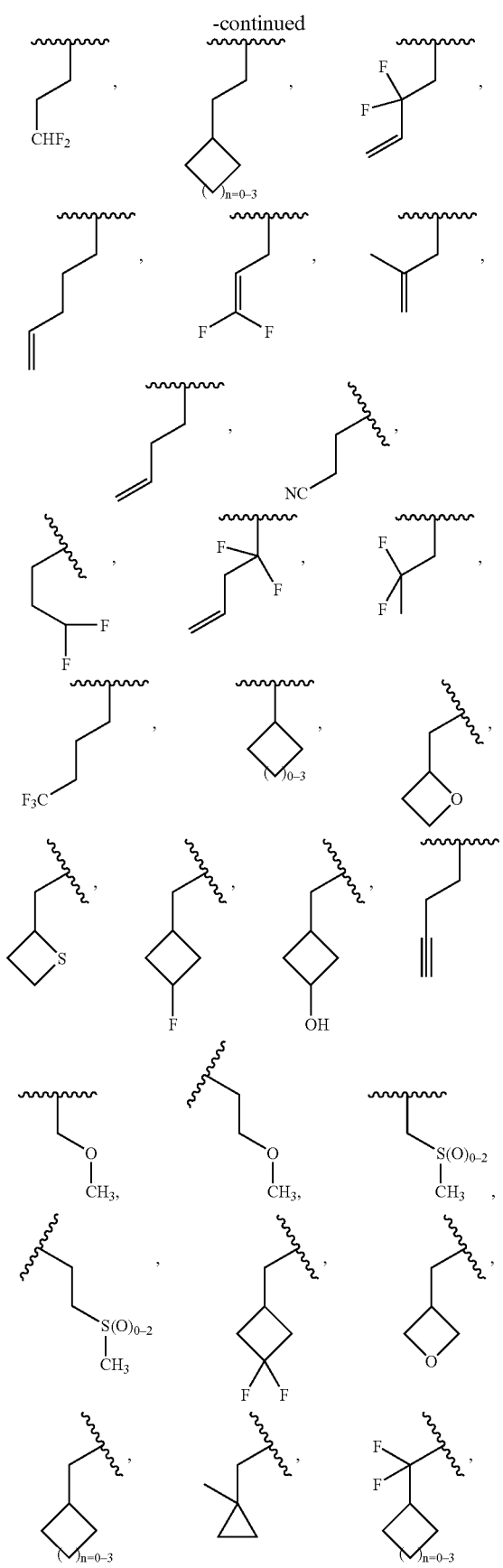
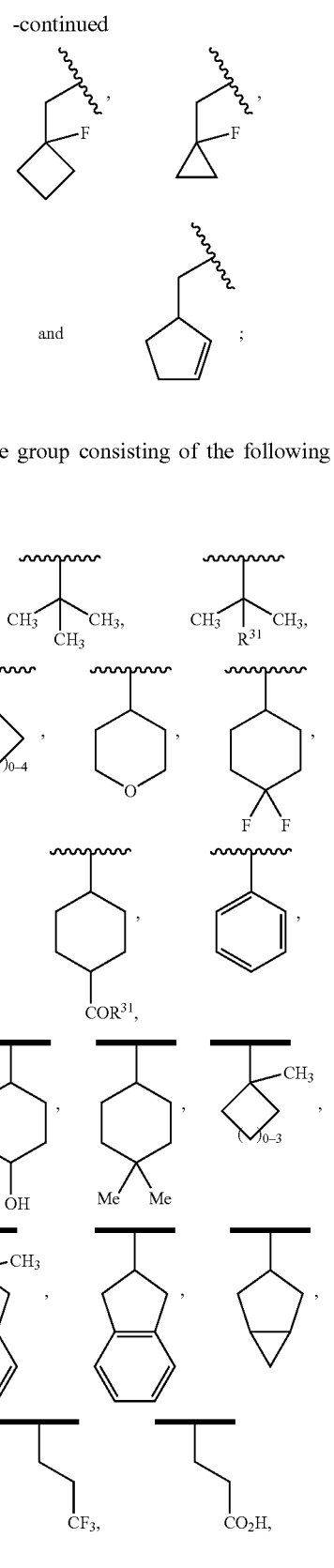
R[3] is selected from the group consisting of the following moieties:

331
-continued
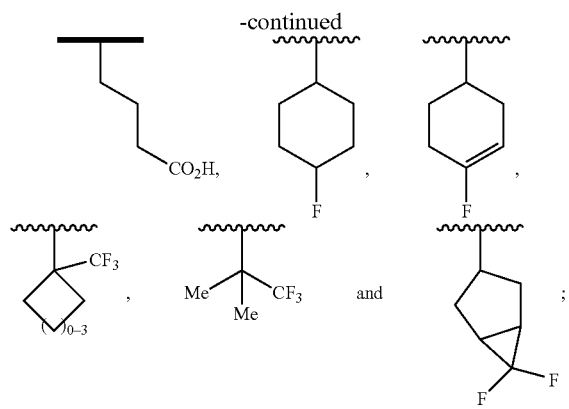
the moiety:
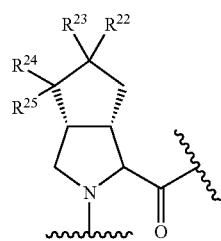
is selected from
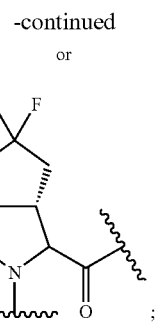
332
-continued or
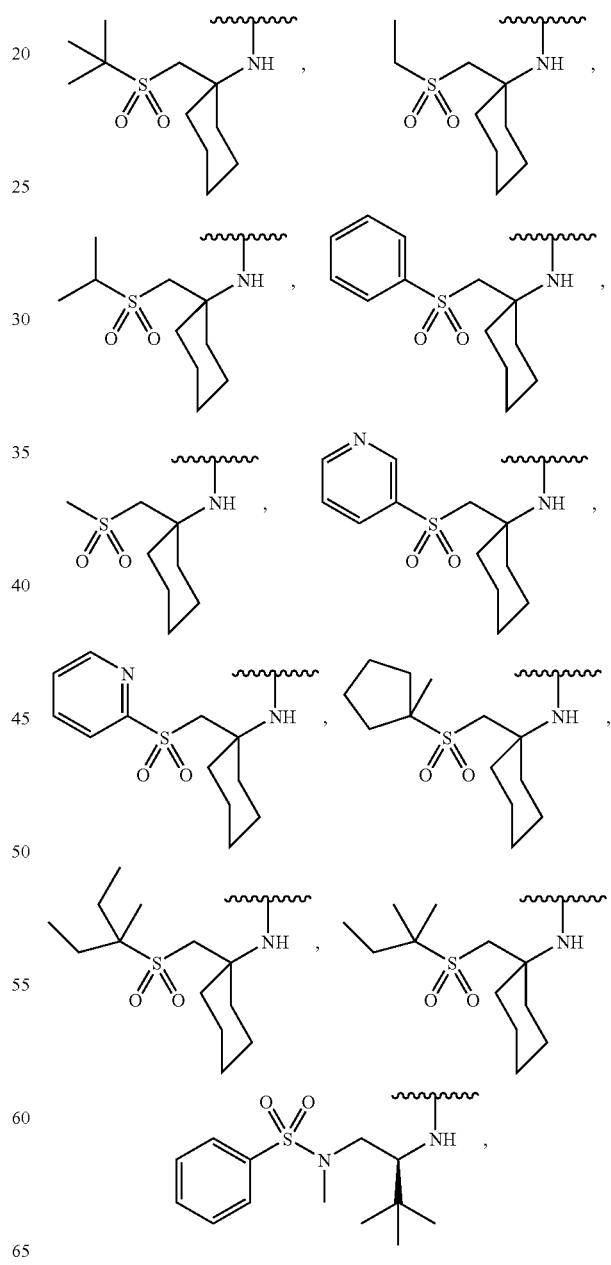
and Y is selected from:

-continued
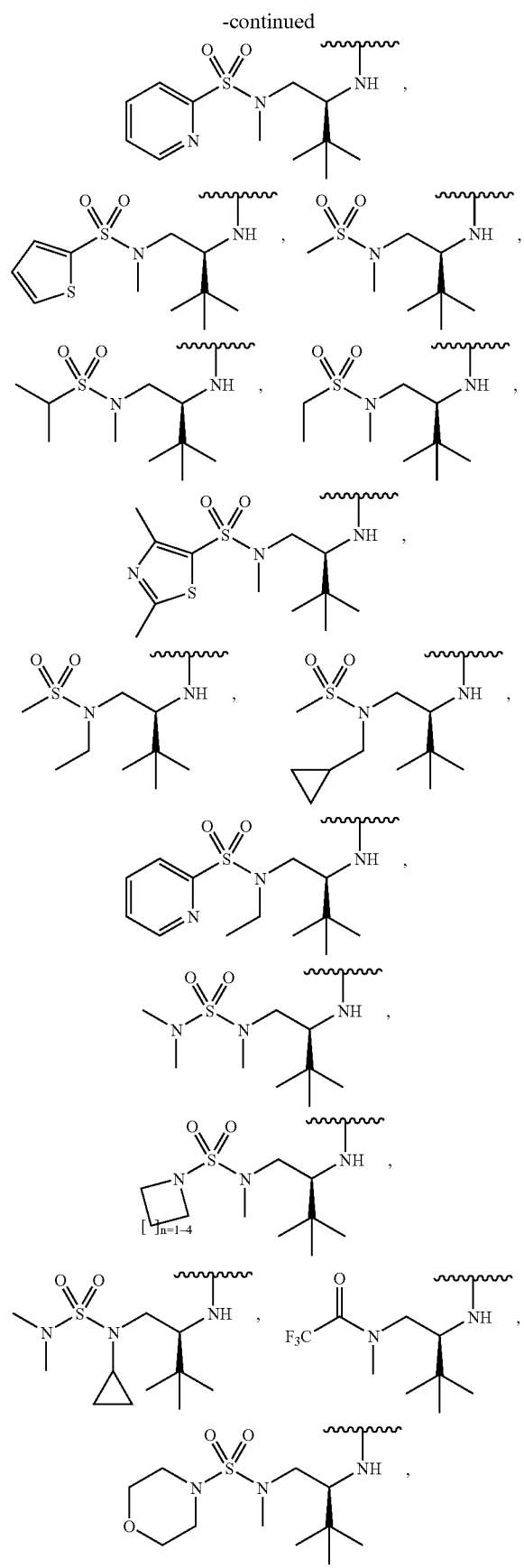
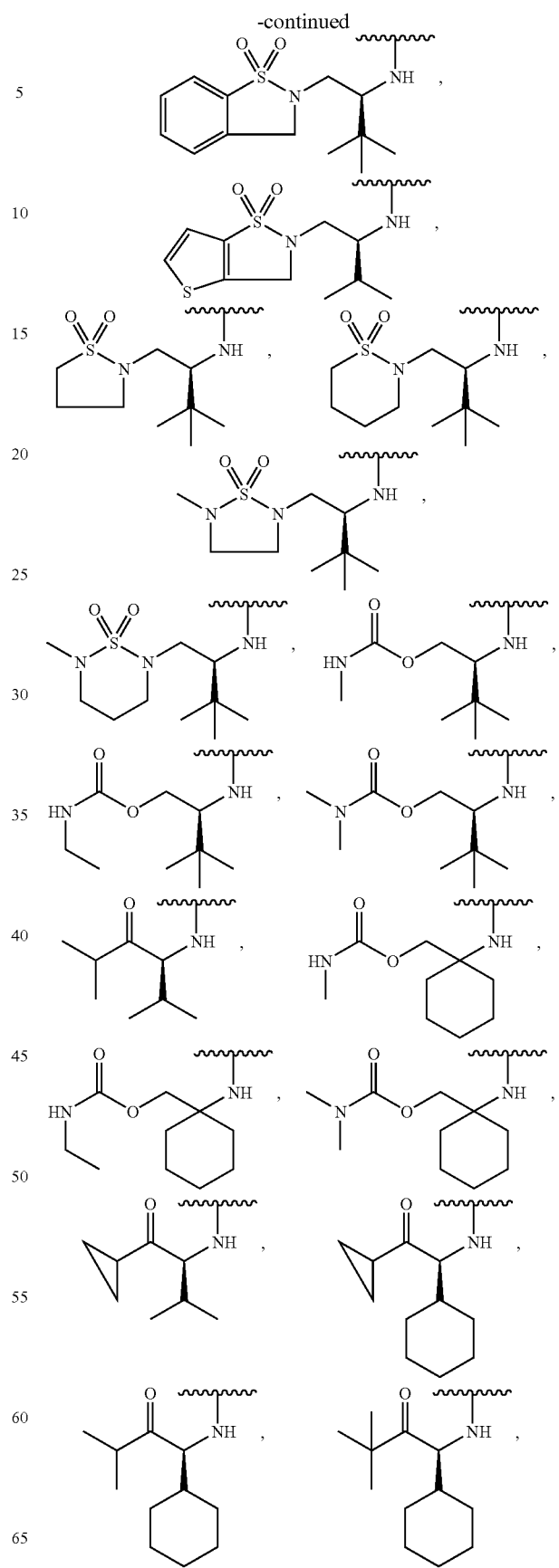

-continued

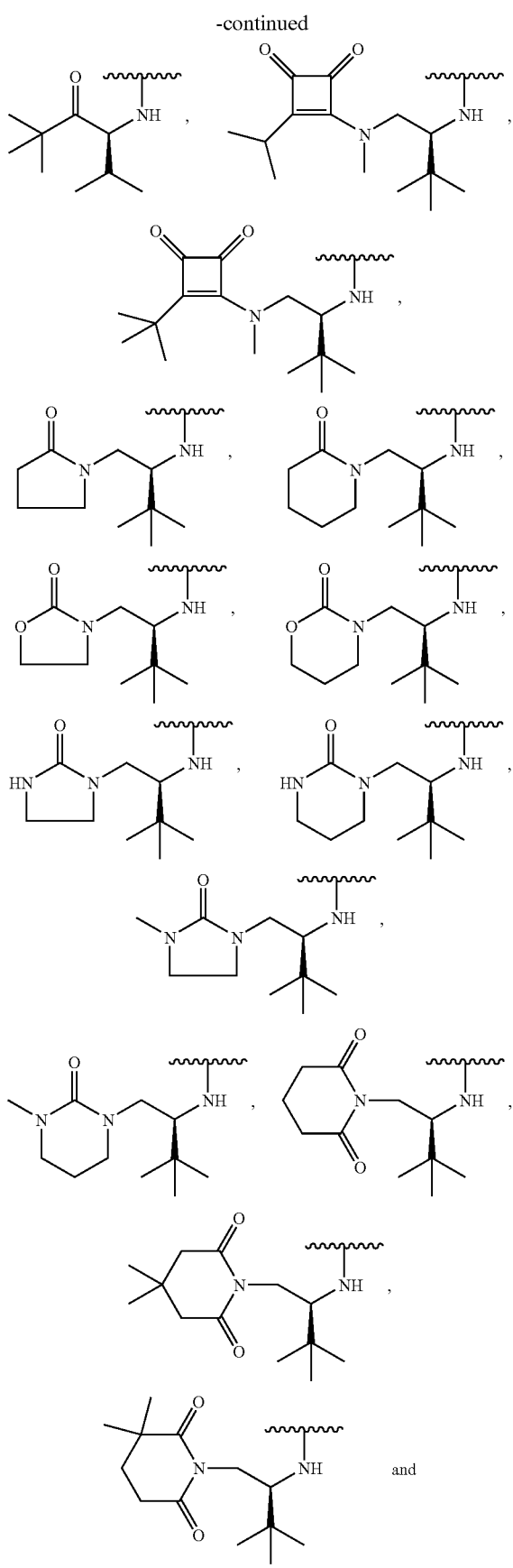

-continued

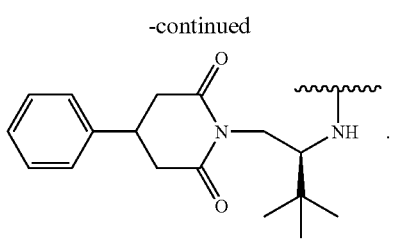

13. A pharmaceutical composition comprising as an active ingredient at least one compound of claim 1.

14. The pharmaceutical composition of claim 13 for use in treating an infection by HCV.

15. The pharmaceutical composition of claim 14 additionally comprising at least one pharmaceutically acceptable carrier.

16. The pharmaceutical composition of claim 15, additionally containing at least one antiviral agent.

17. The pharmaceutical composition of claim 16, still additionally containing at least one interferon.

18. The pharmaceutical composition of claim 17, wherein said at least one antiviral agent is ribavirin and said at least one interferon is α-interferon or pegylated interferon.

19. A method of treating an infection by HCV, said method comprising administering to a patient in need of such treatment a pharmaceutical composition which comprises therapeutically effective amounts of at least one compound of claim 1.

20. The method of claim 19, wherein said administration is oral or subcutaneous.

21. A method of preparing a pharmaceutical composition for treating the an infection by the HCV, said method comprising bringing into intimate physical contact at least one compound of claim 1 and at least one pharmaceutically acceptable carrier.

22. A compound exhibiting HCV protease inhibitory activity, or enantiomers, stereoisomers, rotamers, tautomers, diastereomers or racemates of said compound, or a pharmaceutically acceptable salt, solvate or ester of said compound, said compound being selected from the compounds of structures listed below:

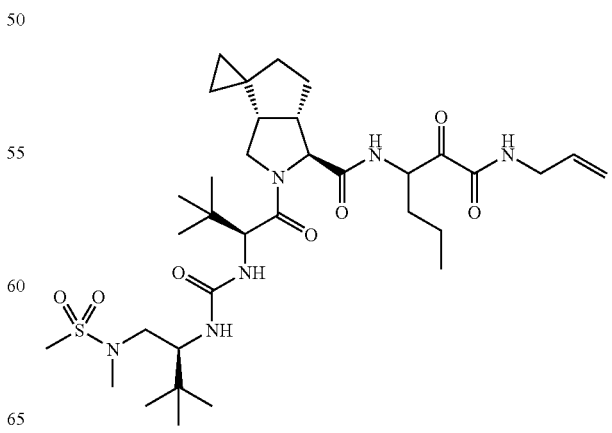

337
-continued
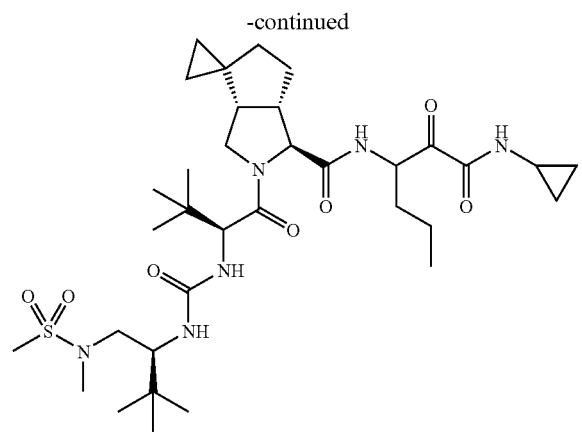
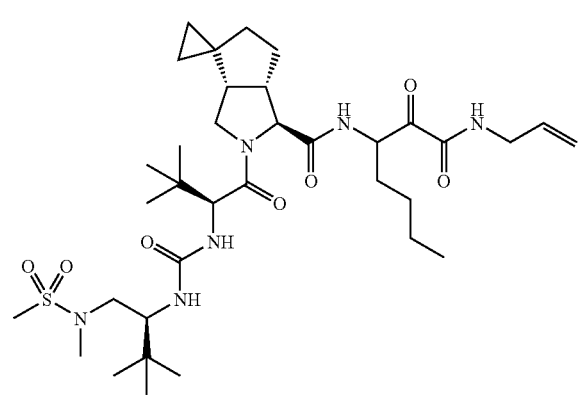
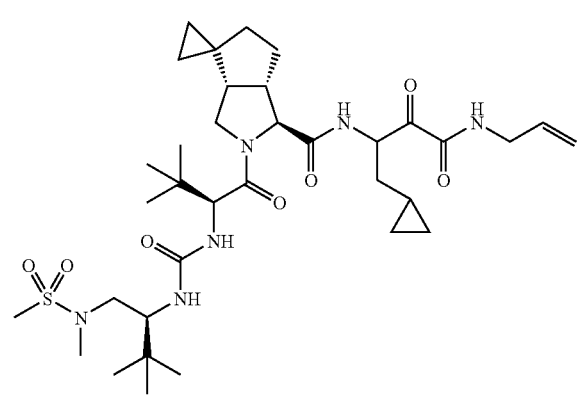
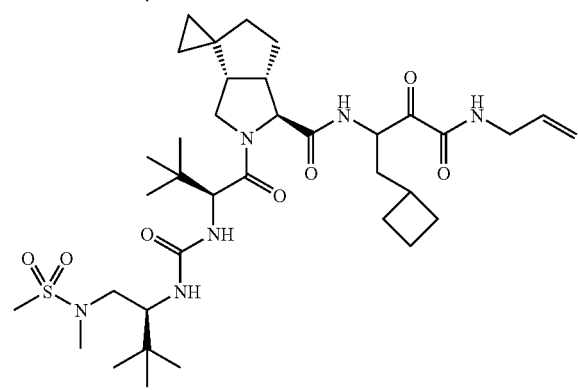
338
-continued
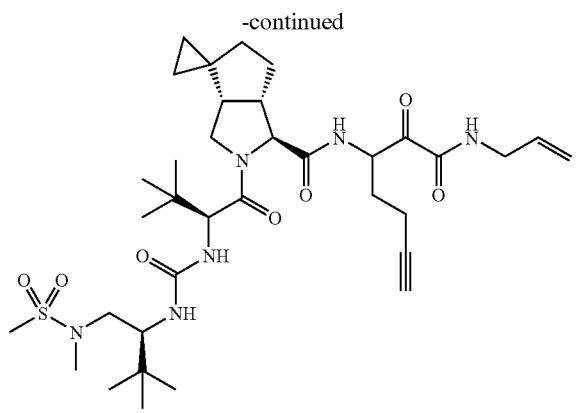
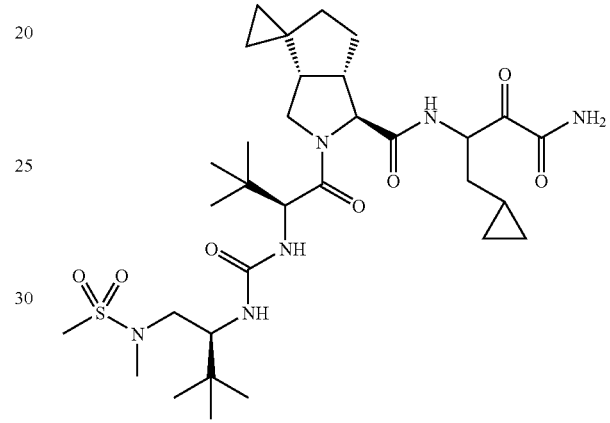
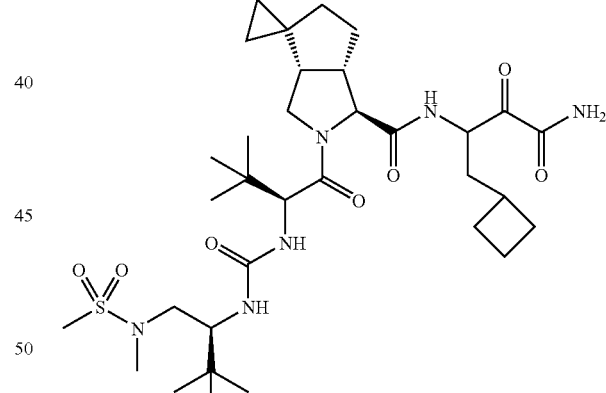
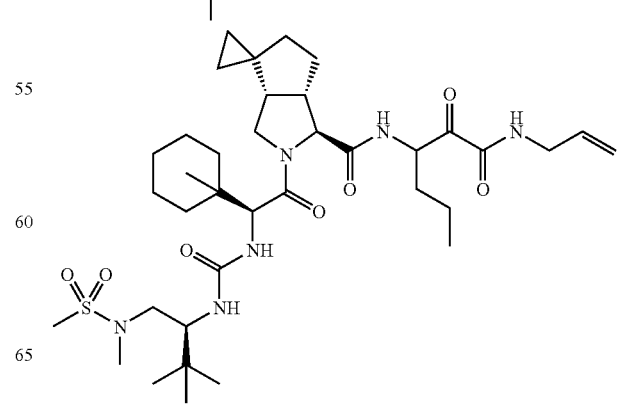

339

-continued

340

-continued

-continued
341
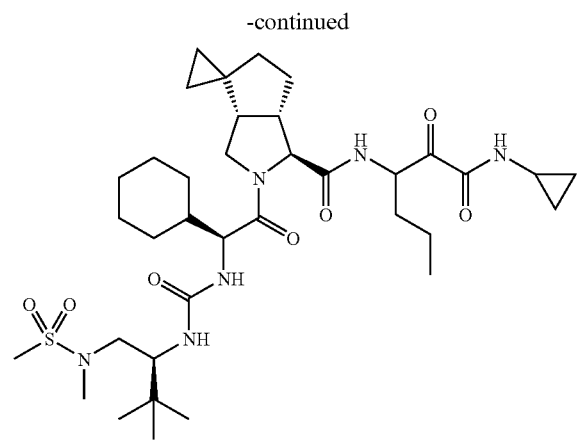
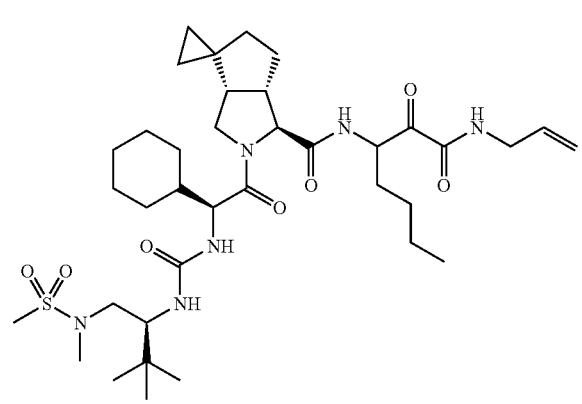
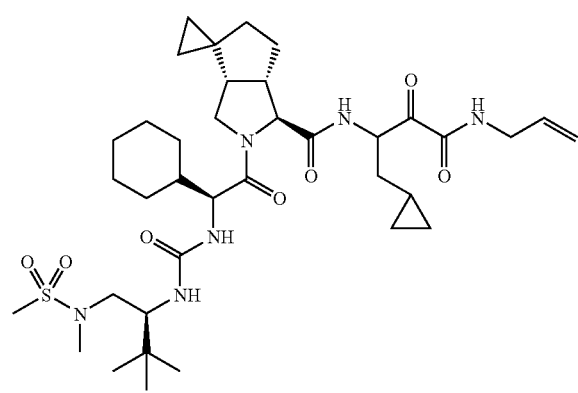
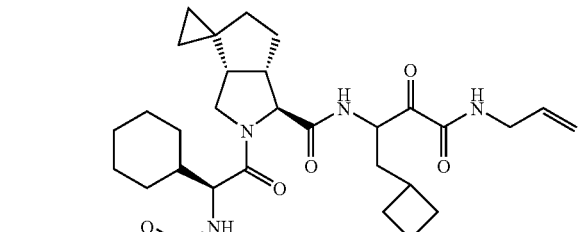
342
-continued
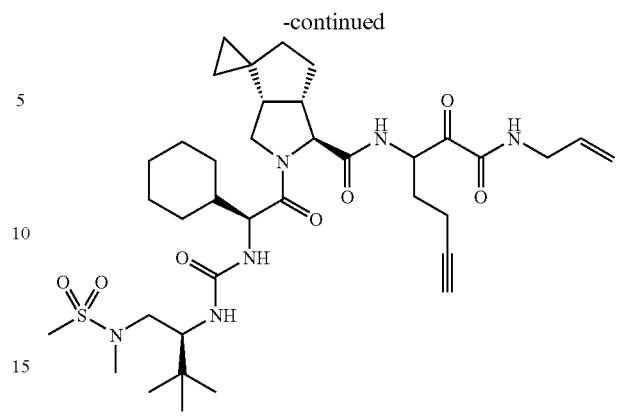
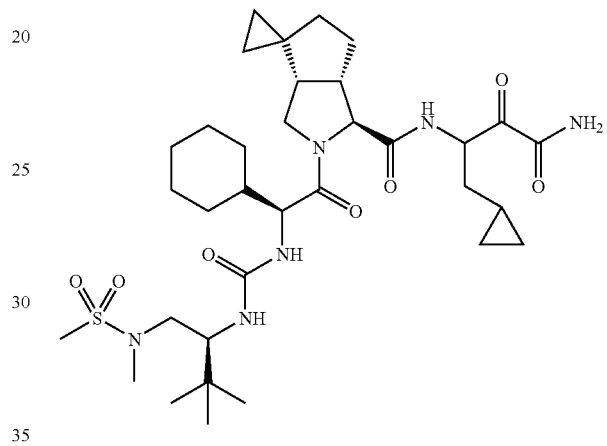
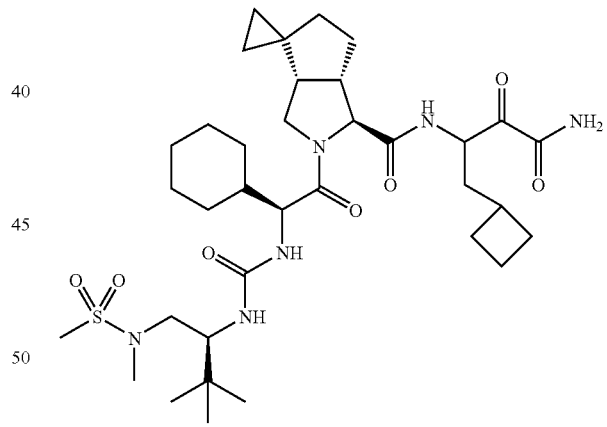
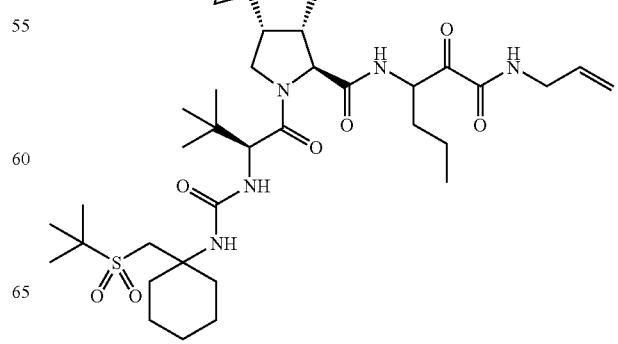

343
-continued
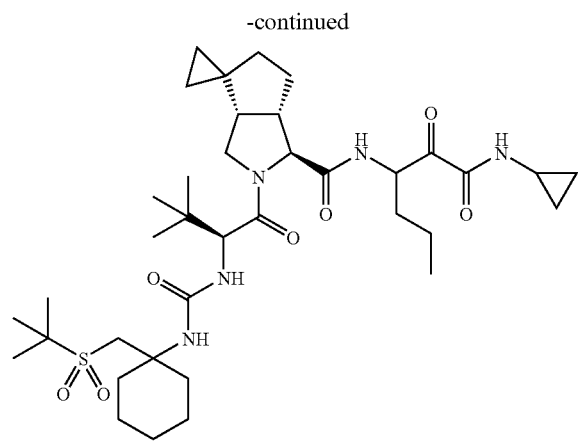
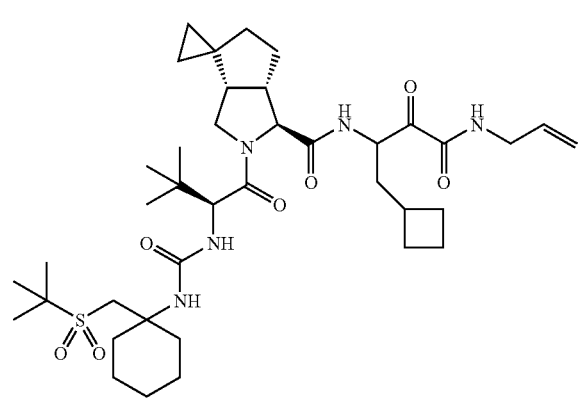
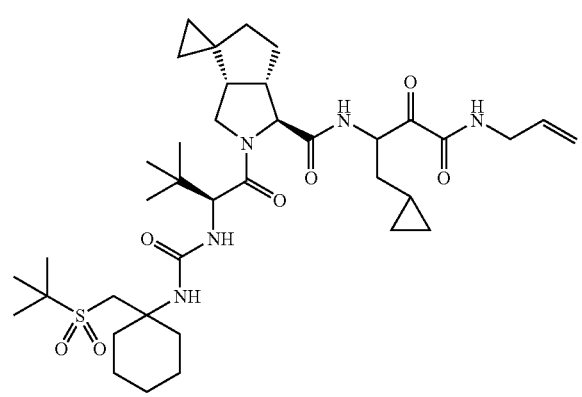
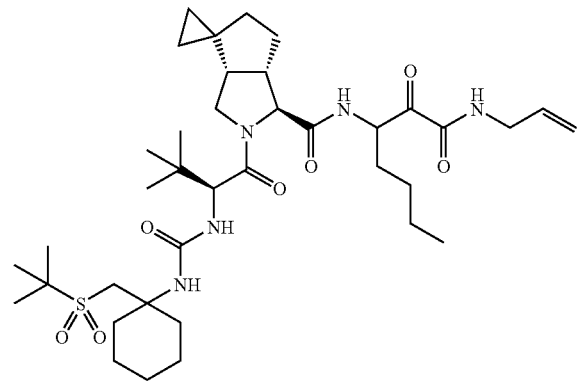
344
-continued
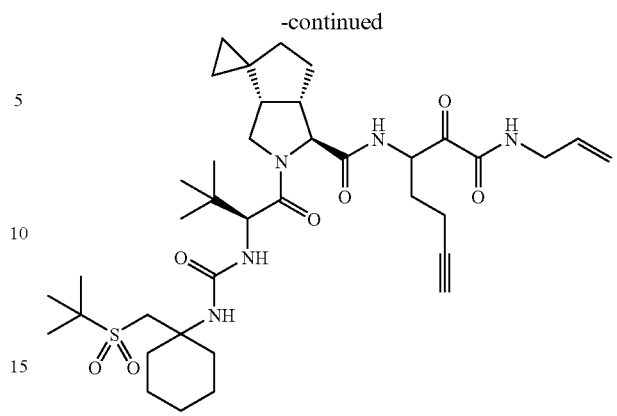
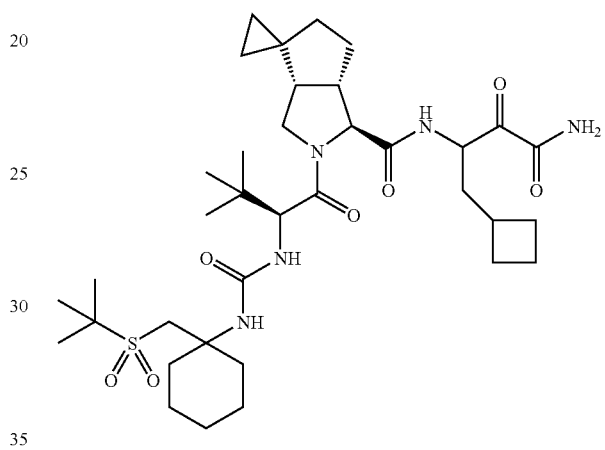
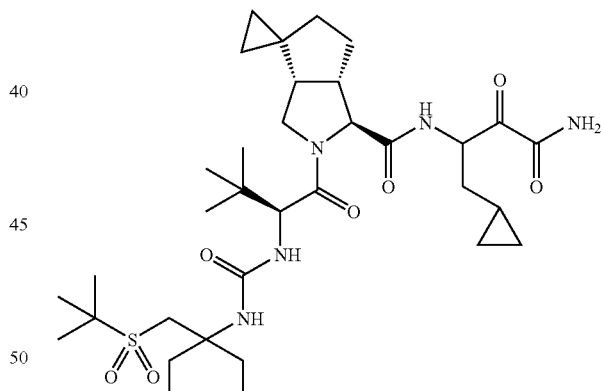
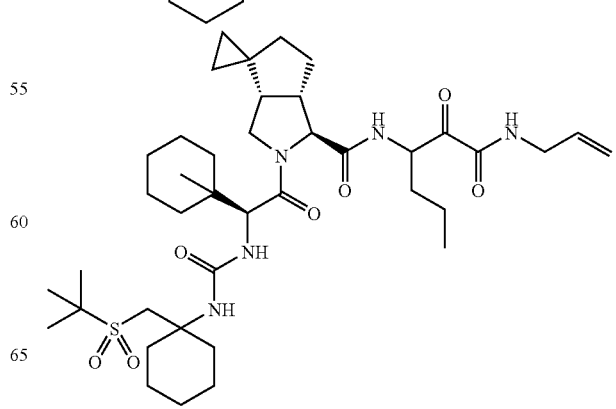

345
-continued
346
-continued
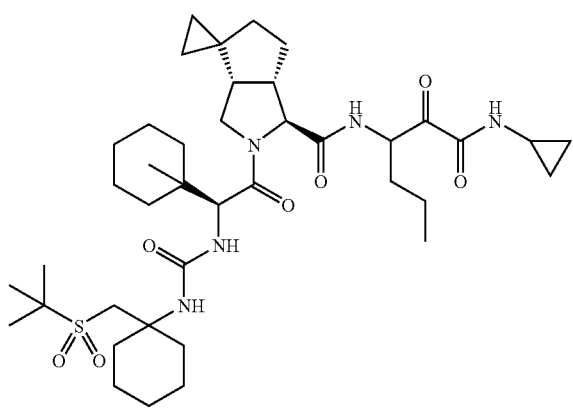
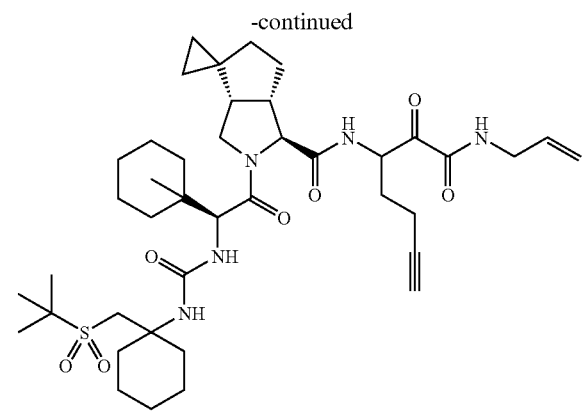

347
-continued
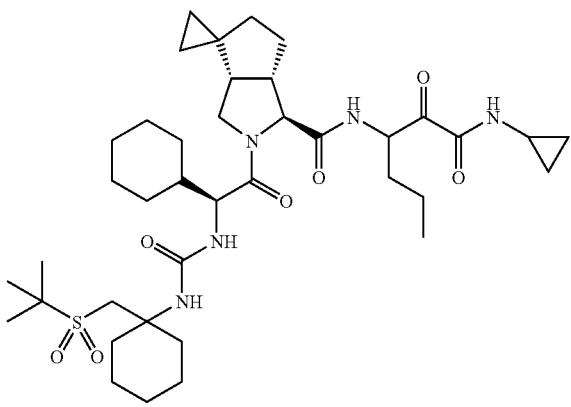
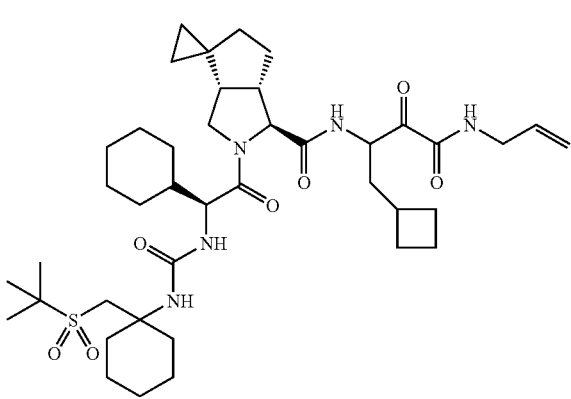
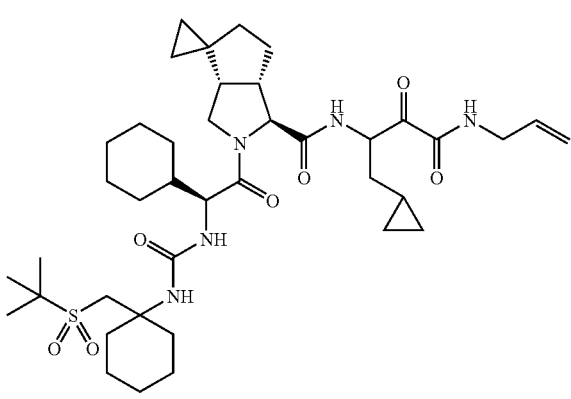
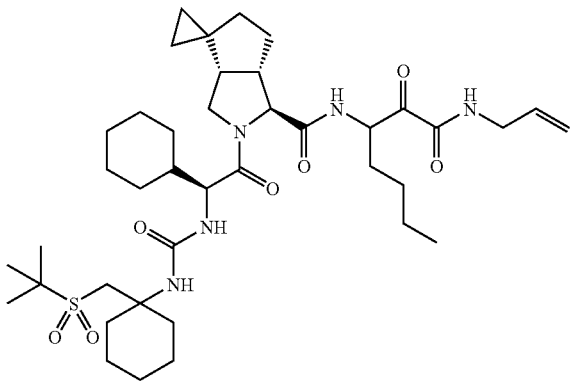
348
-continued
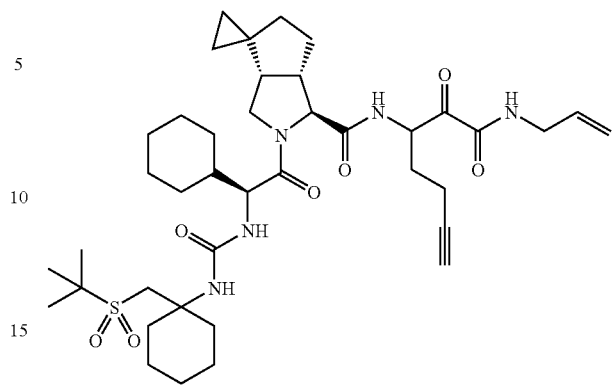
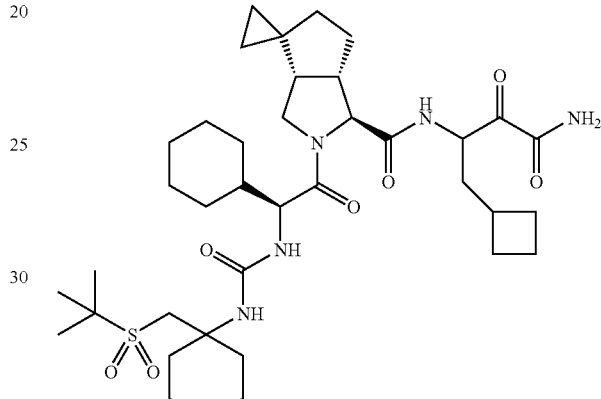
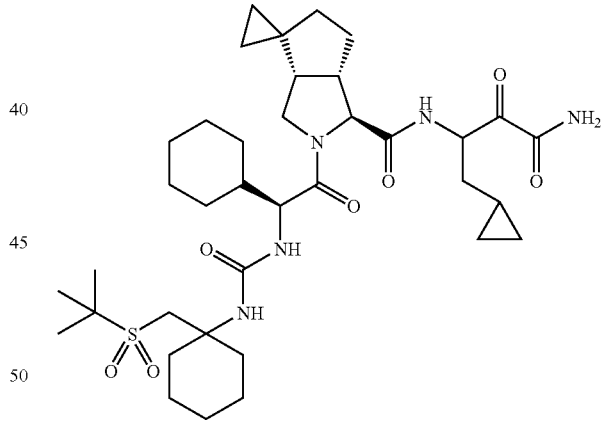
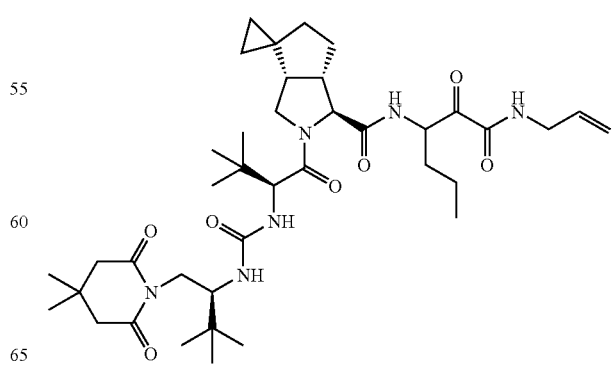

349
-continued
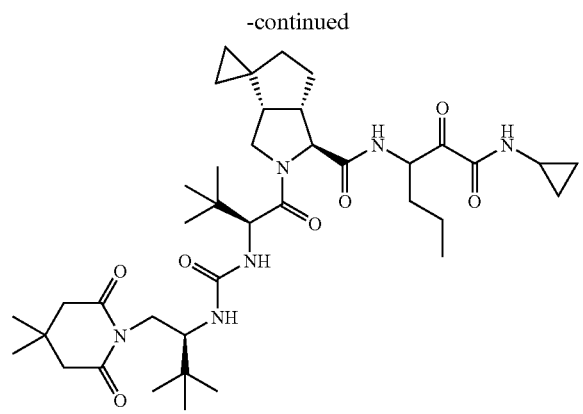
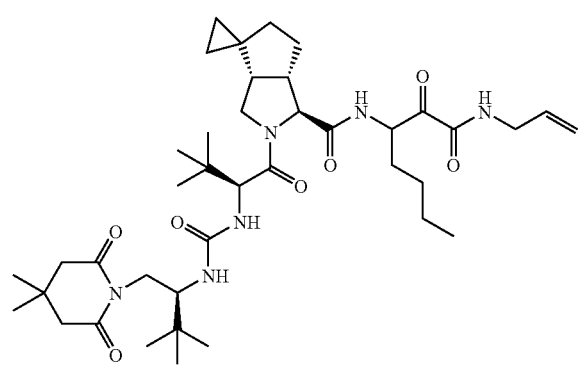
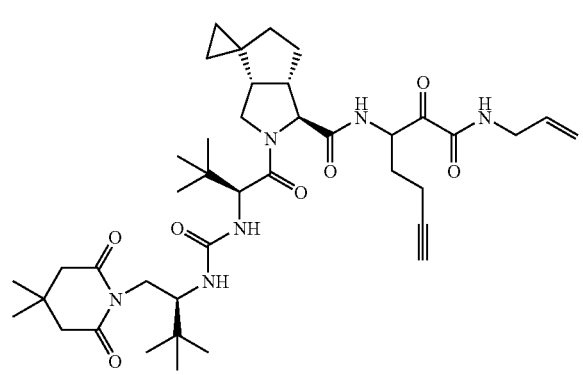
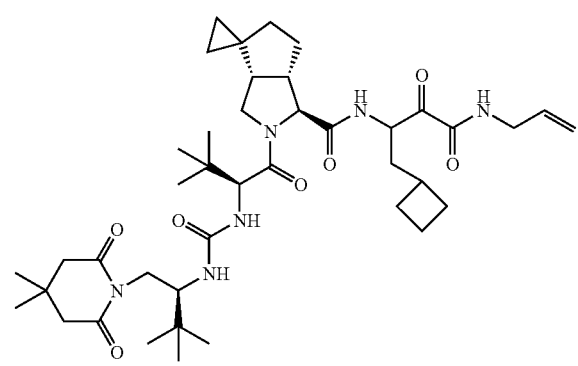
350
-continued
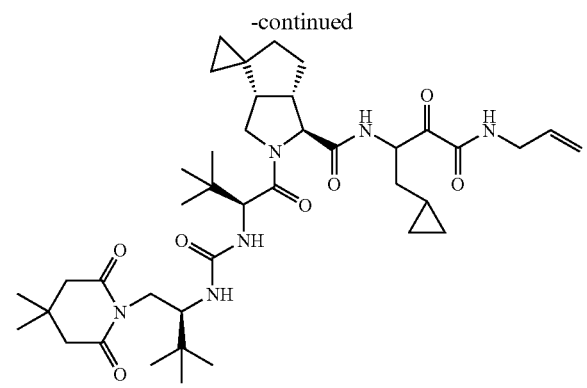
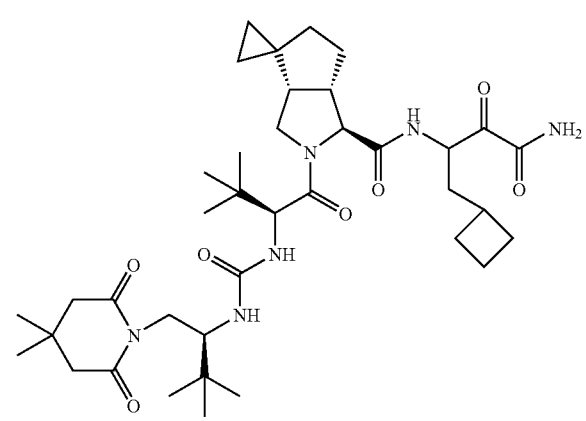
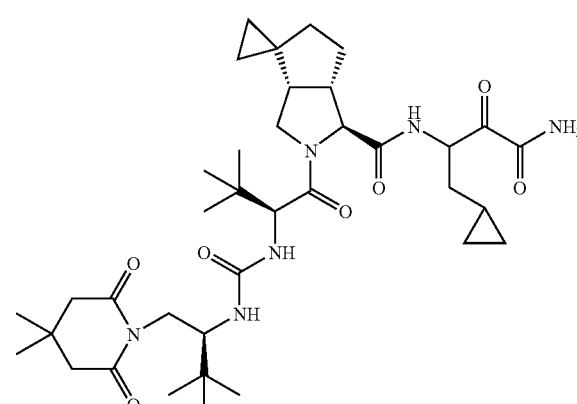
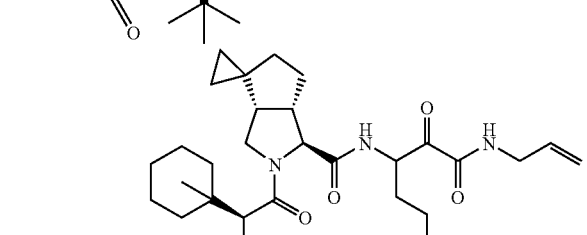
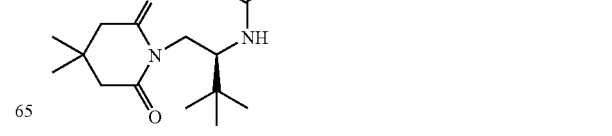

351
-continued
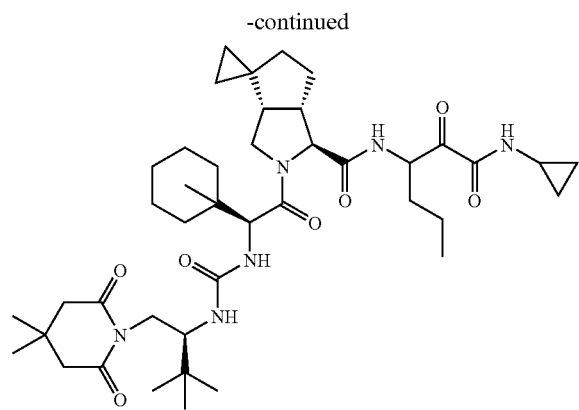
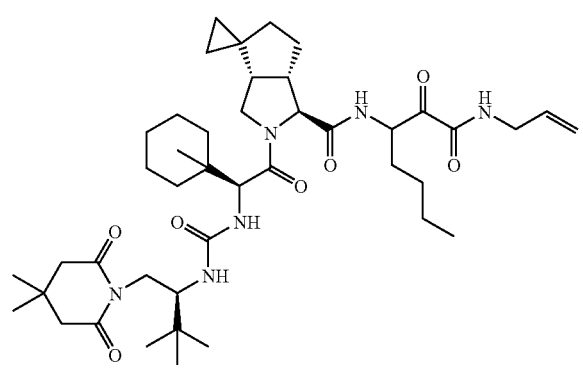
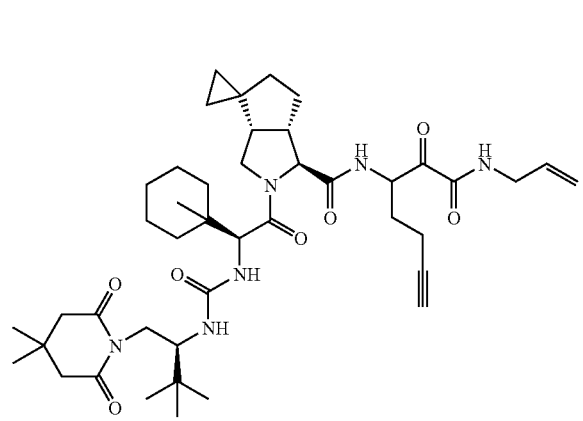
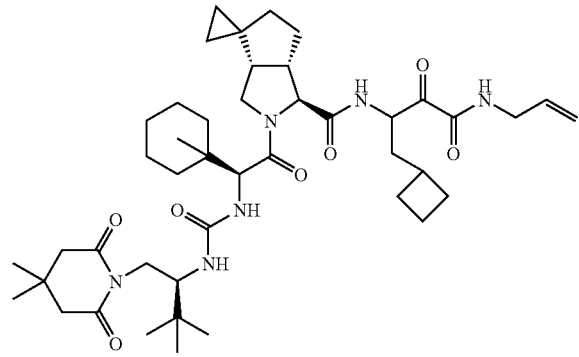
352
-continued
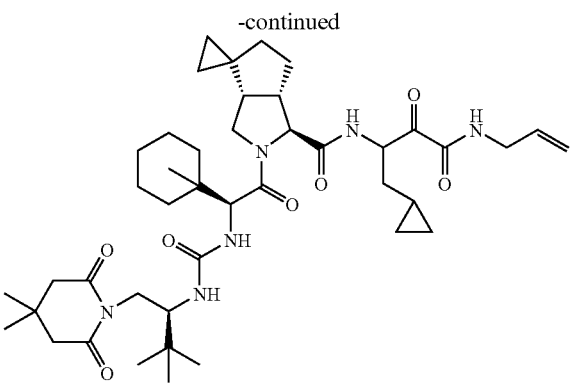
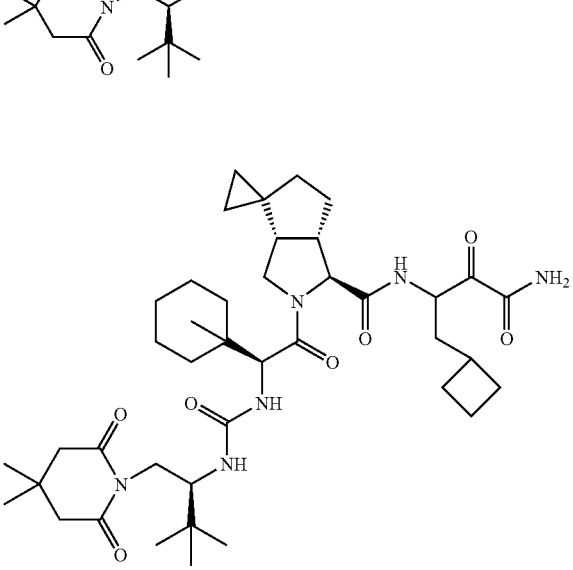
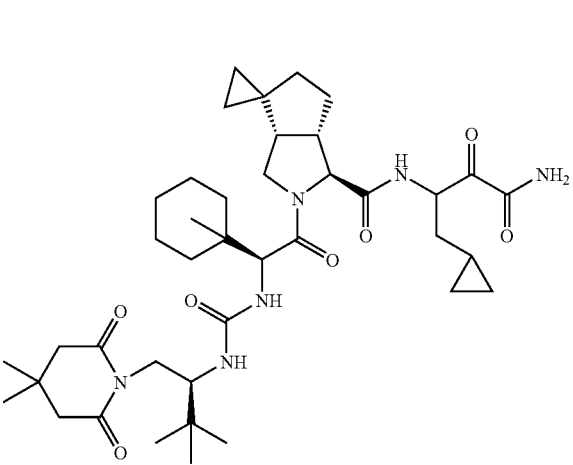
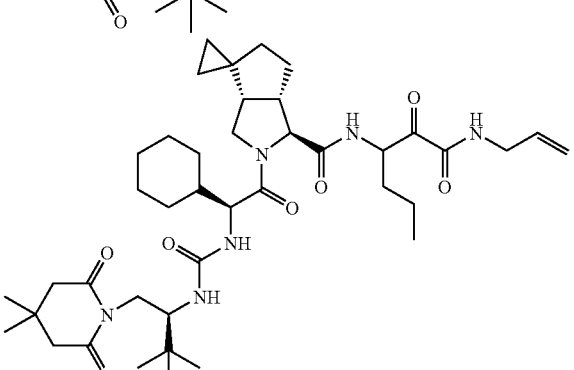

353 354
-continued -continued
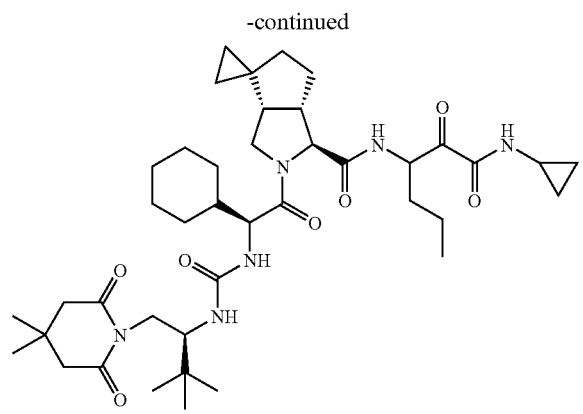
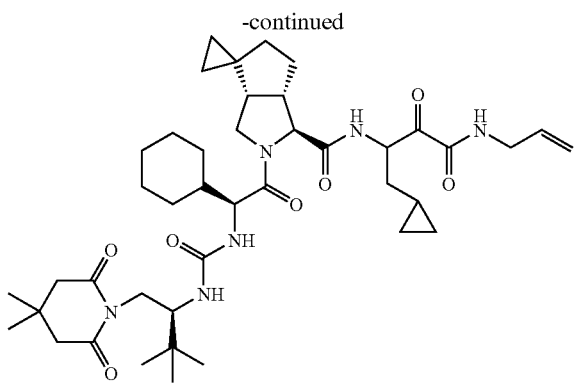
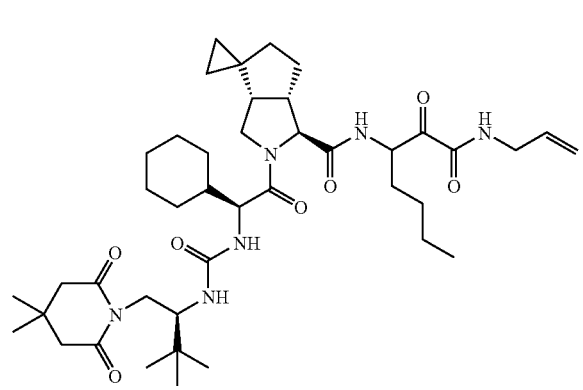
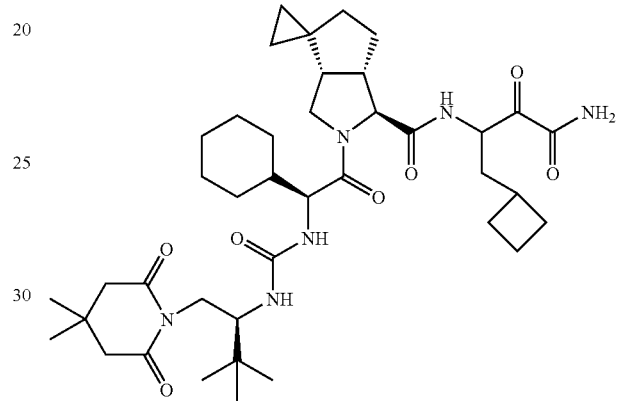
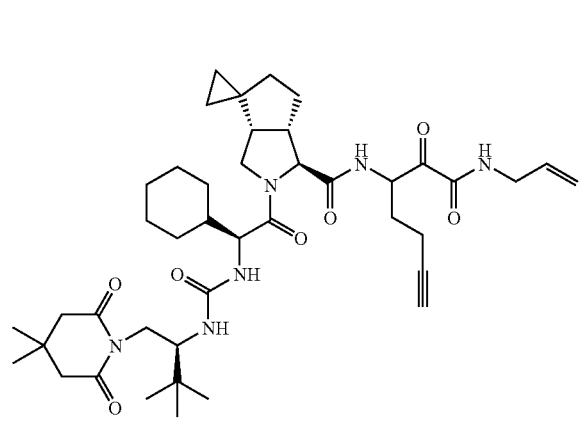
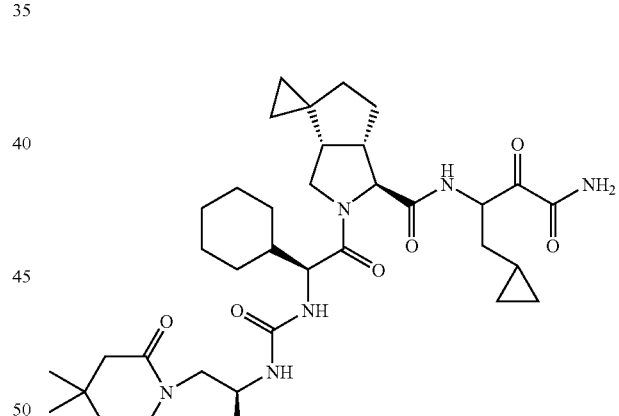
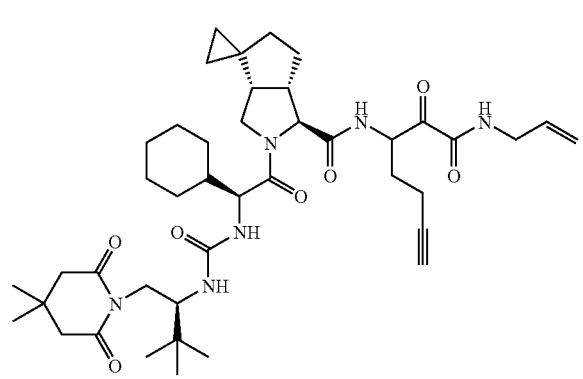
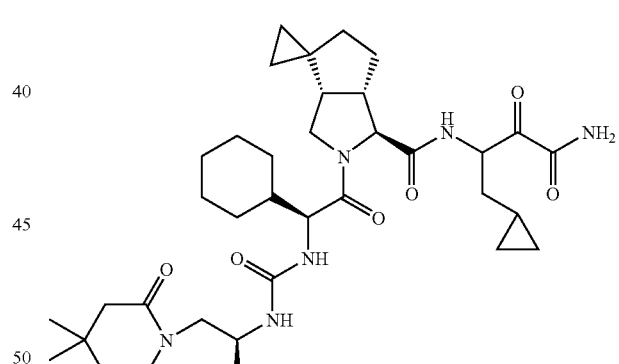

355 356
-continued -continued
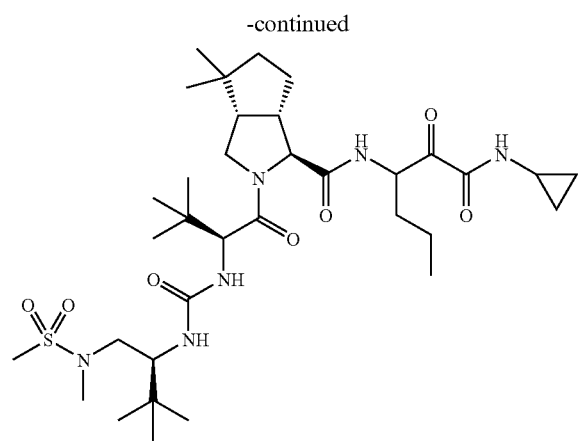
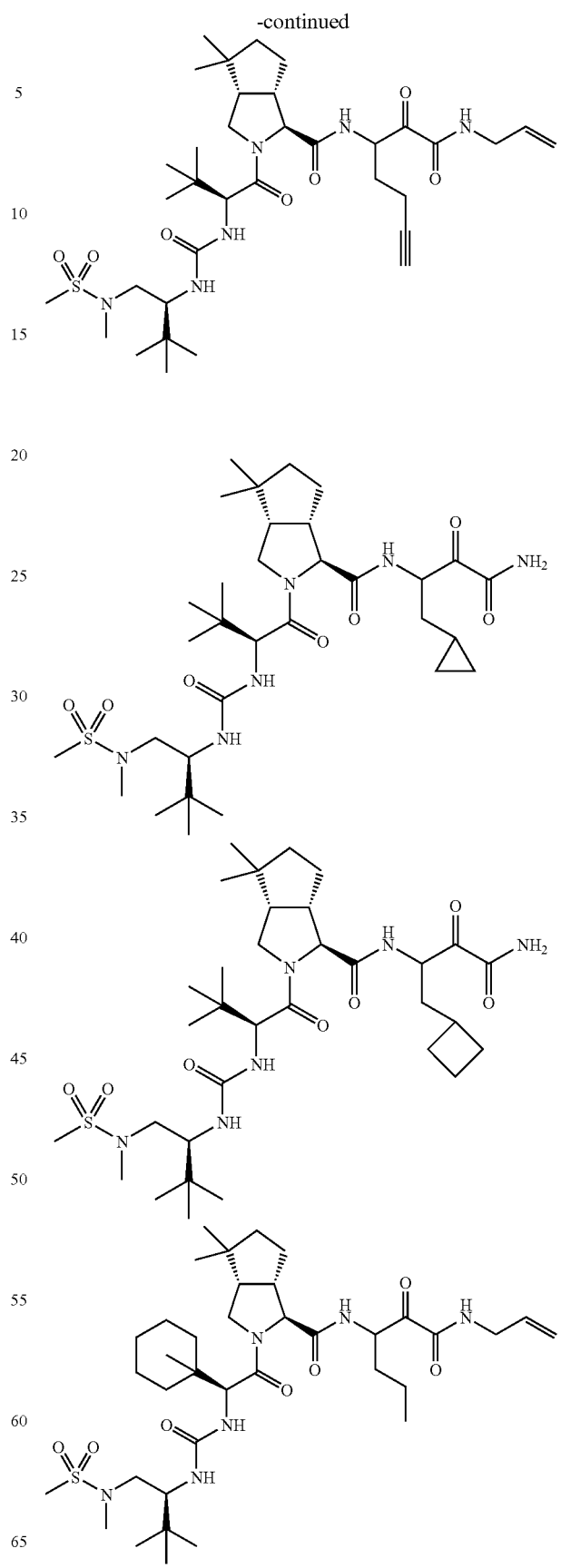

357
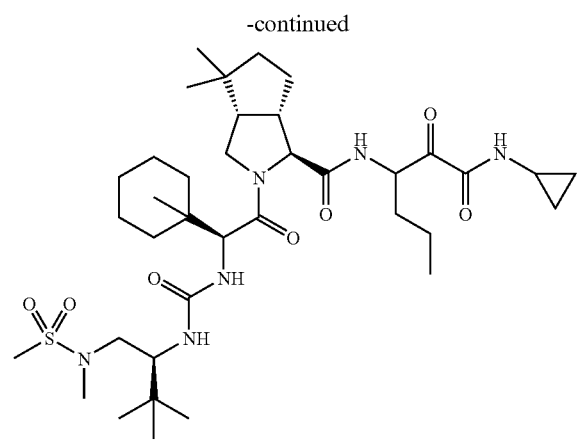
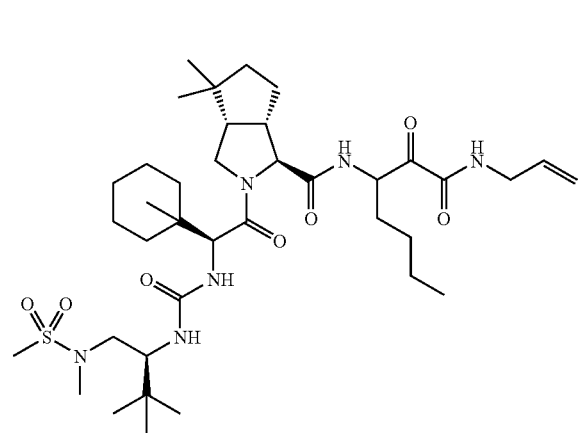
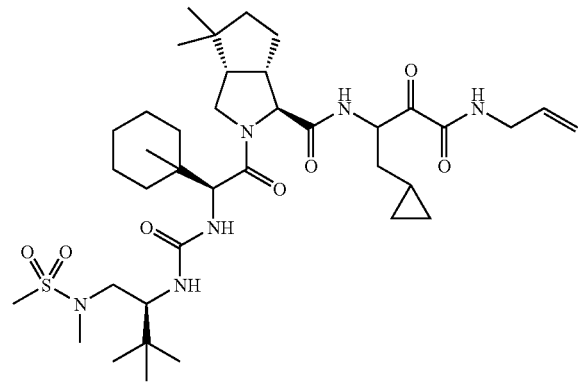
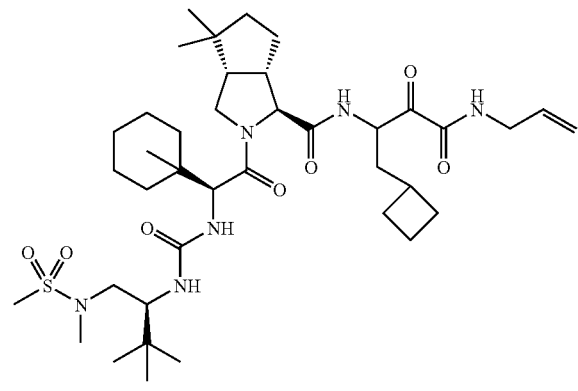
358
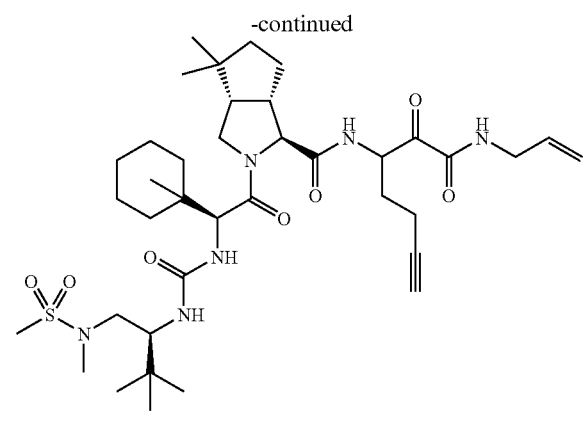
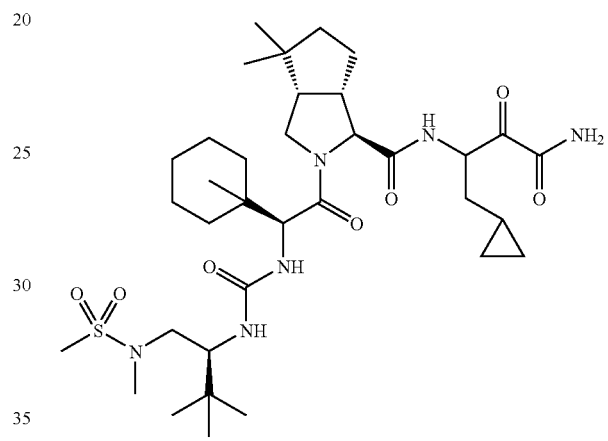
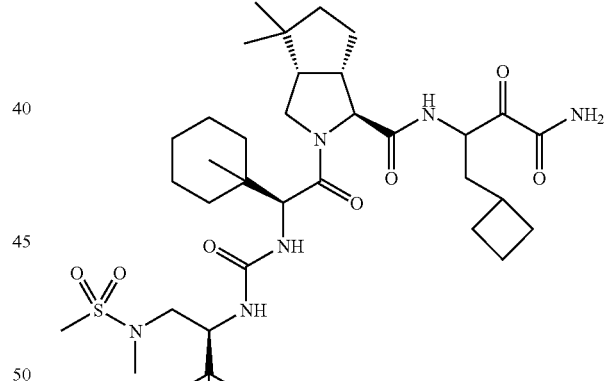
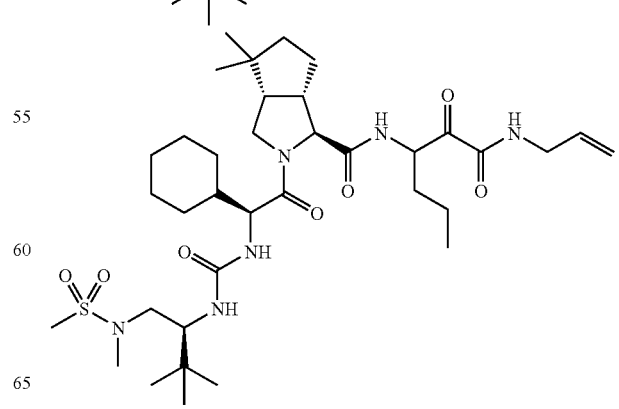

-continued
| 359 | 360 |
|---|---|
| 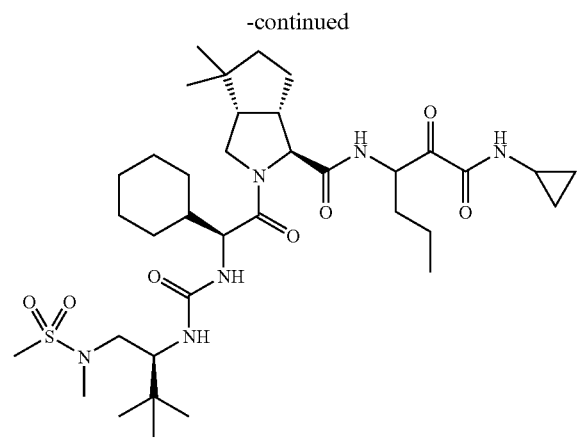 | 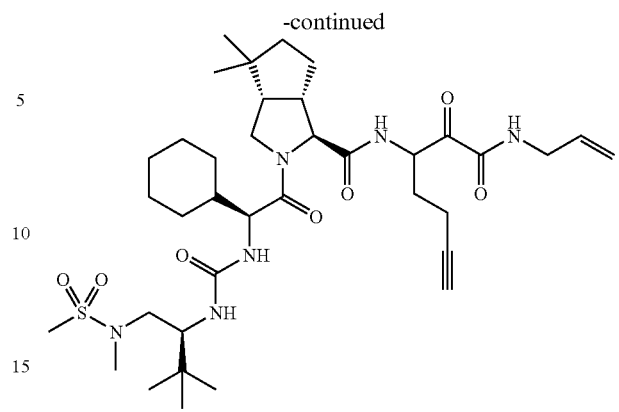 |
| 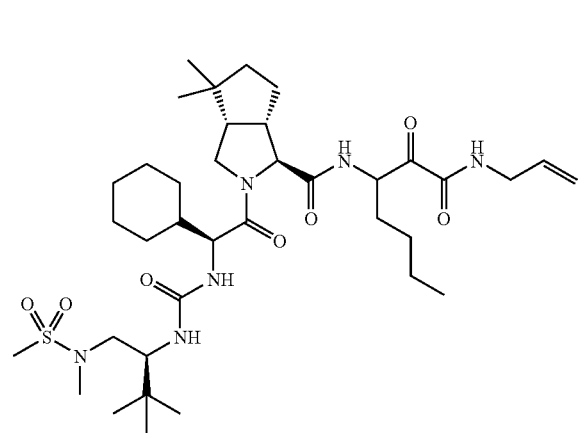 | 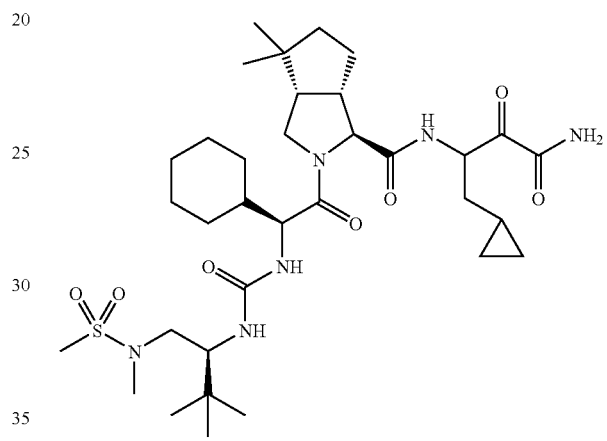 |
| 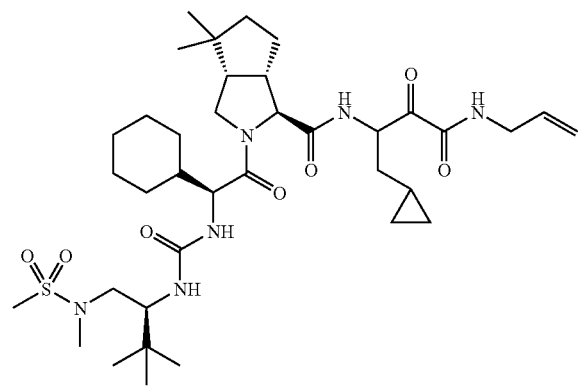 | 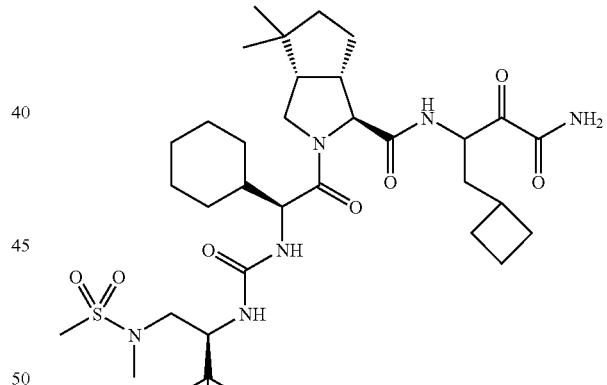 |
| 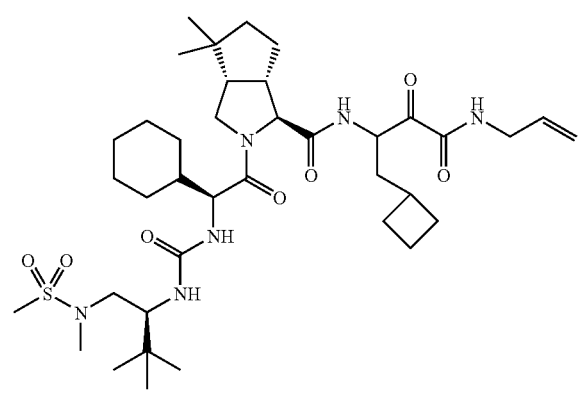 | 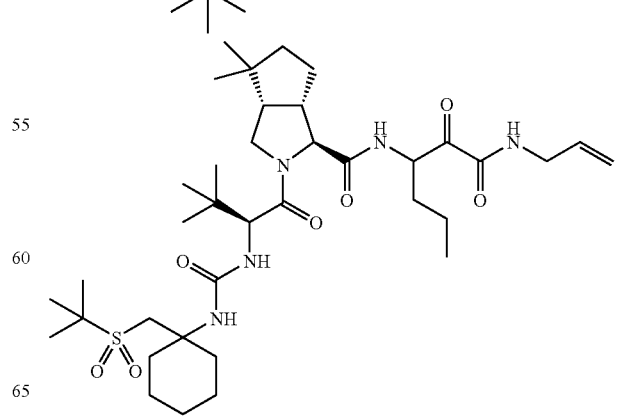 |

361
-continued
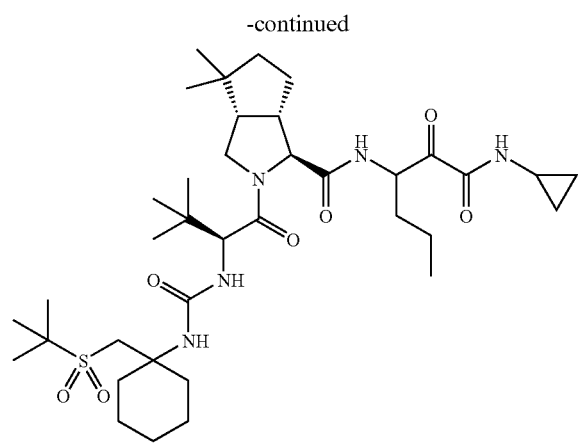
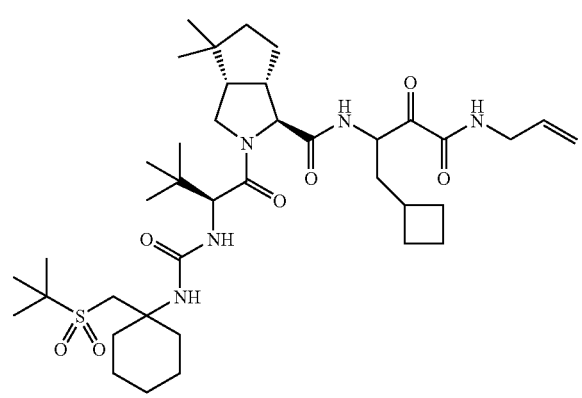
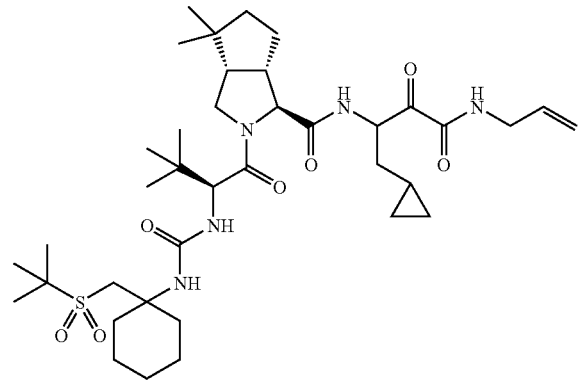
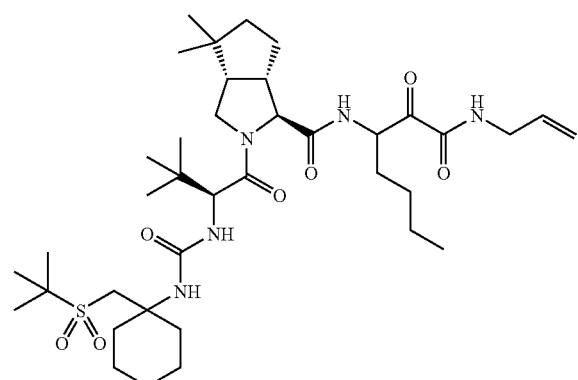
362
-continued
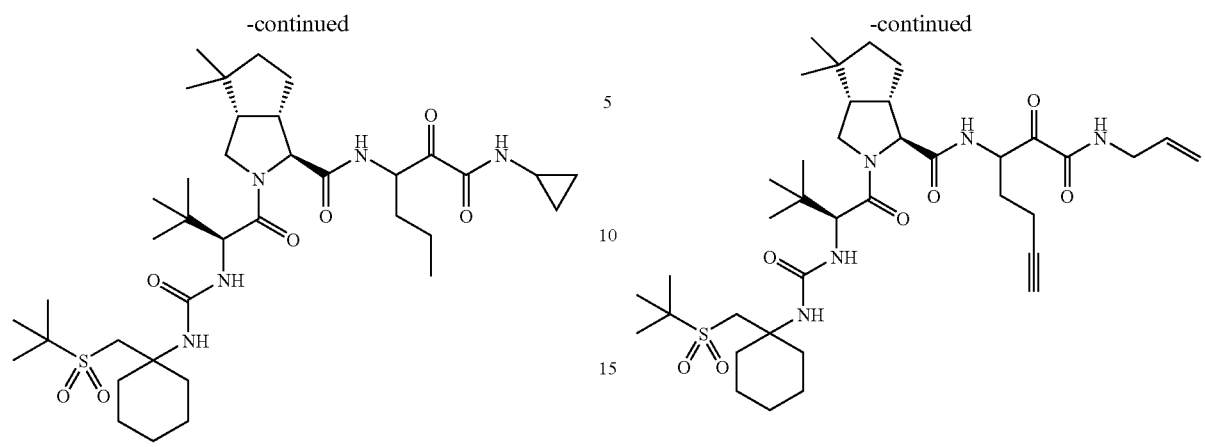
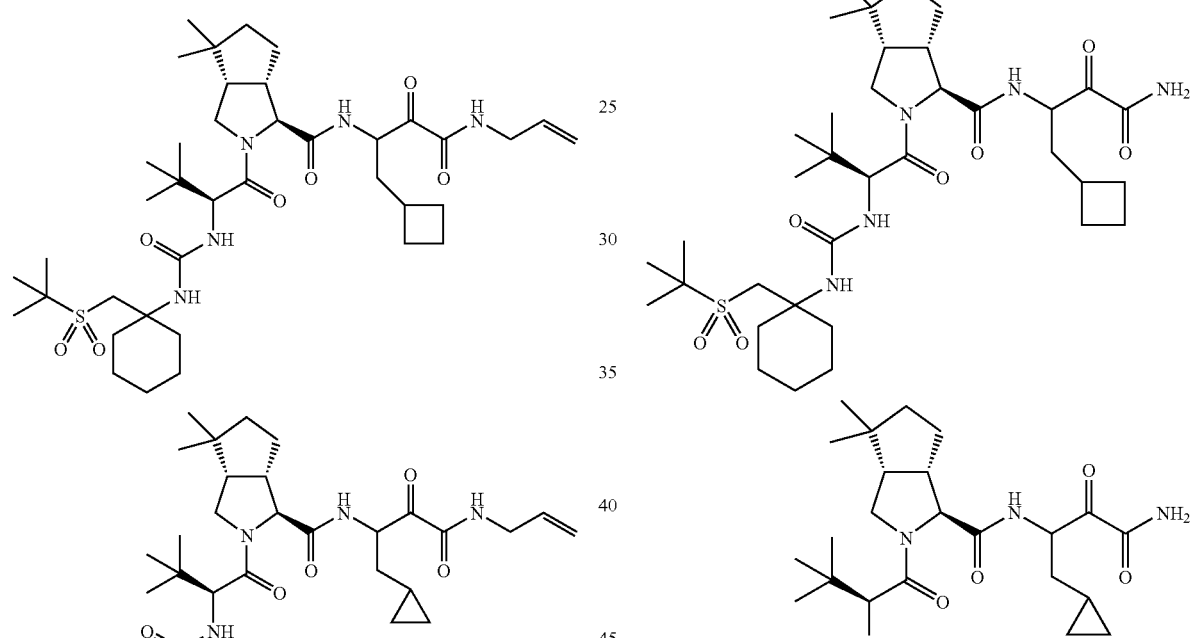
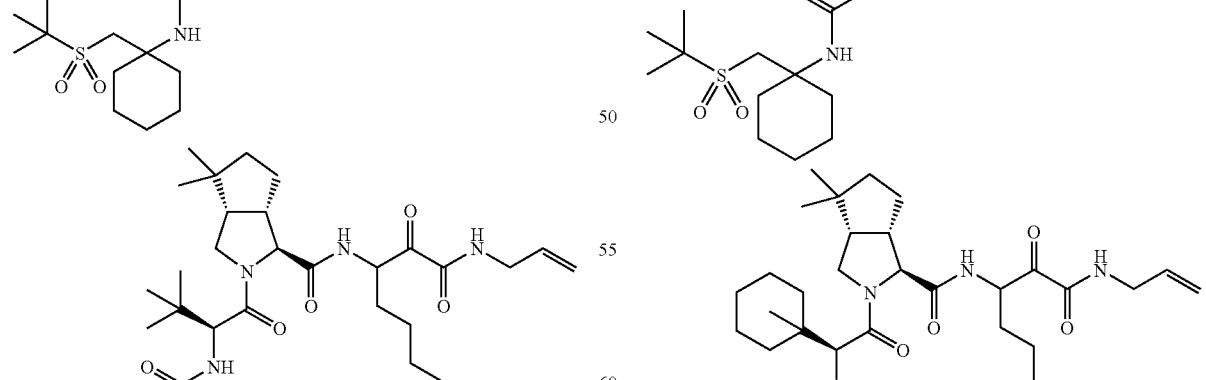
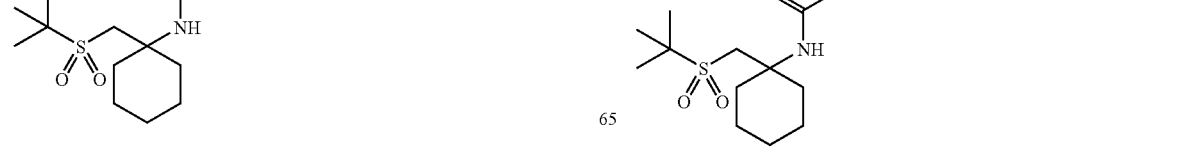

-continued
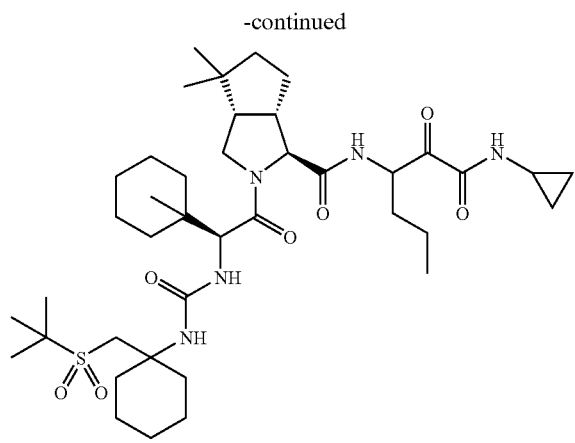
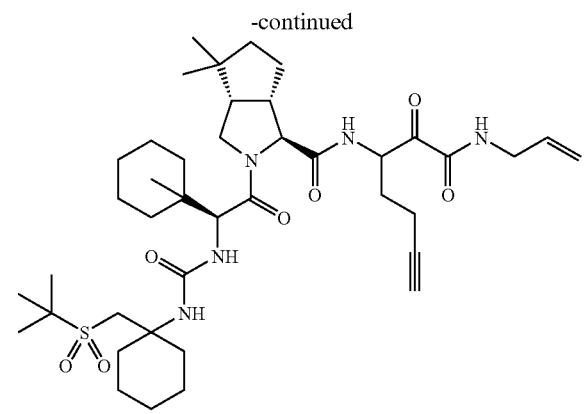
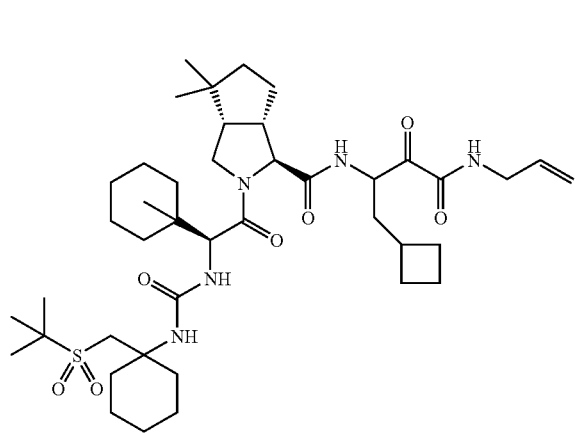
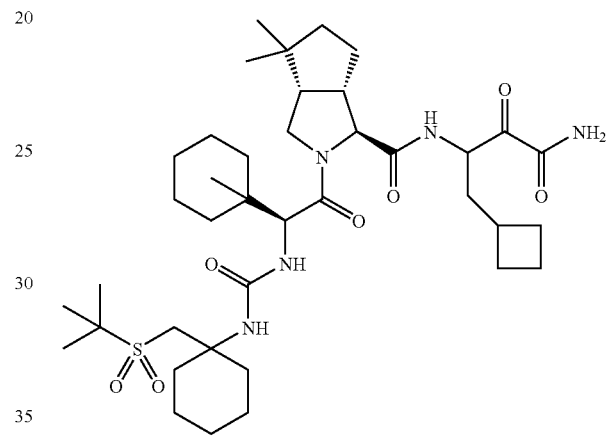
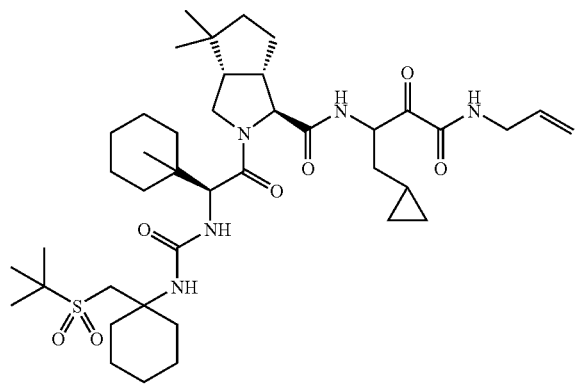
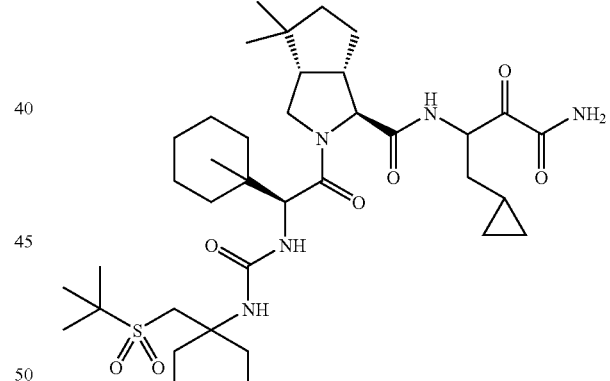
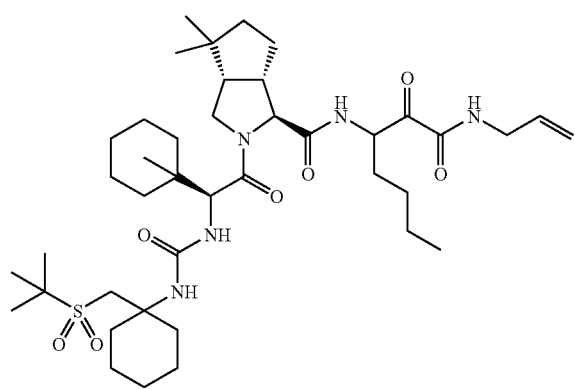
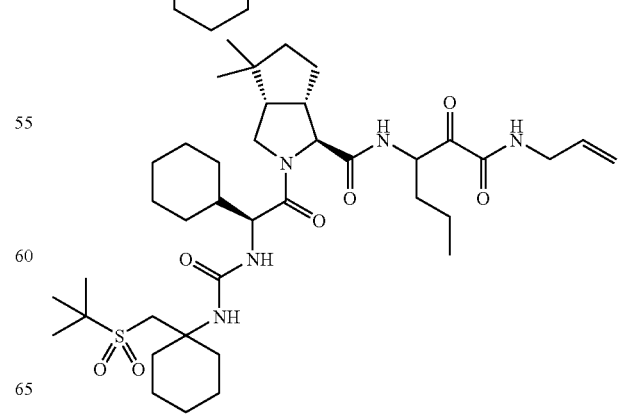

365 366
-continued -continued
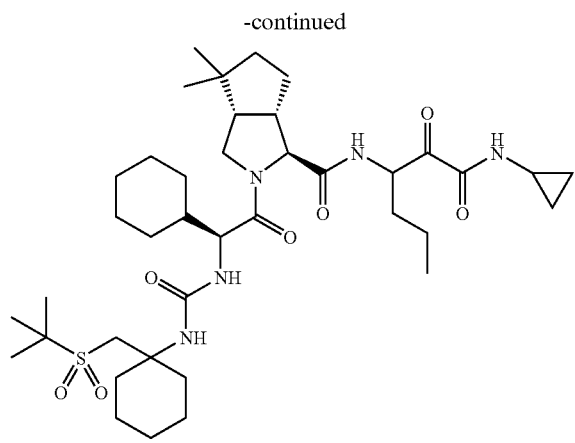
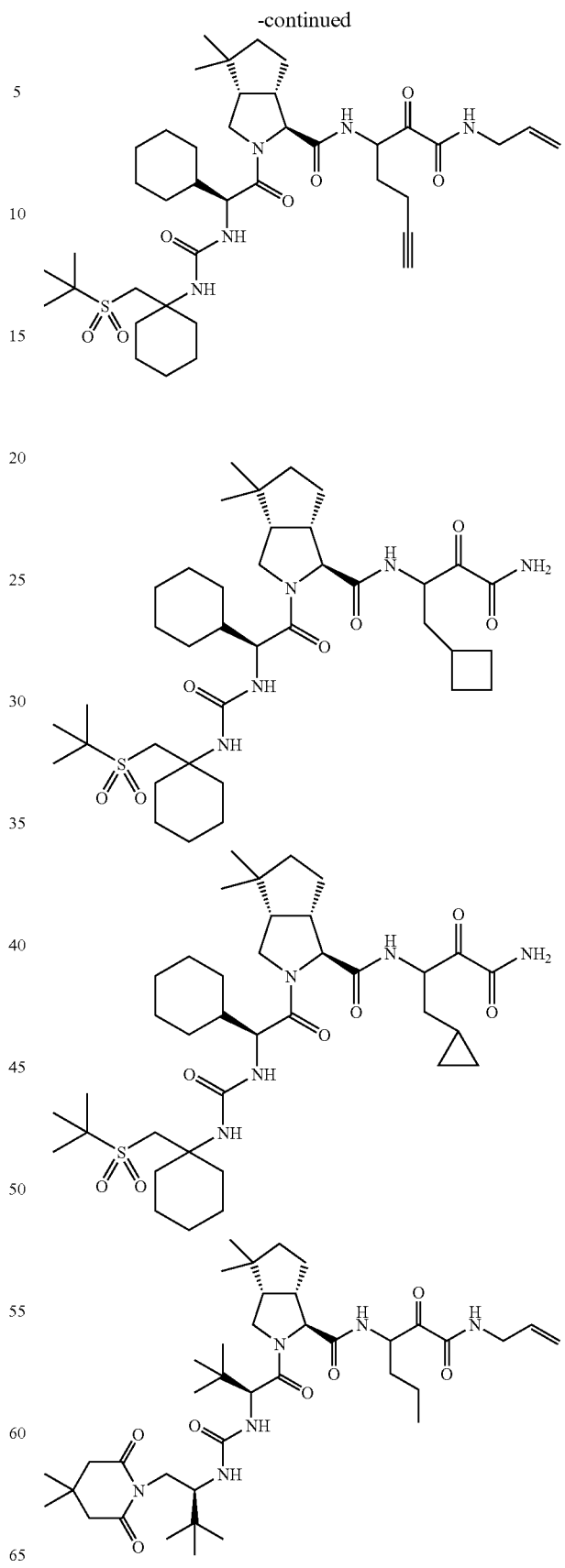

367
-continued
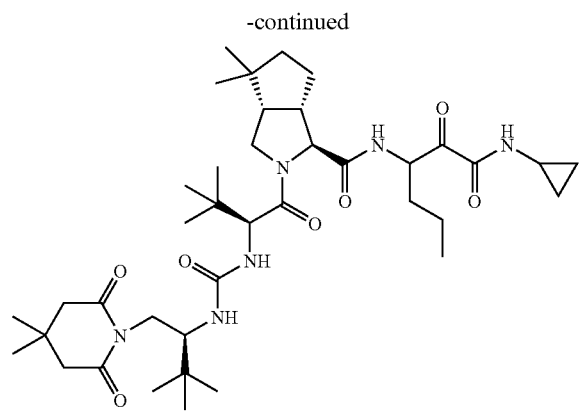
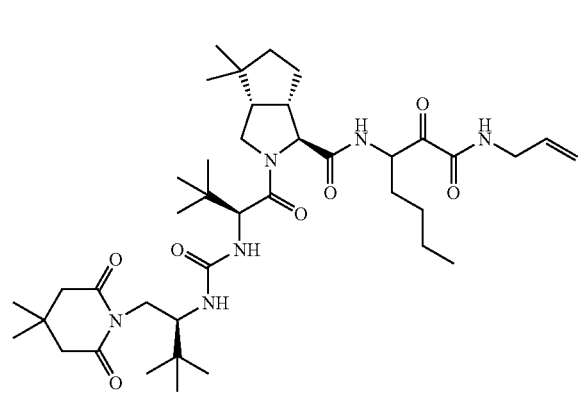
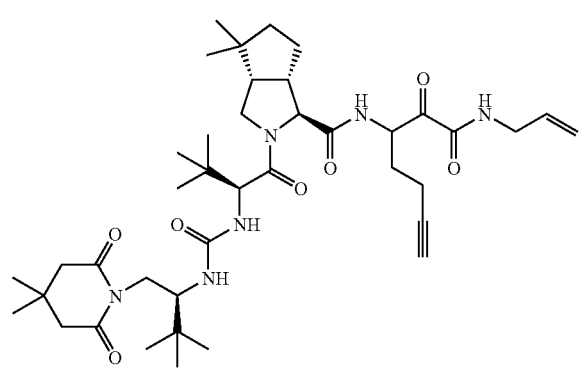
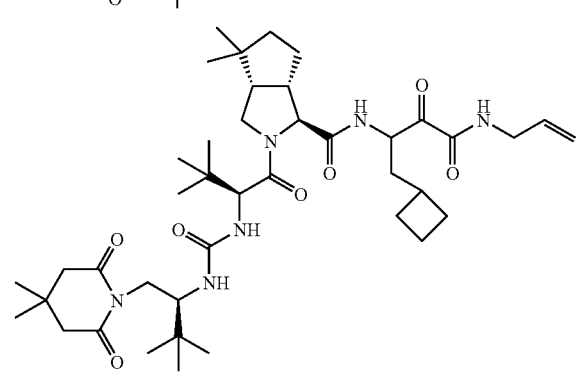
368
-continued
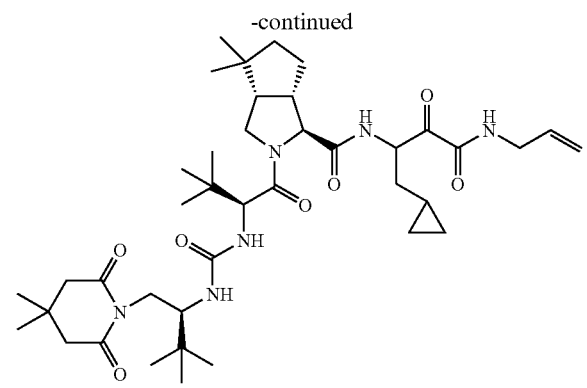
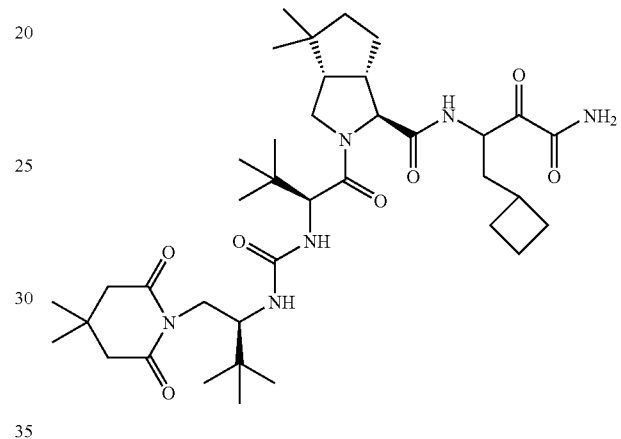
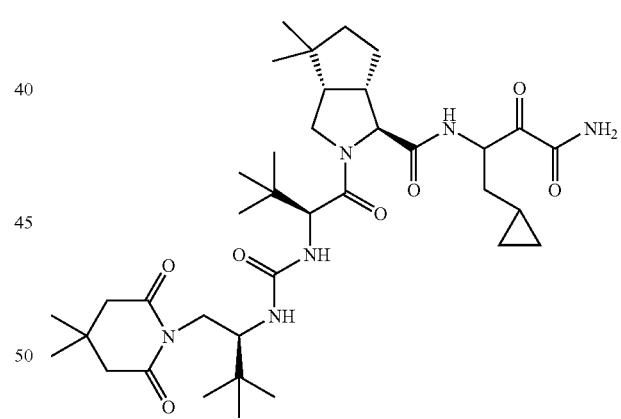
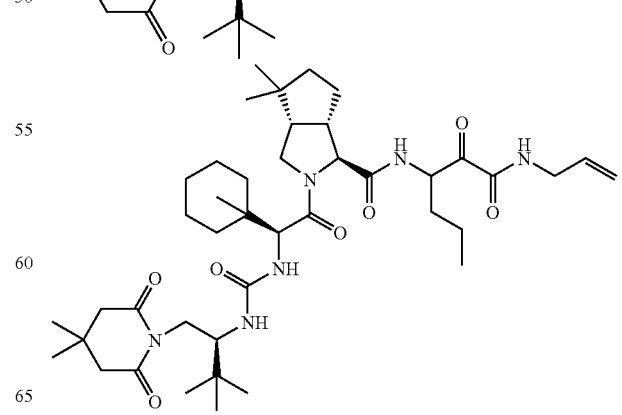

369
-continued
370
-continued
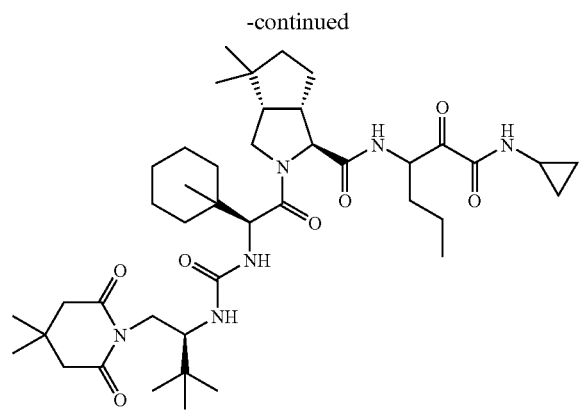
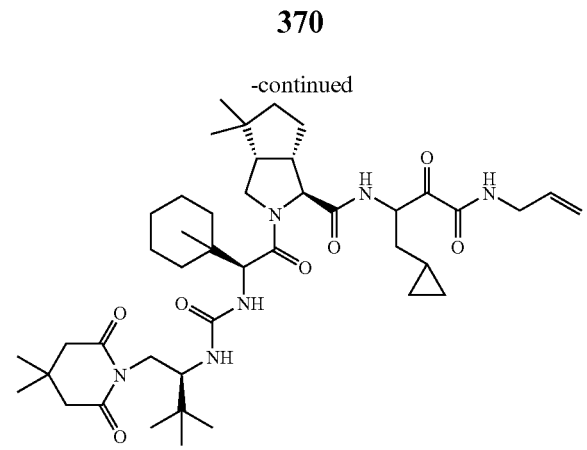
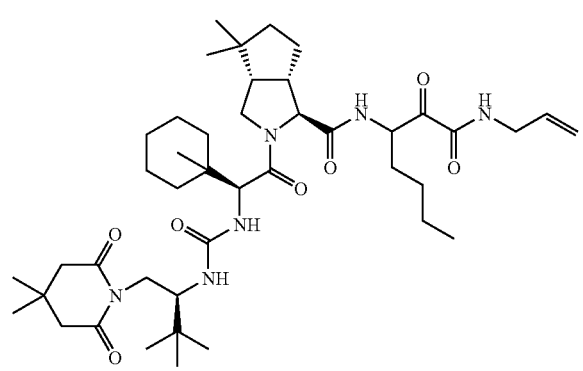
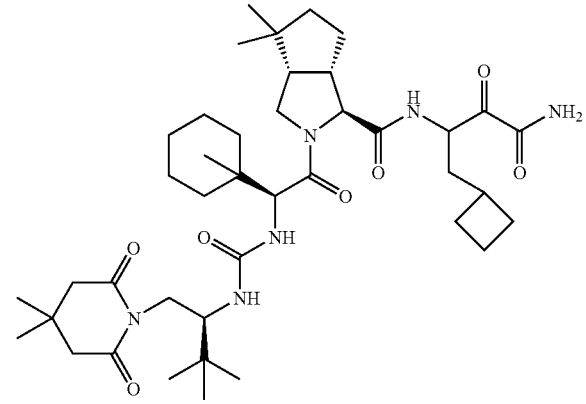
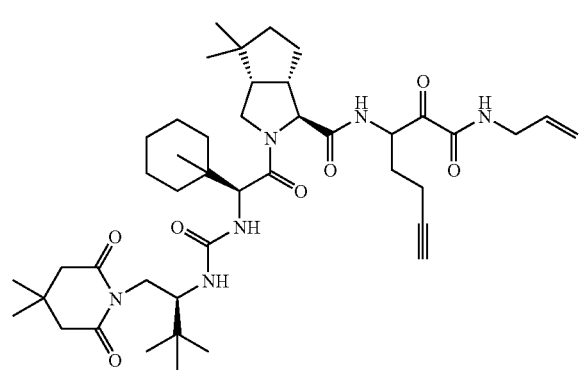
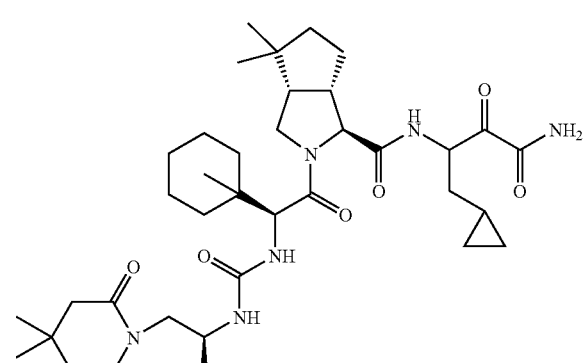
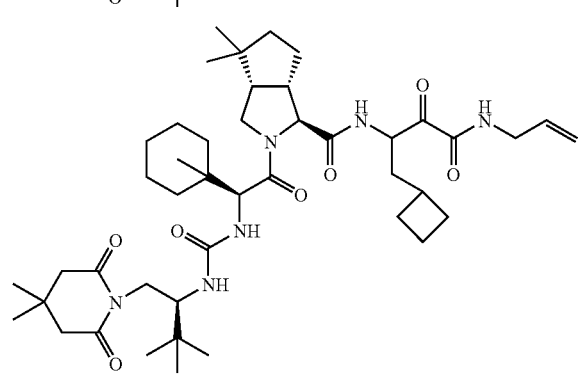
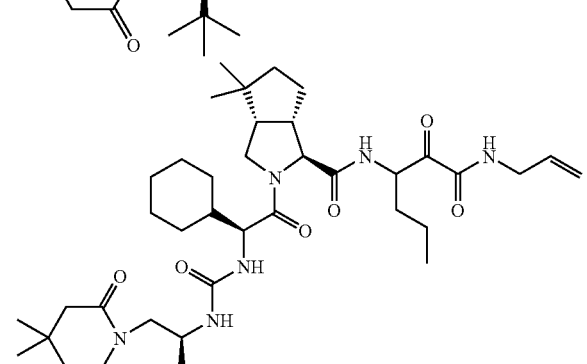

371
-continued
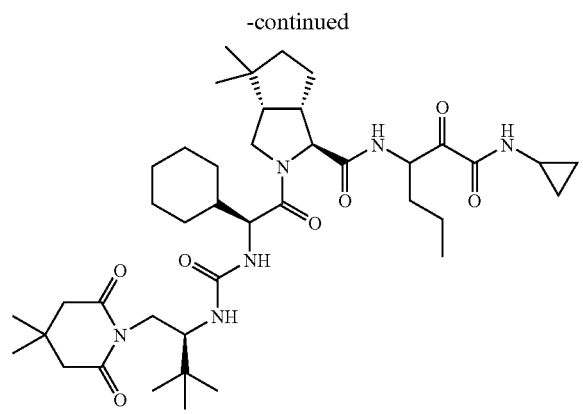
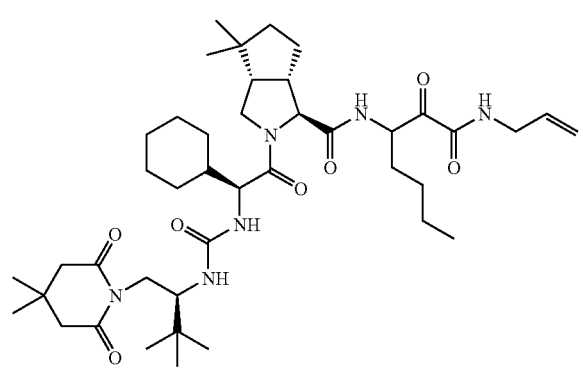
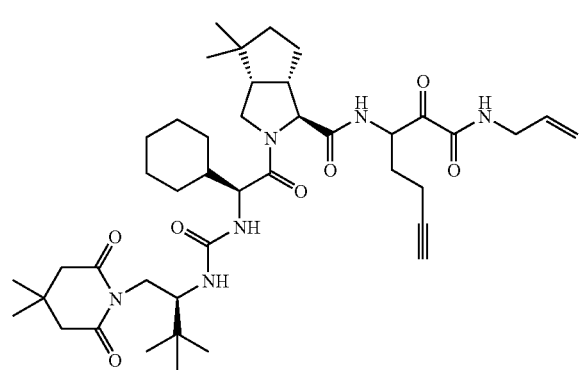
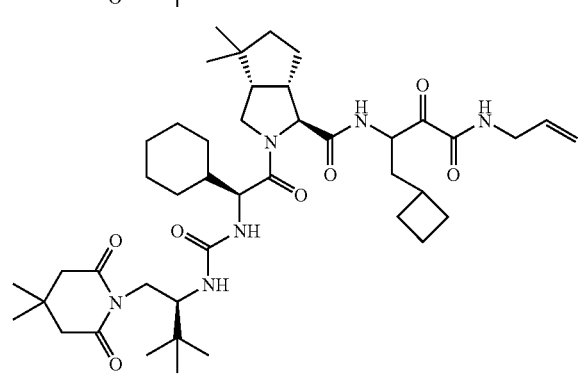
372
-continued
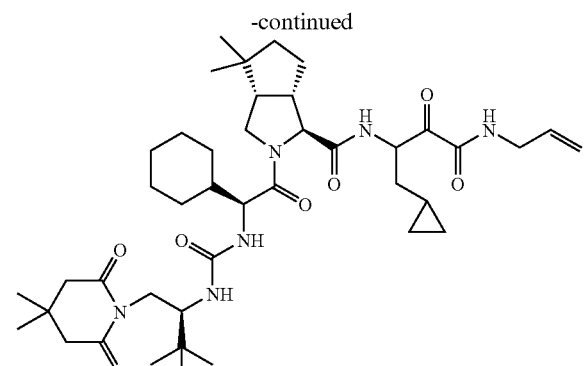
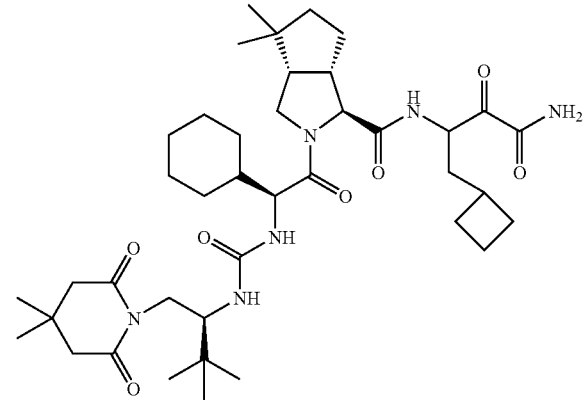
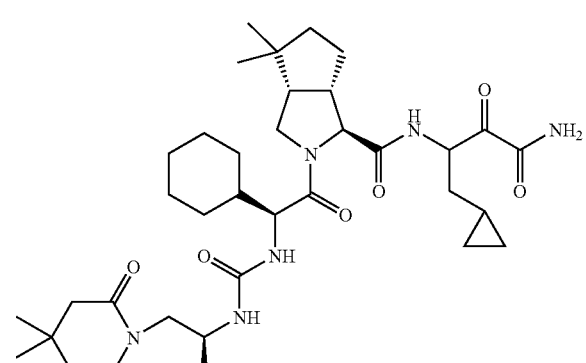
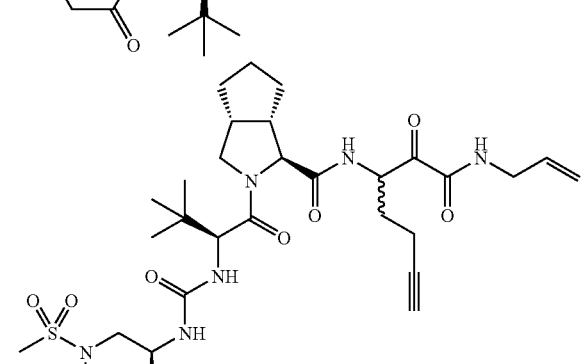

373                                           374
-continued                                   -continued
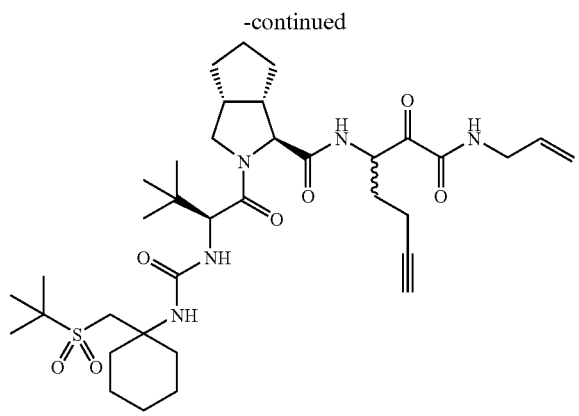
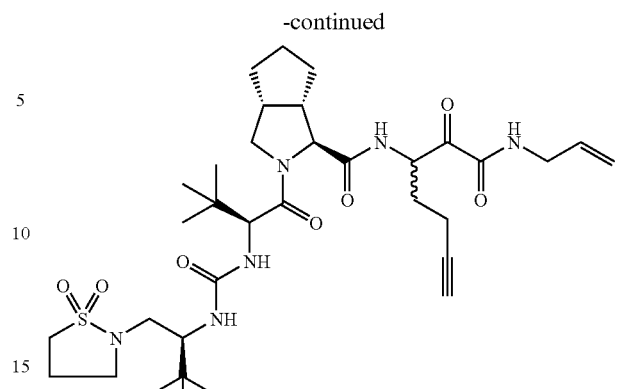
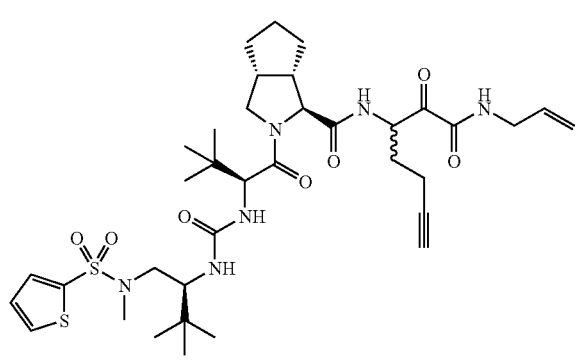
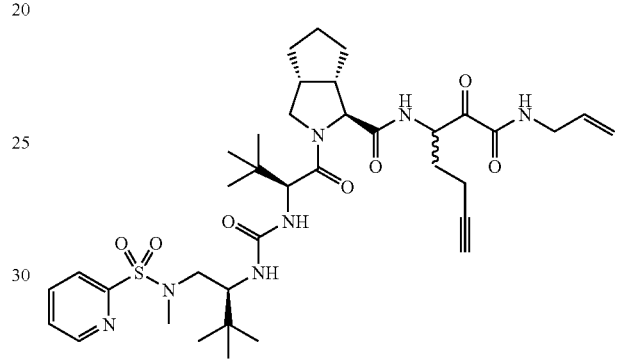
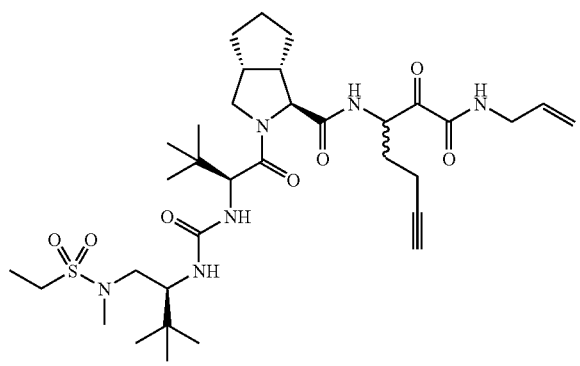
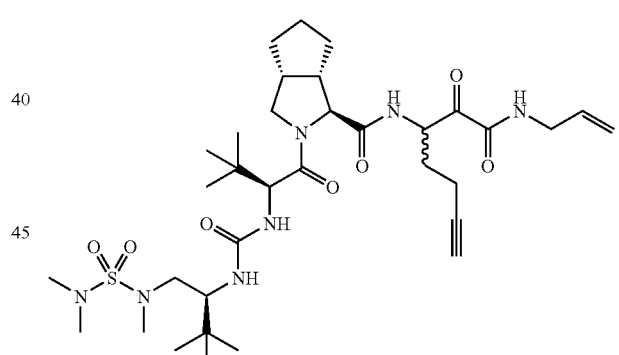
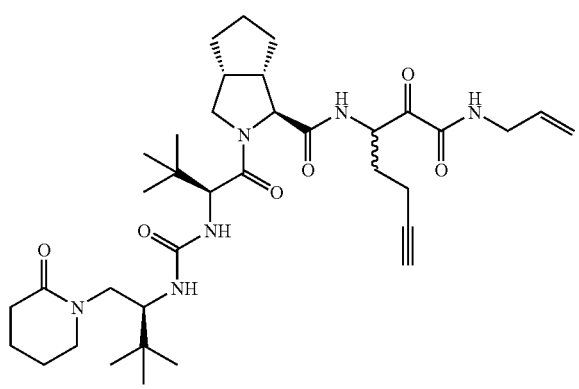
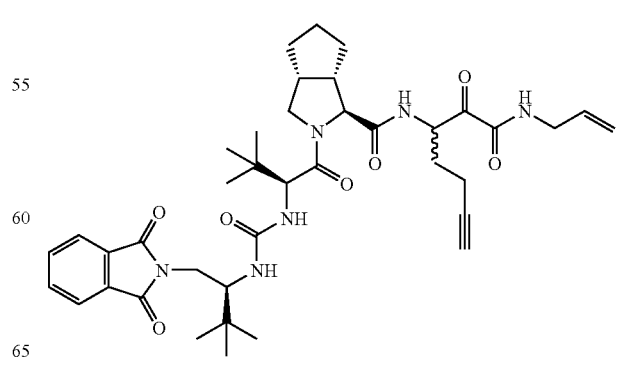

375 376
-continued -continued
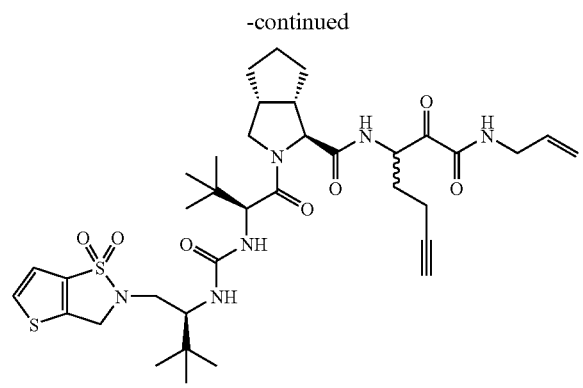 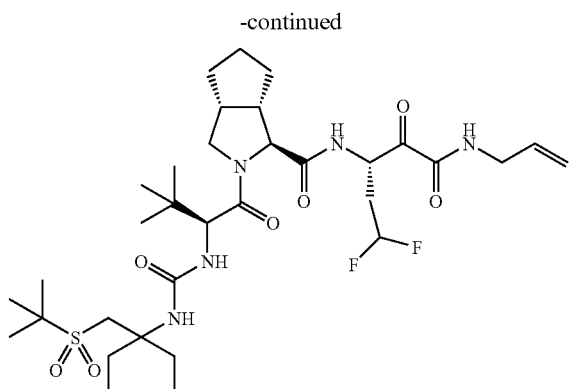
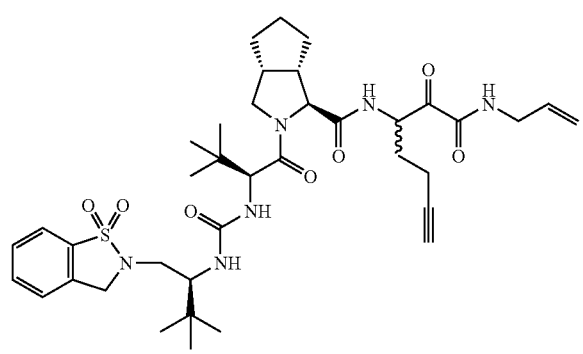 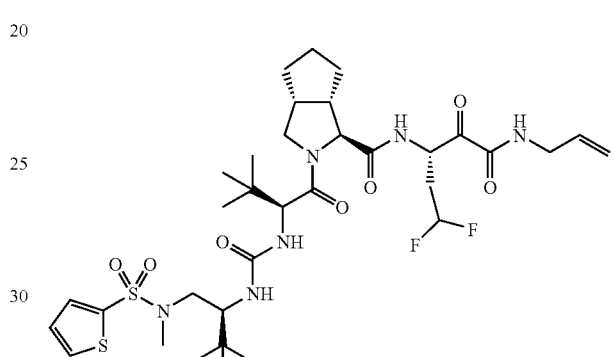
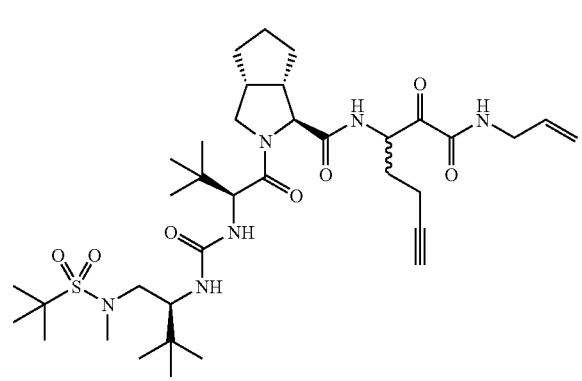 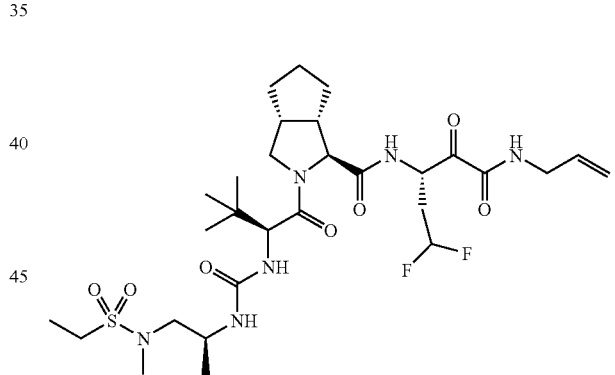
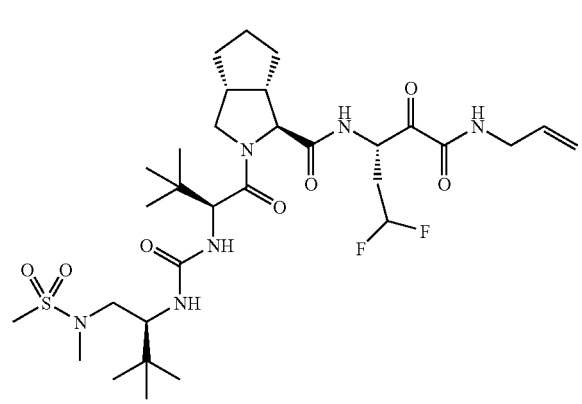 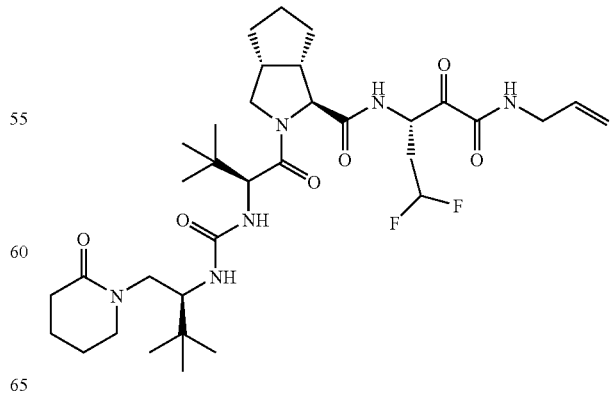

377
-continued
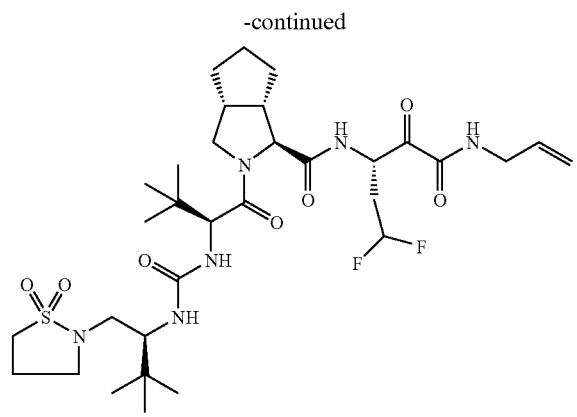
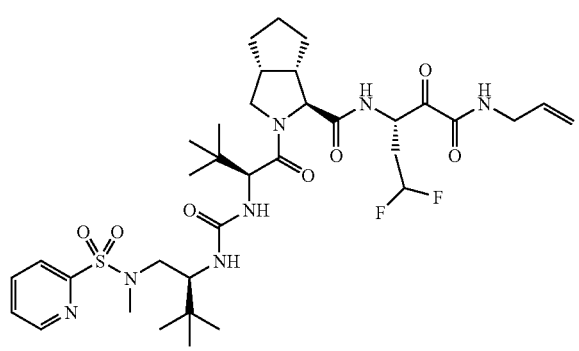
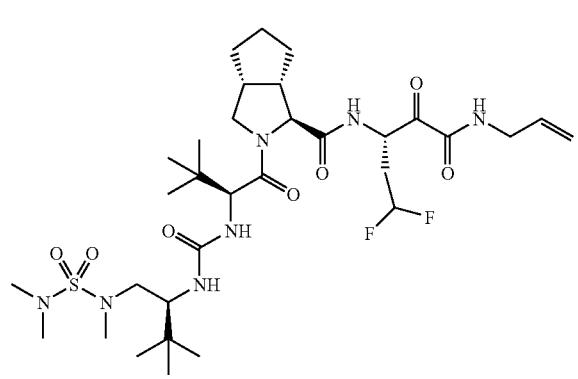
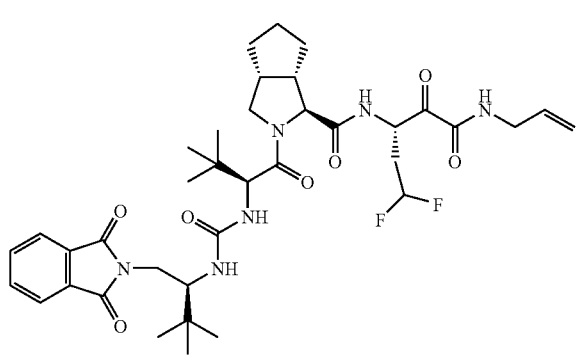
378
-continued
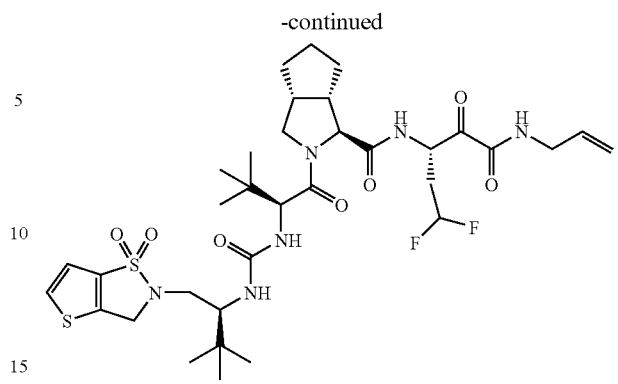
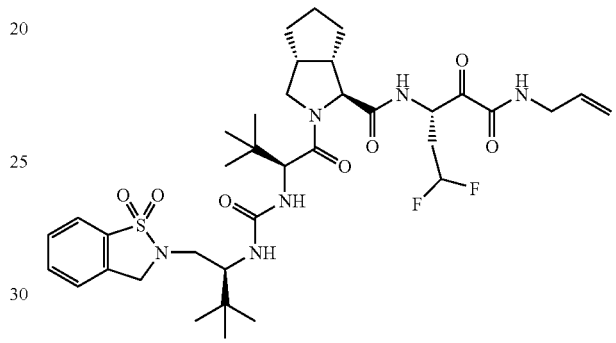
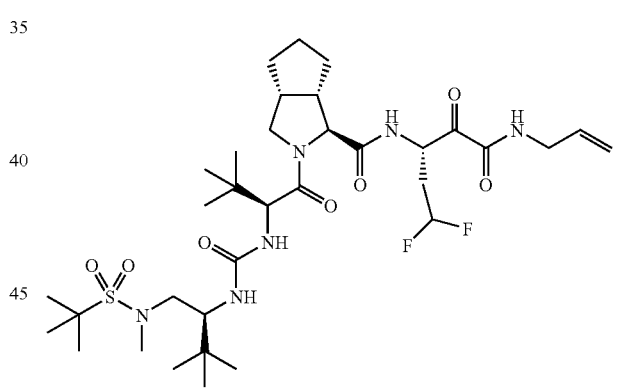
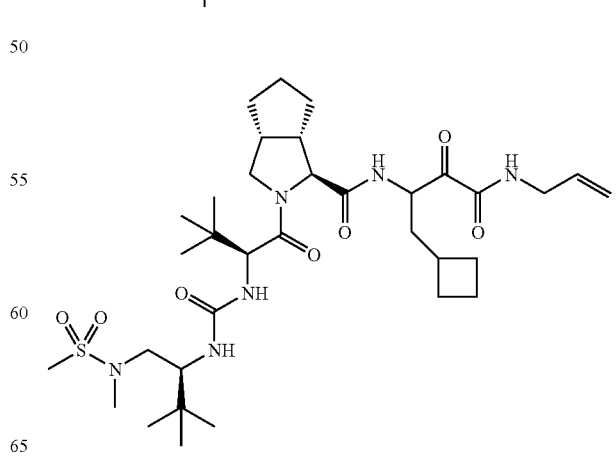

-continued
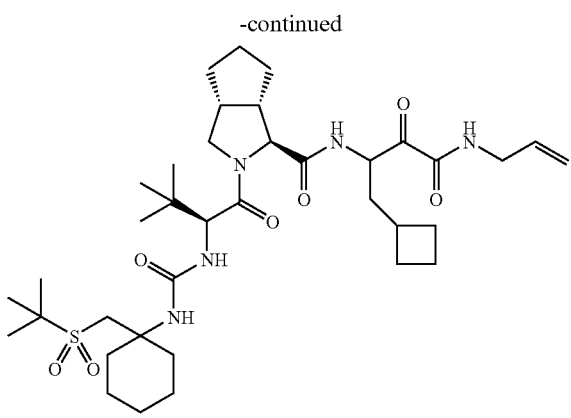
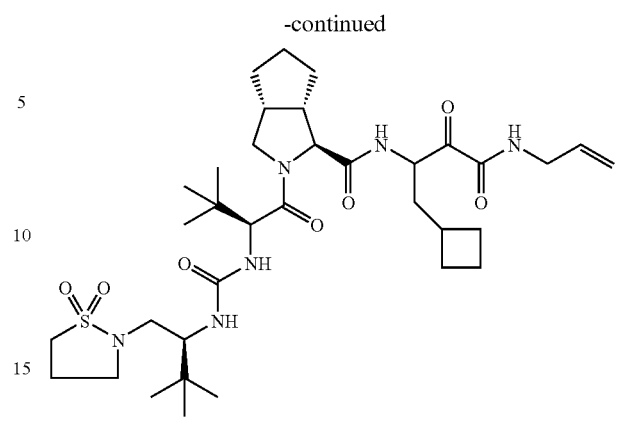
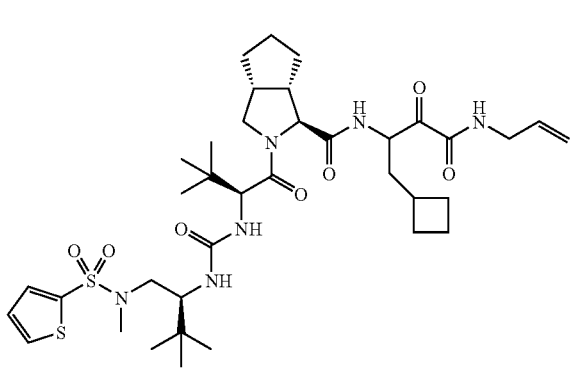
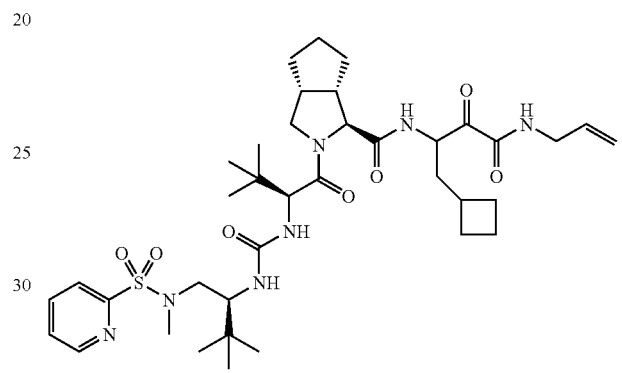
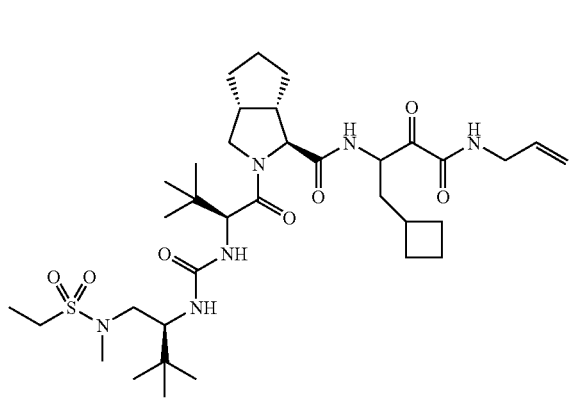
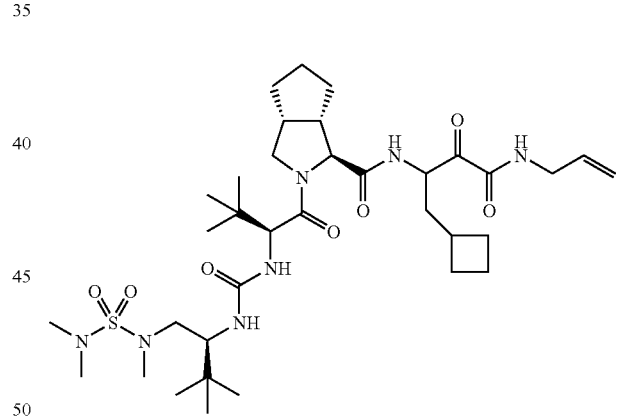
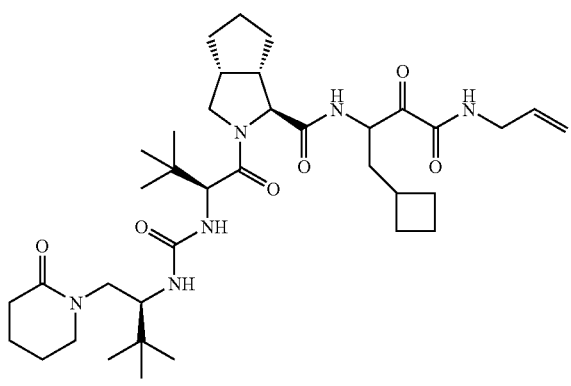
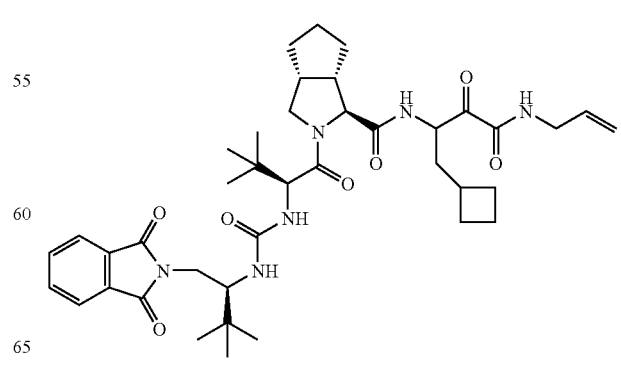

381 382
-continued -continued
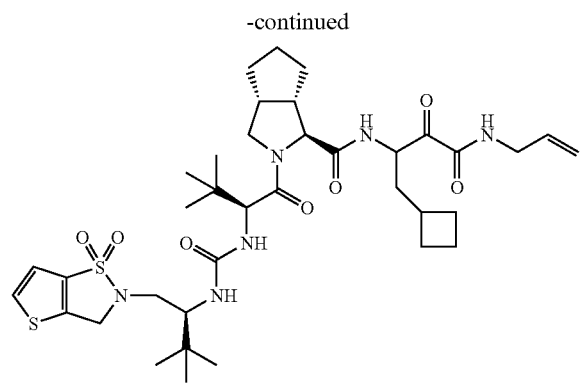 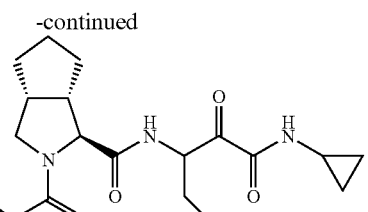
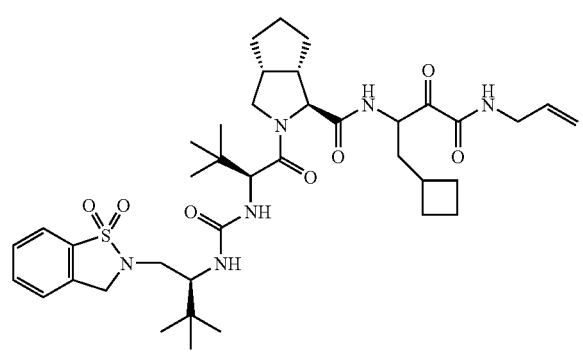 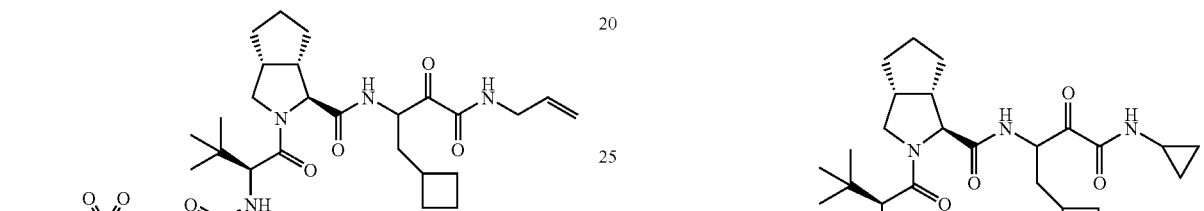
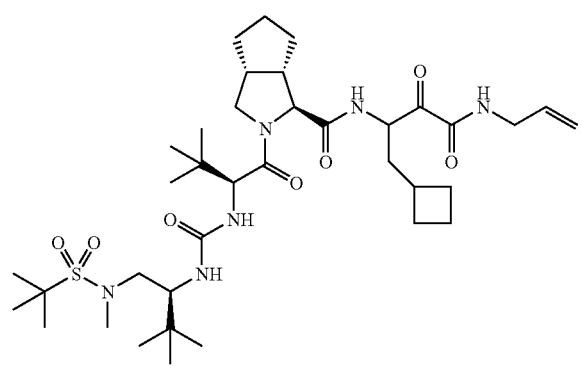 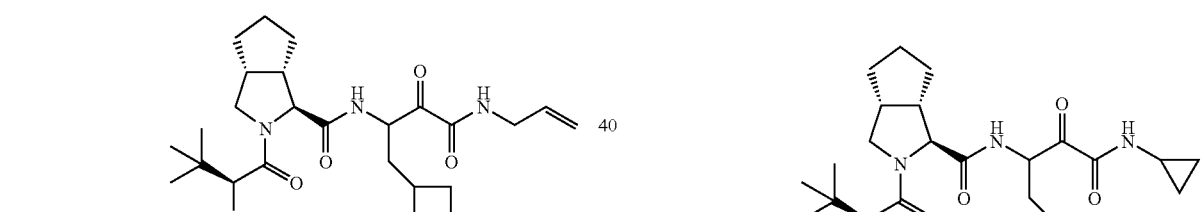
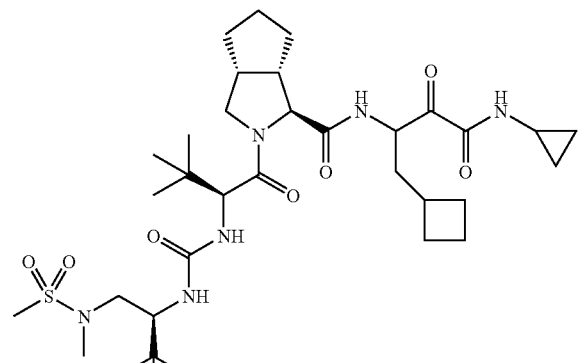 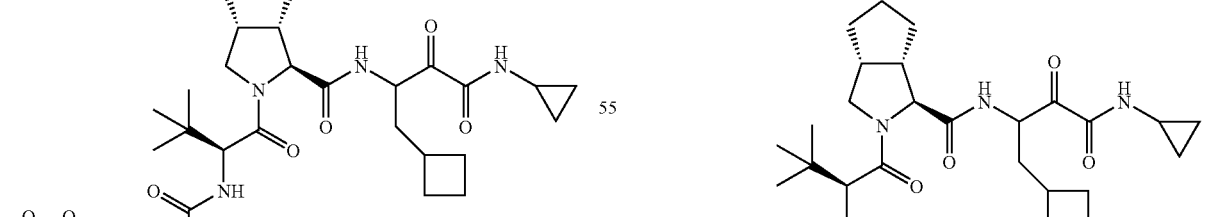

-continued
383
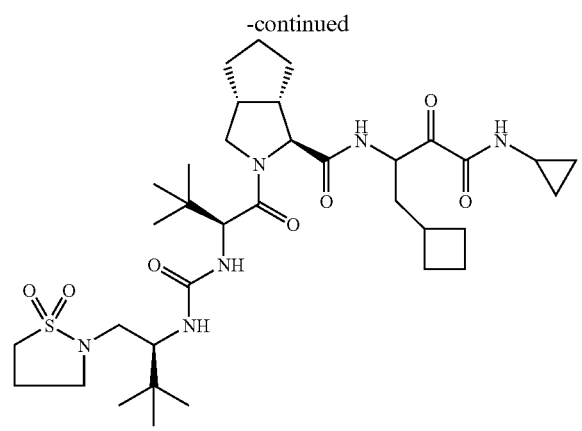
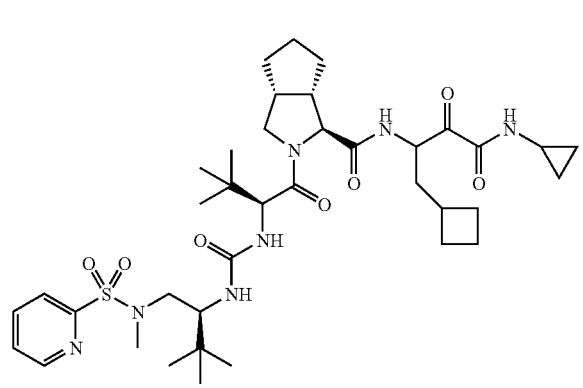
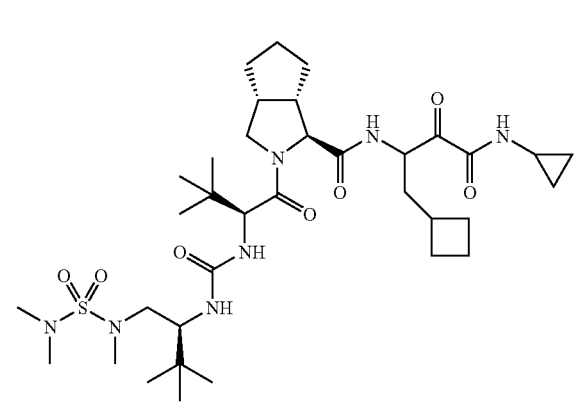
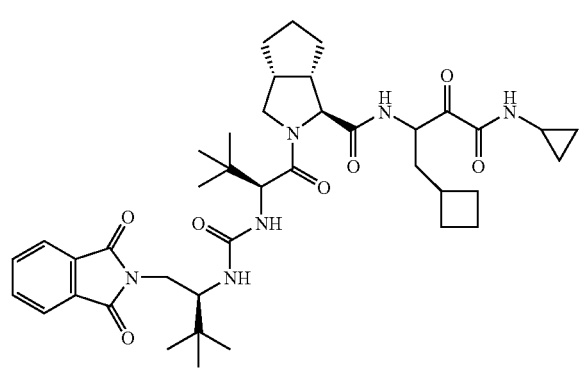
384
-continued
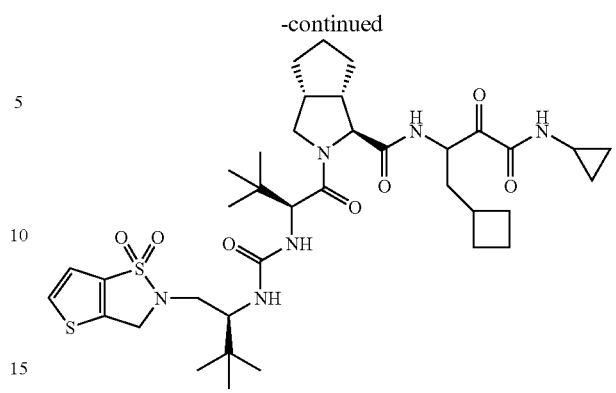
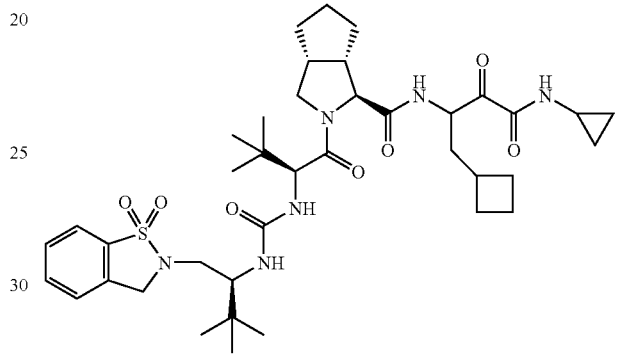
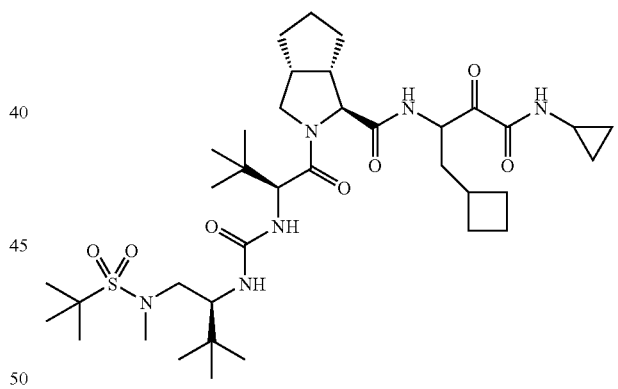
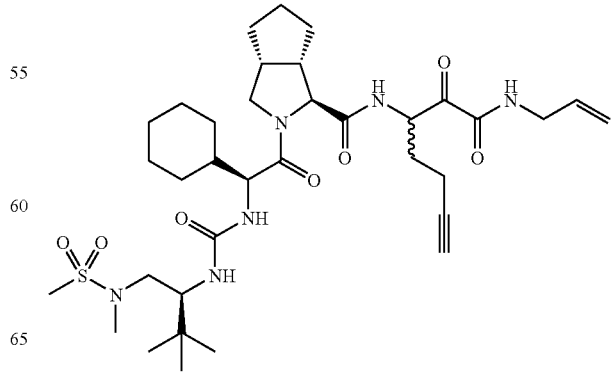

385
-continued
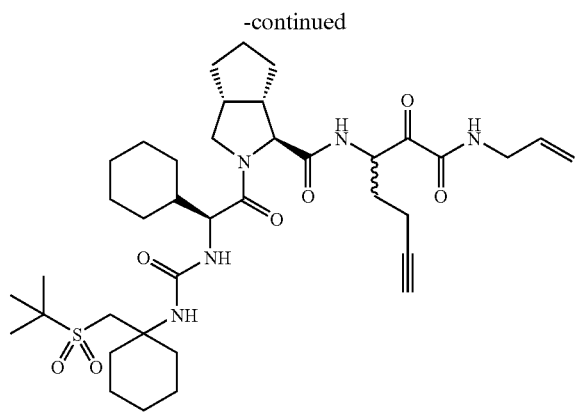
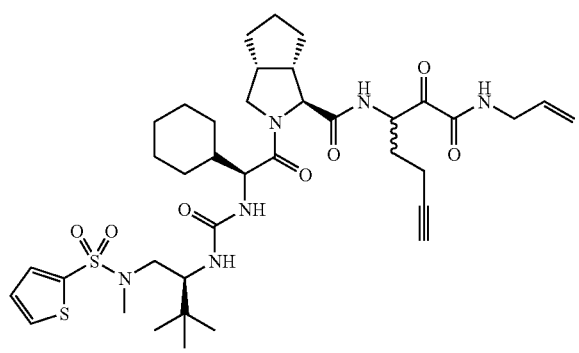
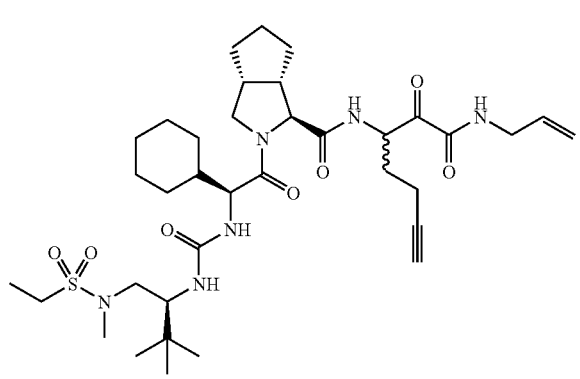
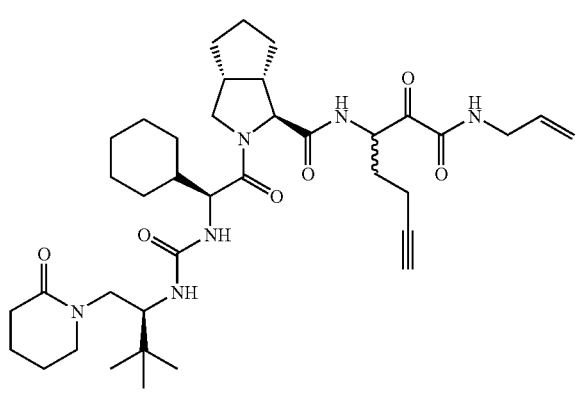
386
-continued
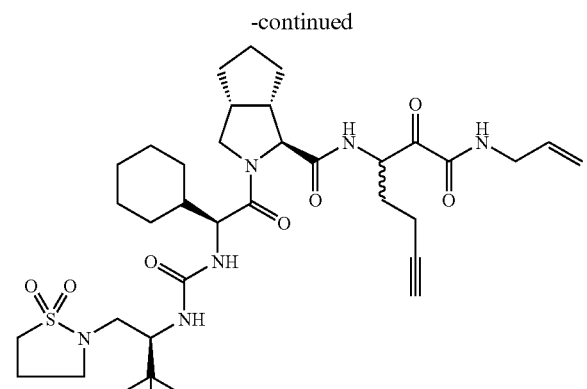
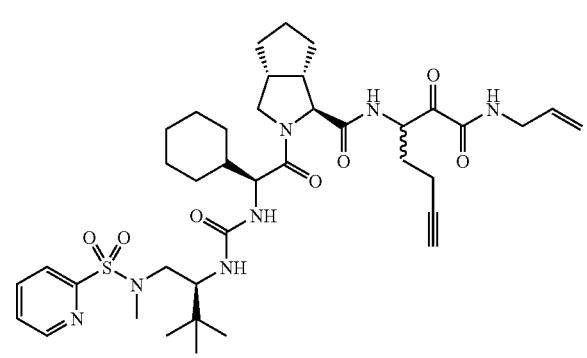
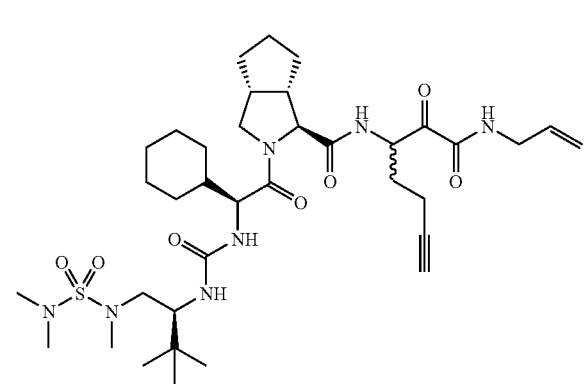
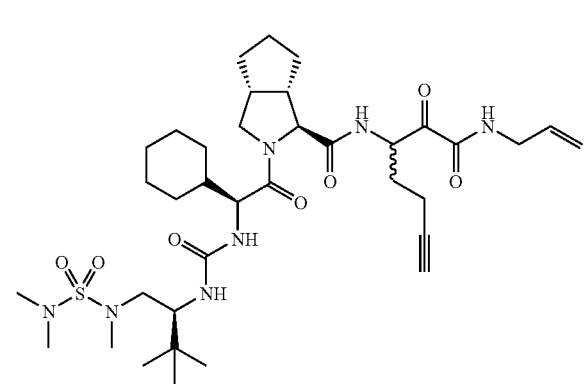

387
-continued
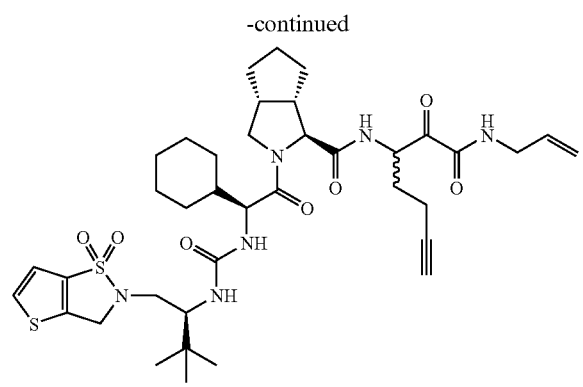
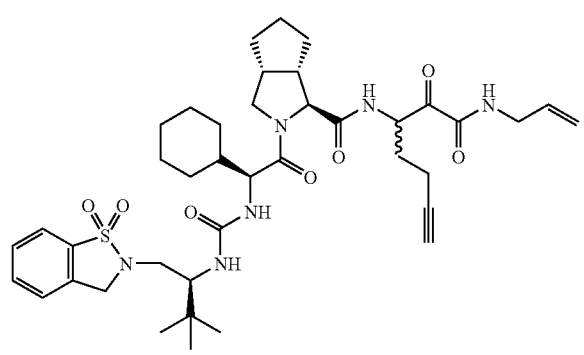
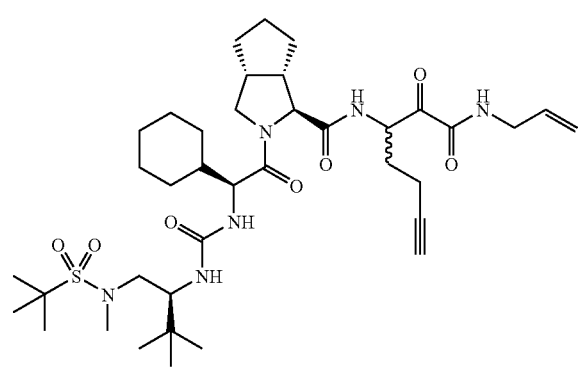
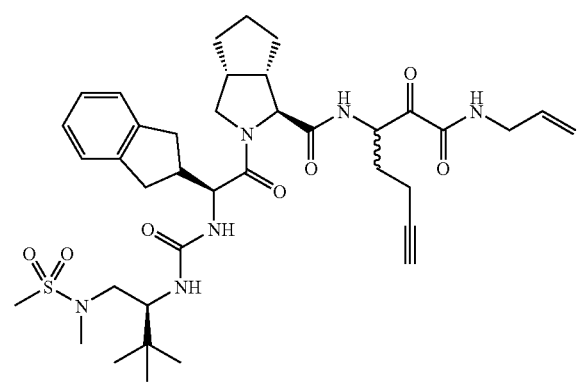
388
-continued
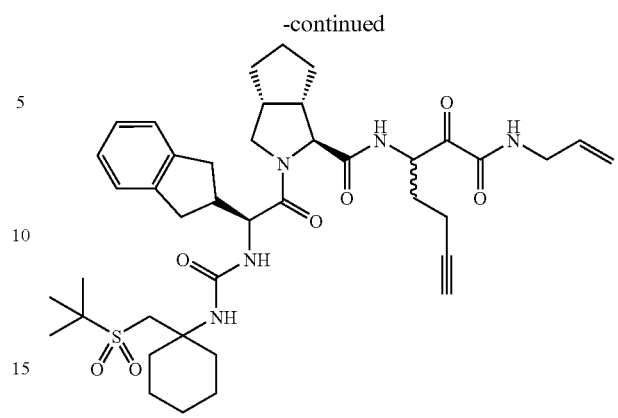
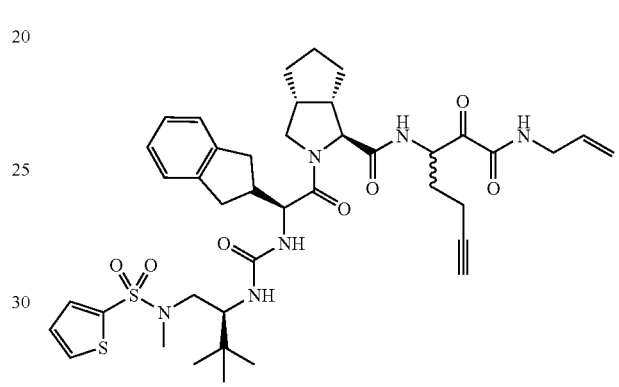
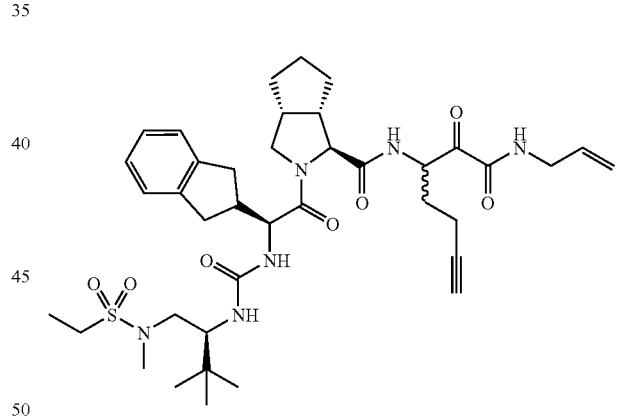
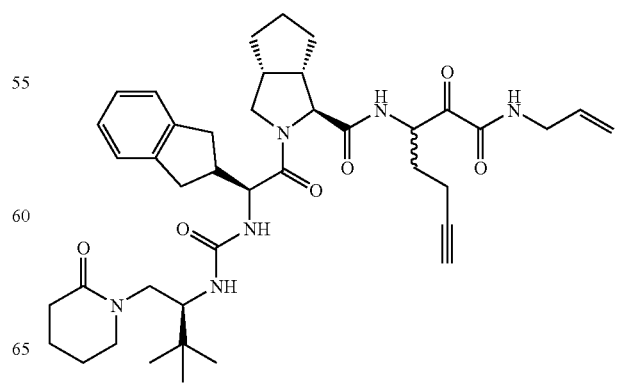

389 390
-continued -continued
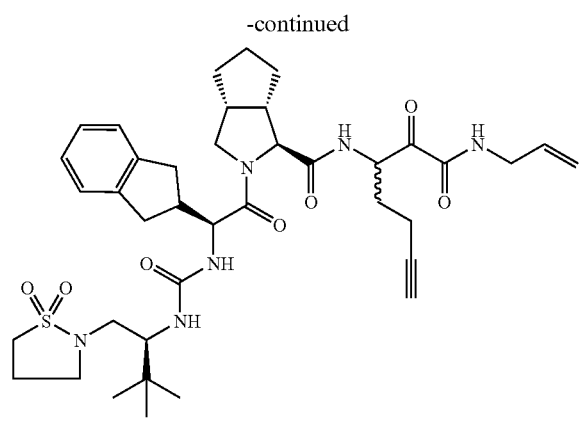
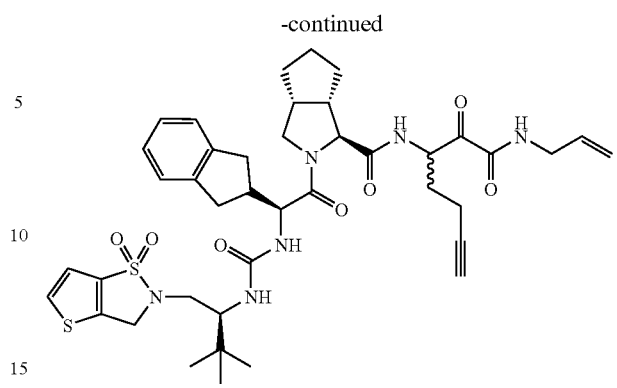
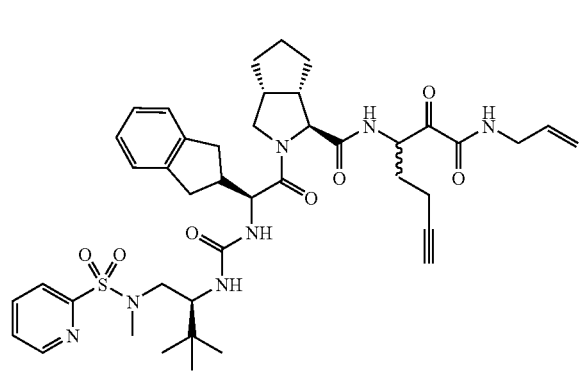
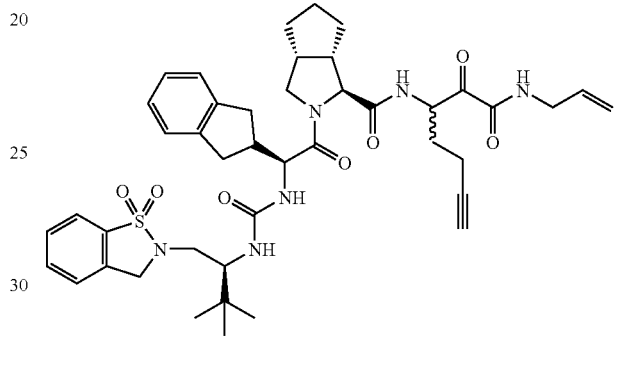
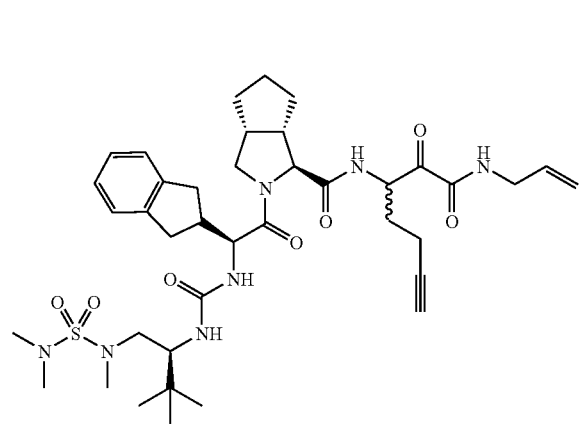
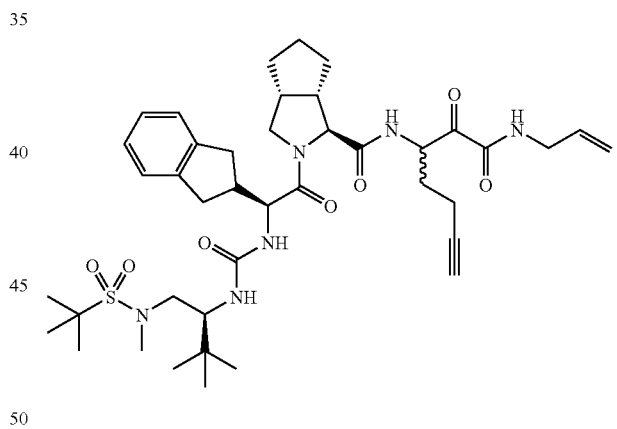
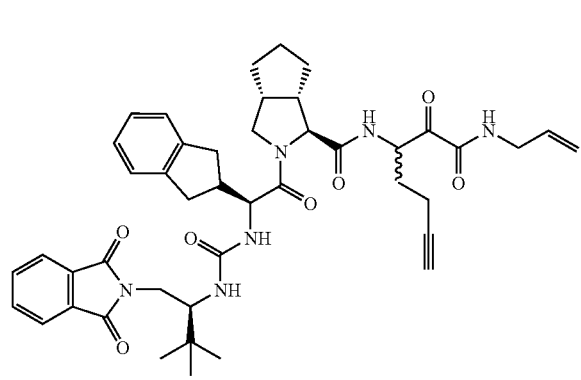
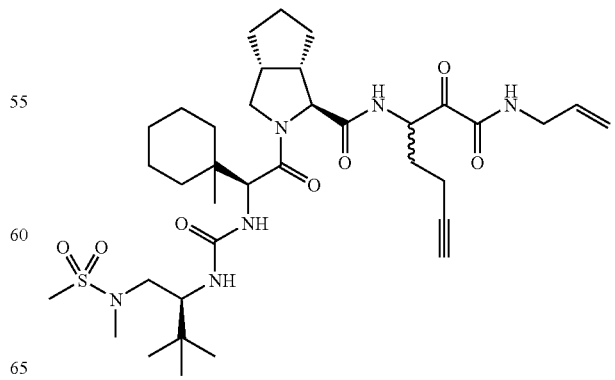

391
-continued
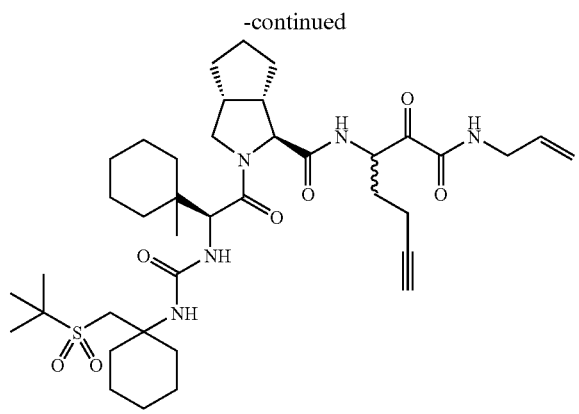
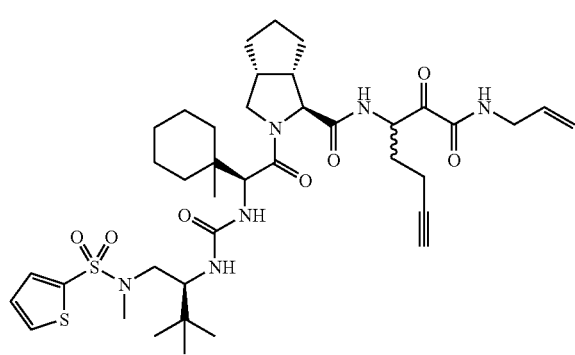
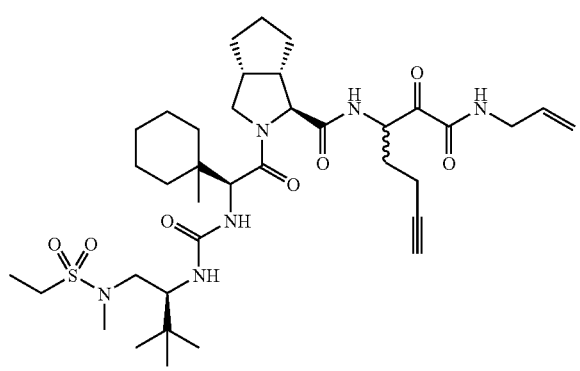
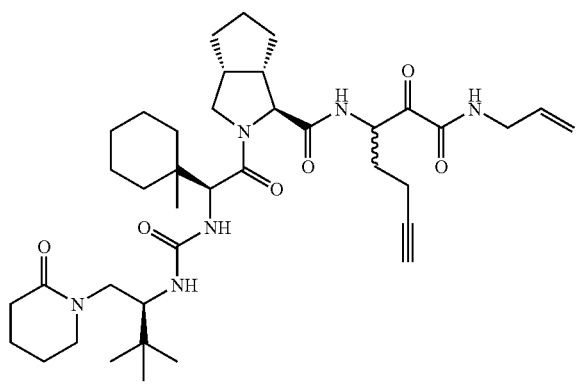
392
-continued
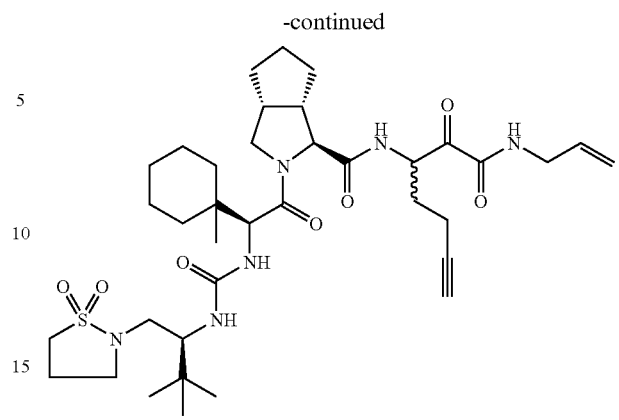
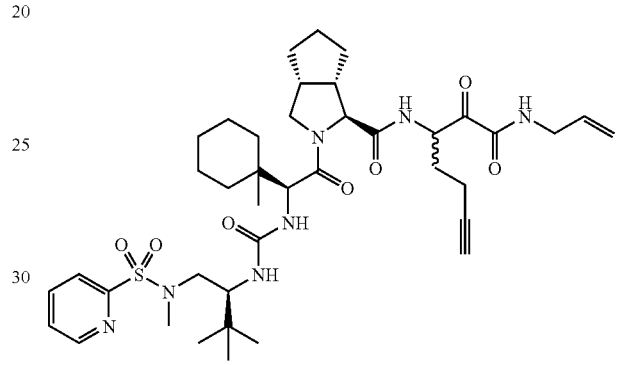
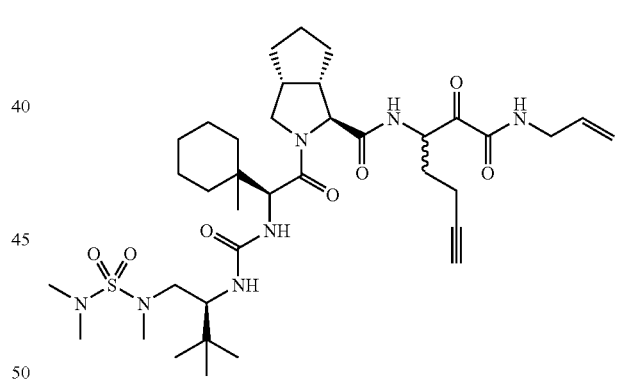
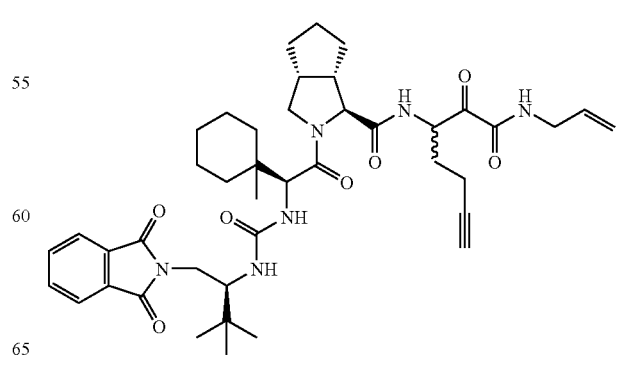

-continued

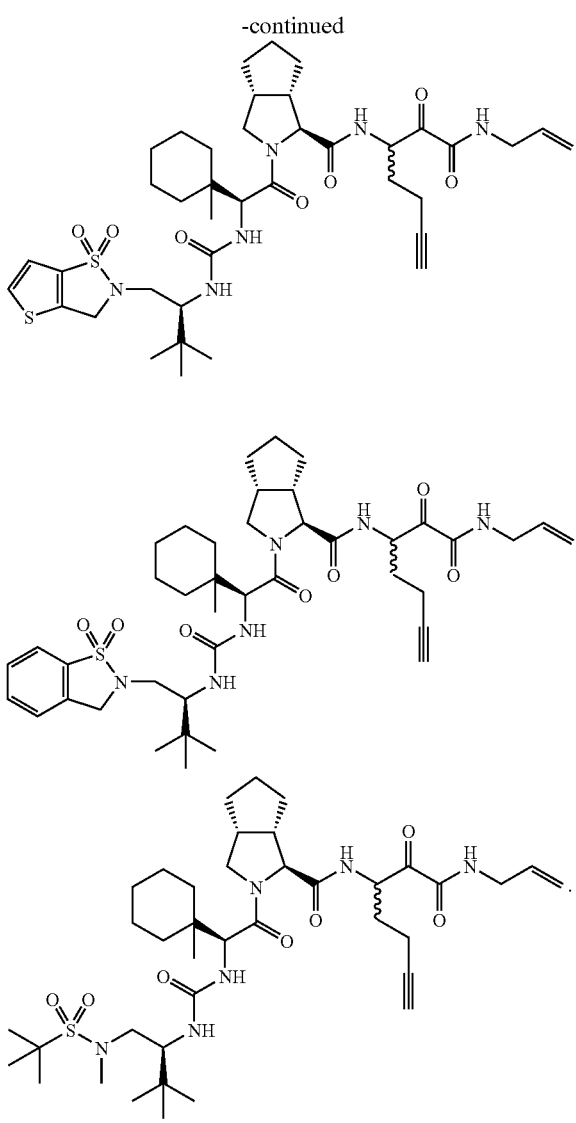

23. A pharmaceutical composition for treating an infection by HCV, said composition comprising therapeutically effective amount of one or more compounds in claim 22 and a pharmaceutically acceptable carrier.

24. The pharmaceutical composition of claim 23, additionally containing at least one antiviral agent.

25. The pharmaceutical composition of claim 24, still additionally containing at least one interferon or PEG-interferon alpha conjugate.

26. The pharmaceutical composition of claim 25, wherein said at least one antiviral agent is ribavirin and said at least one interferon is α-interferon or pegylated interferon.

27. A method of treatment of a hepatitis C virus infection comprising administering an effective amount of one or more compounds of claim 22.

28. A method of modulating the activity of hepatitis C virus (HCV) protease, comprising contacting HCV protease with one or more compounds of claim 22.

29. A method of treating or ameliorating one or more symptoms of hepatitis C, comprising administering a therapeutically effective amount of one or more compounds of claim 22.

30. The method of claim 29, wherein the HCV protease is the NS3/NS4a protease.

31. The method of claim 30, wherein the compound or compounds inhibit HCV NS3/NS4a protease.

32. A method of modulating the processing of hepatitis C virus (HCV) polypeptide, comprising contacting a composition containing the HCV polypeptide under conditions in which said polypeptide is processed with one or more compounds of claim 22.

33. A method of treating an infection by HCV, said method comprising administering to a patient in need of such treatment, a pharmaceutical composition which comprises therapeutically effective amounts of at least one compound, or enantiomers, stereoisomers, rotamers, tautomers, diastereomers or racemates of said compound, or a pharmaceutically acceptable salt, solvate or ester of said compound, said compound being selected from the following:

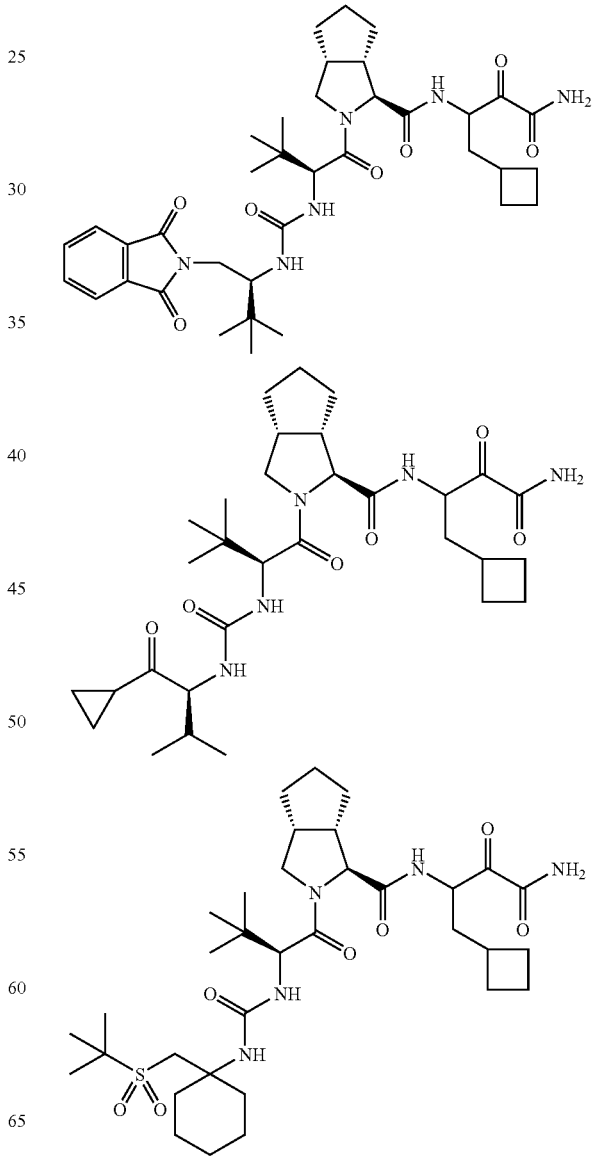

-continued
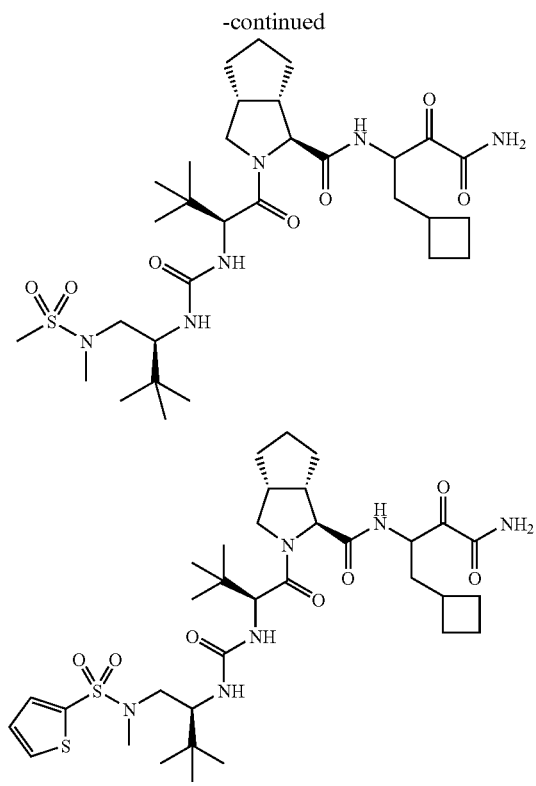
-continued
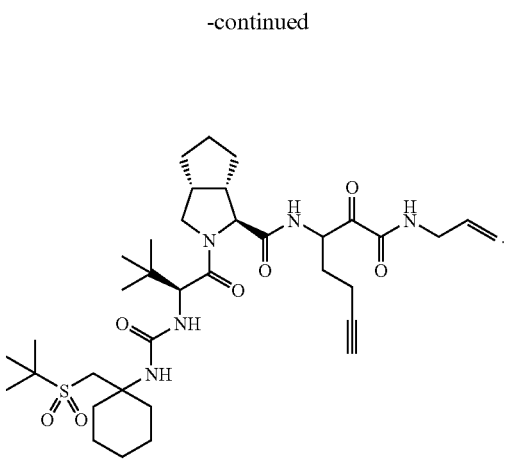
34. A compound of claim 1 in purified form.
\* \* \* \* \*

UNITED STATES PATENT AND TRADEMARK OFFICE
CERTIFICATE OF CORRECTION

PATENT NO. : 7,342,041 B2  Page 1 of 1
APPLICATION NO. : 11/064757
DATED : March 11, 2008
INVENTOR(S) : Njoroge et al.

It is certified that error appears in the above-identified patent and that said Letters Patent is hereby corrected as shown below:

Column 320

Claim 8, Line 48, replace "from" with -- form --.

Signed and Sealed this

Eighth Day of July, 2008

JON W. DUDAS
*Director of the United States Patent and Trademark Office*